(12) United States Patent
Kreider et al.

(10) Patent No.: US 10,294,200 B2
(45) Date of Patent: May 21, 2019

(54) MIXED BRANCHED EICOSYL POLYSULFIDE COMPOSITIONS AND METHODS OF MAKING SAME

(71) Applicant: Chevron Phillips Chemical Company LP, The Woodlands, TX (US)

(72) Inventors: Jason L. Kreider, Copan, OK (US); R. Shawn Childress, Bartlesville, OK (US); Michael S. Matson, Bartlesville, OK (US); Jim D. Byers, Bartlesville, OK (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 0 days.

(21) Appl. No.: 16/021,736

(22) Filed: Jun. 28, 2018

(65) Prior Publication Data

US 2018/0305306 A1    Oct. 25, 2018

Related U.S. Application Data

(60) Continuation-in-part of application No. 15/825,555, filed on Nov. 29, 2017, now Pat. No. 10,040,758, (Continued)

(51) Int. Cl.
*C07C 319/04* (2006.01)
*C07C 319/24* (2006.01)
(Continued)

(52) U.S. Cl.
CPC .......... *C07C 319/04* (2013.01); *B01J 19/123* (2013.01); *C07C 319/16* (2013.01); (Continued)

(58) Field of Classification Search
CPC ... C07C 319/04; C07C 319/16; C07C 321/04; B01J 19/123; B01J 2219/0877; B01J 2219/1203
See application file for complete search history.

(56) References Cited

U.S. PATENT DOCUMENTS 1,774,183 A    8/1930 Moses et al.
2,125,337 A    8/1938 Gaudin
(Continued)

FOREIGN PATENT DOCUMENTS

CN    105985774 A    10/2016
EP    2397503 A1    12/2011
(Continued)

OTHER PUBLICATIONS

Duffey, H. R., et al., "Effect of Catalysts on the Reaction between Olefins and Hydrogen Sulfide," Industrial and Engineering chemistry, Jan. 1, 1934, pp. 91-93, vol. 26, No. 1.
(Continued)

*Primary Examiner* — Peter F Godenschwager
*Assistant Examiner* — Andrew J. Oyer
(74) *Attorney, Agent, or Firm* — Conley Rose, P.C.

(57) ABSTRACT

A composition comprising polysulfides, wherein at least about 50 wt. % of the polysulfides are branched $C_{20}$ to $C_{60}$ polysulfides represented by general formula $R^{15}S^1$—$[S]_n$—$S^2R^{16}$ wherein $R^{15}$ and $R^{16}$ are each independently a branched $C_{10}$ to $C_{30}$ alkyl group and wherein n is an integer from 1 to 10. A process of producing a polysulfides crude product comprising one or more branched $C_{20}$ to $C_{60}$ polysulfides comprising: (A) reacting a feedstock comprising one or more branched $C_{10}$ to $C_{30}$ mercaptans and sulfur in the presence of a catalyst and (B) collecting the polysulfides crude product.

32 Claims, 10 Drawing Sheets

R, R', R" = H or $C_1$ to $C_{16}$ alkyl and R + R' + R" = 8 to 16 carbon atoms

Related U.S. Application Data which is a continuation-in-part of application No. 15/669,097, filed on Aug. 4, 2017, now Pat. No. 10,011,564, which is a continuation-in-part of application No. 15/632,910, filed on Jun. 26, 2017, now Pat. No. 9,938,237, which is a continuation of application No. 15/296,837, filed on Oct. 18, 2016, now Pat. No. 9,738,601, which is a division of application No. 14/981,469, filed on Dec. 28, 2015, now Pat. No. 9,512,071, said application No. 15/669,097 is a continuation-in-part of application No. 15/463,867, filed on Mar. 20, 2017, now Pat. No. 9,879,102, which is a continuation of application No. 15/284,802, filed on Oct. 4, 2016, now Pat. No. 9,631,039, which is a division of application No. 14/981,428, filed on Dec. 28, 2015, now Pat. No. 9,512,248.

(51) Int. Cl.
*B01J 19/12* (2006.01)
*C07C 321/04* (2006.01)
*C07C 319/16* (2006.01)

(52) U.S. Cl.
CPC .......... *C07C 319/24* (2013.01); *C07C 321/04* (2013.01); *B01J 2219/0877* (2013.01); *B01J 2219/1203* (2013.01)

(56) References Cited

U.S. PATENT DOCUMENTS

| | | | |
|---|---|---|---|
| 2,374,983 A | 5/1945 | Simó et al. | |
| 2,411,961 A | 12/1946 | Evans et al. | |
| 2,551,813 A | 5/1951 | Pinkney et al. | |
| 2,820,831 A | 1/1958 | Doumani | |
| 3,051,758 A * | 8/1962 | Franz | C07C 319/04 568/21 |
| 3,059,774 A | 10/1962 | Wilson | |
| 3,219,709 A | 11/1965 | Louthan | |
| 3,221,056 A | 11/1965 | Louthan | |
| 3,419,614 A | 12/1968 | Doss | |
| 3,454,651 A | 7/1969 | Warner et al. | |
| 3,567,608 A | 3/1971 | Warner | |
| 4,119,549 A | 10/1978 | Davis | |
| 4,211,644 A | 7/1980 | Wiechers | |
| 4,233,128 A | 11/1980 | Ollivier et al. | |
| 4,274,950 A | 6/1981 | Larribau | |
| 4,439,314 A | 3/1984 | Parlman et al. | |
| 4,594,151 A | 6/1986 | Delourme et al. | |
| 4,822,483 A | 4/1989 | Klimpel et al. | |
| 5,183,856 A | 2/1993 | Kitagawa et al. | |
| 5,304,683 A | 4/1994 | Sattich | |
| 5,310,683 A | 5/1994 | Godec et al. | |
| 6,242,489 B1 | 6/2001 | Pinney | |
| 6,288,006 B1 * | 9/2001 | Arretz | B01J 37/20 502/216 |
| 6,417,306 B1 | 7/2002 | Ueda et al. | |
| 6,827,220 B1 | 12/2004 | Young et al. | |
| 6,844,290 B1 | 1/2005 | Maas et al. | |
| 7,014,048 B2 | 3/2006 | Anglerot et al. | |
| 7,105,602 B1 | 9/2006 | Sunagawa et al. | |
| 7,217,843 B2 | 5/2007 | Hasenberg et al. | |
| 7,461,745 B2 | 12/2008 | Young et al. | |
| 7,989,655 B2 | 8/2011 | Refvik et al. | |
| 8,592,550 B2 | 11/2013 | Frijns et al. | |
| 8,883,907 B2 | 11/2014 | Moraru et al. | |
| 9,505,011 B1 | 11/2016 | Byers et al. | |
| 9,512,071 B1 | 12/2016 | Matson et al. | |
| 9,512,248 B1 | 12/2016 | Kreider et al. | |
| 9,527,090 B1 | 12/2016 | Byers et al. | |
| 9,631,039 B1 | 4/2017 | Kreider et al. | |
| 9,738,601 B2 | 8/2017 | Matson et al. | |
| 9,879,102 B2 | 1/2018 | Kreider et al. | |
| 9,938,237 B2 | 4/2018 | Matson et al. | |
| 10,000,590 B2 | 6/2018 | Kreider et al. | |
| 10,011,564 B2 | 7/2018 | Matson et al. | |
| 10,040,758 B2 | 8/2018 | Matson et al. | |
| 2005/0187391 A1 | 8/2005 | Knudsen et al. | |
| 2006/0173218 A1 | 8/2006 | Muller et al. | |
| 2007/0244248 A1 | 10/2007 | Behles | |
| 2009/0264669 A1 | 10/2009 | Upshaw | |
| 2010/0274065 A1 | 10/2010 | Sydora | |
| 2011/0269930 A1 | 11/2011 | Edel et al. | |
| 2013/0267739 A1 * | 10/2013 | Fremy | C07C 319/24 568/26 |
| 2014/0221692 A1 | 8/2014 | Netemeyer et al. | |

FOREIGN PATENT DOCUMENTS

| | | |
|---|---|---|
| WO | 8606983 A1 | 12/1986 |
| WO | 0147839 A1 | 7/2001 |
| WO | 2014094114 A1 | 6/2014 |
| WO | 2017010998 A1 | 1/2017 |

OTHER PUBLICATIONS

Foreign communication from a related counterpart application—International Search Report and Written Opinion, PCT/US2015/040433, dated Feb. 23, 2016, 14 pages.

Foreign communication from a related counterpart application—International Search Report and Written Opinion, PCT/US2016/058822, dated Jan. 16, 2017, 8 pages.

Foreign communication from a related counterpart application—International Search Report and Written Opinion, PCT/US2016/058818, dated Jan. 23, 2017, 14 pages.

"Group notation revised in periodic table," Feb. 4, 1985, pp. 26-27, C&EN.

Matsumoto, Y., et al,. "Mfr of polyurethane of resin for waterproof fabric—by radical polymerisation of polyoxyethylene mono:alkyl:ether (meth)acrylate with mercaptan-based chain transfter agent, poly:ol, and organic poly: isocyanate," WPI, 1992, 2 pages, XP-002755753, Thomson.

McNaught, Alan D., et al., "Compendium of Chemical Terminology," IUPAC Recommendations, Second edition, 1997, 5 pages, Wiley-Blackwell.

Sorokina, L. I., et al., "Chain transfer reactions by aliphatic mercaptans in the high-tempurature polymerization of methlmethacrylate," Polymer Science U.S.S.R., Jan. 1, 1983, pp. 2414-2418, vol. 25, No. 10, Pergamon Press ltd.

Vaughan, W. E., et al. "The Photo-Additions of Hydrogen Sulfide to Olefinic Bonds," The Journal of Organic Chemistry, Nov. 6, 1942, pp. 472-476, vol. 7, No. 6.

Van Zijll Langhout, W. C., et al., "The addition of hydrogen sulphide to alkenes," Journal of Applied Chemistry, Jun. 4, 1954, pp. 285-288, vol. 4, No. 6, Journal of Applied Chemistry.

Technical Data Sheet entitled NEODENE® 14/16 Higher Olefins, Nov. 2015, 2 pages, Shell Chemicals.

Technical Data Sheet entitled NEODENE® 134 IO Higher Olefins, Nov. 2015, 2 pages, Shell Chemicals.

Technical Data Sheet entitled NEODENE® 1112 IO Higher Olefins, Nov. 2015, 2 pages, Shell Chemicals.

* cited by examiner

MIXED BRANCHED EICOSYL POLYSULFIDE COMPOSITIONS AND METHODS OF MAKING SAME

CROSS-REFERENCE TO RELATED APPLICATIONS

This application is a continuation-in-part application of U.S. patent application Ser. No. 15/825,555 filed Nov. 29, 2017, published as U.S. Patent Application Publication No. U.S. 2018/0079718 A1, which is a continuation-in-part application of U.S. patent application Ser. No. 15/669,097 filed Aug. 4, 2017, published as U.S. Patent Application Publication No. U.S. 2017/0334843 A1, which is a continuation-in-part application of U.S. patent application Ser. No. 15/632,910 filed Jun. 26, 2017, now U.S. Pat. No. 9,938,237, which is a continuation of and claims priority to U.S. patent application Ser. No. 15/296,837 filed Oct. 18, 2016, now U.S. Pat. No. 9,738,601, which is a divisional of and claims priority to U.S. patent application Ser. No. 14/981,469 filed Dec. 28, 2015, now U.S. Pat. No. 9,512,071, and entitled "Mixed Decyl Mercaptans Compositions and Methods of Making Same," each of which is incorporated by reference herein in its entirety.

U.S. patent application Ser. No. 15/669,097 is also a continuation-in-part application of U.S. patent application Ser. No. 15/463,867 filed Mar. 20, 2017, now U.S. Pat. No. 9,879,102, which is a continuation of and claims priority to U.S. patent application Ser. No. 15/284,802 filed Oct. 4, 2016, now U.S. Pat. No. 9,631,039, which is a divisional of and claims priority to U.S. patent application Ser. No. 14/981,428 filed Dec. 28, 2015, now U.S. Pat. No. 9,512,248, and entitled "Mixed Decyl Mercaptans Compositions and Use Thereof as Chain Transfer Agents," each of which is incorporated by reference herein in its entirety.

This application is related to U.S. patent application Ser. No. 15/284,809 filed Oct. 4, 2016, now U.S. Pat. No. 9,527,090, which is a divisional of and claims priority to U.S. patent application Ser. No. 14/981,475 filed Dec. 28, 2015, now U.S. Pat. No. 9,505,011, and entitled "Mixed Decyl Mercaptans Compositions and Use Thereof as Mining Chemical Collectors," each of which is incorporated by reference herein in its entirety.

TECHNICAL FIELD

The present disclosure relates to compositions containing $C_{20+}$ polysulfides and/or $C_{20+}$ monosulfides and methods of making same. More specifically, the present disclosure relates to compositions containing mixed $C_{20+}$ polysulfides and/or mixed $C_{20+}$ monosulfides, and methods of making same.

BACKGROUND

Polysulfides of the type disclosed herein are individual organic molecules containing chains of multiple sulfur atoms. Polysulfides are used in diverse applications including lubricants for the mining industry; sealants for automotive, construction, and marine uses; and to some extent as flexibilizing hardeners for epoxy adhesives. Polysulfides are also used as sulfiding agents in synthetic chemistry processes. While processes for making polysulfides from mercaptans are available, preparing individual mercaptans can be costly due numerous purification steps required for the feedstock and/or mercaptan product. Some mercaptans can be used as precursors for agriculture chemicals or as natural gas additives. However, many applications may not require a single pure mercaptan compound, but could utilize mercaptan mixtures. Thus, there is a need to develop mercaptan compositions suitable for such applications, and methods of making same.

SUMMARY

Disclosed herein is a composition comprising polysulfides, wherein at least about 50 wt. % of the polysulfides are branched $C_{20}$ to $C_{60}$ polysulfides represented by general formula $R^{15}S^1$—$[S]_n$—$S^2R^{16}$ wherein $R^{15}$ and $R^{16}$ are each independently a branched $C_{10}$ to $C_{30}$ alkyl group and wherein n is an integer from 1 to 10.

Also disclosed herein is a process of producing a polysulfides crude product comprising one or more branched $C_{20}$ to $C_{60}$ polysulfides comprising: (A) reacting a feedstock comprising one or more branched $C_{10}$ to $C_{30}$ mercaptans and sulfur in the presence of a catalyst and (B) collecting the polysulfides crude product.

Also disclosed herein is a process of producing one or more branched $C_{20}$ to $C_{60}$ polysulfides comprising: (a) reacting hydrogen sulfide ($H_2S$) and a feedstock comprising one or more branched $C_{10}$ to $C_{30}$ olefins in the presence of an initiating agent to produce a branched $C_{10+}$ mercaptans crude composition; (b) recovering an intermediate reaction product comprising one or more branched $C_{10}$ to $C_{30}$ mercaptans from the branched $C_{10+}$ mercaptans crude composition; (c) reacting sulfur and the intermediate reaction product comprising one or more branched $C_{10}$ to $C_{30}$ mercaptans in the presence of a catalyst; and (d) collecting a $C_{20+}$ polysulfides crude product comprising the one or more branched $C_{20}$ to $C_{60}$ polysulfides.

Also disclosed herein is a composition comprising: (A) at least about 25 wt. % branched $C_{20}$ to $C_{60}$ polysulfides represented by general formula $R^{15}S^1$—$[S]_n$—$S^2R^{16}$, wherein n is an integer from 1 to 10, wherein $R^{15}$ and $R^{16}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group; and (B) at least about 5 wt. % branched $C_{20}$ to $C_{60}$ monosulfides represented by general formula $R^{17}$—S—$R^{18}$, wherein $R^{17}$ and $R^{18}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an attachment point with a sulfur atom of the branched $C_{20}$ to $C_{60}$ monosulfide, and wherein $R^9$ is a $C_1$ to $C_{21}$ alkyl group.

Also disclosed herein is a composition comprising: (A) from at least about 50 wt. % to at least about 90 wt. % polysulfides, wherein at least about 50 wt. % of the polysulfides are branched $C_{20}$ to $C_{60}$ polysulfides represented by general formula $R^{15}S^1$—$[S]_n$—$S^2R^{16}$, wherein n is an integer from 1 to 10, wherein $R^{15}$ and $R^{16}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group; and (B) from at least about 10 wt. % to at least about 30 wt. % monosulfides, wherein at least 50 wt. % of the monosulfides are branched $C_{20}$ to $C_{60}$ monosulfides represented by general formula $R^{17}$—S—$R^{18}$, wherein $R^{17}$ and $R^{18}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an attachment point with a sulfur atom of the branched $C_{20}$ to $C_{60}$ monosulfide, and wherein $R^9$ is a $C_1$ to $C_{21}$ alkyl group.

Also disclosed herein is a composition comprising: (A) at least about 25 wt. % branched $C_{20}$ to $C_{60}$ polysulfides represented by general formula $R^{15}S^1$—$[S]_n$—$S^2R^{16}$, wherein n is an integer from 1 to 10, wherein $R^{15}$ and $R^{16}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group; and (B) at least about 5 wt. % branched $C_{20}$ to $C_{60}$ monosulfides represented by general formula $R^{17}$—S—$R^{18}$, wherein $R^{17}$ and $R^{18}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an attachment point with a sulfur atom of the branched $C_{20}$ to $C_{60}$ monosulfide, and wherein $R^9$ is a $C_1$ to $C_{21}$ alkyl group; and one or more of the following components (C)-(I): (C) less than about 5 wt. % branched $C_{16}$ polysulfides; (D) less than about 15 wt. % branched $C_{64}$ polysulfides; (E) less than about 15 wt. % branched $C_{68}$ polysulfides; (F) less than about 5 wt. % branched $C_{72}$ polysulfides and/or branched $C_{76}$ polysulfides; (G) less than about 1 wt. % branched $C_{16}$ to $C_{76}$ monosulfides represented by general formula $R^{17}$—S—$R^{18}$, wherein $R^{17}$ and $R^{18}$ are each independently a functional group derived from an olefin selected from the group consisting of $C_8$ monoolefins, $C_{32}$ monoolefins, $C_{34}$ monoolefins, $C_{36}$ monoolefins, and $C_{38}$ monoolefins, wherein $R^{17}$ and $R^{18}$ are not both branched $C_{30}$ monoolefins; (H) less than about 10 wt. % unreacted $C_8$ to $C_{38}$ mercaptans; and (I) less than about 10 wt. % non-mercaptan impurities selected from the group consisting of $C_8$ to $C_{38}$ olefins, $C_8$ to $C_{14}$ alkanes, cyclohexane, methylcyclopentane, methylcyclohexane, benzene, toluene, ethylbenzene, xylene, mesitylene, hexamethylbenzene, $C_4$ to $C_{12}$ alcohols, 2-ethyl-1-hexanol, and 2-ethylhexyl-2-ethylhexanoate.

BRIEF DESCRIPTION OF THE DRAWINGS

For a detailed description of the preferred embodiments of the disclosed compositions and methods of making same, reference will now be made to the accompanying drawings in which.

DETAILED DESCRIPTION

Figure 1:
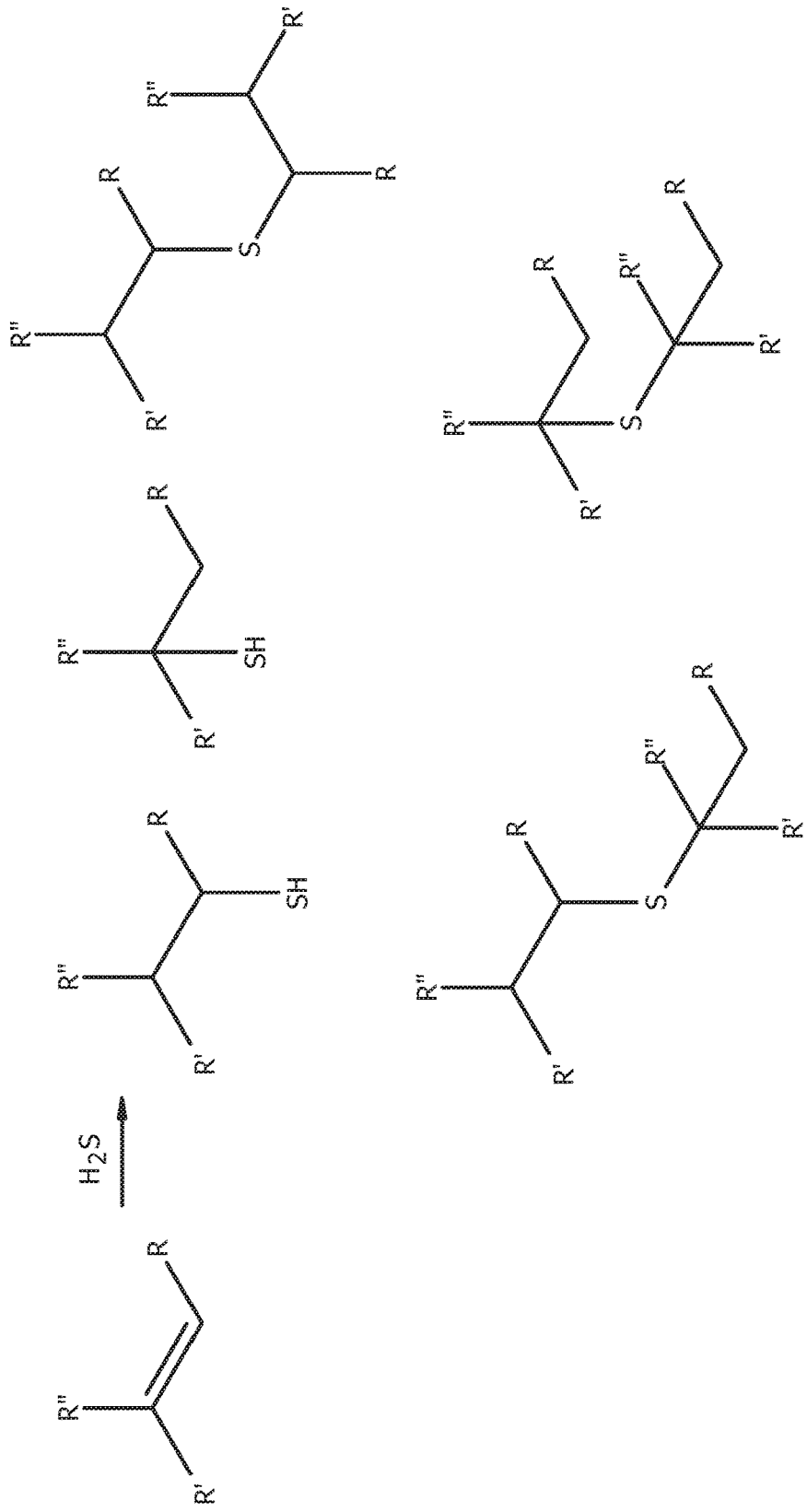
FIG. 1 displays a reaction schematic for addition of hydrogen sulfide ($H_2S$) to an olefin.

To define more clearly the terms used herein, the following definitions are provided. Unless otherwise indicated, the following definitions are applicable to this disclosure. If a term is used in this disclosure, but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the Periodic Table are indicated using the numbering scheme indicated in the version of the Periodic Table of elements published in *Chemical and Engineering News,* 63(5), 27, 1985. In some instances, a group of elements can be indicated using a common name assigned to the group; for example, alkali metals for Group 1 elements, alkaline earth metals (or alkaline metals) for Group 2 elements, transition metals for Groups 3-12 elements, and halogens for Group 17 elements.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting of" limits the scope of a claim to the specified materials or steps and those that do not materially affect the basic and novel characteristic(s) of the present disclosure as claimed. The term "consisting essentially of" occupies a middle ground between closed terms like "consisting of" and fully open terms like "comprising." Absent an indication to the contrary, when describing a compound or composition, "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which is utilized and it is possible to have different transitional terms or phrases utilized with different features within a claim. For example, a method can comprise several recited steps (and other non-recited steps), but utilize a catalyst system preparation consisting of specific steps, or alternatively, consisting essentially of specific steps, but utilize a catalyst system comprising recited components and other non-recited components.

While compositions and methods are described in terms of "comprising" (or other broad term) various components and/or steps, the compositions and methods can also be described using narrower terms, such as "consist essentially of" or "consist of" the various components and/or steps.

The terms "a," "an," and "the" are intended, unless specifically indicated otherwise, to include plural alternatives, e.g., at least one.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers, unless explicitly indicated otherwise; e.g., a general reference to pentane includes n-pentane, 2-methyl-butane, and 2,2-dimethylpropane, while a general reference to a butyl group includes an n-butyl group, a sec-butyl group, an iso-butyl group, and a tert-butyl group. Additionally, the reference to a general structure or name encompasses all enantiomers, diastereomers, and other optical isomers, whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" can formally be derived by removing one hydrogen atom from an alkane, while an "alkylene group" can formally be derived by removing two hydrogen atoms from an alkane. Moreover, a more general term can be used to encompass a variety of groups that formally are derived by removing any number ("one or more") of hydrogen atoms from a parent compound, which in this example can be described as an "alkane group," and which encompasses an "alkyl group," an "alkylene group," and materials having three or more hydrogens atoms, as necessary for the situation, removed from the alkane. Throughout, the disclosure of a substituent, ligand, or other chemical moiety that can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g., halogenated alkane indicates the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl group are derived by removal of a hydrogen atom from a primary, secondary, and tertiary carbon atom, respectively, of an alkane. The n-alkyl group can be derived by removal of a hydrogen atom from a terminal carbon atom of a linear alkane.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from a carbon atom of an aliphatic compound. Thus, an aliphatic compound is an acyclic or cyclic, saturated or unsaturated carbon compound, excluding aromatic compounds. That is, an aliphatic compound is a non-aromatic organic compound. Aliphatic compounds and therefore aliphatic groups can contain organic functional group(s) and/or atom(s) other than carbon and hydrogen.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms, such as "non-substituted," which refers to the original group in which a non-hydrogen moiety does not replace a hydrogen within that group. "Substituted" is intended to be nonlimiting and include inorganic substituents or organic substituents.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "alkene" whenever used in this specification and claims refers to a linear or branched aliphatic hydrocarbon olefin that has one or more carbon-carbon double bonds. Alkenes having only one, only two, only three, etc., such multiple bonds can be identified by use of the term "mono," "di," "tri," etc., within the name. For example, alkaminoenes, alkadienes, and alkatrienes refer to linear or branched acyclic hydrocarbon olefins having only one carbon-carbon double bond (acyclic having a general formula of $C_nH_{2n}$), only two carbon-carbon double bonds (acyclic having a general formula of $C_nH_{2n-2}$), and only three carbon-carbon double bonds (acyclic having a general formula of $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2 position (a vinylidene) and/or the 3 position or higher with respect to the olefin double bond. The term "vinylidene" whenever used in this specification and claims refers to an alpha olefin having a branch at the 2 position with respect to the olefin double bond. By itself, the term "alpha olefin" does not indicate the presence or absence of other carbon-carbon double bonds unless explicitly indicated.

The term "normal alpha olefin" whenever used in this specification and claims refers to a linear aliphatic monoolefin having a carbon-carbon double bond between the first and second carbon atoms. It is noted that "normal alpha olefin" is not synonymous with "linear alpha olefin" as the term "linear alpha olefin" can include linear olefinic compounds having a double bond between the first and second carbon atoms.

The terms "lights," "light fraction," or "light compounds" whenever used in this specification and claims refers to compounds present in the reaction product with equal to or less than about 9 carbon atoms ($C_{9-}$) per molecule. Nonlimiting examples of $C_{9-}$ compounds that can be in the reaction product include $C_{9-}$ monoolefins (e.g., unreacted $C_{9-}$ monoolefins), $C_{9-}$ mercaptans, $C_{9-}$ alkanes, $C_{9-}$ alcohols, cyclohexane, methylcyclopentane, methylcyclohexane, benzene, toluene, ethylbenzene, xylene, mesitylene, 2-ethyl-1-hexanol, and the like, or combinations thereof. Unless otherwise specifically indicated herein, the terms "lights," "light fraction," or "light compounds" whenever used in this specification and claims excludes hydrogen sulfide, as $H_2S$ is typically substantially consumed during the preceding reaction and/or removed from the reaction product (as discussed in more detail herein) prior to further processing of the reaction product (e.g., distillation thereof). For example, $H_2S$ can be removed from the reaction product via distillation, stripping, flashing, or other suitable means known to those of skill in the art without removing any substantial amounts of the "lights," "light fraction," or "light compounds" from the reaction product. Not wanting to be limited by theory, this definition of "lights," "light fraction," or "light compounds" includes any compounds with about nine or less carbon atoms present in the reaction product that can be detected, even in trace amounts. As is known to one of skill in the art, the light fraction can also contain trace amounts of lower carbon number sulfides.

The terms "intermediates" or "intermediate fraction" whenever used in this specification and claims typically refers to compounds with about ten to seventeen carbon atoms ($C_{10-17}$) per molecule. Nonlimiting examples of $C_{10-17}$ compounds include $C_{10}$ mercaptans (including both branched and non-branched $C_{10}$ mercaptans), $C_{12-17}$ mercaptan isomers, $C_{12}$-$C_{17}$ sulfides, and the like, or combinations thereof. Not wanting to be limited by theory, this definition of "intermediates" or "intermediate fraction" includes any compounds with about ten to seventeen carbon atoms present in the reaction product that can be detected, even in trace amounts. As is known to one skilled in the art, the intermediate fraction can also contain trace amounts of lower carbon number compounds, including sulfides. In some embodiments (e.g., in the Examples described herein), a product can be recovered from the intermediate fraction (e.g., a $C_{10}$ mercaptan fraction), and the remaining $C_{11}$ to $C_{17}$ compounds (e.g., $C_{12-16}$ mercaptans) can be referred to as the intermediate fraction.

The terms "heavies" or "heavy fraction" whenever used in this specification and claims refers to compounds with about eighteen or more carbon atoms ($C_{18+}$) per molecule. Nonlimiting examples of $C_{18+}$ products include $C_{18}$ sulfides, $C_{20}$ sulfides, $C_{24}$ sulfides, $C_{28}$ sulfides, $C_{32}$ sulfides, $C_{18}$ mercaptans, and the like, or combinations thereof. As is known to those of skill in the art, the heavy fraction can also contain trace amounts of lower carbon number compounds, including mercaptans and sulfides.

These light, intermediate, and heavy fractions can be referred to as "rough-cuts," in that they contain a plurality of compounds spread across a range of carbon atoms, i.e., a plurality of compounds having a different number of carbon atoms (e.g., a rough cut comprising $C_{10}$, $C_{11}$, $C_{12}$, $C_{13}$, $C_{14}$, $C_{15}$, $C_{16}$, $C_{17}$, etc. compounds). These rough cuts are in contrast to one or more "fine-cuts" that contain a fewer number of compounds than the rough-cuts, for example, a $C_{10}$ fine cut (e.g., a $C_{10}$ mercaptan fraction) derived from or otherwise recovered separately from the rough cut. Accordingly, a rough cut can be comprised of a number of fine cuts, for example where a plurality of cuts are taken via distillation over a period of time and across a ramped temperature range, and referred to collectively as a rough cut or individually as fine cuts. Those of ordinary skill in the art can produce a fine-cut fraction from a rough-cut fraction, for example via further distillation (e.g., a $C_{10}$ splitter, a $C_{20}$ splitter, etc.) or other purification technique.

The terms "room temperature" or "ambient temperature" are used herein to describe any temperature from 15° C. to 35° C. wherein no external heat or cooling source is directly applied to the reaction vessel. Accordingly, the terms "room temperature" and "ambient temperature" encompass the individual temperatures and any and all ranges, subranges, and combinations of subranges of temperatures from 15° C. to 35° C. wherein no external heating or cooling source is directly applied to the reaction vessel. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

Features within this disclosure that are provided as a minimum value can be alternatively stated as "at least" or "greater than or equal to" any recited minimum value for the feature disclosed herein. Features within this disclosure that are provided as a maximum value can be alternatively stated as "less than or equal to" or "below" any recited maximum value for the feature disclosed herein.

Within this disclosure, the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using comprising or some other alternative language. For example, a reference to a phenyl group comprising a substituent at the 4 position refers to a phenyl group having a non-hydrogen substituent group at the 4 position and hydrogen or any non-hydrogen group at the 2, 3, 5, and 6 positions.

Use of the term "optionally" with respect to any element of a claim is intended to mean that the subject element is required, or alternatively, is not required. Both alternatives are intended to be within the scope of the claim.

Unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms. Moreover, other identifiers or qualifying terms can be utilized to indicate the presence or absence of a particular substituent, a particular regiochemistry and/or stereochemistry, or the presence or absence of a branched underlying structure or backbone.

Processes and/or methods described herein utilize steps, features, and compounds which are independently described herein. The process and methods described herein may or may not utilize step identifiers (e.g., 1), 2), etc., a), b), etc., or i), ii), etc.), features (e.g., 1), 2), etc., a), b), etc., or i), ii), etc.), and/or compound identifiers (e.g., first, second, etc.). However, it should be noted that processes and/or methods described herein can have multiple steps, features (e.g., reagent ratios, formation conditions, among other considerations), and/or multiple compounds having the same general descriptor. Consequently, it should be noted that the processes and/or methods described herein can be modified to use an appropriate step or feature identifier (e.g., 1), 2), etc., a), b), etc., or i), ii), etc.) and/or compound identifier (e.g., first, second, etc.) regardless of step, feature, and/or compound identifier utilized in a particular aspect and/or embodiment described herein and that step or feature identifiers can be added and/or modified to indicate individual different steps/features/compounds utilized within the process and/or methods without detracting from the general disclosure.

Embodiments disclosed herein can provide the materials listed as suitable for satisfying a particular feature of the embodiment delimited by the term "or." For example, a particular feature of the disclosed subject matter can be disclosed as follows: Feature X can be A, B, or C. It is also contemplated that for each feature the statement can also be phrased as a listing of alternatives such that the statement "Feature X is A, alternatively B, or alternatively C" is also an embodiment of the present disclosure whether or not the statement is explicitly recited.

The weight percent compositional aspects of the various compositions described herein (e.g., the weight percent of one or more compounds present in a composition) can be determined by gas chromatography (GC), gas chromatography-mass spectroscopy (GC-MS), Raman spectroscopy, nuclear magnetic resonance (NMR) spectroscopy, or any other suitable analytical method known to those of skill in the art. For example, unless otherwise indicated, the weight percent compositional aspects of the various compositions described herein (e.g., the weight percent of the various sulfur-containing compounds such as $C_{10}$ mercaptans and $C_{20}$ sulfides present in the compositions such as the crude, light fraction, intermediate fraction, heavy faction, etc.) can be determined using a gas chromatograph with a flame ionization detector (GC-FID) detector based on the total GC peak areas (as described herein) and reported as gas chromatography (GC) area percent (GC area %), which is a common analytical technique for compositions comprising sulfur-containing compounds. While not wishing to be bound by this theory, it is believed that the amount in area % is very similar to the amount in weight percent (wt. %), and these respective amounts need not be exactly equivalent or interchangeable in order to be understood by a person of ordinary skill.

In an embodiment, a process of the present disclosure comprises reacting, in a reactor, hydrogen sulfide ($H_2S$) and a feedstock comprising one or more branched $C_{10}$ monoolefins in the presence of an initiating agent to produce a crude composition (also referred to as a crude product); wherein the branched $C_{10}$ monoolefins comprise 5-methyl-1-nonene, 3-propyl-1-heptene, 4-ethyl-1-octene, 2-butyl-1-hexene, or combinations thereof; and wherein the crude composition comprises branched $C_{10}$ mercaptans and branched $C_{20}$ sulfides.

The crude composition can be further processed, for example via distillation, to yield one or more products (also referred to as distilled, purified, refined, finished, or final products) selected from the group consisting of mercaptan compositions (e.g., a composition comprising one or more branched $C_{10}$ mercaptans), sulfide compositions (e.g., a composition comprising one or more branched $C_{20}$ sulfides); and compositions having both mercaptans (e.g., branched $C_{10}$ mercaptans) and sulfides (e.g., branched $C_{20}$ sulfides), referred to as mercaptan/sulfide compositions.

In an embodiment, a mercaptan composition comprises branched $C_{10}$ mercaptans selected from the group consisting of 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, and combinations thereof.

In an embodiment, a sulfide composition comprises branched $C_{20}$ sulfides represented by the structure $R^1$—S—$R^2$, wherein $R^1$ and $R^2$ are each independently a functional group derived from an olefin, wherein the olefin comprises 5-methyl-1-nonene, 3-propyl-1-heptene, 4-ethyl-1-octene, 2-butyl-1-hexene, or combinations thereof.

In an embodiment, a mercaptan/sulfide composition comprises (A) branched $C_{10}$ mercaptans selected from the group consisting of 5-methyl-1-mercapto-nonane, 3-propyl-1-mercapto-heptane, 4-ethyl-1-mercapto-octane, 2-butyl-1-mercapto-hexane, 5-methyl-2-mercapto-nonane, 3-propyl-2-mercapto-heptane, 4-ethyl-2-mercapto-octane, 5-methyl-5-mercapto-nonane, and combinations thereof; and (B) branched $C_{20}$ sulfides represented by the structure $R^1$—S—$R^2$, wherein $R^1$ and $R^2$ are each independently a functional group derived from an olefin, wherein the olefin comprises 5-methyl-1-nonene, 3-propyl-1-heptene, 4-ethyl-1-octene, 2-butyl-1-hexene, or combinations thereof.

The mercaptan compositions, sulfide compositions, and mercaptan/sulfide compositions can be salable or otherwise used for a variety of end uses such as mining ore collector compositions and chain transfer agents.

In an embodiment, the compositions disclosed herein can be prepared by a process comprising reacting, in a reactor, hydrogen sulfide ($H_2S$) and a feedstock comprising one or more branched $C_{10}$ monoolefins in the presence of an initiating agent to produce a crude (reaction product) composition, wherein the branched $C_{10}$ monoolefins comprise 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

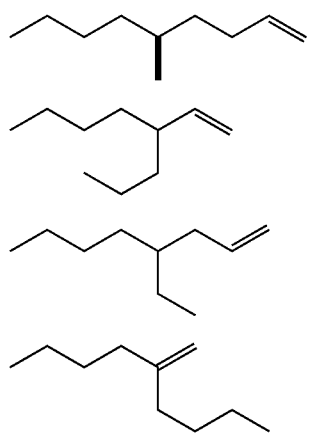

Structure I

Structure J

Structure K

Structure L

Any feedstock comprising one or more branched $C_{10}$ monoolefins of the type described herein can be used, for example a feedstock obtained from a commercial petroleum refining or petrochemical process. Such feedstocks can comprise other olefins in addition to the one or more branched $C_{10}$ monoolefins of the type described herein, for example linear $C_{10}$ monoolefins as well as olefins having more or less than 10 carbon atoms. In an embodiment, the feedstock comprises one or more branched $C_{10}$ monoolefins and is obtained from a 1-hexene production process effluent stream. In various embodiments, a feedstock obtained from a 1-hexene production process effluent stream can comprise $C_{10}$ monoolefins (e.g., branched and/or linear $C_{10}$ monoolefins) as well as olefins having more or less than 10 carbon atoms.

In an embodiment, the feedstock can comprise (a) at least about 76 mol %, alternatively at least about 78 mol %, alternatively at least about 80 mol %, or alternatively at least about 82 mol % $C_{10}$ monoolefins, and (b) at least about 1 mol %, alternatively at least about 2 mol %, alternatively at least about 3 mol %, or alternatively at least about 4 mol % $C_{14}$ monoolefins. In an embodiment, the feedstock can comprise (a) from about 76 mol % to about 92 mol %, alternatively from about 78 mol % to about 90 mol %, alternatively from about 80 mol % to about 88 mol %, or alternatively from about 82 mol % to about 86 mol % $C_{10}$ monoolefins; and (b) from about 1 mol % to about 12 mol %, alternatively from about 2 mol % to about 10 mol %, alternatively from about 3 mol % to about 8 mol %, or alternatively from about 4 mol % to about 7 mol % $C_{14}$ monoolefins. For purposes of the disclosure herein, a feedstock comprising (a) at least about 76 mol % $C_{10}$ monoolefins, and (b) at least about 1 mol % $C_{14}$ monoolefins can also be referred to as a "first feedstock." In an embodiment, the first feedstock is obtained from a 1-hexene production process effluent stream, for example an effluent stream obtained from a 1-hexene production process of the type disclosed in co-pending International Patent Application PCT/US2015/40433, which is incorporated by reference herein in its entirety.

In another embodiment, the feedstock can comprise at least about 95 mol %, alternatively at least about 96 mol %, alternatively at least about 97 mol %, alternatively at least about 98 mol %, or alternatively at least about 99 mol % $C_{10}$ monoolefins. For purposes of the disclosure herein, a feedstock comprising at least about 95 mol % $C_{10}$ monoolefins can also be referred to as a "second feedstock." In an embodiment, the second feedstock can be produced by purifying the first feedstock, such as for example by distillation of an effluent stream obtained from a 1-hexene production process of the type disclosed in co-pending International Patent Application PCT/US2015/40433, which is incorporated by reference herein in its entirety.

In an embodiment, the $C_{10}$ monoolefins of any feedstock described herein (e.g., a first feedstock or a second feedstock) can comprise, can consist essentially of, or can be, 2-butyl-1-hexene, 3-propyl-1-heptene, 4-ethyl-1-octene, and 5-methyl-1-nonene. In an embodiment, the $C_{10}$ monoolefins of any feedstock described herein can comprise i) at least about 3 mol %, alternatively at least about 4 mol %, alternatively at least about 5 mol %, alternatively at least about 6 mol %, alternatively at least about 7 mol %, or alternatively at least about 8 mol % 2-butyl-1-hexene (represented by Structure L), ii) at least about 8 mol %, alternatively at least about 9 mol %, alternatively at least about 10 mol %, alternatively at least about 11 mol %, alternatively at least about 12 mol %, or alternatively at least about 13 mol % 3-propyl-1-heptene (represented by Structure J), iii) at least about 6 mol %, alternatively at least about 7 mol %, alternatively at least about 8 mol %, alternatively at least about 9 mol %, alternatively at least about 10 mol %, or alternatively at least about 11 mol % 4-ethyl-1-octene (represented by Structure K), and iv) at least about 20 mol %, alternatively at least about 22 mol %, alternatively at least about 24 mol %, alternatively at least about 26 mol %, alternatively at least about 28 mol %, or alternatively at least about 30 mol % 5-methyl-1-nonene (represented by Structure I).

In an embodiment, the $C_{10}$ monoolefins of any feedstock described herein (e.g., a first feedstock or a second feedstock) can have a molar ratio of 2-butyl-1-hexene to 5-methyl-1-nonene of at least about 2:1, alternatively at least about 2.4:1, alternatively at least about 2.6:1, or alternatively at least about 2.8:1. In an embodiment, the $C_{10}$ monoolefins of any feedstock described herein can have a molar ratio of 3-propyl-1-heptene to 5-methyl-1-nonene of at least about 1.2:1, alternatively at least about 1.4:1, alternatively at least about 1.6:1, or alternatively at least about 1.8:1. In an embodiment, the $C_{10}$ monoolefins of any feedstock described herein can have a molar ratio of 4-ethyl-1-octene to 5-methyl-1-nonene of at least about 1.6:1, alternatively at least about 1.7:1, alternatively at least about 1.9:1, or alternatively at least about 2.1:1. In an embodiment, the $C_{10}$ monoolefins of any feedstock described herein can have a molar ratio of 2-butyl-1-hexene to 5-methyl-1-nonene of at least about 2:1, alternatively at least about 2.4:1, alternatively at least about 2.6:1, or alternatively at least about 2.8:1; a molar ratio of 3-propyl-1-heptene to 5-methyl-1-nonene of at least about 1.2:1, alternatively at least about 1.4:1, alternatively at least about 1.6:1, or alternatively at least about 1.8:1; and a molar ratio of 4-ethyl-1-octene to 5-methyl-1-nonene of at least about 1.6:1, alternatively at least about 1.7:1, alternatively at least about 1.9:1, or alternatively at least about 2.1:1.

In an embodiment, the $C_{10}$ monoolefins of any feedstock described herein (e.g., a first feedstock or a second feedstock) can comprise linear $C_{10}$ monoolefins. In such embodiment, the linear $C_{10}$ monoolefins can comprise, can consist essentially of, or can be, 1-decene, 4-decene, 5-decene, or combinations thereof; alternatively, 1-decene; alternatively, 4-decene and/or 5-decene; alternatively, 4-decene; or alternatively, 5-decene. In an embodiment, the $C_{10}$ monoolefins of any feedstock described herein can comprise less than or equal to about 26 mol %, alternatively less than or equal to about 24 mol %, alternatively less than or equal to about 22 mol %, alternatively less than or equal to about 20 mol %, or alternatively less than or equal to about 18 mol % linear $C_{10}$ monoolefins. In an embodiment, the $C_{10}$ monoolefins of any feedstock described herein can comprise from about 1 mol % to about 16 mol %, alternatively from about 2 mol % to about 15 mol %, alternatively from about 3 mol % to about 14 mol %, alternatively from about 4 mol % to about 13 mol %, or alternatively from about 6 mol % to about 12 mol % 4-decene and/or 5-decene. In some embodiments, the $C_{10}$ monoolefins of any feedstock described herein can comprise less than or equal to about 10 mol %, alternatively less than or equal to about 9 mol %, alternatively less than or equal to about 8 mol %, alternatively less than or equal to about 7 mol %, or alternatively less than or equal to about 6 mol % 1-decene. In other embodiments, the $C_{10}$ monoolefins of any feedstock described herein can comprise from about 0.5 mol % to about 9 mol %, alternatively from about 1 mol % to about 8 mol %, alternatively from about 1.5 mol % to about 7 mol %, or alternatively from about 2 mol % to about 6 mol % 1-decene.

In an embodiment, the first feedstock disclosed herein can further comprise $C_{9-}$ monoolefins, $C_{11+}$ monoolefins, or combinations thereof; alternatively, $C_{9-}$ monoolefins; or alternatively, $C_{11+}$ monoolefins. In an embodiment, the $C_{9-}$ monoolefins can comprise, can consist essentially of, or can be, a $C_7$ monoolefin, a $C_8$ monoolefin, a $C_9$ monoolefin, or combinations thereof; alternatively, a $C_7$ monoolefin; alternatively, a $C_8$ monoolefin; or alternatively, a $C_9$ monoolefin. In some embodiments, the $C_{9-}$ monoolefins can comprise, can consist essentially of, or can be, a $C_8$ monoolefin. In an embodiment, the monoolefins can comprise, can consist essentially of, or can be, a $C_{11}$ monoolefin, a $C_{12}$ monoolefin, a $C_{13}$ monoolefin, a $C_{14}$ monoolefin, a $C_{15}$ monoolefin, a $C_{16}$ monoolefin, a $C_{17}$ monoolefin, a $C_{18}$ monoolefin, or combinations thereof; alternatively, a $C_{11}$ monoolefin; alternatively, a $C_{12}$ monoolefin; alternatively, a $C_{13}$ monoolefin; alternatively, a $C_{14}$ monoolefin; alternatively, a $C_{15}$ monoolefin; alternatively, a $C_{16}$ monoolefin; alternatively, a $C_{17}$ monoolefin; or alternatively, a $C_{18}$ monoolefin. In some embodiments, the $C_{11+}$ monoolefins can comprise, can consist essentially of, or can be, a $C_{12}$ monoolefin, a $C_{16}$ monoolefin, a $C_{18}$ monoolefin, or combinations thereof; alternatively, a $C_{12}$ monoolefin; alternatively, a $C_{16}$ monoolefin; or alternatively, a $C_{18}$ monoolefin.

In an embodiment, the first feedstock disclosed herein can further comprise $C_8$ monoolefins, $C_{12}$ monoolefins, $C_{16}$ monoolefins, $C_{18}$ monoolefins, or combinations thereof; alternatively, $C_8$ monoolefins; alternatively, $C_{12}$ monoolefins; alternatively, $C_{16}$ monoolefins and/or $C_{18}$ monoolefins; alternatively, $C_{16}$ monoolefins; or alternatively, $C_{18}$ monoolefins. In an embodiment, the $C_8$ monoolefins can comprise 1-octene. In an embodiment, the $C_{12}$ monoolefins can comprise 1-dodecene.

In an embodiment, the first feedstock can further comprise from about 0.1 mol % to about 5 mol %, alternatively from about 0.25 mol % to about 4 mol %, or alternatively from about 0.5 mol % to about 3 mol % $C_{12}$ monoolefins. In such embodiment, the $C_{12}$ monoolefins can comprise from about 54 mol % to about 74 mol %, alternatively from about 56 mol % to about 72 mol %, alternatively from about 58 mol % to about 70 mol %, or alternatively from about 60 mol % to about 68 mol % 1-dodecene.

In an embodiment, the first feedstock can further comprise from about 0.1 mol % to about 5 mol %, alternatively from about 0.25 mol % to about 4 mol %, or alternatively from about 0.5 mol % to about 3 mol % $C_8$ monoolefins. In such embodiment, the $C_8$ monoolefins can comprise at least about 95 mol %, alternatively at least about 96 mol %, alternatively at least about 97 mol %, alternatively at least about 98 mol %, or alternatively at least about 99 mol % 1-octene.

In an embodiment, the first feedstock can further comprise from about 0.05 mol % to about 2 mol %, alternatively from about 0.04 mol % to about 1.5 mol %, alternatively from about 0.06 mol % to about 1.25 mol %, alternatively from about 0.08 mol % to about 1 mol %, or alternatively from about 0.1 mol % to about 0.75 mol % $C_{16}$ monoolefins and/or $C_{18}$ monoolefins.

In an embodiment, a feedstock comprising branched $C_{10}$ monoolefins produced in a 1-hexene process can be purified to produce a second feedstock of the type described herein, for example to improve olefin reactivity and resultant mercaptan and/or sulfide purity. A light fraction, comprising $C_{9-}$, can be removed from the feedstock and any $C_{10}$ olefin isomers can be collected overhead to obtain a high purity (>95%) $C_{10}$ monoolefin fraction as the second feedstock. This high purity $C_{10}$ monoolefin fraction (i.e., second feedstock) comprises little or no non-olefin impurities or $C_{11}$ to $C_{17}$ compounds. The high purity $C_{10}$ olefin can be reacted with $H_2S$ to produce a crude composition. Reaction conditions to produce a crude composition from the high purity $C_{10}$ monoolefin fraction (i.e., a second feedstock) can be identical to the reaction conditions disclosed for the feedstock comprising branched $C_{10}$ monoolefins produced in a 1-hexene process used as received without further purification (i.e., a first feedstock). The major difference between reacting a first feedstock and a second feedstock is the composition of the crude composition and any resulting purified or partially purified products (e.g., fractions or cuts taken from the crude composition). For the second feedstock (e.g., a high purity (>95%) $C_{10}$ monoolefin fraction), the crude composition can comprise residual $H_2S$, unreacted $C_{10}$ olefin, $C_{10}$ mercaptan isomers, and $C_{10}H_{21}$—S—$C_{10}H_{21}$ sulfides and minimal other mercaptans or sulfides. After removal of $H_2S$ and $C_{9-}$ lights from the crude composition, the resultant partially purified product will contain $C_{10}$ mercaptan isomers and $C_{20}$ sulfides, but will not contain any of the intermediate mercaptans and asymmetric sulfide components formed by reactions of olefins having less than or greater than 10 carbon atoms (because there were minimal, if any, such olefins having less than or greater than 10 carbon atoms in the purified feedstock). While not wishing to be bound by theory, it is believed that the intermediate mercaptans and asymmetric sulfide components can be produced from the reaction of $C_{10}$ mercaptans with other non-$C_{10}$ olefins.

In an embodiment, $H_2S$ and a feedstock comprising one or more branched $C_{10}$ monoolefins can be reacted at an $H_2S$ to olefin molar ratio of from about 1:1 to about 20:1, alternatively from about 2:1 to about 15:1, or alternatively from about 3:1 to about 10:1.

In an embodiment, $H_2S$ and a feedstock comprising one or more branched $C_{10}$ monoolefins can be reacted at a pressure of from about 30 psig (206 kPag) to about 1,500 psig (10,300 kPag), alternatively from about 100 psig (690 kPag) to about 1,250 psig (8,600 kPag), or alternatively from about 250 psig (1,700 kPag) to about 1,000 psig (6,900 kPag).

In an embodiment, $H_2S$ and a feedstock comprising one or more branched $C_{10}$ monoolefins can be reacted to produce olefin conversion of equal to or greater than about 80%, alternatively equal to or greater than about 85%, or alternatively equal to or greater than about 90%. For purposes of the disclosure herein, an olefin conversion refers to the mol % of olefins that have reacted during the reaction between $H_2S$ and a feedstock in a reactor, with respect to the amount of olefins introduced into the reactor during the same time period.

In an embodiment, the process can comprise reacting $H_2S$ and a feedstock (e.g., a first or second feedstock as described herein) comprising one or more branched $C_{10}$ monoolefins in the presence of an initiating agent to produce a crude composition; wherein the initiating agent comprises ultraviolet (UV) radiation. In such embodiment, the UV radiation can be any UV radiation capable of initiating the reaction of the olefins present in the feedstock and $H_2S$. In some embodiments, the UV radiation can be generated by a medium pressure mercury lamp. As will be appreciated by one of skill in the art, and with the help of this disclosure, although UV radiation can be the initiating agent, other suitable types of light sources can be used.

In an embodiment, $H_2S$ and a feedstock comprising one or more branched $C_{10}$ monoolefins can be reacted in the presence of an initiating agent comprising UV radiation in a batch reactor or a continuous reactor. Nonlimiting examples of continuous reactors suitable for use in the present disclosure include continuous flow reactors, continuous stirred reactors, fixed bed reactors, and the like, or combinations thereof. Nonlimiting examples of batch reactors suitable for use in the present disclosure include UV batch reactors. As will be appreciated by one of skill in the art, and with the help of this disclosure, any other suitable type of batch and continuous reactors can be used for reacting $H_2S$ and a feedstock comprising one or more branched $C_{10}$ monoolefins in the presence of UV radiation. UV reactors and conditions suitable for reacting $H_2S$ and a feedstock comprising one or more branched $C_{10}$ monoolefins in the presence of UV radiation are described in more detail in U.S. Pat. No. 7,989,655, and U.S. Publication No. 20140221692 A1, each of which is incorporated by reference herein in its entirety.

In embodiments where $H_2S$ and a feedstock comprising one or more branched $C_{10}$ monoolefins are reacted in the presence of UV radiation in a continuous reactor, the continuous reactor can be sized and configured to the desired continuous production rate. That is, a person skilled in the art will be able to select an appropriate reaction vessel size, geometry and material (e.g., a transparent material for sidewalls, windows, or internal chambers); along with an appropriate number of UV sources; and arrange the sources and reactor vessel (e.g., place UV sources adjacent a transparent exterior portion of the reaction vessel and/or disposed in transparent chambers within the reactor vessel) to yield a desired continuous production rate.

In embodiments where $H_2S$ and a feedstock comprising one or more branched $C_{10}$ monoolefins are reacted in the presence of UV radiation in a batch reactor, the batch reactor can be characterized by a reaction time of from about 1 minute to about 4 hours, alternatively from about 10 minutes to about 2 hours, or alternatively from about 30 minutes to about 1.5 hours.

In an embodiment, $H_2S$ and a feedstock comprising one or more branched $C_{10}$ monoolefins can be reacted in the presence of UV radiation at a temperature of from about 0° C. to about 100° C., alternatively from about 10° C. to about 70° C., or alternatively from about 15° C. to about 35° C.

In an embodiment, $H_2S$ and a feedstock comprising one or more branched $C_{10}$ monoolefins can be reacted in the presence of UV radiation at a $H_2S$ to olefin molar ratio of from about 1:1 to about 15:1, alternatively from about 2:1 to about 12.5:1, or alternatively from about 5:1 to about 10:1.

Multiple In an embodiment, the process can comprise reacting $H_2S$ and a feedstock comprising one or more branched $C_{10}$ monoolefins in the presence of an initiating agent to produce a crude composition; wherein the initiating agent comprises ultraviolet (UV) radiation, and wherein the initiating agent further comprises a phosphite promoter, a photoinitiator, or both.

In an embodiment, the phosphite promoter can be used in an amount of from about 0.01 wt. % to about 5 wt. %, alternatively from about 0.1 wt. % to about 4 wt. %, or alternatively from about 1 wt. % to about 2.5 wt. %, based on a weight of olefins.

In an embodiment, the phosphite promoter can be characterized by formula $P(OR^5)_3$, wherein each $R^5$ can independently be a $C_1$-$C_{18}$ hydrocarbyl group, alternatively $C_1$-$C_{10}$ hydrocarbyl group, alternatively $C_1$-$C_5$ hydrocarbyl group; alternatively a $C_1$-$C_{18}$ alkyl group, alternatively $C_1$-$C_{10}$ alkyl group, alternatively $C_1$-$C_5$ alkyl group; alternatively, a $C_6$-$C_{18}$ aryl group, or alternatively, a $C_6$-$C_{10}$ aryl group. Nonlimiting examples of $R^5$ groups suitable for use in the present disclosure in the phosphite promoter include a methyl group, an ethyl group, a propyl group, a butyl group, a pentyl group, a hexyl group, a heptyl group, an octyl group, a nonyl group, a decyl group; a phenyl group, a tolyl group, a xylyl group, a naphthyl group; and the like, or combinations thereof.

Nonlimiting examples of phosphite promoters suitable for use in the present disclosure include a trialkylphosphite, trimethylphosphite, triethylphosphite, tributylphosphite; a triarylphosphite, triphenylphosphite; and the like, or combinations thereof.

In an embodiment, the photoinitiator can be used in an amount of from about 0.05 wt. % to about 5 wt. %, alternatively from about 0.1 wt. % to about 4 wt. %, or alternatively from about 1 wt. % to about 2.5 wt. %, based on the weight of olefins present in the feed mixture.

Nonlimiting examples of photoinitiators suitable for use in the present disclosure include 1-hydroxy-cyclohexyl-phenyl-ketone, benzophenone, Bis-(2,4,6-trimethylbenzoyl)-phenylphosphineoxide, 2-hydroxy-1-{4-[4-(2-hydroxy-2-methyl-propionyl)-benzyl]-phenyl}-2-methy-1-propan-1-one, 2-hydroxy-2-methyl-1-phenyl-1-propanone, and the like, or combinations thereof.

In an embodiment, the process can comprise reacting $H_2S$ and a feedstock comprising one or more branched $C_{10}$ monoolefins in the presence of UV radiation to produce a crude composition (wherein the crude composition comprises from 50-100 wt. % $C_{10}$ mercaptans, alternatively from 50-90 wt. % $C_{10}$ mercaptans, alternatively from 75-85 wt. % $C_{10}$ mercaptans); wherein the $C_{10}$ mercaptans present in the crude composition further comprise from about 70 wt. % to about 100 wt. %, alternatively from about 70 wt. % to about 95 wt. %, alternatively from about 80 wt. % to about 90 wt. %, or alternatively from about 79 wt. % to about 85 wt. % $C_{10}$ primary mercaptans; from about 0 wt. % to about 30 wt. %, alternatively from about 0 wt. % to about 20 wt. %, alternatively from about 10 wt. % to about 20 wt. %, or alternatively from about 5 wt. % to about 19 wt. % $C_{10}$ secondary mercaptans; and from about 0 wt. % to about 10 wt. %, alternatively from about 0 wt. % to about 5 wt. %, or alternatively from about 0 wt. % to about 3 wt. % $C_{10}$ tertiary mercaptans. For purposes of the disclosure herein, a primary mercaptan is a mercaptan that has the thiol group (—SH) attached to a primary carbon (e.g., a carbon atom that is attached to one and only one other carbon atom). Further, for purposes of the disclosure herein, a secondary mercaptan is a mercaptan that has the thiol group (—SH) attached to a secondary carbon (e.g., a carbon atom that is attached to two and only two other carbon atoms). Further, for purposes of the disclosure herein, a tertiary mercaptan is a mercaptan that has the thiol group (—SH) attached to a tertiary carbon (e.g., a carbon atom that is attached to three and only three other carbon atoms). As will be appreciated by one of skill in the art, and with the help of this disclosure, the make-up of the crude composition, in terms of primary, secondary, and tertiary mercaptans, will depend on the make-up of the feedstock, as well as on the reaction conditions. Further, as will be appreciated by one of skill in the art, and with the help of this disclosure, the make-up of each of the primary, secondary, and tertiary mercaptans will depend on the make-up of the feedstock, as well as on the reaction conditions.

In an embodiment, the $C_{10}$ primary mercaptans can comprise 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 1-mercapto-decane (represented by Structure M), or combinations thereof.

In an embodiment, the $C_{10}$ secondary mercaptans can comprise 4-mercapto-decane (represented by Structure N), 5-mercapto-decane (represented by Structure O), 5-methyl-2-mercapto-nonane (represented by Structure E), 3-propyl-2-mercapto-heptane (represented by Structure F), 4-ethyl-2-mercapto-octane (represented by Structure G), 2-mercapto-decane (represented by Structure P), or combinations thereof.

In an embodiment, the $C_{10}$ tertiary mercaptans can comprise equal to or greater than about 90 wt. %, alternatively equal to or greater than about 95 wt. %, or alternatively equal to or greater than about 99 wt. % 5-methyl-5-mercapto-nonane (represented by Structure H).

In an embodiment, the process can comprise reacting $H_2S$ and a feedstock (e.g., a first or second feedstock as described herein) comprising one or more branched $C_{10}$ monoolefins in the presence of an initiating agent (e.g., catalyst) to produce a crude composition; wherein the initiating agent comprises an acid catalyst. Nonlimiting examples of acid catalysts suitable for use in the present disclosure include acid washed clays (such as, but not limited to, Filtrol® 24 or Filtrol® 24X); acid washed bentonite; a tetrafluoroethylene polymer resin modified with perfluorovinyl ether groups terminated with sulfonate groups; a macroreticular, sulfonated, crosslinked copolymer of styrene and divinyl benzene; and the like, or combinations thereof.

In an embodiment, $H_2S$ and a feedstock comprising one or more branched $C_{10}$ monoolefins can be reacted in the presence of an acid catalyst in a continuous reactor, such as for example continuous flow reactor, continuous stirred reactors, fixed bed reactors, packed bed reactors, and the like, or combinations thereof.

In embodiments where $H_2S$ and a feedstock comprising one or more branched $C_{10}$ monoolefins are reacted in the presence of an acid catalyst in a continuous reactor, the continuous reactor can be characterized by a weight hourly space velocity (WHSV) of from about $0.1\ h^{-1}$ to about $5\ h^{-1}$, alternatively from about $0.5\ h^{-1}$ to about $4\ h^{-1}$, or alternatively from about $1\ h^{-1}$ to about $3\ h^{-1}$, based on mass of olefin per mass of catalyst per hour.

In an embodiment, $H_2S$ and a feedstock comprising one or more branched $C_{10}$ monoolefins can be reacted in the presence of an acid catalyst at a temperature of from about 100° C. to about 300° C., alternatively from about 120° C. to about 220° C., or alternatively from about 180° C. to about 200° C.

In an embodiment, $H_2S$ and a feedstock comprising one or more branched $C_{10}$ monoolefins can be reacted in the presence of an acid catalyst at a $H_2S$ to olefin molar ratio of from about 1:1 to about 10:1, alternatively from about 2:1 to about 7.5:1, or alternatively from about 2.5:1 to about 5:1.

In an embodiment, the process can comprise reacting $H_2S$ and a feedstock comprising one or more branched $C_{10}$ monoolefins in the presence of an acid catalyst to produce a crude composition (wherein the crude composition comprises from 50-100 wt. % $C_{10}$ mercaptans, alternatively from 50-90 wt. % $C_{10}$ mercaptans, alternatively from 75-85 wt. % $C_{10}$ mercaptans); wherein the $C_{10}$ mercaptans comprise from about 0 wt. % to about 5 wt. % alternatively from about 0.1 wt. % to about 4 wt. %, or alternatively from about 0.5 wt. % to about 2.5 wt. % $C_{10}$ primary mercaptans; from about 80 wt. % to about 95 wt. %, alternatively from about 82.5 wt. % to about 92.5 wt. %, or alternatively from about 85 wt. % to about 90 wt. % $C_{10}$ secondary mercaptans; and from about 5 wt. % to about 20 wt. %, alternatively from about 7.5 wt. % to about 17.5 wt. %, or alternatively from about 10 wt. % to about 15 wt. % $C_{10}$ tertiary mercaptans.

In an embodiment, the process can comprise reacting $H_2S$ and a feedstock (e.g., a first or second feedstock as described herein) comprising one or more branched $C_{10}$ monoolefins in the presence of an initiating agent to produce a crude composition; wherein the initiating agent comprises a hydrodesulfurization (HDS) catalyst.

In an embodiment, the HDS catalyst comprises a comprises a metal, a transition metal, Ru, Co, Mo, Ni, W, sulfides thereof, disulfides thereof, and the like, or combinations thereof.

In an embodiment, the HDS catalyst can be Haldor Topsoe TK-554 or TK-570, and the like, or combinations thereof.

In an embodiment, the HDS catalyst can further comprise a support, such as for example alumina, silica, and the like, or combinations thereof.

In an embodiment, $H_2S$ and a feedstock comprising one or more branched $C_{10}$ monoolefins can be reacted in the presence of an HDS catalyst in a continuous reactor, such as for example continuous flow reactor, continuous stirred reactors, fixed bed reactors, packed bed reactors, and the like, or combinations thereof.

In embodiments where $H_2S$ and a feedstock comprising one or more branched $C_{10}$ monoolefins are reacted in the presence of an HDS catalyst in a continuous reactor, the continuous reactor can be characterized by a WHSV of from about $0.1\ h^{-1}$ to about $5\ h^{-1}$, alternatively from about $0.5\ h^{-1}$ to about $4\ h^{-1}$, or alternatively from about $1\ h^{-1}$ to about $3\ h^{-1}$, based on mass of olefin per mass of catalyst per hour.

In an embodiment, $H_2S$ and a feedstock comprising one or more branched $C_{10}$ monoolefins can be reacted in the presence of an HDS catalyst at a temperature of from about 100° C. to about 300° C., alternatively from about 120° C. to about 220° C., or alternatively from about 180° C. to about 200° C.

In an embodiment, $H_2S$ and a feedstock comprising one or more branched $C_{10}$ monoolefins can be reacted in the presence of an HDS catalyst at a $H_2S$ to olefin molar ratio of from about 1:1 to about 10:1, alternatively from about 2:1 to about 7.5:1, or alternatively from about 2.5:1 to about 5:1.

In an embodiment, the process can comprise reacting $H_2S$ and a feedstock comprising one or more branched $C_{10}$ monoolefins in the presence of an HDS catalyst to produce a crude composition (wherein the crude composition comprises from 50-100 wt. % $C_{10}$ mercaptans, alternatively from 50-90 wt. % $C_{10}$ mercaptans, alternatively from 75-85 wt. % $C_{10}$ mercaptans); wherein the $C_{10}$ mercaptans comprise from about 5 wt. % to about 30 wt. % alternatively from about 10 wt. % to about 25 wt. %, or alternatively from about 15 wt. % to about 20 wt. % $C_{10}$ primary mercaptans; from about 60 wt. % to about 75 wt. %, alternatively from about 62.5 wt. % to about 72.5 wt. %, or alternatively from about 65 wt. % to about 70 wt. % $C_{10}$ secondary mercaptans; and from about 5 wt. % to about 15 wt. %, alternatively from about 7.5 wt. % to about 13.5 wt. %, or alternatively from about 9 wt. % to about 12 wt. % $C_{10}$ tertiary mercaptans.

As noted previously, any such feedstocks comprising one or more branched $C_{10}$ monoolefins can be reacted with hydrogen sulfide ($H_2S$) in the presence of an initiating agent to produce a crude composition, and the crude composition can be further refined (e.g., distilled or otherwise separated into one or more fractions such as lights, intermediate, and heavies) to yield the various compositions described herein. As described in more detail herein, the type and/or amounts of the constituent components that form the crude composition can vary depending upon the feedstock (e.g., the amount and types of olefins therein), the reaction conditions, the catalysts employed, etc., and one skilled in the art can tailor the post reactor processing of the crude composition to account for the specific compounds present in a given crude composition to yield various desired products and compositions of the types described herein.

Upon completion of the reaction of a feedstock comprising one or more branched $C_{10}$ monoolefins with hydrogen sulfide ($H_2S$), a reactor effluent can be recovered from the reactor and $H_2S$ removed therefrom to yield a crude composition. The term "crude composition" or "crude product" refers to an unrefined effluent stream recovered from the reactor after removal of $H_2S$, and in particular to an $H_2S$-free effluent stream that has not undergone any additional post-reactor processing such as flashing, distillation, or other separation techniques or processes to remove any components from the effluent stream other than the initial removal of $H_2S$.

Hydrogen sulfide ($H_2S$) is a highly corrosive, poisonous, flammable, explosive gas. As such, it is typically removed before the crude composition can be further processed or utilized. Bulk $H_2S$ can be removed under conditions of reduced pressure, and residual $H_2S$ can be removed at reduced temperature and pressure without removing any substantial quantities of the lights. Alternatively, $H_2S$ can also be removed by sparging inert gas into the liquid phase. Alternatively, there are other methods for removing $H_2S$ (i.e., absorption, stripping, etc.) that are known to those of skill in the art. In an embodiment, under appropriate conditions, a reactor effluent can be treated to remove essentially all of any excess and/or unreacted hydrogen sulfide ($H_2S$).

The crude composition comprises branched $C_{10}$ mercaptans and branched $C_{20}$ sulfides formed by the reaction of $H_2S$ and the one or more branched $C_{10}$ monoolefins, and the structures of these branched $C_{10}$ mercaptans and branched $C_{20}$ sulfides are described in more detail herein. In addition to branched $C_{10}$ mercaptans and branched $C_{20}$ sulfides, the crude composition can comprise a number of other compounds such as unreacted olefins, inert compounds (e.g., alkanes), non-branched $C_{10}$ mercaptans, non-branched $C_{20}$ sulfides, non-$C_{10}$ mercaptans, non-$C_{20}$ sulfides, and other impurities. The constituent components contained within the crude composition can vary depending upon the composition of the feedstock (e.g., an unpurified first feedstock as compared to a purified second feedstock as described herein) as well as reaction conditions, catalyst, etc. In various embodiments, a crude composition can comprise light, intermediate, and heavy fractions as described herein.

In an embodiment, the crude compositions can contain a variety of other non-$C_{10}$ mercaptan and non-$C_{20}$ sulfides components (e.g., impurities) such as $C_8$ mercaptans; $C_{12}$ mercaptans; $C_{14}$ mercaptans; $C_{16}$ mercaptans; $C_{18}$ mercaptans; $C_{16-36}$ sulfides represented by the structure $R^3$—S—$R^4$, wherein $R^3$ and $R^4$ are each independently a functional group derived from an olefin selected from the group consisting of $C_8$ monoolefins, $C_{10}$ monoolefins, $C_{12}$ monoolefins, $C_{14}$ monoolefins, $C_{16}$ monoolefins, and $C_{18}$ monoolefins, wherein $R^3$ and $R^4$ are not both branched $C_{10}$ monoolefins; unreacted $C_{8-18}$ monoolefins; non-olefin impurities selected from the group consisting of $C_{8-14}$ alkanes, cyclohexane, methylcyclopentane, methylcyclohexane, benzene, toluene, ethylbenzene, xylene, mesitylene, hexamethylbenzene, $C_{4-12}$ alcohols, 2-ethyl-1-hexanol, and 2-ethylhexyl-2-ethylhexanoate; and combinations thereof.

In an embodiment, a crude composition comprising branched $C_{10}$ mercaptans and branched $C_{20}$ sulfides can be separated by any process or unit operation known in the art. For example, a crude composition can be processed (e.g., distilled) to remove a fraction of light compounds. Alternatively, a crude composition can be processed to recover both a lights fraction and an intermediates fraction (e.g., a rough cut), followed by further processing to obtain one or more fine cuts. Alternatively, a crude composition can be processed to recover a heavies fraction (e.g., a $C_{20}$ sulfide fraction). Alternatively, a crude composition can be processed to separate out any combination of a lights fraction, an intermediates fraction (e.g., comprising $C_{10}$ mercaptans, including branched $C_{10}$ mercaptans), and a heavies fraction (e.g., comprising $C_{20}$ sulfides, including branched $C_{20}$ sulfides). Furthermore, a light, intermediate or heavy fraction (e.g., a rough cut) can be further processed or parsed to obtain one or more desired fine cuts (e.g., a $C_{10}$ mercaptan fraction). Alternatively, a crude composition can be separated to produce a high-purity $C_{10}$ mercaptan stream and/or a high-purity $C_{20}$ sulfide stream (e.g., to obtain a desired fine cut or fraction such as a $C_{10}$ mercaptan fraction). Further, these separated streams can be blended in any combination of ratios to produce a mixture with specific concentrations of one of more components (e.g., desired blend ratios of branched $C_{10}$ mercaptans and/or branched $C_{20}$ sulfides, for example to aid in a particular end use). The unit operations/processes used for these separations are known to one of skill and the art and include, but are not limited to, distillation, fractionation, flashing, stripping, and absorption, and others. The unit operation conditions, such as for example, temperature, pressure, flow rates, and others at which these unit operations produce one or more of the desired fractions can easily be determined by one of ordinary skill in the art.

In an embodiment, a lights fraction is removed from the crude composition, for example by flashing, distillation, fractionation, stripping, absorption, etc.

In an embodiment, the lights fraction can comprise at least about 90 wt. %, alternatively at least about 90 wt. %, alternatively at least about 95 wt. %, alternatively at least about 96 wt. %, alternatively at least about 97 wt. %, alternatively at least about 98 wt. %, alternatively at least about 99 wt. % $C_{9-}$ compounds, based on the total weight of the lights fraction. Nonlimiting examples of $C_{9-}$ compounds include $C_{9-}$ monoolefins (e.g., unreacted $C_{9-}$ monoolefins), $C_{9-}$ mercaptans, $C_{9-}$ alkanes, cyclohexane, methylcyclopentane, methylcyclohexane, benzene, toluene, ethylbenzene, xylene, mesitylene, $C_{9-}$ alcohols, 2-ethyl-1-hexanol, and the like, or combinations thereof. In an embodiment, the lights fraction can comprise less than about 10 wt. %, alternatively less than about 5 wt. %, alternatively less than about 4 wt. %, alternatively at less than about 3 wt. %, alternatively less than about 2 wt. %, alternatively less than about 1 wt. % $C_{10+}$ compounds, based on the total weight of the lights fraction.

In an embodiment, the $C_{9-}$ monoolefins can comprise, can consist essentially of, or can be, a $C_7$ monoolefin, a $C_8$ monoolefin, a $C_9$ monoolefin, or combinations thereof; alternatively, a $C_7$ monoolefin; alternatively, a $C_8$ monoolefin; or alternatively, a $C_9$ monoolefin. In some embodiments, the $C_{9-}$ monoolefins can comprise, can consist essentially of, or can be, a $C_8$ monoolefin (e.g., 1-octene).

In an embodiment, the $C_{9-}$ mercaptans can comprise, can consist essentially of, or can be, a $C_7$ mercaptan, a $C_8$ mercaptan, a $C_9$ mercaptan, or combinations thereof; alternatively, a $C_7$ mercaptan; alternatively, a $C_8$ mercaptan; or alternatively, a $C_9$ mercaptan. In some embodiments, the $C_{9-}$ mercaptans can comprise, can consist essentially of, or can be, a $C_8$ mercaptan.

Following removal of the lights (for example, via flash), a combined intermediate and heavy fraction (i.e., $C_{10+}$ compounds sometimes referred to as a kettle product in the Examples) can remain, and the combined intermediate and heavy fraction can be used "as is" or can be further processed, for example separated or split into separate intermediate and heavy fractions (and said separate intermediate and heavy fractions can be subsequently recombined in various blends and associated blend ratios), as described in more detail herein. In an embodiment, a combined intermediate and heavy fraction (i.e., $C_{10+}$ compounds) formed by removal of the lights fraction from the crude composition can comprise less than about 15 wt. %, alternatively less than about 10 wt. %, alternatively less than about 9 wt. %, alternatively less than about 8 wt. %, alternatively less than about 7 wt. %, alternatively less than about 6 wt. %, alternatively less than about 5 wt. %, alternatively less than about 4 wt. %, alternatively less than about 3 wt. %, alternatively less than about 2 wt. %, alternatively less than about 1 wt. % $C_{9-}$ products, based on the total weight of the combined intermediate and heavy fraction (i.e., $C_{10+}$ compounds).

In an embodiment, a combined intermediate and heavy fraction (i.e., $C_{10+}$ compounds) can comprise (A) at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % mercaptans; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof; and (B) at least about 10 wt. %, alternatively at least about 15 wt. %, alternatively at least about 20 wt. %, alternatively at least about 25 wt. % sulfides, or alternatively at least about 30 wt. % sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In an embodiment, the crude composition can be flashed to remove a lights fraction as described herein to produce a combined intermediate and heavy fraction (i.e., $C_{10+}$ compounds) comprising: (A) at least about 25, 30, 35, 40, 45, 50, 55, 60, 65, 70, 75, 80, or 85 wt. % $C_{10}$ branched mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof; and (B) at least about 5 wt. %, alternatively at least about 10 wt. %, alternatively at least about 15 wt. %, alternatively at least about 20 wt. %, alternatively at least about 25 wt. %, or alternatively at least about 30 wt. % branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In an embodiment, the crude composition can be flashed to remove a lights fraction as described herein to produce a combined intermediate and heavy fraction (i.e., $C_{10+}$ compounds) comprising: (A) from at least about 50 wt. % to at least about 90 wt. %, alternatively from at least about 55 wt. % to at least about 85 wt. %, or alternatively from at least about 60 wt. % to at least about 80 wt. % mercaptans, wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof; and (B) from at least about 10 wt. % to at least about 30 wt. %, alternatively from at least about 10 wt. % to at least about 25 wt. %, alternatively from at least about 12.5 wt. % to at least about 22.5 wt. %, or alternatively from at least about 15 wt. % to at least about 20 wt. % sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In an embodiment, the crude composition can be flashed to remove a lights fraction and subsequently further separated to produce an intermediate fraction and a heavies fraction. The intermediate fraction and the heavies fractions can then be optionally further processed (e.g., polished) and mixed in any appropriate ratio to produce a blended composition comprising: (A) at least about 25 wt. %, alternatively at least about 30 wt. %, alternatively at least about 40 wt. %, alternatively at least about 50 wt. %, alternatively at least about 80 wt. %, or alternatively at least about 90 wt. % $C_{10}$ mercaptans (e.g., branched $C_{10}$ mercaptans) selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof; (B) at least about 5 wt. %, alternatively at least about 10 wt. %, alternatively at least about 15 wt. %, alternatively at least about 20 wt. %, alternatively at least about 25 wt. %, or alternatively at least about 30 wt. % $C_{20}$ sulfides (e.g., branched $C_{20}$ sulfides) represented by structure $R^1$—S—$R^2$, wherein $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof; and one or more of the following components (C)-(I): (C) less than about 5 wt. %, alternatively less than about 4 wt. %, alternatively less than about 3 wt. %, alternatively less than about 2 wt. %, or alternatively less than about 1 wt. % $C_8$ mercaptans; (D) less than about 15 wt. %, alternatively less than about 10 wt. %, or alternatively less than about 5 wt. % $C_{12}$ mercaptans; (E) less than about 15 wt. %, alternatively less than about 10 wt. %, or alternatively less than about 5 wt. % $C_{14}$ mercaptans; (F) less than about 5 wt. %, alternatively less than about 4 wt. %, alternatively less than about 3 wt. %, alternatively less than about 2 wt. %, or alternatively less than about 1 wt. % $C_{16}$ mercaptans and/or $C_{18}$ mercaptans; (G) less than about 1 wt. %, alternatively less than about 0.5 wt. %, alternatively less than about 0.4 wt. %, alternatively less than about 0.3 wt. %, alternatively less than about 0.2 wt. %, or alternatively less than about 0.1 wt. % $C_{16-36}$ sulfides represented by the structure $R^3$—S—$R^4$, wherein $R^3$ and $R^4$ are each independently a functional group derived from an olefin selected from the group consisting of $C_8$ monoolefins, $C_{10}$ monoolefins, $C_{12}$ monoolefins, $C_{14}$ monoolefins, $C_{16}$ monoolefins, and $C_{18}$ monoolefins, wherein $R^3$ and $R^4$ are not both branched $C_{10}$ monoolefins; (H) less than about 10 wt. %, alternatively less than about 5 wt. %, alternatively less than about 4 wt. %, alternatively less than about 3 wt. %, alternatively less than about 2 wt. %, or alternatively less than about 1 wt. % unreacted $C_{8-18}$ monoolefins; and (I) less than about 10 wt. %, alternatively less than about 5 wt. %, alternatively less than about 4 wt. %, alternatively less than about 3 wt. %, alternatively less than about 2 wt. %, or alternatively less than about 1 wt. % non-olefin impurities selected from the group consisting of $C_{8-14}$ alkanes, cyclohexane, methylcyclopentane, methylcyclohexane, benzene, toluene, ethylbenzene, xylene, mesitylene, hexamethylbenzene, $C_{4-12}$ alcohols, 2-ethyl-1-hexanol, and 2-ethylhexyl-2-ethylhexanoate. In various embodiments, the blended composition can comprise varying amounts of each of components (C)-(I), and the presence of each component (C)-(I) and the amount thereof can be independently formulated and/or controlled. In various embodiments, the blended composition can comprise an amount of one or more components (C)-(I) that is greater than zero (i.e., above a detection limit associated with the component) and less than the upper range endpoint set forth above (e.g., component (C) is present in the composition in an amount greater than zero and less than about 5 wt. %, and so forth as set forth above).

In some embodiments, a mercaptan/sulfide composition of the type disclosed herein can be prepared by combining at least a portion of a first mercaptan/sulfide composition (wherein only a lights fraction has been removed from the crude product to yield a combined intermediate and heavy fraction, e.g., $C_{10+}$ compounds) with at least a portion of a heavies fraction comprising a sulfide composition to yield a second mercaptan/sulfide composition, wherein a sulfide content of the second mercaptan/sulfide composition is greater than a sulfide content of the first mercaptan/sulfide composition.

In an embodiment, the crude can be separated into light, intermediate, and heavy fractions by distillation, for example in a single distillation column having a light fraction recovered as an overhead stream, an intermediate fraction (e.g., comprising branched $C_{10}$ mercaptans) recovered as a side stream, and a heavy fraction (e.g., comprising branched $C_{20}$ sulfides) recovered as a bottom stream. In alternative embodiments, the separation can be in sequential steps such as removal of the lights fraction in a first distillation column, followed by separation of the intermediate fraction (e.g., comprising branched $C_{10}$ mercaptans) as an overhead stream in a second distillation column and the heavy fraction (e.g., comprising $C_{11+}$ compounds, including branched $C_{20}$ sulfides) as a bottom stream of the second distillation column. These "rough-cut" light, intermediate, and heavy streams can be used "as is" or they can be further processed (e.g., further refined or polished, for example by additional distillation or other separation techniques to produce "fine-cuts") and/or blended to obtain a variety of products that are salable or otherwise available for a variety of end uses such as mining ore collector compositions or chain transfer agents. For example, a variety of mercaptan compositions, sulfide compositions, and mixed mercaptan/sulfide compositions can be produced of the type disclosed in more detail herein.

In an embodiment, an intermediate fraction can comprise at least about 25 wt. %, alternatively at least about 30 wt. %, alternatively at least about 40 wt. %, alternatively at least about 50 wt. % branched $C_{10}$ mercaptans, alternatively at least 75 wt. % branched $C_{10}$ mercaptans, or alternatively at least about 85 wt. % branched $C_{10}$ mercaptans. In such embodiment, the branched $C_{10}$ mercaptans can be selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In an embodiment, the heavy fraction can comprise at least about 5, 10, 15, 20, 25, 30, 35, 40, 45, 50, 55, 60, 65, 70, 75, 80, or 85 wt. %, branched $C_{20}$ sulfides represented by structure $R^1$—S—$R^2$, wherein both $R^1$ and $R^2$ are each independently a branched $C_{10}$ alkyl group derived from the branched $C_{10}$ monoolefin, and wherein the branched $C_{10}$ alkyl group is selected from the group consisting of

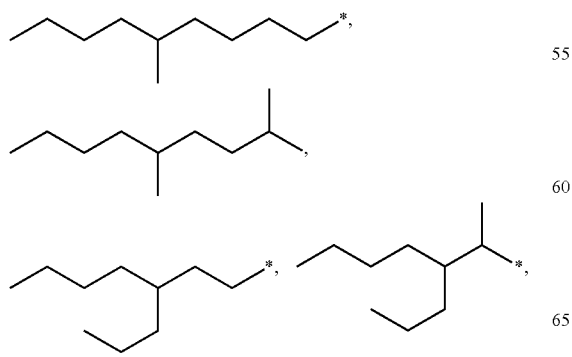

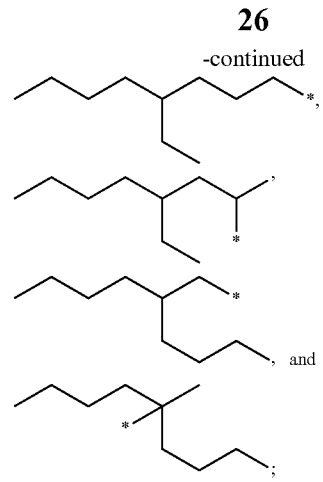

wherein * designates the attachment point to the S atom of the branched $C_{20}$ sulfide.

In an embodiment, a mercaptan composition can comprise mercaptans, wherein at least a portion of the mercaptans comprise $C_{10}$ mercaptans, and wherein at least a portion of the $C_{10}$ mercaptans comprise branched $C_{10}$ mercaptans. In an embodiment, the branched $C_{10}$ mercaptans can comprise 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), or combinations thereof.

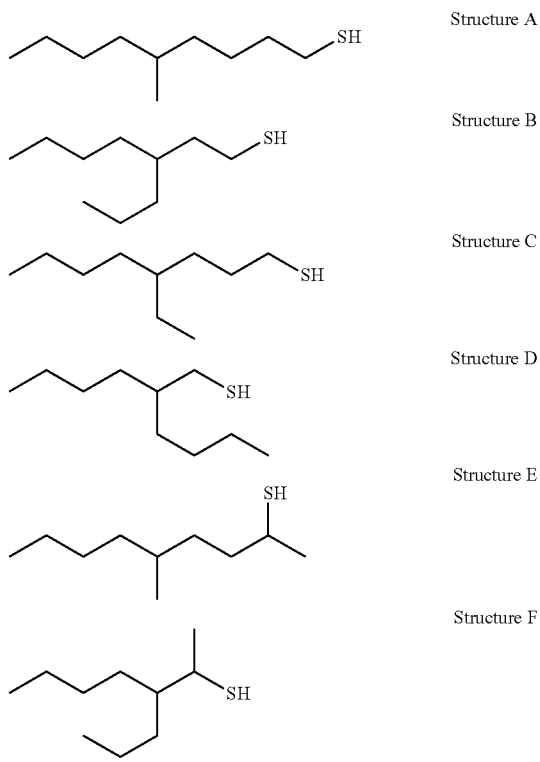

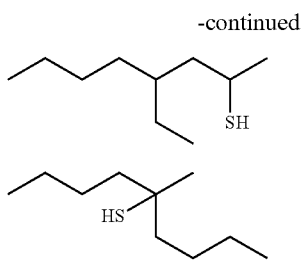

Structure G

Structure H

For purposes of the disclosure herein, branched $C_{10}$ mercaptans refer to mercaptans (or thiols) that are characterized by the general formula R—SH, wherein R is a branched alkyl group (as opposed to a linear alkyl group), i.e., an alkyl group substituted with alkyl substituents; and wherein R has a total of 10 carbon atoms. Further, for purposes of the disclosure herein, a composition comprising mercaptans, wherein at least a portion of the mercaptans are branched $C_{10}$ mercaptans (e.g., 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), or combinations thereof), can also be referred to as a "branched $C_{10}$ mercaptan composition." In an embodiment, the mercaptan composition can comprise any suitable amount of branched $C_{10}$ mercaptans.

In an embodiment, the $C_{10}$ mercaptans can further comprise non-branched $C_{10}$ mercaptans, such as for example 1-mercapto-decane (represented by Structure M), 4-mercapto-decane (represented by Structure N), 5-mercapto-decane (represented by Structure O), 2-mercapto-decane (represented by Structure P), or combinations thereof.

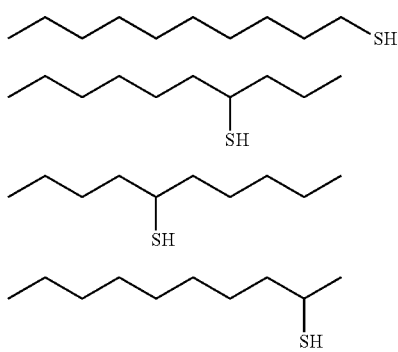

Structure M

Structure N

Structure O

Structure P

In some embodiments, a mercaptan composition can comprise mercaptans, wherein at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In other embodiments, a mercaptan composition can comprise at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % mercaptans, wherein at least a portion of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In yet other embodiments, a mercaptan composition can comprise at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % mercaptans; wherein at least about 50 wt. %, alternatively at least about 60 wt. %, alternatively at least about 70 wt. %, alternatively at least about 75 wt. %, alternatively at least about 80 wt. %, or alternatively at least 85 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In yet other embodiments, a mercaptan composition can comprise at least about 50, 55, 60, 65, 70, 75, 80, 85, 90, 95, or 99 wt. % mercaptans; wherein at least about 25, 30, 35, 40, 45, 50, 55, 60, 65, 70, 75, 80, 85, 90, 95, or 99 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In still yet other embodiments, a mercaptan composition can comprise from at least about 50 wt. % to at least about 90 wt. %, alternatively from at least about 55 wt. % to at least about 85 wt. %, or alternatively from at least about 60 wt. % to at least about 80 wt. % mercaptans, wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In still yet other embodiments, a mercaptan composition can consist of or consist essentially of branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In still yet other embodiments, a mercaptan composition can comprise at least about 1, 5, 10, 15, 20, 25, 30, 35, 40, 45, 50, 55, 60, 65, 70, 75, 80, 85, 90, 95, or 99 wt. % branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In still yet other embodiments, a composition can comprise mercaptans, wherein at least about 50, 55, 60, 65, 70, 75, 80, 85, 90, 95, or 99 wt. % of the mercaptans are branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof.

In an embodiment, a sulfide composition can comprise sulfides, wherein at least a portion of the sulfides comprise $C_{20}$ sulfides, and wherein at least a portion of the $C_{20}$ sulfides comprise branched $C_{20}$ sulfides represented by structure $R^1$—S—$R^2$, wherein $R^1$ and $R^2$ can each independently be an alkyl group, and wherein at least a portion of the alkyl groups comprises a branched $C_{10}$ alkyl group. In an embodiment, the alkyl group (e.g., a branched $C_{10}$ alkyl group as $R^1$, $R^2$) can comprise a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

Structure I

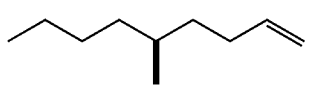

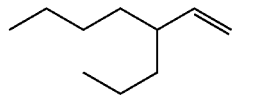

Structure J

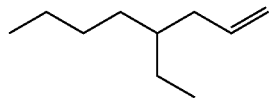

Structure K

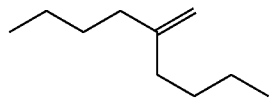

Structure L

For purposes of the disclosure herein a sulfide will be referred to by the total number of carbon atoms (as opposed to the number of carbons of only one of the alkyl groups present in a dialkyl sulfide). For example, a $H_{21}C_{10}$—S—$C_{10}H_{21}$ sulfide will be referred to as a $C_{20}$ sulfide (rather than a $C_{10}$ sulfide). For purposes of the disclosure herein, branched $C_{20}$ sulfides refer to sulfides (or thioethers) that are characterized by the general formula $R^1$—S—$R^2$, wherein both $R^1$ and $R^2$ are each independently a branched $C_{10}$ alkyl group (as opposed to a linear alkyl group), i.e., an alkyl group substituted with alkyl substituents. Stated alternatively, branched $C_{20}$ sulfides refer to sulfides wherein both $R^1$ and $R^2$ are branched $C_{10}$ alkyl groups, wherein $R^1$ and $R^2$ can be the same or different. Further, for purposes of the disclosure herein, a composition comprising sulfides, wherein at least a portion of the sulfides are branched $C_{20}$ sulfides represented by structure $R^1$—S—$R^2$, wherein both $R^1$ and $R^2$ are each independently an alkyl group, wherein at least a portion of the alkyl group comprises a branched $C_{10}$ alkyl group (e.g., a functional group derived from an olefin, and wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof), can also be referred to as a "branched $C_{20}$ sulfide composition." In an embodiment, the sulfide composition can comprise any suitable amount of branched $C_{20}$ sulfides.

In an embodiment, a sulfide composition can comprise sulfides, wherein at least a portion of the sulfides comprise $C_{20}$ sulfides, and wherein at least a portion of the $C_{20}$ sulfides comprise branched $C_{20}$ sulfides represented by structure $R^1$—S—$R^2$, wherein both $R^1$ and $R^2$ can each independently be a branched $C_{10}$ alkyl group derived from a branched $C_{10}$ monoolefin, and wherein the branched $C_{10}$ alkyl group is selected from the group consisting of

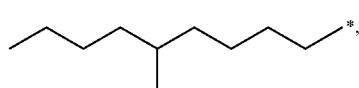

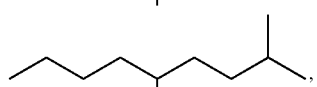

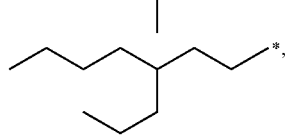

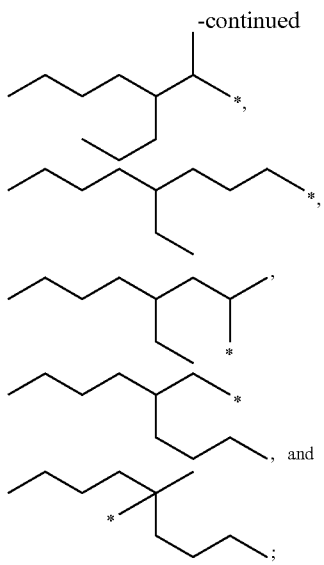

wherein * designates the attachment point to the S atom of the branched $C_{20}$ sulfide. In an embodiment, the branched $C_{10}$ monoolefin can comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof. Generally, a monoolefin is a linear or branched aliphatic hydrocarbon olefin that has one and only one carbon-carbon double bond. Generally, a $C_n$ monoolefin is a linear or branched aliphatic hydrocarbon olefin that has n and only n carbon atoms, and one and only one carbon-carbon double bond. A $C_{10}$ monoolefin is a linear or branched aliphatic hydrocarbon olefin that has ten and only ten carbon atoms, and one and only one carbon-carbon double bond. A branched $C_{10}$ monoolefin is a branched aliphatic hydrocarbon olefin that has ten and only ten carbon atoms, and one and only one carbon-carbon double bond.

In an embodiment, the $C_{20}$ sulfides can further comprise non-branched $C_{20}$ sulfides and/or partially branched $C_{20}$ sulfides represented by structure $R^1$—S—$R^2$, wherein both $R^1$ and $R^2$ (in the case of non-branched $C_{20}$ sulfides) or one of the $R^1$ and $R^2$ (in the case of partially-branched $C_{20}$ sulfides) can be a linear $C_{10}$ alkyl group derived from a linear $C_{10}$ monoolefin, such as for example 4-decene (represented by Structure Q), 5-decene (represented by Structure R), 1-decene (represented by Structure S), or combinations thereof.

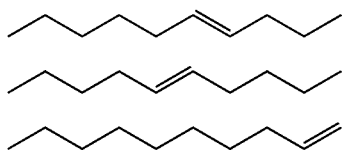

Structure Q

Structure R

Structure S

For purposes of the disclosure herein, the non-branched $C_{20}$ sulfides represented by structure $R^1$—S—$R^2$ are the sulfides wherein both $R^1$ and $R^2$ are each independently a linear $C_{10}$ alkyl group derived from a linear $C_{10}$ monoolefin. Further, for purposes of the disclosure herein, the partially branched $C_{20}$ sulfides represented by structure $R^1$—S—$R^2$ are the sulfides wherein one of the $R^1$ and $R^2$ is a linear $C_{10}$ alkyl group derived from a linear $C_{10}$ monoolefin, while the other one of the $R^1$ and $R^2$ is a branched $C_{10}$ alkyl group derived from a branched $C_{10}$ monoolefin as described herein.

In some embodiments, a sulfide composition can comprise sulfides, wherein at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In other embodiments, a sulfide composition can comprise at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % sulfides, wherein at least a portion of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In other embodiments, a sulfide composition can comprise at least about 1, 5, 10, 15, 20, 25, 30, 35, 40, 45, 50, 55, 60, 65, 70, 75, 80, 85, 90, 95, or 99 wt. %, sulfides, wherein at least about 1, 5, 10, 15, 20, 25, 30, 35, 40, 45, 50, 55, 60, 65, 70, 75, 80, 85, 90, 95, or 99 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In yet other embodiments, a sulfide composition can comprise at least about 10 wt. %, alternatively at least about 15 wt. %, alternatively at least about 20 wt. %, or alternatively at least about 25 wt. % sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In still yet other embodiments, a sulfide composition can comprise from at least about 10 wt. % to at least about 30 wt. %, alternatively from at least about 12.5 wt. % to at least about 22.5 wt. %, or alternatively from at least about 15 wt. % to at least about 20 wt. % sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In still yet other embodiments, a sulfide composition can consist of or consist essentially of branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In still yet other embodiments, a sulfide composition can comprise at least about 5 wt. %, alternatively at least about 10 wt. %, alternatively at least about 15 wt. %, or alternatively at least about 20 wt. % $C_{20}$ sulfides (e.g., branched $C_{20}$ sulfides) represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In still yet other embodiments, a sulfide composition comprises at least about 1, 5, 10, 15, 20, 25, 30, 35, 40, 45, 50, 55, 60, 65, 70, 75, 80, 85, 90, 95, or 99 wt. % branched $C_{20}$ sulfides represented by the structure $R^1$—S—$R^2$, wherein $R^1$ and $R^2$ are each independently a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In an embodiment, a mercaptan/sulfide composition can comprise one or more mercaptans and one or more sulfides of the type disclosed herein. For purposes of the disclosure herein, a composition comprising (i) mercaptans, wherein at least a portion of the mercaptans are branched $C_{10}$ mercaptans, and (ii) sulfides, wherein at least a portion of the sulfides are branched $C_{20}$ sulfides, can also be referred to as a "branched $C_{10}$ mercaptan/$C_{20}$ sulfide composition." In an embodiment, the mercaptan/sulfide composition can comprise any suitable amount of branched $C_{10}$ mercaptans, and any suitable amount of branched $C_{20}$ sulfides.

In an embodiment, a mercaptan/sulfide composition can comprise (A) at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % mercaptans, wherein at least a portion of the mercaptans can be branched $C_{10}$ mercaptans selected from the group consisting of 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), and combinations thereof; and (B) at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % sulfides, wherein at least a portion of the sulfides can be branched $C_{20}$ sulfides represented by structure $R^1$—S—$R^2$, wherein both $R^1$ and $R^2$ can each independently be a functional group derived from an olefin, wherein the olefin comprises 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

In an embodiment, a mercaptan/sulfide composition can comprise $C_{10}$ mercaptans represented by the general formula R—SH and/or $C_{20}$ sulfides represented by structure $R^1$—S—$R^2$ that are formed by reacting an olefin feedstock comprising olefins with $H_2S$ as described in more detail herein, wherein the olefins present in the olefin feedstock provide the alkyl group represented by R, $R^1$, and $R^2$. In such embodiments, the R group of the $C_{10}$ mercaptans and/or the $R^1$ and $R^2$ groups of the $C_{20}$ sulfides are provided by or derived from the counterpart R, $R^1$, and $R^2$ groups present in the olefins in the olefin feedstock. In an embodiment, R, $R^1$ and $R^2$ can each independently be an alkyl group, wherein at least a portion of the alkyl groups can comprise a functional group derived from an olefin, wherein the olefin is present in a feedstock (e.g., a first feedstock as described herein) comprising a) at least about 76 mol %, alternatively at least about 78 mol %, alternatively at least about 80 mol %, or alternatively at least about 82 mol % $C_{10}$ monoolefins; and b) at least about 1 mol %, alternatively at least about 2 mol %, alternatively at least about 3 mol %, or alternatively at least about 4 mol % $C_{14}$ monoolefins. In such embodiment, the $C_{10}$ monoolefins can comprise i) at least about 3 mol %, alternatively at least about 4 mol %, alternatively at least about 5 mol %, alternatively at least about 6 mol %, alternatively at least about 7 mol %, or alternatively at least about 8 mol % 2-butyl-1-hexene (represented by Structure L), ii) at least about 8 mol %, alternatively at least about 9 mol %, alternatively at least about 10 mol %, alternatively at least about 11 mol %, alternatively at least about 12 mol %, or alternatively at least about 13 mol % 3-propyl-1-heptene (represented by Structure J), iii) at least about 6 mol %, alternatively at least about 7 mol %, alternatively at least about 8 mol %, alternatively at least about 9 mol %, alternatively at least about 10 mol %, or alternatively at least about 11 mol % 4-ethyl-1-octene (represented by Structure K), and iv) at least about 20 mol %, alternatively at least about 22 mol %, alternatively at least about 24 mol %, alternatively at least about 26 mol %, alternatively at least about 28 mol %, or alternatively at least about 30 mol % 5-methyl-1-nonene (represented by Structure I). In an embodiment, the $C_{10}$ monoolefins can comprise from about 1 mol % to about 16 mol %, alternatively from about 2 mol % to about 15 mol %, alternatively from about 3 mol % to about 14 mol %, alternatively from about 4 mol % to about 13 mol %, or alternatively from about 6 mol % to about 12 mol % 4-decene and/or 5-decene. In an embodiment, the $C_{10}$ monoolefins can comprise from about 0.5 mol % to about 9 mol %, alternatively from about 1 mol % to about 8 mol %, alternatively from about 1.5 mol % to about 7 mol %, or alternatively from about 2 mol % to about 6 mol % 1-decene.

In an embodiment, the olefin (e.g., corresponding to R, $R^1$ or $R^2$) present in the olefin feedstock (e.g., a first feedstock as described herein) can further comprise from about 0.1 mol % to about 5 mol %, alternatively from about 0.25 mol % to about 4 mol %, or alternatively from about 0.5 mol % to about 3 mol % $C_{12}$ monoolefins. In such embodiment, the $C_{12}$ monoolefins can comprise from about 54 mol % to about 74 mol %, alternatively from about 56 mol % to about 72 mol %, alternatively from about 58 mol % to about 70 mol %, or alternatively from about 60 mol % to about 68 mol % 1-dodecene.

In an embodiment, the olefin (e.g., corresponding to R, $R^1$ or $R^2$) present in the olefin feedstock (e.g., a first feedstock as described herein) can further comprise from about 0.1 mol % to about 5 mol %, alternatively from about 0.25 mol % to about 4 mol %, or alternatively from about 0.5 mol % to about 3 mol % $C_8$ monoolefins. In such embodiment, the $C_8$ monoolefins can comprise at least about 95 mol %, alternatively at least about 96 mol %, alternatively at least about 97 mol %, alternatively at least about 98 mol %, or alternatively at least about 99 mol % 1-octene.

In an embodiment, the olefin (e.g., corresponding to R, $R^1$ or $R^2$) present in the olefin feedstock (e.g., a first feedstock as described herein) can further comprise from about 0.05 mol % to about 2 mol %, alternatively from about 0.04 mol % to about 1.5 mol %, alternatively from about 0.06 mol % to about 1.25 mol %, alternatively from about 0.08 mol % to about 1 mol %, or alternatively from about 0.1 mol % to about 0.75 mol % $C_{16}$ monoolefins and/or $C_{18}$ monoolefins.

In an embodiment where the R group of the $C_{10}$ mercaptans and/or the $R^1$ and $R^2$ groups of the $C_{20}$ sulfides are provided by or derived from the counterpart R, $R^1$, and $R^2$ groups present in the olefins in the olefin feedstock (e.g., a first feedstock obtained from a 1-hexene process as described herein), the resultant mercaptan/sulfide composition can be a crude composition that can be further separated and refined into other compositions as described herein.

In an embodiment, mercaptan compositions, sulfide compositions, and/or mercaptan/sulfide compositions as disclosed herein advantageously display improvements in one or more composition characteristics when compared to otherwise similar compositions lacking branched $C_{10}$ mercaptans.

In an embodiment, a mercaptan composition and/or a mercaptan/sulfide composition comprising equal to or greater than about 25 wt. % $C_{10}$ branched mercaptans as disclosed herein can advantageously have an odor less unpleasant and less offensive than an odor of an otherwise similar composition comprising equal to or greater than about 25 wt. % n-decyl mercaptan, as perceived by equal to or greater than about 51% of human subjects exposed to the odor of each composition.

In an embodiment, a mercaptan composition and/or a mercaptan/sulfide composition comprising equal to or greater than about 25 wt. % $C_{10}$ branched mercaptans as disclosed herein can advantageously have an odor less unpleasant than an odor of an otherwise similar composition comprising equal to or greater than about 25 wt. % n-dodecyl mercaptan and/or tert-dodecyl mercaptan, as perceived by equal to or greater than about 51% of human subjects exposed to the odor of each composition. Additional advantages of the mercaptan compositions, sulfide compositions, and/or mercaptan/sulfide compositions and processes of producing same as disclosed herein can be apparent to one of skill in the art viewing this disclosure.

In an aspect, a process of the present disclosure comprises reacting, in a reactor, a sulfur source (e.g., $H_2S$) and a feedstock comprising one or more $C_{11+}$ monoolefins in the presence of an initiating agent, as previously described herein for the branched $C_{10}$ monoolefins, to produce a crude composition (also referred to as a crude product); wherein the crude composition comprises mercaptans and $C_{22+}$ sulfides.

In an aspect, a process of the present disclosure comprises reacting, in a reactor, a sulfur source (e.g., $H_2S$) and a feedstock comprising one or more $C_{11+}$ monoolefins in the presence of an initiating agent, as previously described herein for the branched $C_{10}$ monoolefins, to produce a $C_{11+}$ mercaptans crude composition; wherein the $C_{11+}$ monoolefins comprise $C_{11}$ and $C_{12}$ internal monoolefins, $C_{13}$ and $C_{14}$ internal monoolefins, $C_{14}$ and $C_{16}$ linear alpha monoolefins, and the like, or combinations thereof.

In an aspect, a process of the present disclosure comprises reacting, in a reactor, a sulfur source (e.g., $H_2S$) and a feedstock comprising one or more $C_{11+}$ monoolefins in the presence of an initiating agent, as previously described herein for the branched $C_{10}$ monoolefins, to produce a $C_{11+}$ mercaptans crude composition; wherein the one or more $C_{11+}$ monoolefins is selected from the group consisting of $C_{11}$ and $C_{12}$ internal monoolefins, $C_{13}$ and $C_{14}$ internal monoolefins, $C_{14}$ and $C_{16}$ linear alpha monoolefins, and combinations thereof.

In an aspect, a process of the present disclosure comprises reacting, in a reactor, a sulfur source (e.g., $H_2S$) and a feedstock comprising one or more $C_{11+}$ monoolefins in the presence of an initiating agent, as previously described herein for the branched $C_{10}$ monoolefins, to produce a $C_{11+}$ mercaptans crude composition; wherein the one or more $C_{11+}$ monoolefins is selected from the group consisting of $C_{11}$ and $C_{12}$ internal monoolefins, $C_{13}$ and $C_{14}$ internal monoolefins, and $C_{14}$ and $C_{16}$ linear alpha monoolefins.

The sulfur source can be any sulfur source suitable to provide sulfur for the conversion of olefins (e.g., $C_{11+}$ monoolefins) to mercaptans (e.g., $C_{11+}$ mercaptans) and sulfides (e.g., $C_{22+}$ sulfides). The sulfur source can comprise $H_2S$, thioacetic acid, and the like, or combinations thereof. In some aspects, the sulfur source can comprise $H_2S$, as previously described herein.

In an aspect, the feedstock can comprise $C_{11}$ and $C_{12}$ internal monoolefins. Any feedstock comprising $C_{11}$ and $C_{12}$ internal monoolefins of the type described herein can be used, for example a feedstock obtained from a commercial petroleum refining or petrochemical process. Such feedstocks can comprise other olefins in addition to the $C_{11}$ and $C_{12}$ internal monoolefins of the type described herein, for example $C_{10-}$ monoolefins, as well as $C_{13+}$ monoolefins. An example of a $C_{11}$ and $C_{12}$ internal monoolefins feedstock suitable for use in the present disclosure include NEODENE 1112 IO higher olefins, which contains a combination of $C_{11}$ and $C_{12}$ internal olefins that is commercially available from Shell Chemicals. A typical composition of NEODENE 1112 IO higher olefins is given in the table below:

| Component of NEODENE 1112 IO | Unit | Value | Method |
|---|---|---|---|
| $C_{10}$ & Lower ($C_{10-}$) | % m/m [% mass/mass] | <1.5 | SMS* 2976 |
| $C_{11}$ | % m/m | 35-56 | SMS 2976 |
| $C_{12}$ | % m/m | 43-64 | SMS 2976 |
| $C_{13}$ & Higher ($C_{13-}$) | % m/m | <2.0 | SMS 2976 |
| Appearance | | Clear and substantially free of visual impurities | Visual |
| Color, Pt•Co | | <10 | ASTM D1209 - 05(2011) |
| Water | mg/kg | <100 | ASTM E1064 - 16 |

*SMS = Shell Modified Spot Test.

In an aspect, the feedstock can comprise at least about 70 wt. %, alternatively at least about 75 wt. %, alternatively at least about 80 wt. %, alternatively at least about 85 wt. %, alternatively at least about 90 wt. %, or alternatively at least about 95 wt. % $C_{11}$ and $C_{12}$ internal monoolefins, based on the total weight of the feedstock. In such aspect, the feedstock can comprise (a) less than about 10 wt. %, alternatively less than about 5 wt. %, or alternatively less than about 1.5 wt. % $C_{10-}$ monoolefins; and (b) less than about 10 wt. %, alternatively less than about 5 wt. %, or alternatively less than about 2 wt. % $C_{13+}$ monoolefins; based on the total weight of the feedstock. For purposes of the disclosure herein, a feedstock comprising at least about 70 wt. % $C_{11}$ and $C_{12}$ internal monoolefins, based on the total weight of the feedstock, can also be referred to as a "first $C_{11}$ and $C_{12}$ feedstock."

In another aspect, the feedstock can comprise at least about 95 wt. %, alternatively at least about 96 wt. %, alternatively at least about 97 wt. %, alternatively at least about 98 wt. %, or alternatively at least about 99 wt. % $C_{11}$ and $C_{12}$ internal monoolefins, based on the total weight of the feedstock. For purposes of the disclosure herein, a feedstock comprising at least about 95 wt. % $C_{11}$ and $C_{12}$ internal monoolefins, based on the total weight of the feedstock, can also be referred to as a "second $C_{11}$ and $C_{12}$ feedstock." In an aspect, the second $C_{11}$ and $C_{12}$ feedstock can be produced by purifying the first $C_{11}$ and $C_{12}$ feedstock, such as for example by distillation of the first $C_{11}$ and $C_{12}$ feedstock.

In some aspects, the $C_{11}$ internal monoolefins and $C_{12}$ internal monoolefins of any feedstock described herein (e.g., a first $C_{11}$ and $C_{12}$ feedstock or a second $C_{11}$ and $C_{12}$ feedstock) can comprise linear $C_{11}$ internal monoolefins and linear $C_{12}$ internal monoolefins, respectively.

In other aspects, the $C_{11}$ internal monoolefins and $C_{12}$ internal monoolefins of any feedstock described herein (e.g., a first $C_{11}$ and $C_{12}$ feedstock or a second $C_{11}$ and $C_{12}$ feedstock) can comprise branched $C_{11}$ internal monoolefins and branched $C_{12}$ internal monoolefins, respectively. The branched $C_{11}$ internal monoolefins can comprise methyl branches. The branched $C_{12}$ internal monoolefins can comprise methyl branches.

In yet other aspects, the $C_{11}$ and $C_{12}$ internal monoolefins can comprise linear $C_{11}$ internal monoolefins, linear $C_{12}$ internal monoolefins, branched $C_{11}$ internal monoolefins, branched $C_{12}$ internal monoolefins, or combinations thereof.

In some aspects, the feedstock can comprise (A) at least about 30 wt. %, alternatively at least about 35 wt. %, or alternatively at least about 40 wt. % $C_{11}$ internal monoolefins, and (B) at least about 40 wt. %, alternatively at least about 45 wt. %, alternatively at least about 50 wt. % $C_{12}$ internal monoolefins, based on the total weight of the feedstock.

In an aspect, the feedstock can comprise $C_{13}$ and $C_{14}$ internal monoolefins. Any feedstock comprising $C_{13}$ and $C_{14}$ internal monoolefins of the type described herein can be used, for example a feedstock obtained from a commercial petroleum refining or petrochemical process. Such feedstocks can comprise other olefins in addition to the $C_{13}$ and $C_{14}$ internal monoolefins of the type described herein, for example $C_{12-}$ monoolefins, as well as $C_{15+}$ monoolefins. An example of a $C_{13}$ and $C_{14}$ internal monoolefins feedstock suitable for use in the present disclosure include NEODENE 1314 IO higher olefins (also known as NEODENE 134 IO higher olefins), which contains a combination of $C_{13}$ and $C_{14}$ internal olefins that is commercially available from Shell Chemicals. A typical composition of NEODENE 1314 IO higher olefins is given in the table below:

| Component of NEODENE 1314 IO | Unit | Value | Method |
|---|---|---|---|
| $C_{12}$ & Lower ($C_{12-}$) | % m/m [% mass/mass] | <2.0 | SMS* 2976 |
| $C_{13}$ | % m/m | 43-55 | SMS 2976 |
| $C_{14}$ | % m/m | 45-55 | SMS 2976 |
| $C_{15}$ & Higher ($C_{15-}$) | % m/m | <2.5 | SMS 2976 |
| Appearance | | Clear and substantially free of visual impurities | Visual |
| Color, Pt•Co | | <10 | ASTM D1209 - 05(2011) |
| Water | mg/kg | <100 | ASTM E1064 - 16 |

*SMS = Shell Modified Spot Test.

In an aspect, the feedstock can comprise at least about 70 wt. %, alternatively at least about 75 wt. %, alternatively at least about 80 wt. %, alternatively at least about 85 wt. %, alternatively at least about 90 wt. %, or alternatively at least about 95 wt. % $C_{13}$ and $C_{14}$ internal monoolefins, based on the total weight of the feedstock. In such aspect, the feedstock can comprise (a) less than about 10 wt. %, alternatively less than about 5 wt. %, or alternatively less than about 2 wt. % $C_{12-}$ monoolefins; and (b) less than about 10 wt. %, alternatively less than about 5 wt. %, or alternatively less than about 2.5 wt. % $C_{15+}$ monoolefins; based on the total weight of the feedstock. For purposes of the disclosure herein, a feedstock comprising at least about 70 wt. % $C_{13}$ and $C_{14}$ internal monoolefins, based on the total weight of the feedstock, can also be referred to as a "first $C_{13}$ and $C_{14}$ feedstock."

In another aspect, the feedstock can comprise at least about 95 wt. %, alternatively at least about 96 wt. %, alternatively at least about 97 wt. %, alternatively at least about 98 wt. %, or alternatively at least about 99 wt. % $C_{13}$ and $C_{14}$ internal monoolefins, based on the total weight of the feedstock. For purposes of the disclosure herein, a feedstock comprising at least about 95 wt. % $C_{13}$ and $C_{14}$ internal monoolefins, based on the total weight of the feedstock, can also be referred to as a "second $C_{13}$ and $C_{14}$ feedstock." In an aspect, the second $C_{13}$ and $C_{14}$ feedstock can be produced by purifying the first $C_{13}$ and $C_{14}$ feedstock, such as for example by distillation of the first $C_{13}$ and $C_{14}$ feedstock.

In some aspects, the $C_{13}$ internal monoolefins and $C_{14}$ internal monoolefins of any feedstock described herein (e.g., a first $C_{13}$ and $C_{14}$ feedstock or a second $C_{13}$ and $C_{14}$ feedstock) can comprise linear $C_{13}$ internal monoolefins and linear $C_{14}$ internal monoolefins, respectively.

In other aspects, the $C_{13}$ internal monoolefins and $C_{14}$ internal monoolefins of any feedstock described herein (e.g., a first $C_{13}$ and $C_{14}$ feedstock or a second $C_{13}$ and $C_{14}$ feedstock) can comprise branched $C_{13}$ internal monoolefins and branched $C_{14}$ internal monoolefins, respectively. The branched $C_{13}$ internal monoolefins can comprise methyl branches. The branched $C_{14}$ internal monoolefins can comprise methyl branches.

In yet other aspects, the $C_{13}$ and $C_{14}$ internal monoolefins can comprise linear $C_{13}$ internal monoolefins, linear $C_{14}$ internal monoolefins, branched $C_{13}$ internal monoolefins, branched $C_{14}$ internal monoolefins, or combinations thereof.

In some aspects, the feedstock can comprise (A) at least about 35 wt. %, alternatively at least about 40 wt. %, or alternatively at least about 45 wt. % $C_{13}$ internal monoolefins, and (B) at least about 35 wt. %, alternatively at least about 40 wt. %, alternatively at least about 45 wt. % $C_{14}$ internal monoolefins; based on the total weight of the feedstock.

In an aspect, the feedstock can comprise $C_{14}$ and $C_{16}$ alpha monoolefins, such as $C_{14}$ and $C_{16}$ linear alpha monoolefins. For purposes of the disclosure herein, the terms "alpha olefin (monoolefin)" and "terminal olefin (monoolefin)" can be used interchangeably. Any feedstock comprising $C_{14}$ and $C_{16}$ alpha monoolefins of the type described herein can be used, for example a feedstock obtained from a commercial petroleum refining or petrochemical process. Such feedstocks can comprise other olefins in addition to the $C_{14}$ and $C_{16}$ alpha monoolefins of the type described herein, for example $C_{13-}$ monoolefins, as well as $C_{17+}$ monoolefins. In some aspects, a feedstock comprising $C_{14}$ and $C_{16}$ alpha monoolefins can further comprise $C_{15}$ monoolefins, such as $C_{15}$ alpha monoolefin, $C_{15}$ linear alpha monoolefins, etc.

As will be appreciated by one of skill in the art, and with the help of this disclosure, a feedstock comprising linear olefins (e.g., linear alpha monoolefins, $C_{14}$ and $C_{16}$ linear alpha monoolefins) can further comprise a minor amount of branched monoolefins; or alternatively can exclude branched monoolefins. In some aspects, the feedstock comprising $C_{14}$ and $C_{16}$ linear alpha monoolefins comprises less than 1 wt. %, alternatively less than 0.1 wt. %, alternatively less than 0.01 wt. %, alternatively less than 0.001 wt. %, or alternatively less than 0.0001 wt. % branched monoolefins, based on the total weight of the feedstock. In an aspect, the feedstock comprising $C_{14}$ and $C_{16}$ linear alpha monoolefins is substantially free of branched monoolefins.

An example of a $C_{14}$ and $C_{16}$ alpha monoolefins feedstock suitable for use in the present disclosure include NEODENE 14/16 higher olefins, which contains a combination of $C_{14}$ and $C_{16}$ alpha olefins (2:1 blend of a high purity 1-tetradecene ($C_{14}$) and 1-hexadecene ($C_{16}$) made by the Shell Higher Olefins Process (SHOP) by the oligomerization of ethylene) that is commercially available from Shell Chemicals. A typical composition of NEODENE 14/16 higher olefins is given in the table below:

| Component of NEODENE 14/16 | Unit | Value | Method |
| --- | --- | --- | --- |
| $C_{12}$ and lower ($C_{12-}$) | % m/m [% mass/mass] | <2 | SMS* 2895 |
| $C_{14}$ | % m/m | 60-70 | SMS 2895 |
| $C_{16}$ | % m/m | 29-40 | SMS 2895 |

-continued

| Component of NEODENE 14/16 | Unit | Value | Method |
| --- | --- | --- | --- |
| $C_{18}$ and higher ($C_{18+}$) | % m/m | <2 | SMS 2895 |
| Total n-Alpha Olefins | % m/m | >92.5 | SMS 2895 |
| Total Branched Olefins | % m/m | <4.5 | SMS 2895 |
| Total Internal Olefins | % m/m | <2.5 | SMS 2895 |
| Paraffin | % m/m | <0.2 | SMS 2895 |
| Appearance | Clear and substantially free of Visual visual impurities | | |
| Color, Pt•Co | | <5 | ASTM D1209 - 05(2011) |
| Water | mg/kg | <100 | ASTM E1064 - 16 |
| Carbonyls as C=O | mg/kg | <15 | SMS 2894 |
| Peroxides as O | mg/kg | <3 | SMS 359 |

*SMS = Shell Modified Spot Test.

In an aspect, the feedstock can comprise at least about 70 wt. %, alternatively at least about 75 wt. %, alternatively at least about 80 wt. %, alternatively at least about 85 wt. %, alternatively at least about 90 wt. %, or alternatively at least about 95 wt. % $C_{14}$ and $C_{16}$ linear alpha monoolefins, based on the total weight of the feedstock. In such aspect, the feedstock can comprise (a) less than about 10 wt. %, alternatively less than about 5 wt. %, or alternatively less than about 2 wt. % $C_{12-}$ monoolefins; and (b) less than about 10 wt. %, alternatively less than about 5 wt. %, or alternatively less than about 2 wt. % $C_{18+}$ monoolefins; based on the total weight of the feedstock. For purposes of the disclosure herein, a feedstock comprising at least about 70 wt. % $C_{14}$ and $C_{16}$ linear alpha monoolefins, based on the total weight of the feedstock, can also be referred to as a "first $C_{14}$ and $C_{16}$ feedstock."

In another aspect, the feedstock can comprise at least about 95 wt. %, alternatively at least about 96 wt. %, alternatively at least about 97 wt. %, alternatively at least about 98 wt. %, or alternatively at least about 99 wt. % $C_{14}$ and $C_{16}$ linear alpha monoolefins, based on the total weight of the feedstock. For purposes of the disclosure herein, a feedstock comprising at least about 95 wt. % $C_{14}$ and $C_{16}$ linear alpha monoolefins, based on the total weight of the feedstock, can also be referred to as a "second $C_{14}$ and $C_{16}$ feedstock." In an aspect, the second $C_{14}$ and $C_{16}$ feedstock can be produced by purifying the first $C_{14}$ and $C_{16}$ feedstock, such as for example by distillation of the first $C_{14}$ and $C_{16}$ feedstock.

The feedstock comprising $C_{14}$ and $C_{16}$ linear alpha monoolefin (e.g., a first $C_{14}$ and $C_{16}$ feedstock or a second $C_{14}$ and $C_{16}$ feedstock) can comprise less than less than about 10 wt. %, alternatively less than about 7.5 wt. %, or alternatively less than about 4.5 wt. % branched olefins, based on the total weight of the feedstock.

In some aspects, the feedstock can comprise (A) at least about 50 wt. %, alternatively at least about 55 wt. %, or alternatively at least about 60 wt. % 1-tetradecene, and (B) at least about 20 wt. %, alternatively at least about 25 wt. %, alternatively at least about 30 wt. % 1-hexadecene, based on the total weight of the feedstock.

In an aspect, a sulfur source (e.g., $H_2S$) and a feedstock comprising one or more $C_{u+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) can be reacted using a sulfur source to olefin molar ratio of from about 1:1 to about 20:1, alternatively from about 2:1 to about 15:1, or alternatively from about 3:1 to about 10:1; as previously described herein for the branched $C_{10}$ monoolefins.

In an aspect, a sulfur source (e.g., $H_2S$) and a feedstock comprising one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) can be reacted at a pressure of from about 30 psig (206 kPag) to about 1,500 psig (10,300 kPag), alternatively from about 100 psig (690 kPag) to about 1,250 psig (8,600 kPag), or alternatively from about 250 psig (1,700 kPag) to about 1,000 psig (6,900 kPag); as previously described herein for the branched $C_{10}$ monoolefins.

In an aspect, a sulfur source (e.g., $H_2S$) and a feedstock comprising one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) can be reacted (as previously described herein for the branched $C_{10}$ monoolefins) to produce olefin conversion of equal to or greater than about 70%, alternatively equal to or greater than about 75%, or alternatively equal to or greater than about 80%, alternatively equal to or greater than about 85%, or alternatively equal to or greater than about 90%.

In an aspect, a sulfur source (e.g., $H_2S$) and a feedstock comprising one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) can be reacted in the presence of an initiating agent to produce a mercaptans crude composition; wherein the initiating agent comprises ultraviolet (UV) radiation; as previously described herein for the branched $C_{10}$ monoolefins. In such aspect, the initiating agent can further comprise a phosphite promoter, a photoinitiator, a sulfur scavenger, an antioxidant, and the like, or combinations thereof.

In an aspect, a sulfur source (e.g., $H_2S$) and a feedstock comprising one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) can be reacted in the presence of an initiating agent to produce a $C_{11+}$ mercaptans crude composition; wherein the initiating agent comprises a acid catalyst; as previously described herein for the branched $C_{10}$ monoolefins.

In an aspect, a sulfur source (e.g., $H_2S$) and a feedstock comprising one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) can be reacted in the presence of an initiating agent to produce a $C_{11+}$ mercaptans crude composition; wherein the initiating agent comprises a hydrodesulfurization (HDS) catalyst; as previously described herein for the branched $C_{10}$ monoolefins.

As noted previously, any suitable feedstocks comprising one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) can be reacted with a sulfur source (e.g., $H_2S$) in the presence of an initiating agent to produce a $C_{11+}$ mercaptans crude composition, and the $C_{11+}$ mercaptans crude composition can be further refined (e.g., distilled or otherwise separated into one or more fractions such as lights, intermediate, and heavies) to yield various compositions described herein. As described in more detail herein, the type and/or amounts of the constituent components that form the $C_{11+}$ mercaptans crude composition can vary depending upon the feedstock (e.g., the amount and types of olefins therein), the reaction conditions, the catalysts employed, etc., and one skilled in the art can tailor the post reactor processing of the $C_{11+}$ mercaptans crude composition to account for the specific compounds present in a given $C_{11+}$ mercaptans crude composition to yield various desired products and compositions of the types described herein.

Upon completion of the reaction of a feedstock comprising one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) with a sulfur source (e.g., $H_2S$), a reactor effluent can be recovered from the reactor and $H_2S$ removed therefrom to yield a $C_{11+}$ mercaptans crude composition. The term "$C_{11+}$ mercaptans crude composition" or "$C_{11+}$ mercaptans crude product" refers to an unrefined effluent stream recovered from the reactor after removal of the sulfur source (e.g., $H_2S$), and in particular to a sulfur source-free effluent stream that has not undergone any additional post-reactor processing such as flashing, distillation, or other separation techniques or processes to remove any components from the effluent stream other than the initial removal of the sulfur source.

The $C_{11+}$ mercaptans crude composition comprises $C_{11+}$ mercaptans and $C_{22+}$ sulfides formed by the reaction of the sulfur source (e.g., $H_2S$) and the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins), wherein the structures of these $C_{11+}$ mercaptans and $C_{22+}$ sulfides are consistent with (e.g., derived from) the structures of the corresponding $C_{11+}$ monoolefins. For example, in aspects where the one or more $C_{11+}$ monoolefins comprise 1-tetradecene ($H_2C=CH-(CH_2)_{11}-CH_3$) and 1-hexadecene ($H_2C=CH-(CH_2)_{13}-CH_3$), the resulting $C_{11+}$ mercaptans ($C_{14}$ mercaptans and $C_{16}$ mercaptans) can be characterized by the following structures that are consistent with (e.g., derived from) the structures of the corresponding 1-tetradecene and 1-hexadecene:

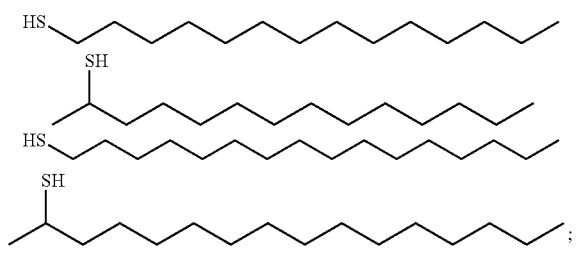

and the resulting $C_{22+}$ sulfides ($C_{28}$ sulfides, $C_{30}$ sulfides, and $C_{32}$ sulfides) can be characterized by the following structures that are consistent with (e.g., derived from) the structures of the corresponding 1-tetradecene and 1-hexadecene:

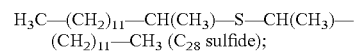

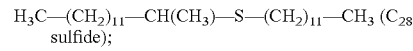

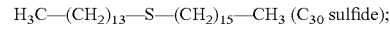

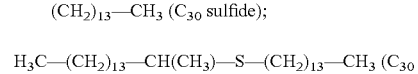

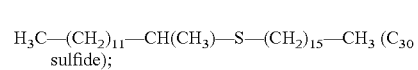

$H_3C-(CH_2)_{15}-S-(CH_2)_{15}-CH_3$ ($C_{32}$ sulfide);

$H_3C-(CH_2)_{13}-CH(CH_3)-S-CH(CH_3)-(CH_2)_{13}-CH_3$ ($C_{32}$ sulfide);

$H_3C-(CH_2)_{13}-CH(CH_3)-S-(CH_2)_{15}-CH_3$ ($C_{32}$ sulfide); etc.

Generally, the $C_{11+}$ mercaptans are characterized by structure $R^6-SH$, wherein $R^6$ is a functional group (e.g., alkyl group) derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein.

Generally, the $C_{22+}$ sulfides are characterized by structure $R^7-S-R^8$, wherein both $R^7$ and $R^8$ can each independently be a functional group derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein. $R^7$ and $R^8$ can be the same or different, e.g., $R^7$ and $R^8$ can have the same structure; $R^7$ and $R^8$ can have different structures; $R^7$ and $R^8$ can have the same chain length; $R^7$ and $R^8$ can have different chain length; etc.

As will be appreciated by one of skill in the art, and with the help of this disclosure, in aspects where the one or more $C_{11+}$ monoolefins (e.g., $C_{11}$ and $C_{12}$ internal monoolefins; $C_{13}$ and $C_{14}$ internal monoolefins) contain methyl branches in their structure, the resulting $C_{11+}$ mercaptans and $C_{22+}$ sulfides would also contain methyl branches consistent with (e.g., derived from) the structures of the corresponding $C_{11+}$ monoolefins.

In addition to $C_{11+}$ mercaptans and $C_{22+}$ sulfides, the $C_{11+}$ mercaptans crude composition can comprise a number of other compounds such as unreacted olefins, inert compounds (e.g., alkanes), $C_{10-}$ mercaptans, $C_{21-}$ sulfides, and other impurities. The constituent components contained within the $C_{11+}$ mercaptans crude composition can vary depending upon the composition of the feedstock (e.g., an unpurified feedstock as compared to a purified feedstock as described herein) as well as reaction conditions, catalyst, etc. In various aspects, a $C_{11+}$ mercaptans crude composition can comprise light, intermediate, and heavy fractions as described herein.

In some aspects, the $C_{11+}$ mercaptans crude composition can comprise less than about 10 wt. %, alternatively less than about 5 wt. %, alternatively less than about 4 wt. %, alternatively at less than about 3 wt. %, alternatively less than about 2 wt. %, or alternatively less than about 1 wt. % $C_{22+}$ sulfides, based on the total weight of the crude composition, wherein the $C_{22+}$ sulfides are characterized by structure $R^7-S-R^8$, wherein both $R^7$ and $R^8$ can each independently be a functional group derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein.

In an aspect, a process of the present disclosure can further comprise recovering a reaction product from the $C_{11+}$ mercaptans crude composition; wherein the reaction product can comprises mercaptans and/or $C_{22+}$ sulfides, wherein the $C_{11+}$ mercaptans are characterized by structure $R^6-SH$, wherein $R^6$ is a functional group (e.g., alkyl group) derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein; and wherein the $C_{22+}$ sulfides are characterized by structure $R^7-S-R^8$, wherein both $R^7$ and $R^8$ can each independently be a functional group derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein.

In an aspect, the reaction product can comprise a $C_{11+}$ mercaptans composition (intermediate fraction), a $C_{22+}$ sulfides composition (heavy fraction), a $C_{11+}$ mercaptans/$C_{22+}$ sulfides composition (intermediate and heavy fractions), or combinations thereof.

In an aspect, a $C_{11+}$ mercaptans crude composition as disclosed herein can be separated into two or more fractions (e.g., light fraction, intermediate fraction, heavy fraction, etc.) by any process or unit operation known in the art. For example, a $C_{11+}$ mercaptans crude composition can be processed (e.g., distilled) to remove a fraction of light compounds. Alternatively, a $C_{11+}$ mercaptans crude composition can be processed to recover both a light fraction and an intermediate fraction (e.g., a rough cut), followed by further processing to obtain one or more fine cuts. Alternatively, a $C_{11+}$ mercaptans crude composition can be processed to recover a heavy fraction (e.g., a $C_{22+}$ sulfide fraction). Alternatively, a $C_{11+}$ mercaptans crude composition can be processed to separate out any combination of a light fraction, an intermediate fraction (e.g., comprising $C_{11+}$ mercaptans), and a heavy fraction (e.g., comprising $C_{22+}$ sulfides). Furthermore, a light, intermediate or heavy fraction (e.g., a rough cut) can be further processed or parsed to obtain one or more desired fine cuts (e.g., a $C_{11+}$ mercaptan fraction). Alternatively, a $C_{11+}$ mercaptans crude composition can be separated to produce a high-purity $C_{11+}$ mercaptan stream and/or a high-purity $C_{22+}$ sulfide stream (e.g., to obtain a desired fine cut or fraction such as a $C_{11+}$ mercaptan fraction). Further, these separated streams can be blended in any combination of ratios to produce a mixture with specific concentrations of one of more components (e.g., desired blend ratios of $C_{11+}$ mercaptans and/or $C_{22+}$ sulfides, for example to aid in a particular end use). The unit operations/processes used for these separations are known to one of skill and the art and include, but are not limited to, distillation, fractionation, flashing, stripping, and absorption, and others. The unit operation conditions, such as for example, temperature, pressure, flow rates, and others at which these unit operations produce one or more of the desired fractions can easily be determined by one of ordinary skill in the art.

In an aspect, a light fraction is removed from the $C_{11+}$ mercaptans crude composition, for example by flashing, distillation, fractionation, stripping, absorption, etc.

In an aspect, the light fraction removed from the $C_{11+}$ mercaptans crude composition can comprise at least about 90 wt. %, alternatively at least about 90 wt. %, alternatively at least about 95 wt. %, alternatively at least about 96 wt. %, alternatively at least about 97 wt. %, alternatively at least about 98 wt. %, alternatively at least about 99 wt. % $C_{10-}$ compounds, based on the total weight of the light fraction. Nonlimiting examples of $C_{10-}$ compounds include $C_{10-}$ monoolefins (e.g., unreacted $C_{10-}$ monoolefins), $C_{10-}$ mercaptans, $C_{10-}$ alkanes, $C_{10-}$ alcohols, and the like, or combinations thereof. In an aspect, the light fraction removed from the $C_{11+}$ mercaptans crude composition can comprise less than about 10 wt. %, alternatively less than about 5 wt. %, alternatively less than about 4 wt. %, alternatively at less than about 3 wt. %, alternatively less than about 2 wt. %, or alternatively less than about 1 wt. % $C_{11+}$ compounds, based on the total weight of the light fraction.

Following removal of the lights (for example, via flashing) from the mercaptans crude composition, a combined intermediate and heavy fraction (i.e., $C_{11+}$ compounds sometimes referred to as a kettle product in the Examples) can remain, and the combined intermediate and heavy fraction can be used "as is" or can be further processed, for example separated or split into separate intermediate and heavy fractions (and said separate intermediate and heavy fractions can be subsequently recombined in various blends and associated blend ratios), as described in more detail herein. In an aspect, a combined intermediate and heavy fraction (i.e., $C_{11+}$ compounds) formed by removal of the light fraction from the mercaptans crude composition can comprise less than about 15 wt. %, alternatively less than about 10 wt. %, alternatively less than about 9 wt. %, alternatively less than about 8 wt. %, alternatively less than about 7 wt. %, alternatively less than about 6 wt. %, alternatively less than about 5 wt. %, alternatively less than about 4 wt. %, alternatively less than about 3 wt. %, alternatively less than about 2 wt. %, alternatively less than about 1 wt. % $C_{10-}$ products, based on the total weight of the combined intermediate and heavy fraction (i.e., $C_{11+}$ compounds).

In an aspect, a combined intermediate and heavy fraction (i.e., $C_{11+}$ compounds) recovered from the from the $C_{11+}$ mercaptans crude composition can comprise (A) at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % $C_{11+}$ mercaptans, based on the total weight of the combined fraction, wherein the $C_{11+}$ mercaptans are characterized by structure $R^6$—SH, wherein $R^6$ is a functional group (e.g., alkyl group) derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein; and (B) less than about 20 wt. %, alternatively less than about 15 wt. %, alternatively less than about 10 wt. %, or alternatively less than about 5 wt. % $C_{22+}$ sulfides, based on the total weight of the combined fraction, wherein the $C_{22+}$ sulfides are characterized by structure $R^7$—S—$R^8$, wherein both $R^7$ and $R^8$ can each independently be a functional group derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein.

In an embodiment, the $C_{11+}$ mercaptans crude composition can be flashed to remove a lights fraction as described herein to produce a combined intermediate and heavy fraction (i.e., $C_{11+}$ compounds) comprising: (A) from at least about 50 wt. % to at least about 99 wt. %, alternatively from at least about 50 wt. % to at least about 95 wt. %, alternatively from at least about 55 wt. % to at least about 85 wt. %, or alternatively from at least about 60 wt. % to at least about 80 wt. % $C_{11+}$ mercaptans, wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the $C_{11+}$ mercaptans can be $C_{11+}$ mercaptans characterized by structure $R^6$—SH, wherein $R^6$ is a functional group (e.g., alkyl group) derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein; and (B) from about 1 wt. % to about 20 wt. %, alternatively from about 5 wt. % to about 20 wt. %, alternatively from about 7.5 wt. % to about 17.5 wt. %, or alternatively from about 10 wt. % to about 15 wt. % $C_{22+}$ sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the $C_{22+}$ sulfides can be $C_{22+}$ sulfides characterized by structure $R^7$—S—$R^8$, wherein both $R^7$ and $R^8$ can each independently be a functional group derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein.

In an aspect, the $C_{11+}$ mercaptans crude composition can be flashed to remove a light fraction and subsequently further separated to produce an intermediate fraction and a heavy fraction (i.e., $C_{11+}$ compounds). The intermediate fraction and the heavy fractions recovered from the $C_{11+}$ mercaptans crude composition can then be optionally further processed (e.g., polished) and mixed in any appropriate ratio to produce blended compositions, as previously described herein for crude compositions derived from branched $C_{10}$ monoolefins.

In an aspect, an intermediate fraction recovered from the $C_{11+}$ mercaptans crude composition can comprise at least about 25 wt. %, alternatively at least about 30 wt. %, alternatively at least about 40 wt. %, alternatively at least about 50 wt. %, alternatively at least about 75 wt. %, or alternatively at least about 85 wt. % $C_{11+}$ mercaptans, based on the total weight of the intermediate fraction, wherein the $C_{11+}$ mercaptans are characterized by structure $R^6$—SH, wherein $R^6$ is a functional group (e.g., alkyl group) derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein.

In an aspect, the heavy fraction recovered from the mercaptans crude composition can comprise at least about 5, 10, 15, 20, 25, 30, 35, 40, 45, 50, 55, 60, 65, 70, 75, 80, or 85 wt. %, $C_{22+}$ sulfides, based on the total weight of the heavy fraction, wherein the $C_{22+}$ sulfides are characterized by structure $R^7$—S—$R^8$, wherein both $R^7$ and $R^8$ can each independently be a functional group derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein.

In an aspect, a $C_{11+}$ mercaptans composition can comprise $C_{11+}$ mercaptans, wherein at least a portion of the $C_{11+}$ mercaptans are characterized by structure $R^6$—SH, wherein $R^6$ is a functional group (e.g., alkyl group) derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein. In an aspect, the $C_{11+}$ mercaptans composition can comprise any suitable amount of $C_{11+}$ mercaptans as disclosed herein.

In some aspects, a $C_{11+}$ mercaptans composition can comprise at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % $C_{11+}$ mercaptans, based on the total weight of the $C_{11+}$ mercaptans composition; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the $C_{11+}$ mercaptans can be $C_{11+}$ mercaptans characterized by structure $R^6$—SH, wherein $R^6$ is a functional group (e.g., alkyl group) derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein.

In other aspects, a $C_{11+}$ mercaptans composition can consist of or consist essentially of $C_{11+}$ mercaptans characterized by structure $R^6$—SH, wherein $R^6$ is a functional group (e.g., alkyl group) derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein.

In yet other aspects, a $C_{11+}$ mercaptans composition can comprise at least about 1, 5, 10, 15, 20, 25, 30, 35, 40, 45, 50, 55, 60, 65, 70, 75, 80, 85, 90, 95, or 99 wt. % $C_{11+}$ mercaptans characterized by structure $R^6$—SH, wherein $R^6$ is a functional group (e.g., alkyl group) derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein.

In an aspect, a $C_{22+}$ sulfides composition can comprise $C_{22+}$ sulfides, wherein at least a portion of the $C_{22+}$ sulfides are characterized by structure $R^7$—S—$R^8$, wherein both $R^7$ and $R^8$ can each independently be a functional group derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein. In an aspect, the $C_{22+}$ sulfides composition can comprise any suitable amount of $C_{22+}$ sulfides as disclosed herein.

In some aspects, a $C_{22+}$ sulfides composition can comprise $C_{22+}$ sulfides, wherein at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % of the $C_{22+}$ sulfides can be $C_{22+}$ sulfides characterized by structure $R^7$—S—$R^8$, wherein both $R^7$ and $R^8$ can each independently be a functional group derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein.

In other aspects, a $C_{22+}$ sulfides composition can consist of or consist essentially of $C_{22+}$ sulfides characterized by structure $R^7$—S—$R^8$, wherein both $R^7$ and $R^8$ can each independently be a functional group derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein.

In yet other aspects, a $C_{22+}$ sulfides composition comprises at least about 1, 5, 10, 15, 20, 25, 30, 35, 40, 45, 50, 55, 60, 65, 70, 75, 80, 85, 90, 95, or 99 wt. % $C_{22+}$ sulfides characterized by structure $R^7$—S—$R^8$, wherein both $R^7$ and $R^8$ can each independently be a functional group derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein.

In an aspect, a $C_{11+}$ mercaptans/$C_{22+}$ sulfides composition can comprise one or more $C_{11+}$ mercaptans and one or more $C_{22+}$ sulfides of the type disclosed herein. In an aspect, the $C_{11+}$ mercaptans/$C_{22+}$ sulfides composition can comprise any suitable amount of $C_{11+}$ mercaptans, and any suitable amount of $C_{22+}$ sulfides.

In an aspect, a $C_{11+}$ mercaptans/$C_{22+}$ sulfides composition can comprise (A) at least about 1 wt. %, alternatively at least about 5 wt. %, alternatively at least about 10 wt. %, alternatively at least about 15 wt. %, alternatively at least about 20 wt. %, alternatively at least about 25 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % $C_{11+}$ mercaptans, based on the total weight of the mercaptans/$C_{22+}$ sulfides composition, wherein at least a portion of the $C_{11+}$ mercaptans can be $C_{11+}$ mercaptans characterized by structure $R^6$—SH, wherein $R^6$ is a functional group (e.g., alkyl group) derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein; and (B) at least about 1 wt. %, alternatively at least about 5 wt. %, alternatively at least about 10 wt. %, alternatively at least about 15 wt. %, alternatively at least about 20 wt. %, alternatively at least about 25 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % $C_{22+}$ sulfides, based on the total weight of the $C_{11+}$ mercaptans/$C_{22+}$ sulfides composition, wherein at least a portion of the $C_{22+}$ sulfides can be $C_{22+}$ sulfides characterized by structure $R^7$—S—$R^8$, wherein both $R^7$ and $R^8$ can each independently be a functional group derived from the one or more $C_{11+}$ monoolefins (e.g., $C_{11}$ and $C_{12}$ internal monoolefins; $C_{13}$ and $C_{14}$ internal monoolefins; or $C_{14}$ and $C_{16}$ linear alpha monoolefins) disclosed herein.

In an aspect, a $C_{11+}$ mercaptans/$C_{22+}$ sulfides composition can comprise $C_{11+}$ mercaptans represented by structure $R^6$—SH and/or $C_{22+}$ sulfides represented by structure $R^7$—S—$R^8$ that are formed by reacting an olefin feedstock comprising $C_{11+}$ monoolefins with $H_2S$ as disclosed herein, wherein the $C_{11+}$ monoolefins present in the olefin feedstock provide the alkyl group represented by $R^6$, $R^7$, and $R^8$. In such aspects, the $R^6$ group of the $C_{11+}$ mercaptans and/or the $R^7$ and $R^8$ groups of the $C_{22+}$ sulfides are provided by or derived from the counterpart $R^6$, $R^7$, and $R^8$ groups present in the $C_{11+}$ monoolefins in the olefin feedstock.

The $C_{11+}$ mercaptans compositions, $C_{22+}$ sulfides compositions, and $C_{11+}$ mercaptans/$C_{22+}$ sulfides compositions can be salable or otherwise used for a variety of end uses such as mining ore collector compositions and chain transfer agents.

In an aspect, the $C_{11+}$ mercaptans as disclosed herein can be further converted to multi-sulfur containing compounds, which could then be used for any suitable applications, such as adhesives, epoxy adhesives, chain transfer agents, catalyst sulfurization, lubricants, mining collectors, etc. In some aspects, the $C_{11+}$ mercaptans as disclosed herein can be further converted to polysulfides, which could then be used for epoxy adhesives. In other aspects, the mercaptans as disclosed herein can be further converted to trithiocarbonates, which could then be used as chain transfer agents.

In an aspect, a $C_{11+}$ mercaptans composition and/or a $C_{11+}$ mercaptans/$C_{22+}$ sulfides composition comprising equal to or greater than about 25 wt. % $C_{11+}$ mercaptans as disclosed herein can advantageously have an odor less unpleasant than an odor of an otherwise similar composition comprising equal to or greater than about 25 wt. % n-dodecyl mercaptan and/or tert-dodecyl mercaptan, as perceived by equal to or greater than about 51% of human subjects exposed to the odor of each composition. Additional advantages of the $C_{11+}$ mercaptans compositions, $C_{22+}$ sulfides compositions, and $C_{11+}$ mercaptans/$C_{22+}$ sulfides compositions and processes of producing same as disclosed herein can be apparent to one of skill in the art viewing this disclosure.

In an aspect, a process of the present disclosure comprises reacting, in a reactor, a sulfur source (e.g., $H_2S$) and a feedstock comprising one or more branched $C_{10+}$ monoolefins in the presence of an initiating agent, as previously described herein for the branched $C_{10}$ monoolefins, to produce a crude composition (also referred to as a crude product); wherein the crude composition comprises branched $C_{10+}$ mercaptans and branched $C_{20+}$ sulfides.

In an aspect, a process of the present disclosure comprises reacting, in a reactor, a sulfur source (e.g., $H_2S$) and a feedstock comprising one or more branched $C_{10+}$ monoolefins in the presence of an initiating agent, as previously described herein for the branched $C_{10}$ monoolefins, to produce a branched $C_{10+}$ mercaptans crude composition (also referred to as a branched $C_{10+}$ mercaptans crude product); wherein the branched $C_{10+}$ monoolefins comprise $C_{10}$ to $C_{30}$ monoolefins, alternatively $C_{11}$ to $C_{30}$ monoolefins, alternatively $C_{12}$ to $C_{30}$ monoolefins, alternatively $C_{14}$ to $C_{30}$ monoolefins, alternatively $C_{16}$ to $C_{28}$ monoolefins, or alternatively $C_{18}$ to $C_{26}$ monoolefins; and wherein the branched $C_{10+}$ mercaptans crude composition comprises branched $C_{10+}$ mercaptans and branched $C_{20+}$ sulfides.

The sulfur source can be any sulfur source suitable to provide sulfur for the conversion of olefins (e.g., branched $C_{10+}$ monoolefins) to mercaptans (e.g., branched $C_{10+}$ mercaptans) and sulfides (e.g., branched $C_{20+}$ sulfides). The sulfur source can comprise $H_2S$, thioacetic acid, and the like, or combinations thereof. In some aspects, the sulfur source can comprise $H_2S$, as previously described herein.

The branched $C_{10+}$ mercaptans crude composition can be further processed, for example via distillation, as previously described herein for the branched $C_{10}$ monoolefins, to yield one or more products (also referred to as distilled, purified, refined, finished, or final products) selected from the group consisting of mercaptan compositions (e.g., a composition comprising one or more branched $C_{m+}$ mercaptans), sulfide compositions (e.g., a composition comprising one or more branched $C_{20+}$ sulfides); and compositions having both mercaptans (e.g., branched $C_{10+}$ mercaptans) and sulfides (e.g., branched $C_{20+}$ sulfides), referred to as mercaptan/sulfide compositions.

In an aspect, a $C_{10+}$ mercaptans composition comprises one or more branched $C_{10+}$ mercaptans, wherein the branched $C_{10+}$ mercaptans comprise $C_{10}$ to $C_{30}$ mercaptans, alternatively $C_{11}$ to $C_{30}$ mercaptans, alternatively $C_{12}$ to $C_{30}$ mercaptans, alternatively $C_{14}$ to $C_{30}$ mercaptans, alternatively $C_{16}$ to $C_{28}$ mercaptans, or alternatively $C_{18}$ to $C_{26}$ mercaptans.

In an aspect, a $C_{20+}$ sulfides composition comprises one or more branched $C_{20+}$ sulfides represented by the structure $R^{10}$—S—$R^{11}$, wherein $R^{10}$ and $R^{11}$ are each independently a functional group derived from an olefin, wherein the olefin comprises a branched $C_{10+}$ monoolefin as disclosed herein. The branched $C_{20+}$ sulfides comprise $C_{20}$ to $C_{60}$ sulfides, alternatively $C_{21}$ to $C_{60}$ sulfides, alternatively $C_{22}$ to $C_{60}$ sulfides, alternatively $C_{24}$ to $C_{60}$ sulfides, alternatively $C_{28}$ to $C_{60}$ sulfides, alternatively $C_{32}$ to $C_{56}$ sulfides, or alternatively $C_{36}$ to $C_{52}$ sulfides.

In an aspect, a $C_{10+}$ mercaptans/$C_{20+}$ sulfides composition comprises (A) one or more branched $C_{10+}$ mercaptans; and (B) one or more branched $C_{20+}$ sulfides represented by the structure $R^{10}$—S—$R^{11}$.

The $C_{10+}$ mercaptans compositions, $C_{20+}$ sulfides compositions, and $C_{10+}$ mercaptans/$C_{20+}$ sulfides compositions can be salable or otherwise used for a variety of end uses such as mining ore collector compositions and chain transfer agents.

In an aspect, the compositions disclosed herein can be prepared by a process comprising reacting, in a reactor, a sulfur source (e.g., $H_2S$) and a feedstock comprising one or more branched $C_{10+}$ monoolefins in the presence of an initiating agent to produce a branched $C_{10+}$ mercaptans crude (reaction product) composition, wherein the branched $C_{10+}$ monoolefins comprise a branched $C_{10+}$ monoolefin represented by Structure I-1, a branched $C_{10+}$ monoolefin represented by Structure J-1, a branched $C_{10+}$ monoolefin represented by Structure K-1, a branched $C_{10+}$ monoolefin represented by Structure L-1, or combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group. The $R^9$ can be a linear $C_1$ to $C_{21}$ alkyl group or a branched $C_1$ to $C_{21}$ alkyl group. As will be appreciated by one of skill in the art, and with the help of this disclosure, the $C_{10+}$ monoolefins comprising the $R^9$ alkyl group are branched monoolefins, regardless of whether $R^9$ is linear or branched, owing to a branched sub-structure that is linked to the $R^9$ alkyl group, as it can be seen in Structures I-1, J-1, K-1, and L-1.

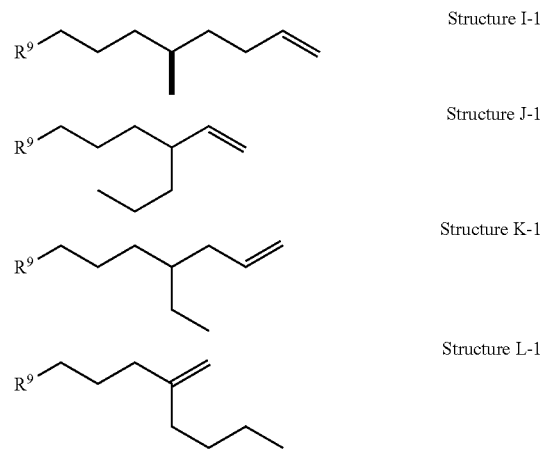

Structure I-1

Structure J-1

Structure K-1

Structure L-1

In some aspects, $R^9$ can be selected from the group consisting of a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a henicosyl group, and combinations thereof.

In aspects where $R^9$ is a methyl group, the branched $C_{10+}$ monoolefins comprise one or more branched $C_{10}$ monoolefins, as previously disclosed herein. The branched $C_{10}$ monoolefins can comprise 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof.

Any feedstock comprising one or more branched $C_{10+}$ monoolefins of the type described herein can be used, for example a feedstock obtained from a commercial petroleum refining or petrochemical process. Such feedstocks can comprise other olefins in addition to the one or more branched $C_{10+}$ monoolefins of the type described herein, for example linear $C_{10+}$ monoolefins as well as olefins having less than 10 carbon atoms.

In an aspect, the feedstock can comprise one or more branched $C_{10}$ to $C_{30}$ monoolefins. Any feedstock comprising branched $C_{10}$ to $C_{30}$ monoolefins of the type described herein can be used, for example a feedstock obtained from a commercial petroleum refining or petrochemical process.

Such feedstocks can comprise other olefins in addition to the branched $C_{10}$ to $C_{30}$ monoolefins of the type described herein, for example $C_{9-}$ monoolefins, $C_{31+}$ monoolefins, as well as linear $C_{10}$ to $C_{30}$ monoolefins.

In an aspect, the feedstock can comprise at least about 70 wt. %, alternatively at least about 75 wt. %, alternatively at least about 80 wt. %, alternatively at least about 85 wt. %, alternatively at least about 90 wt. %, or alternatively at least about 95 wt. % branched $C_{10}$ to $C_{30}$ monoolefins, based on the total weight of the feedstock. In such aspect, the feedstock can comprise (a) less than about 15 wt. %, alternatively less than about 10 wt. %, alternatively less than about 5 wt. %, or alternatively less than about 1 wt. % $C_{9-}$ monoolefins; and (b) less than about 15 wt. %, alternatively less than about 10 wt. %, alternatively less than about 5 wt. %, or alternatively less than about 1 wt. % $C_{31+}$ monoolefins; based on the total weight of the feedstock. For purposes of the disclosure herein, a feedstock comprising at least about 70 wt. % branched $C_{10}$ to $C_{30}$ monoolefins, based on the total weight of the feedstock, can also be referred to as a "first $C_{10}$ to $C_{30}$ feedstock."

In another aspect, the feedstock can comprise at least about 95 wt. %, alternatively at least about 96 wt. %, alternatively at least about 97 wt. %, alternatively at least about 98 wt. %, or alternatively at least about 99 wt. % branched $C_{10}$ to $C_{30}$ monoolefins, based on the total weight of the feedstock. For purposes of the disclosure herein, a feedstock comprising at least about 95 wt. % branched $C_{10}$ to $C_{30}$ monoolefins, based on the total weight of the feedstock, can also be referred to as a "second $C_{10}$ to $C_{30}$ feedstock." In an aspect, the second $C_{10}$ to $C_{30}$ feedstock can be produced by purifying the first $C_{10}$ to $C_{30}$ feedstock, such as for example by distillation of the first $C_{10}$ to $C_{30}$ feedstock.

In an aspect, the $C_{10}$ to $C_{30}$ monoolefins of any feedstock described herein (e.g., a first $C_{10}$ to $C_{30}$ feedstock or a second $C_{10}$ to $C_{30}$ feedstock) can comprise, can consist essentially of, or can be, a branched $C_{10+}$ monoolefin represented by Structure I-1, a branched $C_{10+}$ monoolefin represented by Structure J-1, a branched $C_{10+}$ monoolefin represented by Structure K-1, and a branched $C_{10+}$ monoolefin represented by Structure L-1; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In an aspect, the $C_{10}$ to $C_{30}$ monoolefins of any feedstock described herein (e.g., a first $C_{10}$ to $C_{30}$ feedstock or a second $C_{10}$ to $C_{30}$ feedstock) can comprise linear $C_{10}$ to $C_{30}$ monoolefins. In an aspect, the $C_{10}$ to $C_{30}$ monoolefins of any feedstock described herein can comprise less than or equal to about 26 mol %, alternatively less than or equal to about 24 mol %, alternatively less than or equal to about 22 mol %, alternatively less than or equal to about 20 mol %, or alternatively less than or equal to about 18 mol % linear $C_{10}$ to $C_{30}$ monoolefins. In some aspects, the $C_{10}$ to $C_{30}$ monoolefins of any feedstock described herein can comprise from about 0.1 mol % to about 26 mol %, alternatively from about 0.5 mol % to about 24 mol %, alternatively from about 1 mol % to about 22 mol %, alternatively from about 1.5 mol % to about 20 mol %, or alternatively from about 2.5 mol % to about 18 mol % linear $C_{10}$ to $C_{30}$ monoolefins.

In an aspect, the first $C_{10}$ to $C_{30}$ feedstock disclosed herein can further comprise $C_{9-}$ monoolefins, $C_{31+}$ monoolefins, or combinations thereof; alternatively, $C_{9-}$ monoolefins; or alternatively, $C_{31+}$ monoolefins. In an aspect, the $C_{9-}$ monoolefins can comprise, can consist essentially of, or can be, a $C_7$ monoolefin, a $C_8$ monoolefin, a $C_9$ monoolefin, or combinations thereof; alternatively, a $C_7$ monoolefin; alternatively, a $C_8$ monoolefin; or alternatively, a $C_9$ monoolefin. In some aspects, the $C_{9-}$ monoolefins can comprise, can consist essentially of, or can be, a $C_8$ monoolefin. In an aspect, the $C_{31+}$ monoolefins can comprise, can consist essentially of, or can be, a $C_{31}$ monoolefin, a $C_{32}$ monoolefin, a $C_{33}$ monoolefin, a $C_{34}$ monoolefin, a $C_{35}$ monoolefin, a $C_{36}$ monoolefin, a $C_{37}$ monoolefin, a $C_{38}$ monoolefin, or combinations thereof; alternatively, a $C_{31}$ monoolefin; alternatively, a $C_{32}$ monoolefin; alternatively, a $C_{33}$ monoolefin; alternatively, a $C_{34}$ monoolefin; alternatively, a $C_{35}$ monoolefin; alternatively, a $C_{36}$ monoolefin; alternatively, a $C_{37}$ monoolefin; or alternatively, a $C_{38}$ monoolefin. In some aspects, the $C_{31+}$ monoolefins can comprise, can consist essentially of, or can be, a $C_{32}$ monoolefin, a $C_{36}$ monoolefin, a $C_{38}$ monoolefin, or combinations thereof; alternatively, a $C_{32}$ monoolefin; alternatively, a $C_{36}$ monoolefin; or alternatively, a $C_{38}$ monoolefin.

In an aspect, the first $C_{10}$ to $C_{30}$ feedstock can further comprise from about 0.1 mol % to about 5 mol %, alternatively from about 0.25 mol % to about 4 mol %, or alternatively from about 0.5 mol % to about 3 mol % $C_8$ monoolefins. In such aspect, the $C_8$ monoolefins can comprise at least about 95 mol %, alternatively at least about 96 mol %, alternatively at least about 97 mol %, alternatively at least about 98 mol %, or alternatively at least about 99 mol % 1-octene.

In an aspect, a sulfur source (e.g., $H_2S$) and a feedstock comprising one or more branched $C_{10}$ to $C_{30}$ monoolefins can be reacted using a sulfur source to olefin molar ratio of from about 1:1 to about 20:1, alternatively from about 2:1 to about 15:1, or alternatively from about 3:1 to about 10:1; as previously described herein for the branched $C_{10}$ monoolefins.

In an aspect, a sulfur source (e.g., $H_2S$) and a feedstock comprising one or more branched $C_{10}$ to $C_{30}$ monoolefins can be reacted at a pressure of from about 30 psig (206 kPag) to about 1,500 psig (10,300 kPag), alternatively from about 100 psig (690 kPag) to about 1,250 psig (8,600 kPag), or alternatively from about 250 psig (1,700 kPag) to about 1,000 psig (6,900 kPag); as previously described herein for the branched $C_{10}$ monoolefins.

In an aspect, a sulfur source (e.g., $H_2S$) and a feedstock comprising one or more branched $C_{10}$ to $C_{30}$ monoolefins can be reacted (as previously described herein for the branched $C_{10}$ monoolefins) to produce olefin conversion of equal to or greater than about 70%, alternatively equal to or greater than about 75%, or alternatively equal to or greater than about 80%, alternatively equal to or greater than about 85%, or alternatively equal to or greater than about 90%.

In an aspect, a sulfur source (e.g., $H_2S$) and a feedstock comprising one or more branched $C_{10}$ to $C_{30}$ monoolefins can be reacted in the presence of an initiating agent to produce a branched $C_{10+}$ mercaptans crude composition; wherein the initiating agent comprises ultraviolet (UV) radiation; as previously described herein for the branched $C_{10}$ monoolefins. In such aspect, the initiating agent can further comprise a phosphite promoter, a photoinitiator, a sulfur scavenger, an antioxidant, and the like, or combinations thereof.

In an aspect, $H_2S$ and a feedstock comprising one or more branched $C_{10}$ to $C_{30}$ monoolefins can be reacted in the presence of UV radiation at a $H_2S$ to olefin molar ratio of from about 1:1 to about 15:1, alternatively from about 2:1 to about 12.5:1, or alternatively from about 5:1 to about 10:1; as previously described herein for the branched $C_{10}$ monoolefins.

In an aspect, the process can comprise reacting $H_2S$ and a feedstock comprising one or more branched $C_{10}$ to $C_{30}$ monoolefins in the presence of UV radiation to produce a branched $C_{10+}$ mercaptans crude composition (wherein the branched $C_{10+}$ mercaptans crude composition comprises from 50-100 wt. % $C_{10}$ to $C_{30}$ mercaptans, alternatively from 50-90 wt. % $C_{10}$ to $C_{30}$ mercaptans, or alternatively from 75-85 wt. % $C_{10}$ to $C_{30}$ mercaptans); wherein the $C_{10}$ to $C_{30}$ mercaptans present in the crude composition further comprise from about 70 wt. % to about 100 wt. %, alternatively from about 70 wt. % to about 95 wt. %, alternatively from about 80 wt. % to about 90 wt. %, or alternatively from about 79 wt. % to about 85 wt. % $C_{10}$ to $C_{30}$ primary mercaptans; from about 0 wt. % to about 30 wt. %, alternatively from about 0 wt. % to about 20 wt. %, alternatively from about 10 wt. % to about 20 wt. %, or alternatively from about 5 wt. % to about 19 wt. % $C_{10}$ to $C_{30}$ secondary mercaptans; and from about 0 wt. % to about 10 wt. %, alternatively from about 0 wt. % to about 5 wt. %, or alternatively from about 0 wt. % to about 3 wt. % $C_{10}$ to $C_{30}$ tertiary mercaptans. As will be appreciated by one of skill in the art, and with the help of this disclosure, the make-up of the branched $C_{10+}$ mercaptans crude composition, in terms of primary, secondary, and tertiary mercaptans, will depend on the make-up of the feedstock, as well as on the reaction conditions. Further, as will be appreciated by one of skill in the art, and with the help of this disclosure, the make-up of each of the primary, secondary, and tertiary mercaptans will depend on the make-up of the feedstock, as well as on the reaction conditions.

In an aspect, the $C_{10}$ to $C_{30}$ primary mercaptans can comprise a branched $C_{10+}$ mercaptan represented by Structure A-1, a branched $C_{10+}$ mercaptan represented by Structure B-1, a branched $C_{10+}$ mercaptan represented by Structure C-1, a branched $C_{10+}$ mercaptan represented by Structure D-1, or combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

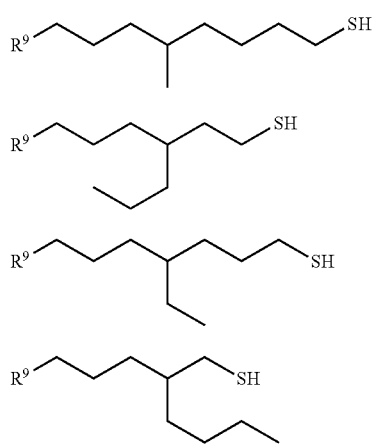

Structure A-1

Structure B-1

Structure C-1

Structure D-1

The $C_{10}$ to $C_{30}$ primary mercaptans can further comprise a linear $C_{10+}$ mercaptan represented by Structure M-1; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

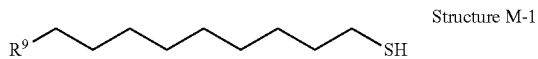

Structure M-1

In aspects where $R^9$ is a methyl group, the $C_{10}$ to $C_{30}$ primary mercaptans comprise one or more branched primary $C_{10}$ mercaptans, as previously disclosed herein. The branched primary $C_{10}$ mercaptans can comprise 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), or combinations thereof. Primary $C_{10}$ mercaptans can further comprise 1-mercapto-decane (represented by Structure M), as disclosed herein.

In an aspect, the $C_{10}$ to $C_{30}$ secondary mercaptans can comprise a branched $C_{10+}$ mercaptan represented by Structure E-1, a branched $C_{10+}$ mercaptan represented by Structure F-1, a branched $C_{10+}$ mercaptan represented by Structure G-1, or combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

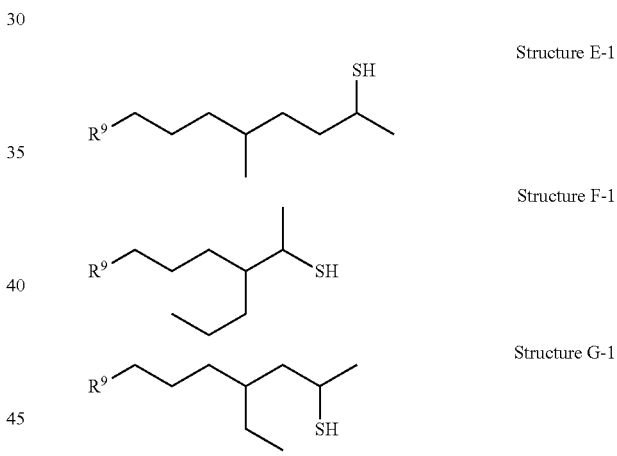

Structure E-1

Structure F-1

Structure G-1

The $C_{10}$ to $C_{30}$ secondary mercaptans can further comprise a linear $C_{10+}$ mercaptan represented by Structure N-1, a linear $C_{10+}$ mercaptan represented by Structure O-1, a linear $C_{10+}$ mercaptan represented by Structure P-1, or combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

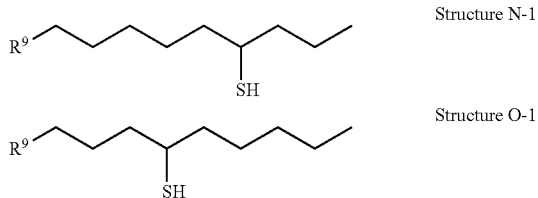

Structure N-1

Structure O-1

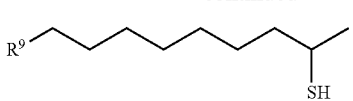
Structure P-1

In aspects where $R^9$ is a methyl group, the $C_{10}$ to $C_{30}$ secondary mercaptans comprise one or more branched secondary $C_{10}$ mercaptans, as previously disclosed herein. The branched secondary $C_{10}$ mercaptans can comprise 5-methyl-2-mercapto-nonane (represented by Structure E), 3-propyl-2-mercapto-heptane (represented by Structure F), 4-ethyl-2-mercapto-octane (represented by Structure G), or combinations thereof. Secondary $C_{10}$ mercaptans can further comprise 4-mercapto-decane (represented by Structure N), 5-mercapto-decane (represented by Structure O), 2-mercapto-decane (represented by Structure P), or combinations thereof; as disclosed herein.

In an aspect, the $C_{10}$ to $C_{30}$ tertiary mercaptans can comprise equal to or greater than about 90 wt. %, alternatively equal to or greater than about 95 wt. %, or alternatively equal to or greater than about 99 wt. % of a branched $C_{10+}$ mercaptan represented by Structure H-1; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

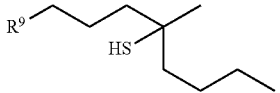
Structure H-1

In aspects where $R^9$ is a methyl group, the $C_{10}$ to $C_{30}$ tertiary mercaptans comprise one or more branched tertiary $C_{10}$ mercaptans, as previously disclosed herein. The branched tertiary $C_{10}$ mercaptans can comprise 5-methyl-5-mercapto-nonane (represented by Structure H), as disclosed herein.

In an aspect, a sulfur source (e.g., $H_2S$) and a feedstock comprising one or more branched $C_{10}$ to $C_{30}$ monoolefins can be reacted in the presence of an initiating agent to produce a branched $C_{10+}$ mercaptans crude composition; wherein the initiating agent comprises an acid catalyst; as previously described herein for the branched $C_{10}$ monoolefins.

In an aspect, $H_2S$ and a feedstock comprising one or more branched $C_{10}$ to $C_{30}$ monoolefins can be reacted in the presence of an acid catalyst at a $H_2S$ to olefin molar ratio of from about 1:1 to about 10:1, alternatively from about 2:1 to about 7.5:1, or alternatively from about 2.5:1 to about 5:1; as previously described herein for the branched $C_{10}$ monoolefins.

In an aspect, the process can comprise reacting $H_2S$ and a feedstock comprising one or more branched $C_{10}$ to $C_{30}$ monoolefins in the presence of an acid catalyst to produce a branched $C_{10+}$ mercaptans crude composition (wherein the branched $C_{10+}$ mercaptans crude composition comprises from 50-100 wt. % $C_{10}$ to $C_{30}$ mercaptans, alternatively from 50-90 wt. % $C_{10}$ to $C_{30}$ mercaptans, or alternatively from 75-85 wt. % $C_{10}$ to $C_{30}$ mercaptans); wherein the $C_{10}$ to $C_{30}$ mercaptans comprise from about 0 wt. % to about 5 wt. % alternatively from about 0.1 wt. % to about 4 wt. %, or alternatively from about 0.5 wt. % to about 2.5 wt. % $C_{10}$ to $C_{30}$ primary mercaptans; from about 80 wt. % to about 95 wt. %, alternatively from about 82.5 wt. % to about 92.5 wt. %, or alternatively from about 85 wt. % to about 90 wt. % $C_{10}$ to $C_{30}$ secondary mercaptans; and from about 5 wt. % to about 20 wt. %, alternatively from about 7.5 wt. % to about 17.5 wt. %, or alternatively from about 10 wt. % to about 15 wt. % $C_{10}$ to $C_{30}$ tertiary mercaptans.

In an aspect, a sulfur source (e.g., $H_2S$) and a feedstock comprising one or more branched $C_{10}$ to $C_{30}$ monoolefins can be reacted in the presence of an initiating agent to produce a branched $C_{10+}$ mercaptans crude composition; wherein the initiating agent comprises a hydrodesulfurization (HDS) catalyst; as previously described herein for the branched $C_{10}$ monoolefins.

In an aspect, $H_2S$ and a feedstock comprising one or more branched $C_{10}$ to $C_{30}$ monoolefins can be reacted in the presence of an HDS catalyst at a $H_2S$ to olefin molar ratio of from about 1:1 to about 10:1, alternatively from about 2:1 to about 7.5:1, or alternatively from about 2.5:1 to about 5:1; as previously described herein for the branched $C_{10}$ monoolefins.

In an aspect, the process can comprise reacting $H_2S$ and a feedstock comprising one or more branched $C_{10}$ to $C_{30}$ monoolefins in the presence of an HDS catalyst to produce a branched $C_{10+}$ mercaptans crude composition (wherein the branched $C_{10+}$ mercaptans crude composition comprises from 50-100 wt. % $C_{10}$ to $C_{30}$ mercaptans, alternatively from 50-90 wt. % $C_{10}$ to $C_{30}$ mercaptans, or alternatively from 75-85 wt. % $C_{10}$ to $C_{30}$ mercaptans); wherein the $C_{10}$ to $C_{30}$ mercaptans comprise from about 5 wt. % to about 30 wt. % alternatively from about 10 wt. % to about 25 wt. %, or alternatively from about 15 wt. % to about 20 wt. % $C_{10}$ to $C_{30}$ primary mercaptans; from about 60 wt. % to about 75 wt. %, alternatively from about 62.5 wt. % to about 72.5 wt. %, or alternatively from about 65 wt. % to about 70 wt. % $C_{10}$ to $C_{30}$ secondary mercaptans; and from about 5 wt. % to about 15 wt. %, alternatively from about 7.5 wt. % to about 13.5 wt. %, or alternatively from about 9 wt. % to about 12 wt. % $C_{10}$ to $C_{30}$ tertiary mercaptans.

As noted previously, any suitable feedstocks comprising one or more branched $C_{10}$ to $C_{30}$ monoolefins can be reacted with a sulfur source (e.g., $H_2S$) in the presence of an initiating agent to produce a branched $C_{10+}$ mercaptans crude composition, and the branched $C_{10+}$ mercaptans crude composition can be further refined (e.g., distilled or otherwise separated into one or more fractions such as lights, intermediate, and heavies) to yield various compositions described herein. As described in more detail herein, the type and/or amounts of the constituent components that form the branched $C_{10+}$ mercaptans crude composition can vary depending upon the feedstock (e.g., the amount and types of olefins therein), the reaction conditions, the catalysts employed, etc., and one skilled in the art can tailor the post reactor processing of the branched $C_{10+}$ mercaptans crude composition to account for the specific compounds present in a given branched $C_{10+}$ mercaptans crude composition to yield various desired products and compositions of the types described herein.

Upon completion of the reaction of a feedstock comprising one or more branched $C_{10}$ to $C_{30}$ monoolefins with a sulfur source (e.g., $H_2S$), a reactor effluent can be recovered from the reactor and sulfur source (e.g., $H_2S$) removed therefrom to yield a branched $C_{10+}$ mercaptans crude composition; as previously described herein for the branched $C_{10}$ monoolefins. The term "branched $C_{10+}$ mercaptans crude composition" or "branched $C_{10+}$ mercaptans crude product" refers to an unrefined effluent stream recovered from the reactor after removal of the sulfur source (e.g., $H_2S$), and in particular to a sulfur source-free effluent stream that has not undergone any additional post-reactor processing such as flashing, distillation, or other separation techniques or processes to remove any components from the effluent stream other than the initial removal of the sulfur source.

The branched $C_{10+}$ mercaptans crude composition comprises branched $C_{10}$ to $C_{30}$ mercaptans and branched $C_{20}$ to $C_{60}$ sulfides formed by the reaction of $H_2S$ and the one or more branched $C_{10}$ to $C_{30}$ monoolefins, and the structures of these branched $C_{10}$ to $C_{30}$ mercaptans and branched $C_{20}$ to $C_{60}$ sulfides are described in more detail herein. In addition to branched $C_{10}$ to $C_{30}$ mercaptans and branched $C_{20}$ to $C_{60}$ sulfides, the branched $C_{10+}$ mercaptans crude composition can comprise a number of other compounds such as unreacted olefins, inert compounds (e.g., alkanes), non-branched $C_{10}$ to $C_{30}$ mercaptans, non-branched $C_{20}$ to $C_{60}$ sulfides, non-$C_{10}$ to $C_{30}$ mercaptans (e.g., $C_{9-}$ mercaptans), non-$C_{20}$ to $C_{60}$ sulfides (e.g., $C_{19-}$ sulfides), and other impurities. The constituent components contained within the branched $C_{10+}$ mercaptans crude composition can vary depending upon the composition of the feedstock (e.g., an unpurified first $C_{10}$ to $C_{30}$ feedstock as compared to a purified second $C_{10}$ to $C_{30}$ feedstock as described herein) as well as reaction conditions, catalyst, etc. In various aspects, a branched $C_{10+}$ mercaptans crude composition can comprise light, intermediate, and heavy fractions as described herein.

In an aspect, the branched $C_{10+}$ mercaptans crude composition can contain a variety of other non-$C_{10}$ to $C_{30}$ mercaptans and non-$C_{20}$ to $C_{60}$ sulfides components (e.g., impurities) such as $C_8$ mercaptans; $C_{16}$ to $C_{19}$ sulfides represented by the structure $R^{12}$—S—$R^{13}$, wherein $R^{12}$ and $R^{13}$ are each independently a functional group derived from a $C_{8+}$ monoolefin, wherein $R^{12}$ and $R^{13}$ are not both derived from a branched $C_{10+}$ monoolefin; unreacted $C_{8+}$ monoolefins; non-olefin impurities selected from the group consisting of $C_{8-14}$ alkanes, cyclohexane, methylcyclopentane, methylcyclohexane, benzene, toluene, ethylbenzene, xylene, mesitylene, hexamethylbenzene, $C_{4-12}$ alcohols, 2-ethyl-1-hexanol, and 2-ethylhexyl-2-ethylhexanoate; and combinations thereof.

In an aspect, a process of the present disclosure can further comprise recovering a reaction product from the branched $C_{10+}$ mercaptans crude composition; wherein the reaction product can comprise branched $C_{10+}$ mercaptans and/or branched $C_{20+}$ sulfides, wherein the branched $C_{10+}$ mercaptans comprise branched $C_{10}$ to $C_{30}$ mercaptans; and wherein the branched $C_{20+}$ sulfides comprise branched $C_{20}$ to $C_{60}$ sulfides represented by the structure $R^{10}$—S—$R^{11}$, wherein $R^{10}$ and $R^{11}$ are each independently a functional group derived from an olefin, wherein the olefin comprises a branched $C_{10+}$ monoolefin as disclosed herein.

In an aspect, the reaction product can comprise a branched $C_{10+}$ mercaptans composition (intermediate fraction; first reaction product), a branched $C_{20+}$ sulfides composition (heavy fraction; second reaction product), a branched $C_{10+}$ mercaptans/branched $C_{20+}$ sulfides composition (intermediate and heavy fractions; first and second reaction products), or combinations thereof.

In an aspect, a branched $C_{10+}$ mercaptans crude composition comprising branched $C_{10+}$ mercaptans and branched $C_{20+}$ sulfides as disclosed herein can be separated into two or more fractions (e.g., light fraction, intermediate fraction, heavy fraction, etc.) by any process or unit operation known in the art. For example, a branched $C_{10+}$ mercaptans crude composition can be processed (e.g., distilled) to remove a fraction of light compounds. Alternatively, a branched $C_{10+}$ mercaptans crude composition can be processed to recover both a light fraction and an intermediate fraction (e.g., a rough cut), followed by further processing to obtain one or more fine cuts. Alternatively, a branched $C_{10+}$ mercaptans crude composition can be processed to recover a heavy fraction (e.g., a $C_{20+}$ sulfides fraction). Alternatively, a branched $C_{10+}$ mercaptans crude composition can be processed to separate out any combination of a light fraction, an intermediate fraction (e.g., comprising $C_{10+}$ mercaptans, including branched $C_{10+}$ mercaptans), and a heavy fraction (e.g., comprising $C_{20+}$ sulfides, including branched $C_{20+}$ sulfides). Furthermore, a light, intermediate or heavy fraction (e.g., a rough cut) can be further processed or parsed to obtain one or more desired fine cuts (e.g., a $C_{10}$ to $C_{30}$ mercaptan fraction). Alternatively, a branched $C_{10+}$ mercaptans crude composition can be separated to produce a high-purity $C_{10+}$ mercaptan stream and/or a high-purity $C_{20+}$ sulfide stream (e.g., to obtain a desired fine cut or fraction such as a $C_{10}$ to $C_{30}$ mercaptan fraction). Further, these separated streams can be blended in any combination of ratios to produce a mixture with specific concentrations of one of more components (e.g., desired blend ratios of branched $C_{10+}$ mercaptans and/or branched $C_{20+}$ sulfides, for example to aid in a particular end use). The unit operations/processes used for these separations are known to one of skill in the art and include, but are not limited to, distillation, fractionation, flashing, stripping, and absorption, and others. The unit operation conditions, such as for example, temperature, pressure, flow rates, and others at which these unit operations produce one or more of the desired fractions can easily be determined by one of ordinary skill in the art.

In an aspect, a light fraction is removed from the branched $C_{10+}$ mercaptans crude composition, for example by flashing, distillation, fractionation, stripping, absorption, etc.

In an aspect, the light fraction removed from the branched $C_{10+}$ mercaptans crude composition can comprise at least about 90 wt. %, alternatively at least about 92 wt. %, alternatively at least about 95 wt. %, alternatively at least about 96 wt. %, alternatively at least about 97 wt. %, alternatively at least about 98 wt. %, alternatively at least about 99 wt. % $C_{9-}$ compounds, based on the total weight of the light fraction. Nonlimiting examples of $C_{9-}$ compounds include $C_{9-}$ monoolefins (e.g., unreacted $C_{9-}$ monoolefins), $C_{9-}$ mercaptans, $C_{9-}$ alkanes, cyclohexane, methylcyclopentane, methylcyclohexane, benzene, toluene, ethylbenzene, xylene, mesitylene, $C_{9-}$ alcohols, 2-ethyl-1-hexanol, and the like, or combinations thereof. In an aspect, the light fraction removed from the branched $C_{10+}$ mercaptans crude composition can comprise less than about 10 wt. %, alternatively less than about 5 wt. %, alternatively less than about 4 wt. %, alternatively at less than about 3 wt. %, alternatively less than about 2 wt. %, alternatively less than about 1 wt. % $C_{10+}$ compounds, based on the total weight of the light fraction.

Following removal of the lights (for example, via flashing) from the branched $C_{10+}$ mercaptans crude composition, a combined intermediate and heavy fraction (i.e., $C_{10+}$ compounds sometimes referred to as a kettle product in the Examples) can remain, and the combined intermediate and heavy fraction can be used "as is" or can be further processed, for example separated or split into separate intermediate and heavy fractions (and said separate intermediate and heavy fractions can be subsequently recombined in various blends and associated blend ratios), as described in more detail herein. In an aspect, a combined intermediate and heavy fraction (i.e., $C_{10+}$ compounds) formed by removal of the light fraction from the branched $C_{10+}$ mercaptans crude composition can comprise less than about 15 wt. %, alternatively less than about 10 wt. %, alternatively less than about 9 wt. %, alternatively less than about 8 wt. %, alternatively less than about 7 wt. %, alternatively less than about 6 wt. %, alternatively less than about 5 wt. %, alternatively less than about 4 wt. %, alternatively less than about 3 wt. %, alternatively less than about 2 wt. %, or alternatively less than about 1 wt. % $C_{9-}$ products, based on the total weight of the combined intermediate and heavy fraction (i.e., $C_{10+}$ compounds).

In an aspect, a combined intermediate and heavy fraction (i.e., $C_{10+}$ compounds) recovered from the branched $C_{10+}$ mercaptans crude composition can comprise (A) at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % mercaptans, based on the total weight of the combined fraction; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the mercaptans can be branched $C_{10}$ to $C_{30}$ mercaptans selected from the group consisting of a branched $C_{10}$ to $C_{30}$ mercaptan represented by Structure A-1, a branched $C_{10}$ to $C_{30}$ mercaptan represented by Structure B-1, a branched $C_{10}$ to $C_{30}$ mercaptan represented by Structure C-1, a branched $C_{10}$ to $C_{30}$ mercaptan represented by Structure D-1, a branched $C_{10}$ to $C_{30}$ mercaptan represented by Structure E-1, a branched $C_{10}$ to $C_{30}$ mercaptan represented by Structure F-1, a branched $C_{10}$ to $C_{30}$ mercaptan represented by Structure G-1, a branched $C_{10}$ to $C_{30}$ mercaptan represented by Structure H-1, and combinations thereof; and (B) at least about 10 wt. %, alternatively at least about 15 wt. %, alternatively at least about 20 wt. %, alternatively at least about 25 wt. % sulfides, or alternatively at least about 30 wt. % sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the sulfides can be branched $C_{20}$ to $C_{60}$ sulfides represented by structure $R^{10}$—S—$R^{11}$, wherein both $R^{10}$ and $R^{11}$ can each independently be a functional group derived from an olefin, wherein the olefin comprises a branched $C_{10}$ to $C_{30}$ monoolefin represented by Structure I-1, a branched $C_{10}$ to $C_{30}$ monoolefin represented by Structure J-1, a branched $C_{10}$ to $C_{30}$ monoolefin represented by Structure K-1, a branched $C_{10}$ to $C_{30}$ monoolefin represented by Structure L-1, or combinations thereof; and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In an aspect, the branched $C_{10+}$ mercaptans crude composition can be flashed to remove a light fraction as described herein to produce a combined intermediate and heavy fraction (i.e., $C_{10+}$ compounds) comprising: (A) at least about 25, 30, 35, 40, 45, 50, 55, 60, 65, 70, 75, 80, or 85 wt. % $C_{10+}$ branched mercaptans selected from the group consisting of a branched $C_{10}$ to $C_{30}$ mercaptan represented by Structure A-1, a branched $C_{10}$ to $C_{30}$ mercaptan represented by Structure B-1, a branched $C_{10}$ to $C_{30}$ mercaptan represented by Structure C-1, a branched $C_{10}$ to $C_{30}$ mercaptan represented by Structure D-1, a branched $C_{10}$ to $C_{30}$ mercaptan represented by Structure E-1, a branched $C_{10}$ to $C_{30}$ mercaptan represented by Structure F-1, a branched $C_{10}$ to $C_{30}$ mercaptan represented by Structure G-1, a branched $C_{10}$ to $C_{30}$ mercaptan represented by Structure H-1, and combinations thereof; and (B) at least about 5 wt. %, alternatively at least about 10 wt. %, alternatively at least about 15 wt. %, alternatively at least about 20 wt. %, alternatively at least about 25 wt. %, or alternatively at least about 30 wt. % branched $C_{20}$ to $C_{60}$ sulfides represented by structure $R^{10}$—S—$R^{11}$, wherein both $R^{10}$ and $R^{11}$ can each independently be a functional group derived from an olefin, wherein the olefin comprises a branched $C_{10}$ to $C_{30}$ monoolefin represented by Structure I-1, a branched $C_{10}$ to $C_{30}$ monoolefin represented by Structure J-1, a branched $C_{10}$ to $C_{30}$ monoolefin represented by Structure K-1, a branched $C_{10}$ to $C_{30}$ monoolefin represented by Structure L-1, or combinations thereof; and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In an aspect, the branched $C_{10+}$ mercaptans crude composition can be flashed to remove a lights fraction as described herein to produce a combined intermediate and heavy fraction (i.e., $C_{10+}$ compounds) comprising: (A) from at least about 50 wt. % to at least about 90 wt. %, alternatively from at least about 55 wt. % to at least about 85 wt. %, or alternatively from at least about 60 wt. % to at least about 80 wt. % mercaptans, wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the mercaptans can be branched $C_{10}$ to $C_{30}$ mercaptans selected from the group consisting of a branched $C_{10}$ to $C_{30}$ mercaptan represented by Structure A-1, a branched $C_{10}$ to $C_{30}$ mercaptan represented by Structure B-1, a branched $C_{10}$ to $C_{30}$ mercaptan represented by Structure C-1, a branched $C_{10}$ to $C_{30}$ mercaptan represented by Structure D-1, a branched $C_{10}$ to $C_{30}$ mercaptan represented by Structure E-1, a branched $C_{10}$ to $C_{30}$ mercaptan represented by Structure F-1, a branched $C_{10}$ to $C_{30}$ mercaptan represented by Structure G-1, a branched $C_{10}$ to $C_{30}$ mercaptan represented by Structure H-1, and combinations thereof; and (B) from at least about 10 wt. % to at least about 30 wt. %, alternatively from at least about 10 wt. % to at least about 25 wt. %, alternatively from at least about 12.5 wt. % to at least about 22.5 wt. %, or alternatively from at least about 15 wt. % to at least about 20 wt. % sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the sulfides can be branched $C_{20}$ to $C_{60}$ sulfides represented by structure $R^{10}$—S—$R^{11}$, wherein both $R^{10}$ and $R^{11}$ can each independently be a functional group derived from an olefin, wherein the olefin comprises a branched $C_{10}$ to $C_{30}$ monoolefin represented by Structure I-1, a branched $C_{10}$ to $C_{30}$ monoolefin represented by Structure J-1, a branched $C_{10}$ to $C_{30}$ monoolefin represented by Structure K-1, a branched $C_{10}$ to $C_{30}$ monoolefin represented by Structure L-1, or combinations thereof; and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In an aspect, the branched $C_{10+}$ mercaptans crude composition can be flashed to remove a light fraction and subsequently further separated to produce an intermediate fraction and a heavy fraction (i.e., $C_{10+}$ compounds). The intermediate fraction and the heavy fractions recovered from the branched $C_{10+}$ mercaptans crude composition can then be optionally further processed (e.g., polished) and mixed in any appropriate ratio to produce blended compositions, as previously described herein for crude compositions derived from branched $C_{10}$ monoolefins.

In an aspect, an intermediate fraction recovered from the branched $C_{10+}$ mercaptans crude composition can comprise at least about 25 wt. %, alternatively at least about 30 wt. %, alternatively at least about 40 wt. %, alternatively at least about 50 wt. %, alternatively at least about 75 wt. %, or alternatively at least about 85 wt. % $C_{10+}$ mercaptans, based on the total weight of the intermediate fraction, wherein the $C_{10+}$ mercaptans are branched $C_{10}$ to $C_{30}$ mercaptans as disclosed herein.

In an aspect, the heavy fraction recovered from the branched $C_{10+}$ mercaptans crude composition can comprise at least about 5, 10, 15, 20, 25, 30, 35, 40, 45, 50, 55, 60, 65, 70, 75, 80, or 85 wt. %, $C_{20+}$ sulfides, based on the total weight of the heavy fraction, wherein the $C_{20+}$ sulfides are branched $C_{20}$ to $C_{60}$ sulfides as disclosed herein.

In an aspect, the branched $C_{10+}$ mercaptans crude composition can be separated into light, intermediate, and heavy fractions by distillation, for example in a single distillation column having a light fraction recovered as an overhead stream, an intermediate fraction (e.g., comprising $C_{10+}$ compounds, including branched $C_{10+}$ mercaptans) recovered as a side stream, and a heavy fraction (e.g., comprising $C_{20+}$ compounds, including branched $C_{20+}$ sulfides) recovered as a bottom stream. In alternative aspects, the separation can be in sequential steps such as removal of the lights fraction in a first distillation column, followed by separation of the intermediate fraction (e.g., comprising $C_{10+}$ compounds, including branched $C_{10+}$ mercaptans) as an overhead stream in a second distillation column and the heavy fraction (e.g., comprising $C_{20+}$ compounds, including branched $C_{20+}$ sulfides) as a bottom stream of the second distillation column. These "rough-cut" light, intermediate, and heavy streams can be used "as is" or they can be further processed (e.g., further refined or polished, for example by additional distillation or other separation techniques to produce "fine-cuts") and/or blended to obtain a variety of products that are salable or otherwise available for a variety of end uses such as mining ore collector compositions or chain transfer agents. For example, a variety of $C_{10+}$ mercaptans compositions, $C_{20+}$ sulfides compositions, and mixed $C_{10+}$ mercaptans/$C_{20+}$ sulfides compositions can be produced of the type disclosed in more detail herein.

In aspects where the olefin feedstock (e.g., olefin feedstock reacted with a sulfur source (e.g., $H_2S$) in the presence of an initiating agent to produce the branched $C_{10+}$ mercaptans crude composition) comprises $C_{10}$ to $C_{19}$ monoolefins, the intermediate fraction comprises $C_{10}$ to $C_{19}$ mercaptans, and the heavy fraction comprises $C_{20}$ to $C_{38}$ sulfides.

In aspects where the olefin feedstock (e.g., olefin feedstock reacted with a sulfur source (e.g., $H_2S$) in the presence of an initiating agent to produce the branched $C_{10+}$ mercaptans crude composition) comprises $C_{20}$ to $C_{30}$ monoolefins, the intermediate fraction comprises $C_{20}$ to $C_{30}$ mercaptans, and the heavy fraction comprises $C_{40}$ to $C_{60}$ sulfides.

In aspects where the olefin feedstock (e.g., olefin feedstock reacted with a sulfur source (e.g., $H_2S$) in the presence of an initiating agent to produce the branched $C_{10+}$ mercaptans crude composition) comprises $C_{10}$ to $C_{30}$ monoolefins, the intermediate and heavy fractions recovered by distillation can comprise mercaptans and sulfides as follows. In some aspects, the intermediate fraction can comprise $C_{10}$ to $C_{19}$ mercaptans, and the heavy fraction can comprise $C_{20}$ to $C_{30}$ mercaptans and $C_{20}$ to $C_{60}$ sulfides. In other aspects, intermediate fraction can comprise $C_{10}$ to $C_{30}$ mercaptans and $C_{20}$ to $C_{30}$ sulfides, and the heavy fraction can comprise $C_{31}$ to $C_{60}$ sulfides. In yet other aspects, a first intermediate fraction can comprise $C_{10}$ to $C_{19}$ mercaptans, a second intermediate fraction can comprise $C_{20}$ to $C_{30}$ mercaptans and $C_{20}$ to $C_{30}$ sulfides, and the heavy fraction can comprise $C_{31}$ to $C_{60}$ sulfides. Intermediate and heavy fractions comprising both mercaptans and sulfides could be used as recovered (e.g., mixed mercaptans/sulfides compositions), or can be further processed to separate and recover further mercaptan compositions and sulfide compositions.

In an aspect, an intermediate fraction can comprise at least about 25 wt. %, alternatively at least about 30 wt. %, alternatively at least about 40 wt. %, alternatively at least about 50 wt. %, alternatively at least about 75 wt. %, or alternatively at least about 85 wt. % branched $C_{10}$, mercaptans. In such aspect, the branched $C_{10}$, mercaptans can be selected from the group consisting of a branched $C_{10}$ to $C_{30}$ mercaptan represented by Structure A-1, a branched $C_{10}$ to $C_{30}$ mercaptan represented by Structure B-1, a branched $C_{10}$ to $C_{30}$ mercaptan represented by Structure C-1, a branched $C_{10}$ to $C_{30}$ mercaptan represented by Structure D-1, a branched $C_{10}$ to $C_{30}$ mercaptan represented by Structure E-1, a branched $C_{10}$ to $C_{30}$ mercaptan represented by Structure F-1, a branched $C_{10}$ to $C_{30}$ mercaptan represented by Structure G-1, a branched $C_{10}$ to $C_{30}$ mercaptan represented by Structure H-1, and combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In an aspect, the heavy fraction can comprise at least about 5, 10, 15, 20, 25, 30, 35, 40, 45, 50, 55, 60, 65, 70, 75, 80, or 85 wt. % branched $C_{20+}$ sulfides represented by structure $R^{10}$—S—$R^{11}$, wherein both $R^{10}$ and $R^{11}$ can each independently be a branched $C_{10}$ to $C_{30}$ alkyl group derived from a branched $C_{10}$ to $C_{30}$ monoolefin, and wherein the branched $C_{10}$ to $C_{30}$ alkyl group is selected from the group consisting of

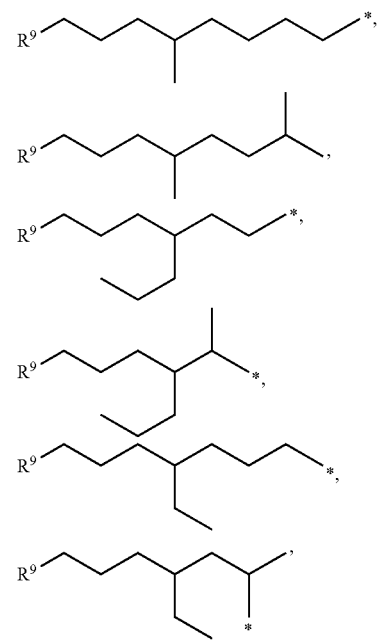

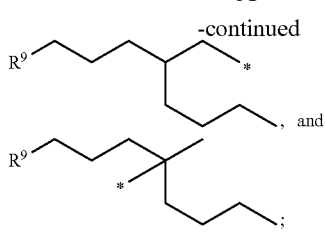

wherein * designates the attachment point to the S atom of the branched $C_{20+}$ sulfide; and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In an aspect, a $C_{10+}$ mercaptans composition can comprise $C_{10+}$ mercaptans, wherein at least a portion of the $C_{10+}$ mercaptans comprise branched $C_{10}$ to $C_{30}$ mercaptans. In an aspect, the branched $C_{10}$ to $C_{30}$ mercaptans can comprise a branched $C_{10}$ to $C_{30}$ mercaptan represented by Structure A-1, a branched $C_{10}$ to $C_{30}$ mercaptan represented by Structure B-1, a branched $C_{10}$ to $C_{30}$ mercaptan represented by Structure C-1, a branched $C_{10}$ to $C_{30}$ mercaptan represented by Structure D-1, a branched $C_{10}$ to $C_{30}$ mercaptan represented by Structure E-1, a branched $C_{10}$ to $C_{30}$ mercaptan represented by Structure F-1, a branched $C_{10}$ to $C_{30}$ mercaptan represented by Structure G-1, a branched $C_{10}$ to $C_{30}$ mercaptan represented by Structure H-1, or combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group. For purposes of the disclosure herein, branched $C_{10+}$ mercaptans refer to mercaptans (or thiols) that are characterized by the general formula $R^{14}$—SH, wherein $R^{14}$ is a branched alkyl group (as opposed to a linear alkyl group), i.e., an alkyl group substituted with alkyl substituents; and wherein $R^{14}$ has from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. Further, for purposes of the disclosure herein, a composition comprising mercaptans, wherein at least a portion of the mercaptans are branched $C_{10+}$ mercaptans (e.g., branched $C_{10}$ to $C_{30}$ mercaptans as disclosed herein), can also be referred to as a "branched $C_{10+}$ mercaptans composition." In an aspect, the $C_{10+}$ mercaptans composition can comprise any suitable amount of branched $C_{10}$ to $C_{30}$ mercaptans.

In an aspect, the $C_{10+}$ mercaptans can further comprise non-branched $C_{10+}$ mercaptans, such as for example a linear $C_{10}$ to $C_{30}$ mercaptan represented by Structure M-1, a linear $C_{10}$ to $C_{30}$ mercaptan represented by Structure N-1, a linear $C_{10}$ to $C_{30}$ mercaptan represented by Structure O-1, a linear $C_{10}$ to $C_{30}$ mercaptan represented by Structure P-1, or combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In aspects where $R^9$ is a methyl group, the $C_{10+}$ mercaptans can further comprise non-branched $C_{10}$ mercaptans, as previously disclosed herein. The non-branched $C_{10}$ mercaptans can comprise 1-mercapto-decane (represented by Structure M), 4-mercapto-decane (represented by Structure N), 5-mercapto-decane (represented by Structure O), 2-mercapto-decane (represented by Structure P), or combinations thereof.

In some aspects, a $C_{10+}$ mercaptans composition can comprise at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % $C_{10+}$ mercaptans, based on the total weight of the $C_{10+}$ mercaptans composition; wherein at least about 50 wt. %, alternatively at least about 60 wt. %, alternatively at least about 70 wt. %, alternatively at least about 75 wt. %, alternatively at least about 80 wt. %, or alternatively at least 85 wt. % of the $C_{10+}$ mercaptans can be branched $C_{10}$ to $C_{30}$ mercaptans characterized by the general formula $R^{14}$—SH, wherein $R^{14}$ is a branched alkyl group; and wherein $R^{14}$ has from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspects, the branched $C_{10}$ to $C_{30}$ mercaptans characterized by the general formula $R^{14}$—SH can be selected from the group consisting of a branched $C_{10}$ to $C_{30}$ mercaptan represented by Structure A-1, a branched $C_{10}$ to $C_{30}$ mercaptan represented by Structure B-1, a branched $C_{10}$ to $C_{30}$ mercaptan represented by Structure C-1, a branched $C_{10}$ to $C_{30}$ mercaptan represented by Structure D-1, a branched $C_{10}$ to $C_{30}$ mercaptan represented by Structure E-1, a branched $C_{10}$ to $C_{30}$ mercaptan represented by Structure F-1, a branched $C_{10}$ to $C_{30}$ mercaptan represented by Structure G-1, a branched $C_{10}$ to $C_{30}$ mercaptan represented by Structure H-1, and combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In other aspects, a $C_{10+}$ mercaptans composition can comprise at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % mercaptans, wherein at least a portion of the mercaptans can be branched $C_{10}$ to $C_{30}$ mercaptans characterized by the general formula $R^{14}$—SH, wherein $R^{14}$ is a branched alkyl group; and wherein $R^{14}$ has from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspects, the branched $C_{10}$ to $C_{30}$ mercaptans characterized by the general formula $R^{14}$—SH can be selected from the group consisting of a branched $C_{10}$ to $C_{30}$ mercaptan represented by Structure A-1, a branched $C_{10}$ to $C_{30}$ mercaptan represented by Structure B-1, a branched $C_{10}$ to $C_{30}$ mercaptan represented by Structure C-1, a branched $C_{10}$ to $C_{30}$ mercaptan represented by Structure D-1, a branched $C_{10}$ to $C_{30}$ mercaptan represented by Structure E-1, a branched $C_{10}$ to $C_{30}$ mercaptan represented by Structure F-1, a branched $C_{10}$ to $C_{30}$ mercaptan represented by Structure G-1, a branched $C_{10}$ to $C_{30}$ mercaptan represented by Structure H-1, and combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In yet other aspects, a $C_{10+}$ mercaptans composition can comprise at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % mercaptans; wherein at least about 50 wt. %, alternatively at least about 60 wt. %, alternatively at least about 70 wt. %, alternatively at least about 75 wt. %, alternatively at least about 80 wt. %, or alternatively at least 85 wt. % of the mercaptans can be branched $C_{10}$ to $C_{30}$ mercaptans characterized by the general formula $R^{14}$—SH, wherein $R^{14}$ is a branched alkyl group; and wherein $R^{14}$ has from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspects, the branched $C_{10}$ to $C_{30}$ mercaptans characterized by the general formula $R^{14}$—SH can be selected from the group consisting of a branched $C_{10}$ to $C_{30}$ mercaptan represented by Structure A-1, a branched $C_{10}$ to $C_{30}$ mercaptan represented by Structure B-1, a branched $C_{10}$ to $C_{30}$ mercaptan represented by Structure C-1, a branched $C_{10}$ to $C_{30}$ mercaptan represented by Structure D-1, a branched $C_{10}$ to $C_{30}$ mercaptan represented by Structure E-1, a branched $C_{10}$ to $C_{30}$ mercaptan represented by Structure F-1, a branched $C_{10}$ to $C_{30}$ mercaptan represented by Structure G-1, a branched $C_{10}$ to $C_{30}$ mercaptan represented by Structure H-1, and combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In still yet other aspects, a $C_{10+}$ mercaptans composition can comprise at least about 50, 55, 60, 65, 70, 75, 80, 85, 90, 95, or 99 wt. % mercaptans; wherein at least about 25, 30, 35, 40, 45, 50, 55, 60, 65, 70, 75, 80, 85, 90, 95, or 99 wt. % of the mercaptans can be branched $C_{10}$ to $C_{30}$ mercaptans characterized by the general formula $R^{14}$—SH, wherein $R^{14}$ is a branched alkyl group; and wherein $R^{14}$ has from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspects, the branched $C_{10}$ to $C_{30}$ mercaptans characterized by the general formula $R^{14}$—SH can be selected from the group consisting of a branched $C_{10}$ to $C_{30}$ mercaptan represented by Structure A-1, a branched $C_{10}$ to $C_{30}$ mercaptan represented by Structure B-1, a branched $C_{10}$ to $C_{30}$ mercaptan represented by Structure C-1, a branched $C_{10}$ to $C_{30}$ mercaptan represented by Structure D-1, a branched $C_{10}$ to $C_{30}$ mercaptan represented by Structure E-1, a branched $C_{10}$ to $C_{30}$ mercaptan represented by Structure F-1, a branched $C_{10}$ to $C_{30}$ mercaptan represented by Structure G-1, a branched $C_{10}$ to $C_{30}$ mercaptan represented by Structure H-1, and combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In still yet other aspects, a $C_{10+}$ mercaptans composition can comprise from at least about 50 wt. % to at least about 90 wt. %, alternatively from at least about 55 wt. % to at least about 85 wt. %, or alternatively from at least about 60 wt. % to at least about 80 wt. % mercaptans, wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the mercaptans can be branched $C_{10}$ to $C_{30}$ mercaptans characterized by the general formula $R^{14}$—SH, wherein $R^{14}$ is a branched alkyl group; and wherein $R^{14}$ has from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspects, the branched $C_{10}$ to $C_{30}$ mercaptans characterized by the general formula $R^{14}$—SH can be selected from the group consisting of a branched $C_{10}$ to $C_{30}$ mercaptan represented by Structure A-1, a branched $C_{10}$ to $C_{30}$ mercaptan represented by Structure B-1, a branched $C_{10}$ to $C_{30}$ mercaptan represented by Structure C-1, a branched $C_{10}$ to $C_{30}$ mercaptan represented by Structure D-1, a branched $C_{10}$ to $C_{30}$ mercaptan represented by Structure E-1, a branched $C_{10}$ to $C_{30}$ mercaptan represented by Structure F-1, a branched $C_{10}$ to $C_{30}$ mercaptan represented by Structure G-1, a branched $C_{10}$ to $C_{30}$ mercaptan represented by Structure H-1, and combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In still yet other aspects, a $C_{10+}$ mercaptans composition can consist of or consist essentially of branched $C_{10}$ to $C_{30}$ mercaptans characterized by the general formula $R^{14}$—SH, wherein $R^{14}$ is a branched alkyl group; and wherein $R^{14}$ has from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspects, the branched $C_{10}$ to $C_{30}$ mercaptans characterized by the general formula $R^{14}$—SH can be selected from the group consisting of a branched $C_{10}$ to $C_{30}$ mercaptan represented by Structure A-1, a branched $C_{10}$ to $C_{30}$ mercaptan represented by Structure B-1, a branched $C_{10}$ to $C_{30}$ mercaptan represented by Structure C-1, a branched $C_{10}$ to $C_{30}$ mercaptan represented by Structure D-1, a branched $C_{10}$ to $C_{30}$ mercaptan represented by Structure E-1, a branched $C_{10}$ to $C_{30}$ mercaptan represented by Structure F-1, a branched $C_{10}$ to $C_{30}$ mercaptan represented by Structure G-1, a branched $C_{10}$ to $C_{30}$ mercaptan represented by Structure H-1, and combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In still yet other aspects, a $C_{10+}$ mercaptans composition can comprise at least about 1, 5, 10, 15, 20, 25, 30, 35, 40, 45, 50, 55, 60, 65, 70, 75, 80, 85, 90, 95, or 99 wt. % branched $C_{10}$ to $C_{30}$ mercaptans characterized by the general formula $R^{14}$—SH, wherein $R^{14}$ is a branched alkyl group; and wherein $R^{14}$ has from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspects, the branched $C_{10}$ to $C_{30}$ mercaptans characterized by the general formula $R^{14}$—SH can be selected from the group consisting of a branched $C_{10}$ to $C_{30}$ mercaptan represented by Structure A-1, a branched $C_{10}$ to $C_{30}$ mercaptan represented by Structure B-1, a branched $C_{10}$ to $C_{30}$ mercaptan represented by Structure C-1, a branched $C_{10}$ to $C_{30}$ mercaptan represented by Structure D-1, a branched $C_{10}$ to $C_{30}$ mercaptan represented by Structure E-1, a branched $C_{10}$ to $C_{30}$ mercaptan represented by Structure F-1, a branched $C_{10}$ to $C_{30}$ mercaptan represented by Structure G-1, a branched $C_{10}$ to $C_{30}$ mercaptan represented by Structure H-1, and combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In still yet other aspects, a $C_{10+}$ mercaptans composition can comprise mercaptans, wherein at least about 50, 55, 60, 65, 70, 75, 80, 85, 90, 95, or 99 wt. % of the mercaptans are branched $C_{10}$ to $C_{30}$ mercaptans characterized by the general formula $R^{14}$—SH, wherein $R^{14}$ is a branched alkyl group; and wherein $R^{14}$ has from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspects, the branched $C_{10}$ to $C_{30}$ mercaptans characterized by the general formula $R^{14}$—SH can be selected from the group consisting of a branched $C_{10}$ to $C_{30}$ mercaptan represented by Structure A-1, a branched $C_{10}$ to $C_{30}$ mercaptan represented by Structure B-1, a branched $C_{10}$ to $C_{30}$ mercaptan represented by Structure C-1, a branched $C_{10}$ to $C_{30}$ mercaptan represented by Structure D-1, a branched $C_{10}$ to $C_{30}$ mercaptan represented by Structure E-1, a branched $C_{10}$ to $C_{30}$ mercaptan represented by Structure F-1, a branched $C_{10}$ to $C_{30}$ mercaptan represented by Structure G-1, a branched $C_{10}$ to $C_{30}$ mercaptan represented by Structure H-1, and combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In an aspect, a $C_{20+}$ sulfides composition can comprise sulfides, wherein at least a portion of the sulfides comprise $C_{20+}$ sulfides, and wherein at least a portion of the $C_{20+}$ sulfides comprise branched $C_{20}$ to $C_{60}$ sulfides represented by structure $R^{10}$—S—$R^{11}$, wherein both $R^{10}$ and $R^{11}$ can each independently be an alkyl group, and wherein at least a portion of the alkyl groups comprises a branched $C_{10}$ to $C_{30}$ alkyl group, alternatively a branched $C_{11}$ to $C_{30}$ alkyl group, alternatively a branched $C_{12}$ to $C_{30}$ alkyl group, alternatively a branched $C_{14}$ to $C_{30}$ alkyl group, alternatively a branched $C_{16}$ to $C_{28}$ alkyl group, or alternatively a branched $C_{18}$ to $C_{26}$ alkyl group. In such aspect, the alkyl group (e.g., a branched $C_{10}$ to $C_{30}$ alkyl group as $R^{10}$, $R^{11}$) can comprise a functional group derived from an olefin, wherein the olefin comprises a branched $C_{10}$ to $C_{30}$ monoolefin represented by Structure I-1, a branched $C_{10}$ to $C_{30}$ monoolefin represented by Structure J-1, a branched $C_{10}$ to $C_{30}$ monoolefin represented by Structure K-1, a branched $C_{10}$ to $C_{30}$ monoolefin represented by Structure L-1, or combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group. As previously disclosed herein, for purposes of the disclosure herein a sulfide (e.g., a branched $C_{20}$ to $C_{60}$ sulfide) will be referred to by the total number of carbon atoms (as opposed to the number of carbons of only one of the alkyl groups present in a dialkyl sulfide). For example, a $H_{21}C_{10}$—S—$C_{10}H_{21}$ sulfide will be referred to as a $C_{20}$ sulfide (rather than a $C_{10}$ sulfide); a $H_{25}C_{12}$—S—$C_{14}H_{29}$ sulfide will be referred to as a $C_{26}$ sulfide (rather than a $C_{12}$ sulfide or a $C_{14}$ sulfide); a $H_{45}C_{22}$—S—$C_{22}H_{45}$ sulfide will be referred to as a $C_{44}$ sulfide (rather than a $C_{22}$ sulfide); etc. For purposes of the disclosure herein, branched $C_{20}$ to $C_{60}$ sulfides refer to sulfides (or thioethers) that are characterized by the general formula $R^{10}$—S—$R^{11}$, wherein both $R^{10}$ and $R^{11}$ are each independently a branched $C_{10}$ to $C_{30}$ alkyl group, alternatively a branched $C_{11}$ to $C_{30}$ alkyl group, alternatively a branched $C_{12}$ to $C_{30}$ alkyl group, alternatively a branched $C_{14}$ to $C_{30}$ alkyl group, alternatively a branched $C_{16}$ to $C_{28}$ alkyl group, or alternatively a branched $C_{18}$ to $C_{26}$ alkyl group (as opposed to a linear alkyl group), i.e., an alkyl group substituted with alkyl substituents. Stated alternatively, branched $C_{20}$ to $C_{60}$ sulfides refer to sulfides wherein both $R^{10}$ and $R^{11}$ are branched $C_{10}$ to $C_{30}$ alkyl groups, wherein $R^{10}$ and $R^{11}$ can be the same or different. Further, for purposes of the disclosure herein, a composition comprising sulfides, wherein at least a portion of the sulfides are branched $C_{20}$ to $C_{60}$ sulfides represented by structure $R^{10}$—S—$R^{11}$, wherein both $R^{10}$ and $R^{11}$ are each independently an alkyl group, wherein the alkyl group comprises a branched $C_{10}$ to $C_{30}$ alkyl group (e.g., a functional group derived from an olefin, and wherein the olefin comprises a branched $C_{10}$ to $C_{30}$ monoolefin as disclosed herein), can also be referred to as a "branched $C_{20+}$ sulfides composition." In an aspect, the $C_{20+}$ sulfides composition can comprise any suitable amount of branched $C_{20}$ to $C_{60}$ sulfides.

In an aspect, a $C_{20+}$ sulfides composition can comprise sulfides, wherein at least a portion of the sulfides comprise $C_{20+}$ sulfides, and wherein at least a portion of the $C_{20+}$ sulfides comprise branched $C_{20}$ to $C_{60}$ sulfides represented by structure $R^{10}$—S—$R^{11}$, wherein both $R^{10}$ and $R^{11}$ can each independently be a branched $C_{10}$ to $C_{30}$ alkyl group derived from a branched $C_{10}$ to $C_{30}$ monoolefin, and wherein the branched $C_{10}$ to $C_{30}$ alkyl group is selected from the group consisting of

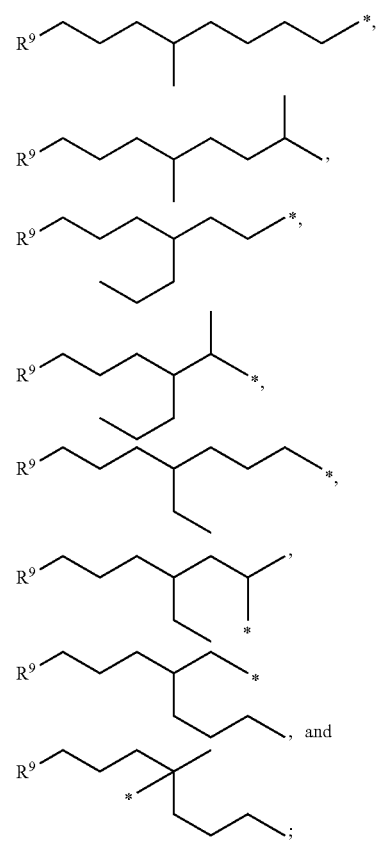

wherein * designates the attachment point to the S atom of the branched $C_{20}$ to $C_{60}$ sulfide; and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group. In an aspect, the branched $C_{10}$ to $C_{30}$ monoolefin can comprise a branched $C_{10}$ to $C_{30}$ monoolefin represented by Structure I-1, a branched $C_{10}$ to $C_{30}$ monoolefin represented by Structure J-1, a branched $C_{10}$ to $C_{30}$ monoolefin represented by Structure K-1, a branched $C_{10}$ to $C_{30}$ monoolefin represented by Structure L-1, or combinations thereof.

In an aspect, the $C_{20}$ to $C_{60}$ sulfides can further comprise non-branched $C_{20}$ to $C_{60}$ sulfides and/or partially branched $C_{20}$ to $C_{60}$ sulfides represented by structure $R^{10}$—S—$R^{11}$, wherein both $R^{10}$ and $R^{11}$ (in the case of non-branched $C_{20}$ to $C_{60}$ sulfides) or one of the $R^{10}$ and $R^{11}$ (in the case of partially-branched $C_{20}$ to $C_{60}$ sulfides) can be a linear $C_{10}$ to $C_{30}$ alkyl group derived from a linear $C_{10}$ to $C_{30}$ monoolefin, such as for example a linear $C_{10}$ to $C_{30}$ monoolefin represented by Structure Q-1, a linear $C_{10}$ to $C_{30}$ monoolefin represented by Structure R-1, a linear $C_{10}$ to $C_{30}$ monoolefin represented by Structure S-1, or combinations thereof; wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

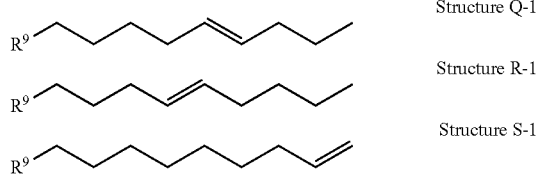

Structure Q-1

Structure R-1

Structure S-1

For purposes of the disclosure herein, the non-branched $C_{20}$ to $C_{60}$ sulfides represented by structure $R^{10}$—S—$R^{11}$ are the sulfides wherein both $R^{10}$ and $R^{11}$ are each independently a linear $C_{10}$ to $C_{30}$ alkyl group derived from a linear $C_{10}$ to $C_{30}$ monoolefin. Further, for purposes of the disclosure herein, the partially branched $C_{20}$ to $C_{60}$ sulfides represented by structure $R^{10}$—S—$R^{11}$ are the sulfides wherein one of the $R^{10}$ and $R^{11}$ is a linear $C_{10}$ to $C_{30}$ alkyl group derived from a linear $C_{10}$ to $C_{30}$ monoolefin, while the other one of the $R^{10}$ and $R^{11}$ is a branched $C_{10}$ to $C_{30}$ alkyl group derived from a branched $C_{10}$ to $C_{30}$ monoolefin as described herein.

In aspects where $R^9$ is a methyl group, the linear $C_{10}$ to $C_{30}$ monoolefin can further comprise linear $C_{10}$ monoolefins, as previously disclosed herein. The linear $C_{10}$ monoolefins can comprise 4-decene (represented by Structure Q), 5-decene (represented by Structure R), 1-decene (represented by Structure S), or combinations thereof.

In some aspects, a $C_{20+}$ sulfides composition can comprise sulfides, wherein at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % of the sulfides can be branched $C_{20}$ to $C_{60}$ sulfides represented by structure $R^{10}$—S—$R^{11}$, wherein both $R^{10}$ and $R^{11}$ can each independently be a functional group derived from an olefin, and wherein the olefin comprises a branched $C_{10}$ to $C_{30}$ monoolefin, alternatively a branched $C_{11}$ to $C_{30}$ monoolefin, alternatively a branched $C_{12}$ to $C_{30}$ monoolefin, alternatively a branched $C_{14}$ to $C_{30}$ monoolefin, alternatively a branched $C_{16}$ to $C_{28}$ monoolefin, or alternatively a branched $C_{18}$ to $C_{26}$ monoolefin. In such aspects, the olefin can comprise a branched $C_{10}$ to $C_{30}$ monoolefin represented by Structure I-1, a branched $C_{10}$ to $C_{30}$ monoolefin represented by Structure J-1, a branched $C_{10}$ to $C_{30}$ monoolefin represented by Structure K-1, a branched $C_{10}$ to $C_{30}$ monoolefin represented by Structure L-1, or combinations thereof.

In other aspects, a $C_{20+}$ sulfides composition can comprise at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % sulfides, wherein at least a portion of the sulfides can be branched $C_{20}$ to $C_{60}$ sulfides represented by structure $R^{10}$—S—$R^{11}$, wherein both $R^{10}$ and $R^{11}$ can each independently be a functional group derived from an olefin, and wherein the olefin comprises a branched $C_{10}$ to $C_{30}$ monoolefin, alternatively a branched $C_{11}$ to $C_{30}$ monoolefin, alternatively a branched $C_{12}$ to $C_{30}$ monoolefin, alternatively a branched $C_{14}$ to $C_{30}$ monoolefin, alternatively a branched $C_{16}$ to $C_{28}$ monoolefin, or alternatively a branched $C_{18}$ to $C_{26}$ monoolefin. In such aspects, the olefin can comprise a branched $C_{10}$ to $C_{30}$ monoolefin represented by Structure I-1, a branched $C_{10}$ to $C_{30}$ monoolefin represented by Structure J-1, a branched $C_{10}$ to $C_{30}$ monoolefin represented by Structure K-1, a branched $C_{10}$ to $C_{30}$ monoolefin represented by Structure L-1, or combinations thereof.

In other aspects, a $C_{20+}$ sulfides composition can comprise at least about 1, 5, 10, 15, 20, 25, 30, 35, 40, 45, 50, 55, 60, 65, 70, 75, 80, 85, 90, 95, or 99 wt. %, sulfides, wherein at least about 1, 5, 10, 15, 20, 25, 30, 35, 40, 45, 50, 55, 60, 65, 70, 75, 80, 85, 90, 95, or 99 wt. % of the sulfides can be branched $C_{20}$ to $C_{60}$ sulfides represented by structure $R^{10}$—S—$R^{11}$, wherein both $R^{10}$ and $R^{11}$ can each independently be a functional group derived from an olefin, and wherein the olefin comprises a branched $C_{10}$ to $C_{30}$ monoolefin, alternatively a branched $C_{11}$ to $C_{30}$ monoolefin, alternatively a branched $C_{12}$ to $C_{30}$ monoolefin, alternatively a branched $C_{14}$ to $C_{30}$ monoolefin, alternatively a branched $C_{16}$ to $C_{28}$ monoolefin, or alternatively a branched $C_{18}$ to $C_{26}$ monoolefin. In such aspects, the olefin can comprise a branched $C_{10}$ to $C_{30}$ monoolefin represented by Structure I-1, a branched $C_{10}$ to $C_{30}$ monoolefin represented by Structure J-1, a branched $C_{10}$ to $C_{30}$ monoolefin represented by Structure K-1, a branched $C_{10}$ to $C_{30}$ monoolefin represented by Structure L-1, or combinations thereof.

In yet other aspects, a $C_{20+}$ sulfides composition can comprise at least about 10 wt. %, alternatively at least about 15 wt. %, alternatively at least about 20 wt. %, or alternatively at least about 25 wt. % sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the sulfides can be branched $C_{20}$ to $C_{60}$ sulfides represented by structure $R^{10}$—S—$R^{11}$, wherein both $R^{10}$ and $R^{11}$ can each independently be a functional group derived from an olefin, and wherein the olefin comprises a branched $C_{10}$ to $C_{30}$ monoolefin, alternatively a branched $C_{11}$ to $C_{30}$ monoolefin, alternatively a branched $C_{12}$ to $C_{30}$ monoolefin, alternatively a branched $C_{14}$ to $C_{30}$ monoolefin, alternatively a branched $C_{16}$ to $C_{28}$ monoolefin, or alternatively a branched $C_{18}$ to $C_{26}$ monoolefin. In such aspects, the olefin can comprise a branched $C_{10}$ to $C_{30}$ monoolefin represented by Structure I-1, a branched $C_{10}$ to $C_{30}$ monoolefin represented by Structure J-1, a branched $C_{10}$ to $C_{30}$ monoolefin represented by Structure K-1, a branched $C_{10}$ to $C_{30}$ monoolefin represented by Structure L-1, or combinations thereof.

In still yet other aspects, a $C_{20+}$ sulfides composition can comprise from at least about 10 wt. % to at least about 30 wt. %, alternatively from at least about 12.5 wt. % to at least about 22.5 wt. %, or alternatively from at least about 15 wt. % to at least about 20 wt. % sulfides; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the sulfides can be branched $C_{20}$ to $C_{60}$ sulfides represented by structure $R^{10}$—S—$R^{11}$, wherein both $R^{10}$ and $R^{11}$ can each independently be a functional group derived from an olefin, and wherein the olefin comprises a branched $C_{10}$ to $C_{30}$ monoolefin, alternatively a branched $C_{11}$ to $C_{30}$ monoolefin, alternatively a branched $C_{12}$ to $C_{30}$ monoolefin, alternatively a branched $C_{14}$ to $C_{30}$ monoolefin, alternatively a branched $C_{16}$ to $C_{28}$ monoolefin, or alternatively a branched $C_{18}$ to $C_{26}$ monoolefin. In such aspects, the olefin can comprise a branched $C_{10}$ to $C_{30}$ monoolefin represented by Structure I-1, a branched $C_{10}$ to $C_{30}$ monoolefin represented by Structure J-1, a branched $C_{10}$ to $C_{30}$ monoolefin represented by Structure K-1, a branched $C_{10}$ to $C_{30}$ monoolefin represented by Structure L-1, or combinations thereof.

In still yet other aspects, a $C_{20+}$ sulfides composition can consist of or consist essentially of branched $C_{20}$ to $C_{60}$ sulfides represented by structure $R^{10}$—S—$R^{11}$, wherein both $R^{10}$ and $R^{11}$ can each independently be a functional group derived from an olefin, and wherein the olefin comprises a branched $C_{10}$ to $C_{30}$ monoolefin, alternatively a branched $C_{11}$ to $C_{30}$ monoolefin, alternatively a branched $C_{12}$ to $C_{30}$ monoolefin, alternatively a branched $C_{14}$ to $C_{30}$ monoolefin, alternatively a branched $C_{16}$ to $C_{28}$ monoolefin, or alternatively a branched $C_{18}$ to $C_{26}$ monoolefin. In such aspects, the olefin can comprise a branched $C_{10}$ to $C_{30}$ monoolefin represented by Structure I-1, a branched $C_{10}$ to $C_{30}$ monoolefin represented by Structure J-1, a branched $C_{10}$ to $C_{30}$ monoolefin represented by Structure K-1, a branched $C_{10}$ to $C_{30}$ monoolefin represented by Structure L-1, or combinations thereof.

In still yet other aspects, a $C_{20+}$ sulfides composition can comprise at least about 5 wt. %, alternatively at least about 10 wt. %, alternatively at least about 15 wt. %, or alternatively at least about 20 wt. % branched $C_{20}$ to $C_{60}$ sulfides represented by structure $R^{10}$—S—$R^{11}$, wherein both $R^{10}$ and $R^{11}$ can each independently be a functional group derived from an olefin, and wherein the olefin comprises a branched $C_{10}$ to $C_{30}$ monoolefin, alternatively a branched $C_{11}$ to $C_{30}$ monoolefin, alternatively a branched $C_{12}$ to $C_{30}$ monoolefin, alternatively a branched $C_{14}$ to $C_{30}$ monoolefin, alternatively a branched $C_{16}$ to $C_{28}$ monoolefin, or alternatively a branched $C_{18}$ to $C_{26}$ monoolefin. In such aspects, the olefin can comprise a branched $C_{10}$ to $C_{30}$ monoolefin represented by Structure I-1, a branched $C_{10}$ to $C_{30}$ monoolefin represented by Structure J-1, a branched $C_{10}$ to $C_{30}$ monoolefin represented by Structure K-1, a branched $C_{10}$ to $C_{30}$ monoolefin represented by Structure L-1, or combinations thereof.

In still yet other aspects, a $C_{20+}$ sulfides composition comprises at least about 1, 5, 10, 15, 20, 25, 30, 35, 40, 45, 50, 55, 60, 65, 70, 75, 80, 85, 90, 95, or 99 wt. % branched $C_{20}$ to $C_{60}$ sulfides represented by structure $R^{10}$—S—$R^{11}$, wherein both $R^{10}$ and $R^{11}$ can each independently be a functional group derived from an olefin, and wherein the olefin comprises a branched $C_{10}$ to $C_{30}$ monoolefin, alternatively a branched $C_{11}$ to $C_{30}$ monoolefin, alternatively a branched $C_{12}$ to $C_{30}$ monoolefin, alternatively a branched $C_{14}$ to $C_{30}$ monoolefin, alternatively a branched $C_{16}$ to $C_{28}$ monoolefin, or alternatively a branched $C_{18}$ to $C_{26}$ monoolefin. In such aspects, the olefin can comprise a branched $C_{10}$ to $C_{30}$ monoolefin represented by Structure I-1, a branched $C_{10}$ to $C_{30}$ monoolefin represented by Structure J-1, a branched $C_{10}$ to $C_{30}$ monoolefin represented by Structure K-1, a branched $C_{10}$ to $C_{30}$ monoolefin represented by Structure L-1, or combinations thereof.

In an aspect, a $C_{10+}$ mercaptans/$C_{20+}$ sulfides composition can comprise one or more mercaptans and one or more sulfides of the type disclosed herein. For purposes of the disclosure herein, a composition comprising (i) mercaptans, wherein at least a portion of the mercaptans are branched $C_{10}$ to $C_{30}$ mercaptans, and (ii) sulfides, wherein at least a portion of the sulfides are branched $C_{20}$ to $C_{60}$ sulfides, can also be referred to as a "branched $C_{10+}$ mercaptans/branched $C_{20+}$ sulfides composition." In an aspect, the $C_{10+}$ mercaptans/$C_{20+}$ sulfides composition can comprise any suitable amount of branched $C_{10}$ to $C_{30}$ mercaptans, and any suitable amount of branched $C_{20}$ to $C_{60}$ sulfides.

In an aspect, a $C_{10+}$ mercaptans/$C_{20+}$ sulfides composition can comprise (A) at least about 1 wt. %, alternatively at least about 5 wt. %, alternatively at least about 10 wt. %, alternatively at least about 15 wt. %, alternatively at least about 20 wt. %, alternatively at least about 25 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % mercaptans, wherein at least a portion of the mercaptans can be branched $C_{10}$ to $C_{30}$ mercaptans characterized by the general formula $R^{14}$—SH, wherein $R^{14}$ is a branched alkyl group; and wherein $R^{14}$ has from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms; and (B) at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % sulfides, wherein at least a portion of the sulfides can be branched $C_{20}$ to $C_{60}$ sulfides represented by structure $R^{10}$—S—$R^{11}$, wherein both $R^{10}$ and $R^{11}$ can each independently be a functional group derived from an olefin, and wherein the olefin comprises a branched $C_{10}$ to $C_{30}$ monoolefin, alternatively a branched $C_{11}$ to $C_{30}$ monoolefin, alternatively a branched $C_{12}$ to $C_{30}$ monoolefin, alternatively a branched $C_{14}$ to $C_{30}$ monoolefin, alternatively a branched $C_{16}$ to $C_{28}$ monoolefin, or alternatively a branched $C_{18}$ to $C_{26}$ monoolefin. In such aspect, the branched $C_{10}$ to $C_{30}$ mercaptans characterized by the general formula $R^{14}$—SH can be selected from the group consisting of a branched $C_{10}$ to $C_{30}$ mercaptan represented by Structure A-1, a branched $C_{10}$ to $C_{30}$ mercaptan represented by Structure B-1, a branched $C_{10}$ to $C_{30}$ mercaptan represented by Structure C-1, a branched $C_{10}$ to $C_{30}$ mercaptan represented by Structure D-1, a branched $C_{10}$ to $C_{30}$ mercaptan represented by Structure E-1, a branched $C_{10}$ to $C_{30}$ mercaptan represented by Structure F-1, a branched $C_{10}$ to $C_{30}$ mercaptan represented by Structure G-1, a branched $C_{10}$ to $C_{30}$ mercaptan represented by Structure H-1, and combinations thereof; and the olefin can comprise a branched $C_{10}$ to $C_{30}$ monoolefin represented by Structure I-1, a branched $C_{10}$ to $C_{30}$ monoolefin represented by Structure J-1, a branched $C_{10}$ to $C_{30}$ monoolefin represented by Structure K-1, a branched $C_{10}$ to $C_{30}$ monoolefin represented by Structure L-1, or combinations thereof.

In an aspect, a $C_{10+}$ mercaptans/$C_{20+}$ sulfides composition can comprise $C_{10}$ to $C_{30}$ mercaptans characterized by the general formula $R^{14}$—SH and/or $C_{20}$ to $C_{60}$ sulfides represented by structure $R^{10}$—S—$R^{11}$ that are formed by reacting an olefin feedstock comprising olefins with $H_2S$ as described in more detail herein, wherein the olefins present in the olefin feedstock provide the alkyl group represented by $R^{10}$, $R^{11}$, and $R^{14}$. In such aspects, the $R^{10}$ and $R^{11}$ groups of the $C_{20}$ to $C_{60}$ sulfides and/or the $R^{14}$ group of the $C_{10}$ to $C_{30}$ mercaptans are provided by or derived from the counterpart $R^{10}$, $R^{11}$, and $R^{14}$ groups present in the olefins in the olefin feedstock. In an aspect, $R^{10}$, $R^{11}$, and $R^{14}$ can each independently be an alkyl group, wherein at least a portion of the alkyl groups can comprise a functional group derived from an olefin, wherein the olefin is present in a feedstock as disclosed herein (e.g., a first $C_{10}$ to $C_{30}$ feedstock; a second $C_{10}$ to $C_{30}$ feedstock).

In an aspect, a $C_{10+}$ mercaptans composition and/or a $C_{10+}$ mercaptans/$C_{20+}$ sulfides composition comprising equal to or greater than about 25 wt. % $C_{10+}$ branched mercaptans as disclosed herein can advantageously have an odor less unpleasant and less offensive than an odor of an otherwise similar composition comprising equal to or greater than about 25 wt. % n-decyl mercaptan, as perceived by equal to or greater than about 51% of human subjects exposed to the odor of each composition.

In an aspect, a $C_{10+}$ mercaptans composition and/or a $C_{10+}$ mercaptans/$C_{20+}$ sulfides composition comprising equal to or greater than about 25 wt. % $C_{10+}$ branched mercaptans as disclosed herein can advantageously have an odor less unpleasant than an odor of an otherwise similar composition comprising equal to or greater than about 25 wt. % n-dodecyl mercaptan and/or tert-dodecyl mercaptan, as perceived by equal to or greater than about 51% of human subjects exposed to the odor of each composition. Additional advantages of the $C_{10+}$ mercaptans compositions, $C_{20+}$ sulfides compositions, and $C_{10+}$ mercaptans/$C_{20+}$ sulfides compositions and processes of producing same as disclosed herein can be apparent to one of skill in the art viewing this disclosure.

In an aspect, a process of the present disclosure comprises reacting branched $C_{10+}$ mercaptans and a sulfur-containing material to produce a $C_{20+}$ crude product. In a further aspect, a process of the present disclosure comprises reacting a feedstock comprising one or more branched $C_{10+}$ mercaptans and a sulfur-containing material in the presence of a catalyst to produce a $C_{20+}$ crude product; wherein the $C_{20+}$ crude product comprises branched $C_{20+}$ polysulfides and branched $C_{20+}$ monosulfides.

In an aspect, a process of the present disclosure comprises reacting feedstock comprising one or more branched $C_{10+}$ mercaptans and a sulfur-containing material (e.g., elemental sulfur) in the presence of a catalyst to produce a branched $C_{20+}$ polysulfides crude product; wherein the branched $C_{10+}$ mercaptans comprise $C_{10}$ to $C_{30}$ mercaptans, alternatively $C_{11}$ to $C_{30}$ mercaptans, alternatively $C_{12}$ to $C_{30}$ mercaptans, alternatively $C_{14}$ to $C_{30}$ mercaptans, alternatively $C_{16}$ to $C_{28}$ mercaptans, or alternatively $C_{18}$ to $C_{26}$ mercaptans; and wherein the branched $C_{20+}$ polysulfides crude product comprises branched $C_{20+}$ polysulfides and branched $C_{20+}$ monosulfides. In a further aspect, the branched $C_{10+}$ mercaptans are derived from one or more branched $C_{10+}$ monoolefins wherein the branched $C_{10+}$ monoolefins are produced by reacting, in a reactor, a sulfur source (e.g., $H_2S$) and a feedstock comprising the branched $C_{10+}$ monoolefins in the presence of an initiating agent, as previously described herein.

The branched $C_{20+}$ polysulfides crude product can be further processed, for example via distillation, as previously described herein for the branched $C_{10+}$ mercaptans, to yield one or more products (also referred to as distilled, purified, refined, finished, or final products) selected from the group consisting of $C_{20+}$ polysulfide compositions (e.g., a composition comprising one or more branched $C_{20+}$ polysulfides); $C_{20+}$ monosulfide compositions (e.g., a composition comprising one or more branched $C_{20+}$ monosulfides); and compositions having both branched $C_{20+}$ polysulfides and branched $C_{20+}$ monosulfides, referred to as $C_{20+}$ metasulfide compositions.

In an aspect, a $C_{20+}$ polysulfides composition comprises one or more branched $C_{20+}$ polysulfides represented by the general formula $R^{15}S^1$—$[S]_n$—$S^2R^{16}$, wherein n is an integer from 1 to 10, and wherein $R^{15}S^1$ and $R^{16}S^2$ are each independently a functional group derived from a mercaptan, wherein the mercaptan comprises a branched $C_{10+}$ mercaptan as disclosed herein. The branched $C_{20+}$ polysulfides may comprise $C_{20}$ to $C_{60}$ polysulfides, alternatively $C_{21}$ to $C_{60}$ polysulfides, alternatively $C_{22}$ to $C_{60}$ polysulfides, alternatively $C_{24}$ to $C_{60}$ polysulfides, alternatively $C_{28}$ to $C_{60}$ polysulfides, alternatively $C_{32}$ to $C_{56}$ polysulfides, or alternatively $C_{36}$ to $C_{52}$ polysulfides.

In an aspect, a $C_{20+}$ monosulfides composition comprises one or more branched $C_{20+}$ monosulfides represented by the general formula $R^{17}$—S—$R^{18}$, wherein $R^{17}$ and $R^{18}$ are each independently an alkyl group, wherein the alkyl group comprises a branched $C_{10+}$ alkyl group as disclosed herein. The branched $C_{20+}$ monosulfides comprise $C_{20}$ to $C_{60}$ monosulfides, alternatively $C_{21}$ to $C_{60}$ monosulfides, alternatively $C_{22}$ to $C_{60}$ monosulfides, alternatively $C_{24}$ to $C_{60}$ monosulfides, alternatively $C_{28}$ to $C_{60}$ monosulfides, alternatively $C_{32}$ to $C_{56}$ monosulfides, or alternatively $C_{36}$ to $C_{52}$ monosulfides.

In an aspect, a $C_{20+}$ metasulfides composition (e.g., a $C_{20+}$ polysulfides/$C_{20+}$ monosulfides composition) comprises (A) one or more branched $C_{20+}$ polysulfides represented by the general formula $R^{15}S^1$—$[S]_n$—$S^2R^{16}$, wherein n is an integer from 1 to 10; and (B) one or more branched $C_{20+}$ monosulfides represented by the general formula $R^{17}$—S—$R^{18}$.

The $C_{20+}$ polysulfide compositions, the $C_{20+}$ monosulfides compositions, and the $C_{20+}$ metasulfides compositions can be salable or otherwise used for a variety of end uses such as mining ore collector compositions and chain transfer agents.

In an aspect, the compositions disclosed herein can be prepared by a process comprising reacting branched $C_{10+}$ mercaptans and a sulfur-containing material to produce a branched $C_{20+}$ polysulfides crude product, wherein the branched $C_{10+}$ mercaptans may comprise a branched $C_{10+}$ mercaptan represented by Structure A-1, Structure B-1, Structure C-1, Structure D-1, Structure E-1, Structure F-1, Structure G-1, Structure H-1, or combinations thereof;

wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group. The $R^9$ group can be a linear $C_1$ to $C_{21}$ alkyl group or a branched $C_1$ to $C_{21}$ alkyl group. As will be appreciated by one of skill in the art, and with the help of this disclosure, the branched $C_{10+}$ mercaptans comprising the $R^9$ alkyl group are branched mercaptans, regardless of whether $R^9$ is linear or branched, owing to a branched sub-structure that is linked to the $R^9$ alkyl group, as it can be seen in Structure A-1, Structure B-1, Structure C-1, Structure D-1, Structure E-1, Structure F-1, Structure G-1, and Structure H-1, as previously disclosed herein.

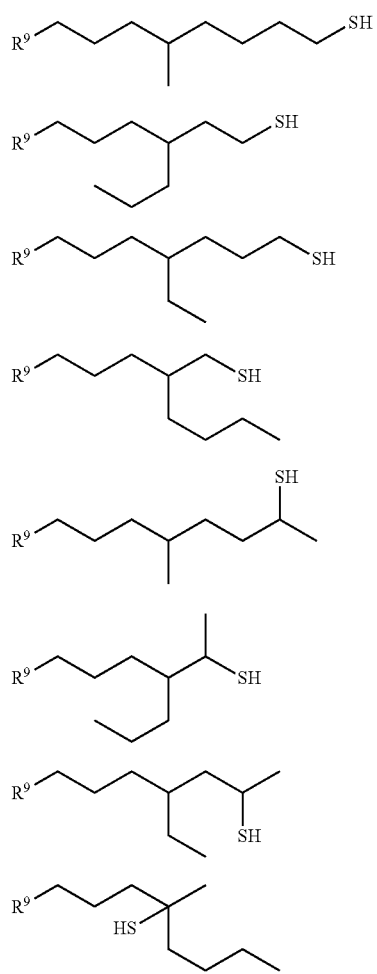

In some aspects, $R^9$ can be selected from the group consisting of a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a henicosyl group, and combinations thereof.

In aspects where $R^9$ is a methyl group, the branched $C_{10+}$ mercaptans comprise one or more branched $C_{10}$ mercaptans, as previously disclosed herein. In an aspect, the branched $C_{10}$ mercaptans may comprise 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), or combinations thereof.

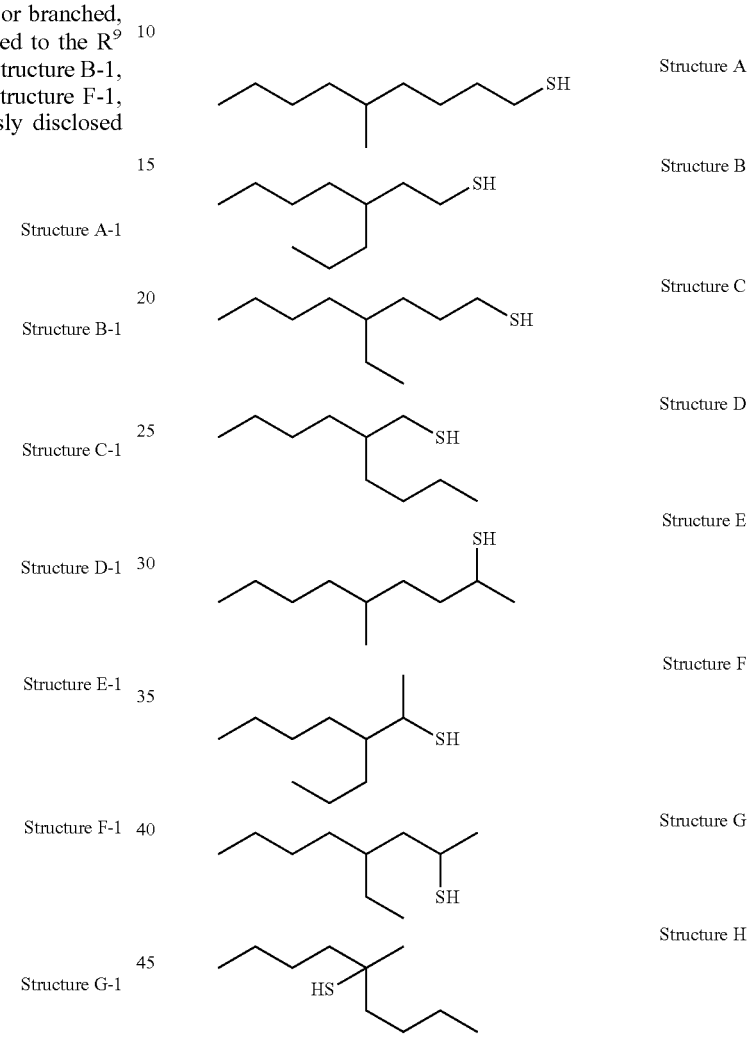

Any feedstock comprising one or more branched $C_{10+}$ mercaptans of the type described herein can be used, for example a reaction product of the process of reacting $H_2S$ and one or more branched $C_{10+}$ monoolefins (alternatively, one or more branched $C_{10}$ monoolefins), in the presence of an initiating agent as previously described herein. In an aspect, a feedstock of branched $C_{10+}$ mercaptans may comprise any mercaptan composition previously described herein such as a "$C_{10+}$ mercaptans composition", a "$C_{11+}$ mercaptans composition", a "mercaptan composition" (also referred to as a "branched $C_{10}$ mercaptan composition"), or combinations thereof. In a further aspect, the feedstock of branched $C_{10+}$ mercaptans may comprise any mercaptan/sulfide composition previously described herein such as a "$C_{10+}$ mercaptans/$C_{20+}$ sulfides composition", a "$C_{11+}$ mercaptans/$C_{22+}$ sulfides composition", a "mercaptan/sulfide composition" (also referred to as a "branched $C_{10}$ mercaptan/$C_{20}$ sulfide composition"), or combinations thereof.

Such feedstocks can comprise other mercaptans in addition to the branched $C_{10+}$ mercaptans of the type described herein, for example linear $C_{10+}$ mercaptans as well as mercaptans having less than 10 carbon atoms.

In an aspect, the feedstock can comprise one or more branched $C_{10}$ to $C_{30}$ mercaptans. Any feedstock comprising branched $C_{10}$ to $C_{30}$ mercaptans of the type described herein can be used, for example a reaction product of the process of reacting $H_2S$ and one or more branched $C_{10+}$ monoolefins in the presence of an initiating agent as described herein. Such feedstocks can comprise other mercaptans in addition to the branched $C_{10}$ to $C_{30}$ mercaptans of the type described herein, for example $C_{9-}$ mercaptans, $C_{31+}$ mercaptans, as well as linear $C_{10}$ to $C_{30}$ mercaptans.

In an aspect, the feedstock can comprise at least about 70 wt. %, alternatively at least about 75 wt. %, alternatively at least about 80 wt. %, alternatively at least about 85 wt. %, alternatively at least about 90 wt. %, or alternatively at least about 95 wt. % branched $C_{10}$ to $C_{30}$ mercaptans, based on the total weight of the feedstock. In such aspect, the feedstock can comprise (a) less than about 15 wt. %, alternatively less than about 10 wt. %, alternatively less than about 5 wt. %, or alternatively less than about 1 wt. % $C_{9-}$ mercaptans; and (b) less than about 15 wt. %, alternatively less than about 10 wt. %, alternatively less than about 5 wt. %, or alternatively less than about 1 wt. % $C_{31+}$ mercaptans; based on the total weight of the feedstock. For purposes of the disclosure herein, a feedstock comprising at least about 70 wt. % branched $C_{10}$ to $C_{30}$ mercaptans, based on the total weight of the feedstock, can also be referred to as a "first $C_{10}$ to $C_{30}$ mercaptans feedstock."

In another aspect, the feedstock can comprise at least about 95 wt. %, alternatively at least about 96 wt. %, alternatively at least about 97 wt. %, alternatively at least about 98 wt. %, or alternatively at least about 99 wt. % branched $C_{10}$ to $C_{30}$ mercaptans, based on the total weight of the feedstock. For purposes of the disclosure herein, a feedstock comprising at least about 95 wt. % branched $C_{10}$ to $C_{30}$ mercaptans, based on the total weight of the feedstock, can also be referred to as a "second $C_{10}$ to $C_{30}$ mercaptans feedstock." In an aspect, the second $C_{10}$ to $C_{30}$ mercaptans feedstock can be produced by purifying the first $C_{10}$ to $C_{30}$ mercaptans feedstock, such as for example by distillation of the first $C_{10}$ to $C_{30}$ mercaptans feedstock.

In an aspect, the branched $C_{10}$ to $C_{30}$ mercaptans of any feedstock described herein (e.g., a first $C_{10}$ to $C_{30}$ mercaptans feedstock or a second $C_{10}$ to $C_{30}$ mercaptans feedstock) can comprise, can consist essentially of, or can be, a branched $C_{10+}$ mercaptan represented by Structure A-1, Structure B-1, Structure C-1, Structure D-1, Structure E-1, Structure F-1, Structure G-1, Structure H-1, wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In an aspect, the $C_{10}$ to $C_{30}$ mercaptans of any feedstock described herein (e.g., a first $C_{10}$ to $C_{30}$ mercaptans feedstock or a second $C_{10}$ to $C_{30}$ mercaptans feedstock) can further comprise non-branched $C_{10+}$ mercaptans, such as for example a linear $C_{10}$ to $C_{30}$ mercaptan represented by Structure M-1, Structure N-1, Structure O-1, Structure P-1, or combinations thereof, wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

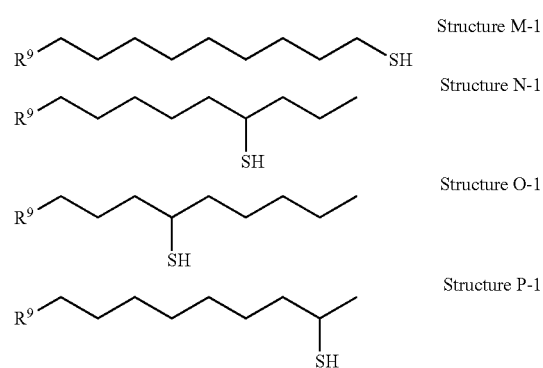

In aspects where $R^9$ is a methyl group, the non-branched $C_{10+}$ mercaptans can further comprise non-branched $C_{10}$ mercaptans, as previously disclosed herein. The non-branched $C_{10}$ mercaptans can comprise 1-mercapto-decane (represented by Structure M), 4-mercapto-decane (represented by Structure N), 5-mercapto-decane (represented by Structure O), 2-mercapto-decane (represented by Structure P), or combinations thereof.

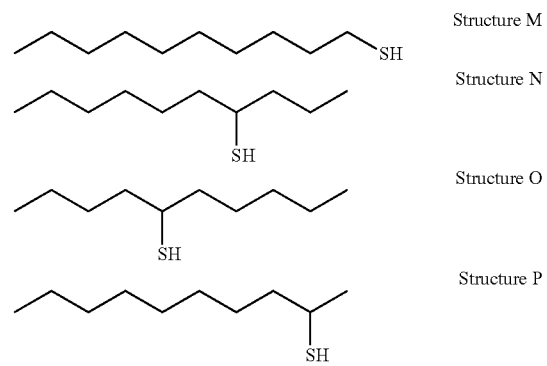

In an aspect, the $C_{10}$ to $C_{30}$ mercaptans of any feedstock described herein (e.g., a first $C_{10}$ to $C_{30}$ feedstock or a second $C_{10}$ to $C_{30}$ feedstock) can comprise linear $C_{10}$ to $C_{30}$ mercaptans. In an aspect, the $C_{10}$ to $C_{30}$ mercaptans of any feedstock described herein can comprise less than or equal to about 26 mol %, alternatively less than or equal to about 24 mol %, alternatively less than or equal to about 22 mol %, alternatively less than or equal to about 20 mol %, or alternatively less than or equal to about 18 mol % linear $C_{10}$ to $C_{30}$ mercaptans. In some aspects, the $C_{10}$ to $C_{30}$ mercaptans of any feedstock described herein can comprise from about 0.1 mol % to about 26 mol %, alternatively from about 0.5 mol % to about 24 mol %, alternatively from about 1 mol % to about 22 mol %, alternatively from about 1.5 mol % to about 20 mol %, or alternatively from about 2.5 mol % to about 18 mol % linear $C_{10}$ to $C_{30}$ mercaptans.

In an aspect, the first $C_{10}$ to $C_{30}$ mercaptans feedstock disclosed herein can further comprise $C_{9-}$ mercaptans, $C_{31+}$ mercaptans, or combinations thereof; alternatively, $C_{9-}$ mercaptans; or alternatively, $C_{31+}$ mercaptans. In an aspect, the $C_{9-}$ mercaptans can comprise, can consist essentially of, or can be, $C_7$ mercaptans, $C_8$ mercaptans, $C_9$ mercaptans, or combinations thereof; alternatively, $C_7$ mercaptans; alternatively, $C_8$ mercaptans; or alternatively, $C_9$ mercaptans. In some aspects, the $C_{9-}$ mercaptans can comprise, can consist essentially of, or can be, $C_8$ mercaptans. In an aspect, the $C_{31+}$ mercaptans can comprise, can consist essentially of, or can be, $C_{31}$ mercaptans, $C_{32}$ mercaptans, $C_{33}$ mercaptans, $C_{34}$ mercaptans, $C_{35}$ mercaptans, $C_{36}$ mercaptans, $C_{37}$ mercaptans, $C_{38}$ mercaptans, or combinations thereof; alternatively, $C_{31}$ mercaptans; alternatively, $C_{32}$ mercaptans; alternatively, $C_{33}$ mercaptans; alternatively, $C_{34}$ mercaptans; alternatively, $C_{35}$ mercaptans; alternatively, $C_{36}$ mercaptans; alternatively, $C_{37}$ mercaptans; or alternatively, $C_{38}$ mercaptans. In some aspects, the $C_{31+}$ mercaptans can comprise, can consist essentially of, or can be, $C_{32}$ mercaptans, $C_{36}$ mercaptans, $C_{38}$ mercaptans, or combinations thereof; alternatively, $C_{32}$ mercaptans; alternatively, $C_{36}$ mercaptans; or alternatively, $C_{38}$ mercaptans.

In an aspect, the first $C_{10}$ to $C_{30}$ mercaptans feedstock can further comprise from about 0.1 mol % to about 5 mol %, alternatively from about 0.25 mol % to about 4 mol %, or alternatively from about 0.5 mol % to about 3 mol % $C_8$ mercaptans. In such aspect, the $C_8$ mercaptans can comprise at least about 95 mol %, alternatively at least about 96 mol %, alternatively at least about 97 mol %, alternatively at least about 98 mol %, or alternatively at least about 99 mol % 1-octanethiol.

In an aspect, a feedstock comprising branched $C_{10+}$ mercaptans and a sulfur-containing material can be reacted in the presence of a catalyst to produce a branched $C_{20+}$ polysulfides crude product wherein the sulfur-containing material comprises any sulfur-containing material suitable to provide sulfur for the conversion of mercaptans to polysulfides. In a particular aspect, the sulfur-containing material comprises elemental sulfur. In a further aspect, elemental sulfur suitable for use herein comprises one or more allotropes of elemental sulfur, e.g., cyclo-$S_8$ or amorphous sulfur. The sulfur-containing material may further comprise one or more polymorphs of elemental sulfur, e.g., α-sulfur (α-cyclo-$S_8$) or β-sulfur (β-cyclo-$S_8$). In a still further aspect, the sulfur-containing material does not comprise hydrogen sulfide ($H_2S$).

In an aspect, an equivalent molar ratio of sulfur-containing material to mercaptans is in a range of from about 0.01:1 to about 20:1, alternatively from about 0.04:1 to about 10:1, alternatively from about 0.07:1 to about 1.2:1, or alternatively, from about 0.4:1 to about 0.8:1.

In an aspect, a feedstock comprising branched $C_{10+}$ mercaptans and a sulfur-containing material can be reacted in the presence of a catalyst to produce a branched $C_{20+}$ polysulfides crude product wherein the catalyst comprises a surfactant and an alkaline material.

In a further aspect, the surfactant may be any surfactant suitable for conversion of mercaptans to polysulfides as disclosed herein. Non-limiting examples of surfactants suitable for use in the present disclosure include nonionic surfactants, ionic surfactants, amphoteric surfactants, or combinations thereof. In an aspect, the surfactant may be a nonionic surfactant. In a further aspect, the surfactant comprises one or more functional groups including but not limited to alkoxylates, polyalkoxylates, ethoxylates, polyethoxylates, glucosides, sulfates, sulfonates, disulfonates, phosphate esters, sulfosuccinates, quaternary ammonium salts, betaines, or combinations thereof. In yet a further aspect, the surfactant may be a nonionic surfactant comprising one or more functional groups including polyalkoxylates, polyethoxylates, or glucosides; alternatively, polyalkoxylates; alternatively, polyethoxylates; or alternatively, glucosides. In a particular aspect, the surfactant may be a nonionic surfactant comprising a polyethoxylated alcohol, a polyethoxylated mercaptan, or a combination thereof; alternatively, a polyethoxylated alcohol; or alternatively, a polyethoxylated mercaptan. The polyethoxylated alcohol may be any polyethoxylated alcohol suitable for conversion of mercaptans to polysulfides. In a particular aspect, the polyethoxylated alcohol is represented by the formula $C_{10-18}H_{21-37}O[C_2H_4O]_xH$; wherein $C_{10-18}H_{21-37}O$ is a functional group derived from a secondary alcohol comprising from about 10 to about 18 carbons atoms; and wherein x is an integer from 3 to 20, alternatively, from 4 to 10, or alternatively, from 6 to 8. In a further aspect, the polyethoxylated mercaptan may be any polyethoxylated mercaptan suitable for conversion of mercaptans to polysulfides. In an aspect, the polyethoxylated mercaptan is represented by the formula $C_{8-16}H_{17-33}S[C_2H_4O]_xH$; wherein $C_{8-16}H_{17-33}S$ is a functional group derived from a tertiary mercaptan comprising from about 8 to about 16 carbons atoms; and wherein x is an integer from 3 to 20, alternatively, from 4 to 10, or alternatively, from 6 to 8.

In a still further aspect, the surfactant may be chosen from the group consisting of 1-Oleoyl-rac-glycerol, Brij® 58, Brij® L23, Brij® L4, Brij® 010, CYMAL-2®, CYMAL-5®, CYMAL-6®, Decaethylene glycol monododecyl ether, Decyl β-D-glucopyranoside, Decyl β-D-maltopyranoside, Deoxy-BigCHAP, Digitonin, ECOSURF™ EH-9, ECO-SURF™ SA-9, Genapol® X-100, Igepal® CA-630, Igepal® CA-720, Kolliphor® P 188, Kolliphor® P 407, Kolliphor® EL, MEGA-8, MEGA-9, MEGA-10, Methoxypolyethylene glycol, N,N-Dimethyldodecylamine N-oxide, n-Dodecyl β-D-maltoside, n-Heptyl β-D-thioglucopyranoside, n-Hexadecyl β-D-maltoside, n-Nonyl-β-D-Glucopyranoside, n-Nonyl-β-D-maltoside, n-Octyl-β-D-maltoside, n-Octyl-β-D-thioglucopyranoside, n-Octyl-b-D-Glucopyranoside, Nonaethylene glycol monododecyl ether, Nonidet™ P40 Substitute, Nonylphenyl-polyethyleneglycol acetate, Octaethylene glycol monododecyl ether, Pluronic® F-127, Pluronic® F-68, Poloxamer 407, Poly(ethylene glycol), Polyoxyethylene (10) tridecyl ether, Polyoxyethylene (40) stearate, Polysorbate 20, Polysorbate 60, Polysorbate 80, Saponin, Span® 20, Span® 40, Span® 60, Span® 80, Span® 85, Sucrose monolaurate, Synperonic® PE/P84, TERGITOL™, TERGITOL™ NP-7, TERGITOL™ NP-9, TERGITOL™ NP-10, TERGITOL™ NP-40, TERGITOL™ 15-S-7, TERGITOL™ 15-S-9, TERGITOL™ 15-S-30, TERGITOL™ 15-S-40, TERGITOL™ TMN 6, TERGITOL™ TMN 10, TERGITOL™ TMN-100X, Tetraethylene glycol monododecyl ether, Tetramethylammonium hydroxide pentahydrate, Thesit®, TRITON™ X-100, TRITON™ X-114, TRITON™ X-165, TRITON™ X-305, TRITON™ X-405, TRITON™ X-405, TRITON™ X-705, TRITON™-CG-110, TWEEN® 20, TWEEN® 40, TWEEN® 60, TWEEN® 65, TWEEN® 80, TWEEN® 85, Tyloxapol, and Undecyl-β-D-maltoside, all of which are available commercially from MilliporeSigma, and AQUA-CLEEN® available commercially from Chemical Products Industries, Inc. In a particular aspect the surfactant may comprise TERGITOL® 15-S-7 or AQUA-CLEEN®.

In a further aspect, the alkaline material may comprise any alkaline material suitable for conversion of mercaptans to polysulfides as disclosed herein. In a particular aspect, the alkaline material may be a metal hydroxide. In an aspect, the metal hydroxide may be a Group 1 metal hydroxide, a Group 2 metal hydroxide, or a combination thereof. In yet a further aspect, the metal hydroxide may be LiOH, NaOH, KOH, RbOH, CsOH, $Mg(OH)_2$, $Ca(OH)_2$, or combinations thereof. The metal hydroxide comprising a catalyst suitable for use in the present disclosure may be a solid or, alternatively, may be a component of an aqueous solution. In yet a further aspect, an amount of metal hydroxide comprising the aqueous solution may be about 5 wt. %; alternatively, about 10 wt. %; alternatively, about 20 wt. %; or alternatively, about 50 wt. % based on the total weight of the aqueous solution.

In a particular aspect, prior to contacting the catalyst with any other component of the reaction process, the surfactant and the alkaline material may be contacted and subsequently heated. In a further aspect, the surfactant and the alkaline material may be heated to a temperature in a range of from about 40° C. to about 120° C., or alternatively, from about 60° C. to about 100° C. In yet a further aspect, the temperature may be maintained for a time period in a range of from 5 min to about 12 h, or alternatively, from about 30 min to about 2 h.

In an aspect, a weight ratio of catalyst to mercaptans is in a range of from about 0.001:1 to about 0.5:1, alternatively from about 0.002:1 to about 0.05:1, alternatively from about 0.005:1 to about 0.013:1, or alternatively from about 0.006:1 to about 0.008:1.

In an aspect, a weight ratio of surfactant to alkaline material is in a range of from about 5:1 to about 500:1, alternatively from about 10:1 to about 200:1, alternatively from about 25:1 to about 40:1, or alternatively from about 30:1 to about 35:1.

In an aspect, a feedstock comprising branched $C_{10+}$ mercaptans and a sulfur-containing material can be reacted in the presence of a catalyst to produce a branched $C_{20+}$ polysulfides crude product wherein a mercaptan scavenger (i.e., quenching agent) may be utilized to produce the branched $C_{20+}$ polysulfides crude product. In an aspect, the mercaptan scavenger may be any mercaptan scavenger suitable for conversion of mercaptans to polysulfides. In a further aspect, the mercaptan scavenger may be an epoxide, an oxetane, or a combination thereof. In a further aspect, the epoxide may be ethylene oxide or propylene oxide; alternatively, ethylene oxide; or alternatively, propylene oxide.

In an aspect, an equivalent molar ratio of mercaptan scavenger to mercaptans is in a range of from about 0.001:1 to about 1:1, alternatively from about 0.01:1 to about 0.5:1, alternatively from about 0.05:1 to about 0.1:1, or alternatively from about 0.06:1 to about 0.08:1.

In an aspect, a feedstock comprising branched $C_{10+}$ mercaptans and a sulfur-containing material can be reacted in the presence of a catalyst to produce a branched $C_{20+}$ polysulfides crude product wherein a decolorizing agent may be utilized to produce the branched $C_{20+}$ polysulfides crude product. In an aspect, the decolorizing agent may be any decolorizing agent suitable for use in the conversion of mercaptans to polysulfides. In a further aspect, the decolorizing agent comprises activated carbon, decolorizing carbon, mineral carbon, charcoal black, graphite (natural), purified charcoal, or a combination thereof. In a further aspect, the decolorizing agent may comprise Darco G-60, Darco®, Norit A® and combinations thereof, available commercially from Sigma-Aldrich, Inc.

In an aspect, a weight ratio of decolorizing agent to mercaptans is in a range of from about 0.001:1 to about 0.2:1, alternatively from about 0.01:1 to about 0.02:1, or alternatively from about 0.015:1 to about 0.018:1.

Disclosed herein are processes of reacting a feedstock comprising branched $C_{10+}$ mercaptans (e.g., a first $C_{10}$ to $C_{30}$ mercaptans feedstock or a second $C_{10}$ to $C_{30}$ mercaptans feedstock) and a sulfur-containing material in the presence of a catalyst to produce a branched $C_{20+}$ polysulfides crude product. In an aspect, such a process may be referred to as a process of producing a $C_{20+}$ polysulfides crude product. It will be appreciated by the ordinary skilled artisan that the entirety of the processes (i.e., each process step), disclosed herein may be conducted under an atmosphere comprising an inert gas. In a further aspect, the inert gas may comprise any inert gas suitable for use in the present disclosure, nonlimiting examples of which include nitrogen, argon, and a combination thereof.

Disclosed herein is a process of producing a $C_{20+}$ polysulfides crude product comprising contacting a feedstock comprising branched $C_{10+}$ mercaptans (e.g., a first $C_{10}$ to $C_{30}$ mercaptans feedstock or a second $C_{10}$ to $C_{30}$ mercaptans feedstock) and a catalyst to form a mixture. In an aspect, the feedstock comprises one or more branched $C_{10}$ to $C_{30}$ mercaptans as disclosed herein. The process further comprises heating the mixture to a temperature in a range of from about 40° C. to about 200° C.; alternatively, from about 60° C. to about 85° C.; or alternatively, from about 70° C. to about 80° C. The mixture may then be contacted with a sulfur-containing material (e.g., elemental sulfur) wherein evolution of a reaction by-product occurs. In an aspect, the reaction by-product may be gas-phase hydrogen sulfide. The mixture may then be agitated for a time period in a range of from 30 min to about 24 h; alternatively, from about 1 h to about 12 h; alternatively, from about 2 h to about 6 h; or alternatively, from about 3 h to about 4 h.

In an aspect, the process of producing a $C_{20+}$ polysulfides crude product comprises raising the temperature of the mixture. The mixture may be heated to a temperature in a range of from about 40° C. to about 250° C.; alternatively, from about 60° C. to about 200° C.; alternatively, from about 90° C. to about 150° C.; or alternatively, from about 90° C. to about 100° C. The mixture may then be agitated for a time period in a range of from 30 min to about 24 h; alternatively, from about 1 h to about 12 h; alternatively, from about 2 h to about 4 h; or alternatively, from about 3 h to about 4 h. The mixture may then be sparged with an inert gas (e.g., nitrogen), for a time period in a range of from 5 min to about 24 h; alternatively, from about 10 min to about 12 h; alternatively, from about 30 min to about 4 h; or alternatively, from about 1 h to about 4 h.

In a further aspect, the process of producing a $C_{20+}$ polysulfides crude product comprises lowering the temperature of the mixture. The temperature of the mixture may be adjusted to a temperature in a range of from about 50° C. to about 100° C.; alternatively, from about 65° C. to about 85° C.; or alternatively, from about 70° C. to about 75° C. The process further comprises addition of a mercaptan scavenger (e.g., propylene oxide), to the mixture. In an aspect, the mercaptan scavenger (e.g., propylene oxide), may be added to the mixture over a time period in a range of from about 1 min to about 10 h; alternatively, from about 5 min to about 6 h; or alternatively, from about 10 min to about 2 h. The mixture may then be agitated for a time period in a range of from 10 min to about 24 h; alternatively, from about 30 min to about 12 h; alternatively, from about 1 h to about 4 h; or alternatively, from about 2 h to about 3 h. The mixture may then be sparged with an inert gas (e.g., nitrogen), for a time period in a range of from 5 min to about 24 h; alternatively, from about 10 min to about 12 h; alternatively, from about 30 min to about 4 h; or alternatively, from about 1 h to about 4 h.

In a particular aspect, the process of producing a $C_{20+}$ polysulfides crude product comprises collecting a $C_{20+}$ polysulfides crude product. The $C_{20+}$ polysulfides crude product may be collected by any suitable liquid/solid separation technique known to the ordinary skilled artisan. Non-limiting examples of techniques for collecting the $C_{20+}$ polysulfides crude product include filtration (e.g., gravity, in-line, membrane, pressure, vacuum), centrifugation, gravimetric settling, hydrocyclone methods, sedimentation, or combinations thereof. In an aspect, subsequent to sparging the mixture with the inert gas, the mixture may be cooled to a temperature in a range of from about 15° C. to about 50° C., or alternatively, from about 20° C. to about 35° C. to form a cooled mixture. In a further aspect, the cooled mixture may be filtered to collect the $C_{20+}$ polysulfides crude product. Alternatively, prior to collecting the $C_{20+}$ polysulfides crude product, activated carbon of the type disclosed herein is added to the cooled mixture and the temperature of the cooled mixture is raised to a temperature in a range of from about 40° C. to about 80° C.; or alternatively, from about 50° C. to about 70° C. The mixture is then agitated for a time period in a range of from 10 min to about 12 h; alternatively, from about 1 h to about 4 h; or alternatively, from about 2 h to about 3 h. The process further comprises cooling the mixture to a temperature in a range of from about 15° C. to about 50° C., or alternatively, from about 20° C. to about 35° C. and collecting (e.g., filtering), the $C_{20+}$ polysulfides crude product.

Disclosed herein is a process of producing a $C_{20+}$ polysulfides crude product comprising contacting a feedstock comprising branched $C_{10+}$ mercaptans (e.g., a first $C_{10}$ to $C_{30}$ mercaptans feedstock or a second $C_{10}$ to $C_{30}$ mercaptans feedstock), a catalyst and a sulfur-containing material to form a mixture. In an aspect the sulfur-containing material comprises elemental sulfur and the feedstock comprises one or more branched $C_{10}$ to $C_{30}$ mercaptans as disclosed herein. The process further comprises heating the mixture to a temperature in a range of from about 40° C. to about 200° C.; alternatively, from about 60° C. to about 85° C.; or alternatively, from about 70° C. to about 80° C. wherein evolution of a reaction by-product occurs. In an aspect, the reaction by-product may be gas-phase hydrogen sulfide. The mixture may then be agitated for a time period in a range of from 30 min to about 24 h; alternatively, from about 1 h to about 12 h; alternatively, from about 2 h to about 6 h; or alternatively, from about 3 h to about 4 h.

In an aspect, the process of producing a $C_{20+}$ polysulfides crude product comprises raising the temperature of the mixture. The mixture may be heated to a temperature in a range of from about 40° C. to about 250° C.; alternatively, from about 60° C. to about 200° C.; alternatively, from about 90° C. to about 150° C.; or alternatively, from about 90° C. to about 100° C. The mixture may then be agitated for a time period in a range of from 30 min to about 24 h; alternatively, from about 1 h to about 12 h; alternatively, from about 2 h to about 4 h; or alternatively, from about 3 h to about 4 h. The mixture may then be sparged with an inert gas (e.g., nitrogen), for a time period in a range of from 5 min to about 24 h; alternatively, from about 10 min to about 12 h; alternatively, from about 30 min to about 4 h; or alternatively, from about 1 h to about 4 h.

In a further aspect, the process of producing a $C_{20+}$ polysulfides crude product comprises lowering the temperature of the mixture. The temperature of the mixture may be adjusted to a temperature in a range of from about 50° C. to about 100° C.; alternatively, from about 65° C. to about 85° C.; or alternatively, from about 70° C. to about 75° C. The process further comprises addition of a mercaptan scavenger (e.g., propylene oxide), to the mixture. In an aspect, the mercaptan scavenger (e.g., propylene oxide), may be added to the mixture over a time period in a range of from about 1 min to about 10 h; alternatively, from about 5 min to about 6 h; or alternatively, from about 10 min to about 2 h. The mixture may then be agitated for a time period in a range of from 10 min to about 24 h; alternatively, from about 30 min to about 12 h; alternatively, from about 1 h to about 4 h; or alternatively, from about 2 h to about 3 h. The mixture may then be sparged with an inert gas (e.g., nitrogen), for a time period in a range of from 5 min to about 24 h; alternatively, from about 10 min to about 12 h; alternatively, from about 30 min to about 4 h; or alternatively, from about 1 h to about 4 h.

In a particular aspect, the process of producing a $C_{20+}$ polysulfides crude product comprises collecting a $C_{20+}$ polysulfides crude product. The $C_{20+}$ polysulfides crude product may be collected by any suitable liquid/solid separation technique known to the ordinary skilled artisan. Non-limiting examples of techniques for collecting the $C_{20+}$ polysulfides crude product include filtration (e.g., gravity, in-line, membrane, pressure, vacuum), centrifugation, gravimetric settling, hydrocyclone methods, sedimentation, or combinations thereof. In an aspect, subsequent to sparging the mixture with the inert gas, the mixture may be cooled to a temperature in a range of from about 15° C. to about 50° C., or alternatively, from about 20° C. to about 35° C. to form a cooled mixture. In a further aspect, the cooled mixture may be filtered to collect the $C_{20+}$ polysulfides crude product. Alternatively, prior to collecting the $C_{20+}$ polysulfides crude product, activated carbon of the type disclosed herein is added to the cooled mixture and the temperature of the cooled mixture is raised to a temperature in a range of from about 40° C. to about 80° C.; or alternatively, from about 50° C. to about 70° C. The mixture is then agitated for a time period in a range of from 10 min to about 12 h; alternatively, from about 1 h to about 4 h; or alternatively, from about 2 h to about 3 h. The process further comprises cooling the mixture to a temperature in a range of from about 15° C. to about 50° C., or alternatively, from about 20° C. to about 35° C. and collecting (e.g., filtering), the $C_{20+}$ polysulfides crude product.

In a particular aspect of the present disclosure, a process of producing a $C_{20+}$ polysulfides crude product comprises reacting, in a reactor, a sulfur source (e.g., $H_2S$) and a feedstock comprising one or more branched $C_{10+}$ monoolefins in the presence of an initiating agent, to produce a branched $C_{10+}$ mercaptans crude composition, i.e., the process previously described herein for the branched $C_{10+}$ monoolefins. The process further comprises recovering an intermediate reaction product from the branched $C_{10+}$ mercaptans crude composition. In an aspect, the intermediate reaction product recovered from the branched $C_{10+}$ mercaptans crude composition may be a branched $C_{10+}$ mercaptans composition, a branched $C_{10+}$ mercaptans/branched $C_{20+}$ sulfides composition, or a combination thereof as previously described herein for the reaction of the branched $C_{10+}$ monoolefins. In a further aspect, the intermediate reaction product comprises one or more branched $C_{10}$ to $C_{30}$ mercaptans as previously described herein. In yet a further aspect, the intermediate reaction product may be recovered from the branched $C_{10+}$ mercaptans crude composition, for example by flashing, distillation, fractionation, stripping, absorption, etc. as previously described herein.

In an aspect, the process of producing a $C_{20+}$ polysulfides crude product comprises contacting the intermediate reaction product and a catalyst to form a mixture. The process further comprises heating the mixture to a temperature in a range of from about 40° C. to about 200° C.; alternatively, from about 60° C. to about 85° C.; or alternatively, from about 70° C. to about 80° C. The mixture may then be contacted with a sulfur-containing material (e.g., elemental sulfur) wherein evolution of a reaction by-product occurs. In an aspect, the reaction by-product may be gas-phase hydrogen sulfide. The mixture may then be agitated for a time period in a range of from 30 min to about 24 h; alternatively, from about 1 h to about 12 h; alternatively, from about 2 h to about 6 h; or alternatively, from about 3 h to about 4 h. In a further aspect, the mixture may be heated to a temperature in a range of from about 40° C. to about 250° C.; alternatively, from about 60° C. to about 200° C.; alternatively, from about 90° C. to about 150° C.; or alternatively, from about 90° C. to about 100° C. The mixture may then may be agitated for a time period in a range of from 30 min to about 24 h; alternatively, from about 1 h to about 12 h; alternatively, from about 2 h to about 4 h; or alternatively, from about 3 h to about 4 h. The mixture may then be sparged with an inert gas (e.g., nitrogen), for a time period in a range of from 5 min to about 24 h; alternatively, from about 10 min to about 12 h; alternatively, from about 30 min to about 4 h; or alternatively, from about 1 h to about 4 h. In a further aspect, the mixture may be cooled to a temperature in a range of from about 50° C. to about 100° C.; alternatively, from about 65° C. to about 85° C.; or alternatively, from about 70° C. to about 75° C. The process further comprises addition of a mercaptan scavenger (e.g., propylene oxide), to the mixture. In an aspect, the mercaptan scavenger (e.g., propylene oxide), may be added to the mixture over a time period in a range of from about 1 min to about 10 h; alternatively, from about 5 min to about 6 h; or alternatively, from about 10 min to about 2 h. The mixture may then be agitated for a time period in a range of from 10 min to about 24 h; alternatively, from about 30 min to about 12 h; alternatively, from about 1 h to about 4 h; or alternatively, from about 2 h to about 3 h. The mixture may be sparged with the inert gas (e.g., nitrogen), for a time period in a range of from 5 min to about 24 h; alternatively, from about 10 min to about 12 h; alternatively, from about 30 min to about 4 h; or alternatively, from about 1 h to about 4 h.

In a particular aspect, the process of producing a $C_{20+}$ polysulfides crude product comprises collecting a $C_{20+}$ polysulfides crude product. The $C_{20+}$ polysulfides crude product may be collected by any suitable liquid/solid separation technique known to the ordinary skilled artisan. Non-limiting examples of techniques for collecting the $C_{20+}$ polysulfides crude product include filtration (e.g., gravity, in-line, membrane, pressure, vacuum), centrifugation, gravimetric settling, hydrocyclone methods, sedimentation, or combinations thereof. In an aspect, subsequent to sparging the mixture with the inert gas, the mixture may be cooled to a temperature in a range of from about 15° C. to about 50° C., or alternatively, from about 20° C. to about 35° C. to form a cooled mixture. In a further aspect, the cooled mixture may be filtered to collect the $C_{20+}$ polysulfides crude product. Alternatively, prior to collecting the $C_{20+}$ polysulfides crude product, activated carbon of the type disclosed herein is added to the cooled mixture and the temperature of the cooled mixture is raised to a temperature in a range of from about 40° C. to about 80° C.; or alternatively, from about 50° C. to about 70° C. The mixture is then agitated for a time period in a range of from 10 min to about 12 h; alternatively, from about 1 h to about 4 h; or alternatively, from about 2 h to about 3 h. The process further comprises cooling the mixture to a temperature in a range of from about 15° C. to about 50° C., or alternatively, from about 20° C. to about 35° C. and collecting (e.g., filtering), the $C_{20+}$ polysulfides crude product.

In an aspect, a feedstock comprising branched $C_{10+}$ mercaptans (e.g., a first $C_{10}$ to $C_{30}$ mercaptans feedstock or a second $C_{10}$ to $C_{30}$ mercaptans feedstock) and a sulfur-containing material can be reacted to produce a $C_{20+}$ crude product wherein a mercaptan conversion is achieved. In an aspect, the mercaptan conversion achieved is equal to or greater than about 70%, alternatively equal to or greater than about 75%, alternatively equal to or greater than about 80%, alternatively equal to or greater than about 85%, or alternatively equal to or greater than about 90%. For purposes of the disclosure herein, a mercaptan conversion refers to the mol % of mercaptans that have reacted during the reaction between the sulfur-containing material (e.g., elemental sulfur) and the feedstock in a reactor, with respect to the amount of mercaptans introduced into the reactor during the same time period.

As noted previously, any suitable feedstock comprising branched $C_{10+}$ mercaptans as described herein (e.g., a first $C_{10}$ to $C_{30}$ mercaptans feedstock or a second $C_{10}$ to $C_{30}$ mercaptans feedstock) can be reacted with a sulfur-containing material in the presence of a catalyst to produce a branched $C_{20+}$ polysulfides crude product. The branched $C_{20+}$ polysulfides crude product can be further refined (e.g., distilled or otherwise separated into one or more fractions such as lights, intermediate, and heavies) to yield various compositions described herein. As described in more detail herein, the type and/or amounts of the constituent components that form the branched $C_{20+}$ polysulfides crude product can vary depending upon the feedstock (e.g., the amount and types of mercaptans therein), the reaction conditions, the catalysts employed, etc., and the ordinary skilled artisan can tailor the post reactor processing of the branched $C_{20+}$ polysulfides crude product to account for the specific compounds present in a given branched $C_{20+}$ polysulfides crude product to yield various desired products and compositions of the types described herein.

Upon completion of the reaction of a feedstock comprising branched $C_{10+}$ mercaptans with a sulfur-containing material, a reactor effluent may be collected (e.g., filtered) to yield a branched $C_{20+}$ polysulfides crude product, as previously described herein. The term "branched $C_{20+}$ polysulfides crude product" or "branched $C_{20+}$ polysulfides crude product" refers to an unrefined effluent stream collected from the reaction process (e.g., filtered), and in particular to an effluent stream that has not undergone any additional post-reactor processing such as flashing, distillation, or other separation techniques or processes to remove any components from the effluent stream other than the initial removal of by-products and/or solid reaction components (e.g., via filtering).

The branched $C_{20+}$ polysulfides crude product comprises branched $C_{20}$ to $C_{60}$ polysulfides and branched $C_{20}$ to $C_{60}$ monosulfides formed by the reaction of one or more branched $C_{10}$ to $C_{30}$ mercaptans and the a sulfur-containing material and the structures of these branched $C_{20}$ to $C_{60}$ polysulfides and branched $C_{20}$ to $C_{60}$ monosulfides are described in more detail herein. In addition to branched $C_{20}$ to $C_{60}$ polysulfides and branched $C_{20}$ to $C_{60}$ monosulfides, the branched $C_{20+}$ polysulfides crude composition can comprise a number of other compounds such as unreacted mercaptans (e.g., unreacted branched $C_{10}$ to $C_{30}$ mercaptans, unreacted $C_{8+}$ mercaptans), non-branched $C_{20}$ to $C_{60}$ polysulfides, non-branched $C_{20}$ to $C_{60}$ monosulfides, non-$C_{20}$ to $C_{60}$ polysulfides, non-$C_{20}$ to $C_{60}$ monosulfides, and other impurities (e.g., inert compounds). The constituent components contained within the branched $C_{20+}$ polysulfides crude product can vary depending upon the composition of the feedstock (e.g., an unpurified first $C_{10}$ to $C_{30}$ mercaptans feedstock as compared to a purified second $C_{10}$ to $C_{30}$ mercaptans feedstock as described herein) as well as reaction conditions, catalyst, etc. In various aspects, a branched $C_{20+}$ polysulfides crude product can comprise light, intermediate, and heavy fractions as described herein.

In an aspect, the branched $C_{20+}$ polysulfides crude product can contain a variety of non-$C_{20}$ to $C_{60}$ polysulfides and non-$C_{20}$ to $C_{60}$ monosulfides components (e.g., impurities) such as $C_{14}$ to $C_{19}$ polysulfides represented by the general formula $R^{19}S-[S]_n-SR^{20}$, wherein n is an integer from 1 to 10, wherein $R^{19}$ and $R^{20}$ are each independently a functional group derived from a $C_{7+}$ mercaptan, and wherein $R^{19}$ and $R^{20}$ are not both derived from a branched $C_{10+}$ mercaptan; $C_{61}$ to $C_{78}$ polysulfides represented by the general formula $R^{19}S-[S]_n-SR^{20}$, wherein n is an integer from 1 to 10, wherein $R^{19}$ and $R^{20}$ are each independently a functional group derived from a $C_{31}$ to $C_{38}$ mercaptan, and wherein $R^{19}$ and $R^{20}$ are not both derived from a branched $C_{10+}$ mercaptan; $C_{14}$ to $C_{19}$ monosulfides represented by the general formula $R^{21}-S-R^{22}$, wherein $R^{21}$ and $R^{22}$ are each independently a functional group derived from a $C_{7+}$ mercaptan, and wherein $R^{21}$ and $R^{22}$ are not both derived from a branched $C_{10+}$ mercaptan; or $C_{61}$ to $C_{78}$ monosulfides represented by the general formula $R^{21}-S-R^{22}$, wherein $R^{21}$ and $R^{22}$ are each independently a functional group derived from a $C_{31}$ to $C_{38}$ mercaptan, and wherein $R^{21}$ and $R^{22}$ are not both derived from a branched $C_{10+}$ mercaptan.

In an aspect, the branched $C_{20+}$ polysulfides crude product can contain a variety of non-branched $C_{20}$ to $C_{60}$ polysulfides and non-branched $C_{20}$ to $C_{60}$ monosulfides, such as $C_{20}$ to $C_{60}$ polysulfides represented by the general formula $R^{19}S-[S]_n-SR^{20}$ wherein n is an integer from 1 to 10, and wherein $R^{19}$ and $R^{20}$ are each independently a non-branched $C_{10}$ to $C_{30}$ alkyl group; and $C_{20}$ to $C_{60}$ monosulfides represented by the general formula $R^{21}-S-R^{22}$ wherein $R^{21}$ and $R^{22}$ are each independently a non-branched $C_{10}$ to $C_{30}$ alkyl group. In a further aspect, the non-branched $C_{20}$ to $C_{60}$ polysulfides can comprise $C_{20}$ to $C_{60}$ polysulfides represented by the general formula $R^{19}S-[S]_n-SR^{20}$ wherein n is an integer from 1 to 10, wherein $SR^{19}$ and $SR^{20}$ are each independently a functional group derived from a linear $C_{10}$ to $C_{30}$ mercaptan represented by Structure M-1, Structure N-1, Structure O-1, or Structure P-1, as previously disclosed herein, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group, as previously disclosed herein; and the non-branched $C_{20}$ to $C_{60}$ monosulfides can comprise $C_{20}$ to $C_{60}$ monosulfides represented by the general formula $R^{21}-S-R^{22}$ wherein $R^{21}$ and $R^{22}$ are each independently a functional group derived from a linear $C_{10}$ to $C_{30}$ olefin represented by Structure Q-1, Structure R-1, or Structure S-1, as previously disclosed herein, wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

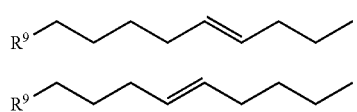

Structure Q-1

Structure R-1

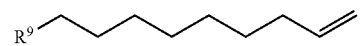

Structure S-1

In a further aspect, the branched $C_{20+}$ polysulfides crude product can contain a variety of non-mercaptan impurities selected from the group consisting of $C_8$ to $C_{78}$ olefins, $C_8$ to $C_{14}$ alkanes, cyclohexane, methylcyclopentane, methylcyclohexane, benzene, toluene, ethylbenzene, xylene, mesitylene, hexamethylbenzene, $C_4$ to $C_{12}$ alcohols, 2-ethyl-1-hexanol, and 2-ethylhexyl-2-ethylhexanoate, and combinations thereof.

In an aspect, a process of reacting a feedstock comprising branched $C_{10+}$ mercaptans and a sulfur-containing material to produce a $C_{20+}$ crude product can further comprise recovering a process product from the branched $C_{20+}$ polysulfides crude product, wherein the process product can comprise branched $C_{20+}$ polysulfides and/or branched $C_{20+}$ monosulfides, wherein the branched $C_{20+}$ polysulfides comprise branched $C_{20}$ to $C_{60}$ polysulfides represented by the general formula $R^{15}S^1-[S]_n-S^2R^{16}$ wherein n is an integer from 1 to 10, wherein the branched $C_{20+}$ monosulfides comprise branched $C_{20}$ to $C_{60}$ monosulfides represented by the general formula $R^{17}-S-R^{18}$, wherein $R^{15}$, $R^{16}$, $R^{17}$, and $R^{18}$ are each independently an alkyl group, and wherein the alkyl group comprises a branched $C_{10}$ to $C_{30}$ alkyl group as disclosed herein.

In an aspect, the process product can comprise a branched $C_{20+}$ polysulfides composition (heavy fraction; primary reaction product), a branched $C_{20+}$ monosulfides composition (intermediate fraction; side reaction product), a branched $C_{20+}$ polysulfides/branched $C_{20+}$ monosulfides composition (intermediate and heavy fractions; primary and side reaction products), or combinations thereof.

In an aspect, a branched $C_{20+}$ polysulfides crude product comprising branched $C_{20+}$ polysulfides and branched $C_{20+}$ monosulfides as disclosed herein can be separated into two or more fractions (e.g., light fraction, intermediate fraction, heavy fraction, etc.) by any process or unit operation known in the art. For example, a branched $C_{20+}$ polysulfides crude product can be processed (e.g., distilled) to remove a fraction of light compounds. Alternatively, a branched $C_{20+}$ polysulfides crude product can be processed to recover both a light fraction and an intermediate fraction (e.g., a rough cut), followed by further processing to obtain one or more fine cuts. Alternatively, a branched $C_{20+}$ polysulfides crude product can be processed to recover a heavy fraction (e.g., a $C_{20+}$ polysulfides fraction). Alternatively, a branched $C_{20+}$ polysulfides crude product can be processed to separate out any combination of a light fraction, an intermediate fraction (e.g., comprising $C_{20+}$ monosulfides, including branched $C_{20+}$ monosulfides), and a heavy fraction (e.g., comprising $C_{20+}$ polysulfides, including branched $C_{20+}$ polysulfides). Furthermore, a light, intermediate or heavy fraction (e.g., a rough cut) can be further processed or parsed to obtain one or more desired fine cuts (e.g., a $C_{20}$ to $C_{60}$ polysulfides fraction). Alternatively, a branched $C_{20+}$ polysulfides crude product can be separated to produce a high-purity $C_{20+}$ polysulfides stream and/or a high-purity $C_{20+}$ monosulfides (e.g., to obtain a desired fine cut or fraction such as a $C_{20}$ to $C_{60}$ polysulfides fraction). Further, these separated streams can be blended in any combination of ratios to produce a mixture with specific concentrations of one or more components (e.g., desired blend ratios of branched $C_{20+}$ polysulfides and/or branched $C_{20+}$ monosulfides, for example to aid in a particular end use). The unit operations/processes used for these separations are known to one of skill and the art and include, but are not limited to, distillation, fractionation, flashing, stripping, and absorption, and others. The unit operation conditions, such as for example, temperature, pressure, flow rates, and others at which these unit operations produce one or more of the desired fractions can be determined by one of ordinary skill in the art.

In an aspect, a light fraction is removed from the $C_{20+}$ polysulfides mercaptans crude composition, for example by flashing, distillation, fractionation, stripping, absorption, etc. In an aspect, the light fraction removed from the branched $C_{20+}$ polysulfides crude product can comprise at least about 90 wt. %, alternatively at least about 92 wt. %, alternatively at least about 95 wt. %, alternatively at least about 96 wt. %, alternatively at least about 97 wt. %, alternatively at least about 98 wt. %, or alternatively at least about 99 wt. % $C_{19-}$ metasulfides based on the total weight of the light fraction, wherein the $C_{19-}$ metasulfides comprise $C_{19-}$ polysulfides, $C_{19-}$ monosulfides, or a combination thereof. In a further aspect, the light fraction removed from the branched $C_{20+}$ polysulfides crude product can comprise at least about 90 wt. %, alternatively at least about 92 wt. %, alternatively at least about 95 wt. %, alternatively at least about 96 wt. %, alternatively at least about 97 wt. %, alternatively at least about 98 wt. %, or alternatively at least about 99 wt. % unreacted mercaptans based on the total weight of the light fraction, wherein the unreacted mercaptans comprise unreacted $C_{10+}$ mercaptans, unreacted $C_{9-}$ mercaptans, or a combination thereof. In a further aspect, the light fraction removed from the branched $C_{20+}$ polysulfides crude product can comprise at least about 90 wt. %, alternatively at least about 92 wt. %, alternatively at least about 95 wt. %, alternatively at least about 96 wt. %, alternatively at least about 97 wt. %, alternatively at least about 98 wt. %, or alternatively at least about 99 wt. % $C_{9-}$ compounds, based on the total weight of the light fraction. Non-limiting examples of $C_{9-}$ compounds include $C_{9-}$ monoolefins, $C_{9-}$ alkanes, cyclohexane, methylcyclopentane, methylcyclohexane, benzene, toluene, ethylbenzene, xylene, mesitylene, $C_{9-}$ alcohols, 2-ethyl-1-hexanol, and the like, or combinations thereof. In an aspect, the light fraction removed from the branched $C_{20+}$ polysulfides crude product can comprise less than about 10 wt. %, alternatively less than about 5 wt. %, alternatively less than about 4 wt. %, alternatively less than about 3 wt. %, alternatively less than about 2 wt. %, or alternatively less than about 1 wt. % $C_{20+}$ compounds, based on the total weight of the light fraction. Non-limiting examples of $C_{20+}$ compounds include $C_{20+}$ polysulfides, $C_{20+}$ monosulfides, $C_{20+}$ monoolefins and $C_{20+}$ alkanes.

Following removal of the lights (for example, via flashing) from the branched $C_{20+}$ polysulfides crude product, a combined intermediate and heavy fraction (i.e., $C_{20+}$ polysulfides and $C_{20+}$ monosulfides), can remain, and the combined intermediate and heavy fraction can be used "as is" or can be further processed, for example separated or split into separate intermediate and heavy fractions (and said separate intermediate and heavy fractions can be subsequently recombined in various blends and associated blend ratios), as described in more detail herein. In an aspect, the combined intermediate and heavy fraction formed by removal of the light fraction from the branched $C_{20+}$ polysulfides crude product can comprise less than about 15 wt. %, alternatively less than about 10 wt. %, alternatively less than about 9 wt. %, alternatively less than about 8 wt. %, alternatively less than about 7 wt. %, alternatively less than about 6 wt. %, alternatively less than about 5 wt. %, alternatively less than about 4 wt. %, alternatively less than about 3 wt. %, alternatively less than about 2 wt. %, or alternatively less than about 1 wt. % $C_{9-}$ products, based on the total weight of the combined intermediate and heavy fraction.

In an aspect, a combined intermediate and heavy fraction (i.e., $C_{20+}$ polysulfides and $C_{20+}$ monosulfides) recovered from the branched $C_{20+}$ polysulfides crude product can comprise (A) at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % polysulfides, based on the total weight of the combined intermediate and heavy fraction; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the polysulfides can be branched $C_{20}$ to $C_{60}$ polysulfides selected from the group consisting of a branched $C_{20}$ to $C_{60}$ polysulfide represented by general formula $R^{15}S^1$—$[S]_nS^2R^{16}$, wherein n is an integer from 1 to 10, wherein $R^{15}$ and $R^{16}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group; and (B) at least about 10 wt. %, alternatively at least about 15 wt. %, alternatively at least about 20 wt. %, alternatively at least about 25 wt. %, or alternatively at least about 30 wt. % monosulfides based on the total weight of the combined intermediate and heavy fraction; wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the monosulfides can be a branched $C_{20}$ to $C_{60}$ monosulfide represented by general formula $R^{17}$—S—$R^{18}$, wherein $R^{17}$ and $R^{18}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an attachment point with a sulfur atom of the branched $C_{20}$ to $C_{60}$ monosulfide, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

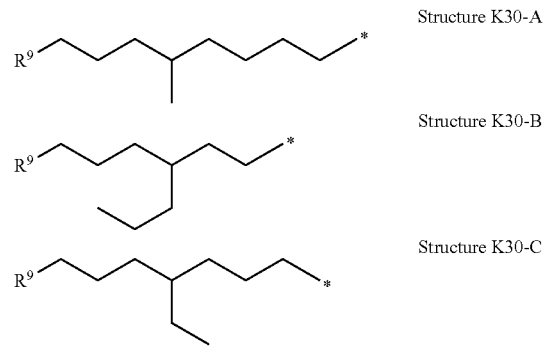

Structure K30-A

Structure K30-B

Structure K30-C

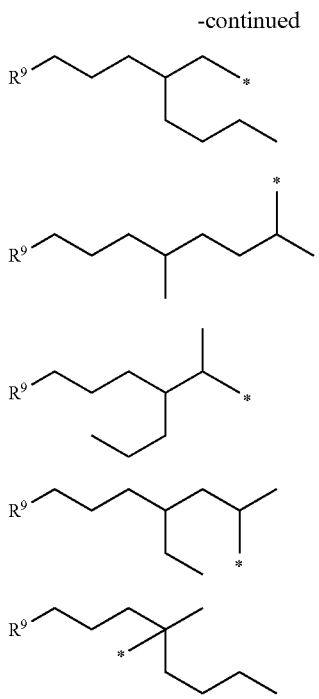

Structure K30-D

Structure K30-E

Structure K30-F

Structure K30-G

Structure K30-H

In an aspect, the branched $C_{20+}$ polysulfides crude product can be flashed to remove a light fraction as described herein to produce a combined intermediate and heavy fraction (i.e., $C_{20+}$ polysulfides and $C_{20+}$ monosulfides), comprising: (A) at least about 25, 30, 35, 40, 45, 50, 55, 60, 65, 70, 75, 80, or 85 wt. % branched $C_{20+}$ polysulfides selected from the group consisting of a branched $C_{20}$ to $C_{60}$ polysulfide represented by structure $R^{15}S^1$—$[S]_n$—$S^2R^{16}$, wherein n is an integer from 1 to 10, wherein $R^{15}$ and $R^{16}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group; and (B) at least about 5, 10, 15, 20, 25, or 30 wt. % branched $C_{20+}$ monosulfides represented by general formula $R^{17}$—S—$R^{18}$, wherein $R^{17}$ and $R^{18}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an attachment point with a sulfur atom of the branched $C_{20+}$ monosulfide, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In an aspect, the branched $C_{20+}$ polysulfides crude product can be flashed to remove a lights fraction as described herein to produce a combined intermediate and heavy fraction (i.e., $C_{20+}$ polysulfides and $C_{20+}$ monosulfides), comprising: (A) from at least about 50 wt. % to at least about 90 wt. %, alternatively from at least about 55 wt. % to at least about 85 wt. %, or alternatively from at least about 60 wt. % to at least about 80 wt. % polysulfides, wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the polysulfides can be branched $C_{20}$ to $C_{60}$ polysulfides selected from the group consisting of a branched $C_{20}$ to $C_{60}$ polysulfide represented by general formula $R^{15}S^1$—$[S]_n$—$S^2R^{16}$, wherein n is an integer from 1 to 10, wherein $R^{15}$ and $R^{16}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group; and (B) from at least about 10 wt. % to at least about 30 wt. %, alternatively from at least about 10 wt. % to at least about 25 wt. %, alternatively from at least about 12.5 wt. % to at least about 22.5 wt. %, or alternatively from at least about 15 wt. % to at least about 20 wt. % monosulfides, wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the monosulfides can be a branched $C_{20}$ to $C_{60}$ monosulfide represented by general formula $R^{17}$—S—$R^{18}$, wherein $R^{17}$ and $R^{18}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an attachment point with a sulfur atom of the branched $C_{20}$ to $C_{60}$ monosulfide, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In an aspect, the branched $C_{20+}$ polysulfides crude product can be flashed to remove a light fraction and subsequently further separated to produce an intermediate fraction and a heavy fraction. Each of the intermediate fraction and the heavy fraction recovered from the branched $C_{20+}$ polysulfides crude product can then be optionally further processed (e.g., polished) and mixed in any appropriate ratio to produce blended compositions, as previously described herein for crude compositions derived from branched $C_{10+}$ monoolefins.

In an aspect, the heavy fraction recovered from the branched $C_{20+}$ polysulfides crude product can comprise at least about 25 wt. %, alternatively at least about 30 wt. %, alternatively at least about 40 wt. %, alternatively at least about 50 wt. %, alternatively at least about 75 wt. %, or alternatively at least about 85 wt. % $C_{20+}$ polysulfides, based on the total weight of the heavy fraction, wherein the $C_{20+}$ polysulfides are branched $C_{20}$ to $C_{60}$ polysulfides as disclosed herein.

In an aspect, an intermediate fraction recovered from the branched $C_{20+}$ polysulfides crude product can comprise at least about 5, 10, 15, 20, 25, 30, 35, 40, 45, 50, 55, 60, 65, 70, 75, 80, or 85 wt. %, $C_{20+}$ monosulfides, based on the total weight of the intermediate fraction, wherein the $C_{20+}$ monosulfides are branched $C_{20}$ to $C_{60}$ monosulfides as disclosed herein.

In an aspect, the branched $C_{20+}$ polysulfides crude product can be separated into light, intermediate, and heavy fractions by distillation, for example in a single distillation column having a light fraction recovered as an overhead stream, an intermediate fraction (e.g., comprising $C_{20+}$ monosulfides)

recovered as a side stream, and a heavy fraction (e.g., comprising $C_{20+}$ polysulfides) recovered as a bottom stream. In alternative aspects, the separation can be in sequential steps such as removal of the lights fraction in a first distillation column, followed by separation of the intermediate fraction (e.g., comprising $C_{20+}$ monosulfides) as an overhead stream in a second distillation column and the heavy fraction (e.g., comprising $C_{20+}$ polysulfides) as a bottom stream of the second distillation column. These "rough-cut" light, intermediate, and heavy streams can be used "as is" or they can be further processed (e.g., further refined or polished, for example by additional distillation or other separation techniques to produce "fine-cuts") and/or blended to obtain a variety of products that are salable or otherwise available for a variety of end uses such as mining ore collector compositions or chain transfer agents. For example, a variety of $C_{20+}$ polysulfides compositions, $C_{20+}$ monosulfides compositions, and $C_{20+}$ metasulfides compositions (i.e., mixed $C_{20+}$ polysulfides/$C_{20+}$ monosulfides compositions) of the type disclosed herein can be produced as disclosed herein.

In aspects where the mercaptan feedstock (e.g., mercaptan feedstock reacted with a sulfur-containing material to produce the branched $C_{20+}$ polysulfides crude product) comprises $C_{10}$ to $C_{19}$ mercaptans, the intermediate fraction comprises $C_{20}$ to $C_{38}$ monosulfides, and the heavy fraction comprises $C_{20}$ to $C_{38}$ polysulfides.

In aspects where the mercaptan feedstock (e.g., mercaptan feedstock reacted with a sulfur-containing to produce the branched $C_{20+}$ polysulfides crude product) comprises $C_{20}$ to $C_{30}$ mercaptans, the intermediate fraction comprises $C_{40}$ to $C_{60}$ monosulfides, and the heavy fraction comprises $C_{40}$ to $C_{60}$ polysulfides.

In aspects where the mercaptan feedstock (e.g., mercaptan feedstock reacted with a sulfur-containing material to produce the branched $C_{20+}$ polysulfides crude product) comprises $C_{10}$ to $C_{30}$ mercaptans, the intermediate and heavy fractions recovered by distillation can comprise mercaptans and sulfides as follows. In some aspects, the intermediate fraction can comprise $C_{10}$ to $C_{19}$ monosulfides, and the heavy fraction can comprise $C_{20}$ to $C_{30}$ monosulfides and $C_{20}$ to $C_{60}$ polysulfides. In other aspects, intermediate fraction can comprise $C_{10}$ to $C_{30}$ monosulfides and $C_{20}$ to $C_{30}$ polysulfides, and the heavy fraction can comprise $C_{31}$ to $C_{60}$ polysulfides. In yet other aspects, a first intermediate fraction can comprise $C_{10}$ to $C_{19}$ monosulfides, a second intermediate fraction can comprise $C_{20}$ to $C_{30}$ monosulfides and $C_{20}$ to $C_{30}$ polysulfides, and the heavy fraction can comprise $C_{31}$ to $C_{60}$ polysulfides. Intermediate and heavy fractions comprising both monosulfides and polysulfides could be used as recovered (e.g., mixed monosulfides/polysulfides compositions) or can be further processed to separate and recover further monosulfides compositions and polysulfides compositions.

In an aspect, an intermediate fraction can comprise at least about 25, 30, 40, 50, 75, or 85 wt. % branched $C_{20+}$ monosulfides. In such aspect, the branched $C_{20+}$ monosulfides can be selected from the group consisting of a branched $C_{20}$ to $C_{60}$ monosulfide represented by general formula $R^{17}$—S—$R^{18}$, wherein $R^{17}$ and $R^{18}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an attachment point with a sulfur atom of the branched $C_{20}$ to $C_{60}$ monosulfide, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In an aspect, the heavy fraction can comprise at least about 5, 10, 15, 20, 25, 30, 35, 40, 45, 50, 55, 60, 65, 70, 75, 80, or 85 wt. % branched $C_{20+}$ polysulfides. In such aspect, the branched $C_{20+}$ polysulfides can be selected from the group consisting of a branched $C_{20}$ to $C_{60}$ polysulfide represented by general formula $R^{15}S^1$—$[S]_n$—$S^2R^{16}$, wherein n is an integer from 1 to 10, wherein $R^{15}$ and $R^{16}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In an aspect, a $C_{20+}$ polysulfides composition can comprise $C_{20+}$ polysulfides, wherein at least a portion of the $C_{20+}$ polysulfides comprise branched $C_{20+}$ polysulfides. Further for purposes of the disclosure herein, branched $C_{20+}$ polysulfides refer to polysulfides that are represented by the general formula $R^{15}S^1$—$[S]_n$—$S^2R^{16}$, wherein n is an integer from 1 to 10, wherein $R^{15}$ and $R^{16}$ are each a branched alkyl group (i.e., a non-linear alkyl group, or in other words an alkyl group substituted with alkyl substituents), and wherein $R^{15}$ and $R^{16}$ can each independently have from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In an aspect, the branched $C_{20+}$ polysulfides of the present disclosure comprise branched $C_{20}$ to $C_{60}$ polysulfides wherein the branched $C_{20}$ to $C_{60}$ polysulfides can comprise a branched $C_{20}$ to $C_{60}$ polysulfide represented by general formula $R^{15}S^1$—$[S]_n$—$S^2R^{16}$, wherein n is an integer from 1 to 10, wherein $R^{15}$ and $R^{16}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group. For purposes of the disclosure herein a polysulfide (e.g., a branched $C_{20}$ to $C_{60}$ polysulfide) will be referred to by the total number of carbon atoms, as opposed to the number of carbons of only one of the alkyl groups present in the polysulfide. For example, wherein x is an integer from 3 to 12, a $H_{21}C_{10}$—$S_x$—$C_{10}H_{21}$ polysulfide will be referred to as a $C_{20}$ polysulfide (rather than a $C_{10}$ polysulfide); a $H_{25}C_{12}$—$S_x$—$C_{14}H_{29}$ polysulfide will be referred to as a $C_{26}$ polysulfide (rather than a $C_{12}$ polysulfide or a $C_{14}$ polysulfide); a $H_{45}C_{22}$—$S_xC_{22}H_{45}$ polysulfide will be referred to as a $C_{44}$ polysulfide (rather than a $C_{22}$ polysulfide); etc. The polysulfides of the present disclosure comprise two alkyl groups linked by a group of sulfur atoms comprising from two to twelve, or alternatively three to six sulfur atoms. Further, for purposes of the disclosure herein, the specific number of sulfur atoms comprising the polysulfide is not distinguished. For example, in regard to $C_{20}$ polysulfides represented by the general formula $H_{21}C_{10}S$—$[S]_n$—$SC_{10}H_{21}$ when n is 1, the corresponding $C_{20}$ trisulfide has formula $H_{21}C_{10}$—SSS—$C_{10}H_{21}$; alternatively, when n is 2, the corresponding $C_{20}$ tetrasulfide has formula $H_{21}C_{10}$—SSSS—$C_{10}H_{21}$; alternatively, when n is 3, the corresponding $C_{20}$ pentasulfide has formula $H_{21}C_{10}$—SSSSS—$C_{10}H_{21}$; etc. In such aspects, the $C_{20}$ trisulfide, the $C_{20}$ tetrasulfide, and the $C_{20}$ pentasulfide are referred to as a $C_{20}$ polysulfide. In a further aspect, a polysulfide of the present disclosure may be termed a "Mixed Intermediate Polysulfide" (MIPS) and described with an average number of sulfur atoms within the polysulfide and a weight percentage of sulfur within the polysulfide. In a nonlimiting example, a $C_{20}$ polysulfide having an average molecular formula $H_{21}C_{10}$—{SSS}—$C_{10}H_{21}$ represents a polysulfide comprising an average of three sulfur atoms (i.e., "{ }" brackets indicate an average number of sulfur atoms) and further comprising 25 wt. % sulfur based on the formula weight of the average molecular formula and may be termed a MIPS 325. In a further nonlimiting example, a $C_{20}$ polysulfide having an average molecular formula $H_{21}C_{10}$—{SSSSS}—$C_{10}H_{21}$ represents a polysulfide comprising an average of five sulfur atoms and further comprising 37 wt. % sulfur based on the formula weight of the average molecular formula and may be termed a MIPS 537. Further for purposes of the disclosure herein a composition comprising polysulfides, wherein at least a portion of the polysulfides are branched $C_{20+}$ polysulfides (e.g., branched $C_{20}$ to $C_{60}$ polysulfides as disclosed herein) can also be referred to as a "branched $C_{20+}$ polysulfides composition." In an aspect, the branched $C_{20+}$ polysulfides composition can comprise any suitable amount of branched $C_{20}$ to $C_{60}$ polysulfides.

In an aspect, the $C_{20+}$ polysulfides can further comprise non-branched $C_{20+}$ polysulfides, such as linear $C_{20}$ to $C_{60}$ polysulfides represented by general formula $R^{15}S^1$—$[S]_n$—$S^2R^{16}$, wherein n is an integer from 1 to 10, wherein $R^{15}S^1$ and $R^{16}S^2$ can each independently be a functional group derived from a mercaptan, wherein the mercaptan may be a $C_{10}$ to $C_{30}$ mercaptan represented by Structure M-1, Structure N-1, Structure O-1, or Structure P-1, as previously disclosed herein, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In aspects where $R^9$ is a methyl group, the $C_{20+}$ polysulfides can further comprise non-branched $C_{10}$ polysulfides. The non-branched $C_{10}$ polysulfides can be represented by general formula $R^{15}S^1$—$[S]_n$—$S^2R^{16}$, wherein n is an integer from 1 to 10, wherein $R^{15}S^1$ and $R^{16}S^2$ can each independently be a functional group derived from a mercaptan, wherein the mercaptan may be a $C_{10}$ mercaptan represented by Structure M, Structure N, Structure O, or Structure P, as previously disclosed herein.

In some aspects, a $C_{20+}$ polysulfides composition can comprise at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % $C_{20+}$ polysulfides, based on the total weight of the $C_{20+}$ polysulfides composition; wherein at least about 50 wt. %, alternatively at least about 60 wt. %, alternatively at least about 70 wt. %, alternatively at least about 75 wt. %, alternatively at least about 80 wt. %, or alternatively at least 85 wt. % of the $C_{20+}$ polysulfides can be $C_{20}$ to $C_{60}$ polysulfides represented by the general formula $R^{15}S^1$—$[S]_n$—$S^2R^{16}$, wherein n is an integer from 1 to 10, wherein $R^{15}$ and $R^{16}$ are each a branched alkyl group, and wherein $R^{15}$ and $R^{16}$ can each independently have from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspects, the branched $C_{20}$ to $C_{60}$ polysulfides can be selected from the group consisting of a branched $C_{20}$ to $C_{60}$ polysulfide represented by the general formula $R^{15}S^1$—$[S]_n$—$S^2R^{16}$, wherein n is an integer from 1 to 10, wherein $R^{15}$ and $R^{16}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In other aspects, a $C_{20+}$ polysulfides composition can comprise at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % polysulfides, wherein at least a portion of the polysulfides can be branched $C_{20}$ to $C_{60}$ polysulfides represented by the general $R^{15}S^1$—$[S]_n$—$S^2R^{16}$, wherein n is an integer from 1 to 10, wherein $R^{15}$ and $R^{16}$ are each a branched alkyl group, and wherein $R^{15}$ and $R^{16}$ can each independently have from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspects, the branched $C_{20}$ to $C_{60}$ polysulfides can be selected from the group consisting of a branched $C_{20}$ to $C_{60}$ polysulfide represented by general formula $R^{15}S^1$—$[S]_n$—$S^2R^{16}$, wherein n is an integer from 1 to 10, wherein $R^{15}$ and $R^{16}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In yet other aspects, a $C_{20+}$ polysulfides composition can comprise at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % polysulfides; wherein at least about 50 wt. %, alternatively at least about 60 wt. %, alternatively at least about 70 wt. %, alternatively at least about 75 wt. %, alternatively at least about 80 wt. %, or alternatively at least 85 wt. % of the polysulfides can be branched $C_{20}$ to $C_{60}$ polysulfides represented by the general formula $R^{15}S^1$—$[S]_n$—$S^2R^{16}$, wherein n is an integer from 1 to 10, wherein $R^{15}$ and $R^{16}$ are each a branched alkyl group, and wherein $R^{15}$ and $R^{16}$ can each independently have from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspects, the branched $C_{20}$ to $C_{60}$ polysulfides can be selected from the group consisting of a branched $C_{20}$ to $C_{60}$ polysulfide represented by general formula $R^{15}S^1$—$[S]_n$—$S^2R^{16}$, wherein n is an integer from 1 to 10, wherein $R^{15}$ and $R^{16}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In still yet other aspects, a $C_{20+}$ polysulfides composition can comprise at least about 50, 55, 60, 65, 70, 75, 80, 85, 90, 95, or 99 wt. % polysulfides; wherein at least about 25, 30, 35, 40, 45, 50, 55, 60, 65, 70, 75, 80, 85, 90, 95, or 99 wt. % of the polysulfides can be branched $C_{20}$ to $C_{60}$ polysulfides represented by the general formula $R^{15}S^1$—$[S]_n$—$S^2R^{16}$, wherein n is an integer from 1 to 10, wherein $R^{15}$ and $R^{16}$ are each a branched alkyl group, and wherein $R^{15}$ and $R^{16}$ can each independently have from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspects, the branched $C_{20}$ to $C_{60}$ polysulfides can be selected from the group consisting of a branched $C_{20}$ to $C_{60}$ polysulfide represented by general formula $R^{15}S^1$—$[S]_n$—$S^2R^{16}$, wherein n is an integer from 1 to 10, wherein $R^{15}$ and $R^{16}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In still yet other aspects, a $C_{20+}$ polysulfides composition can comprise from at least about 50 wt. % to at least about 90 wt. %, alternatively from at least about 55 wt. % to at least about 85 wt. %, or alternatively from at least about 60 wt. % to at least about 80 wt. % polysulfides, wherein at least about 50 wt. %, alternatively at least about 60 wt. %, alternatively at least about 70 wt. %, alternatively at least about 75 wt. %, alternatively at least about 80 wt. %, or alternatively at least about 85 wt. % of the polysulfides can be branched $C_{20}$ to $C_{60}$ polysulfides represented by the general formula $R^{15}S^1$—$[S]_n$—$S^2R^{16}$, wherein n is an integer from 1 to 10, wherein $R^{15}$ and $R^{16}$ are each a branched alkyl group, and wherein $R^{15}$ and $R^{16}$ can each independently have from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspects, the branched $C_{20}$ to $C_{60}$ polysulfides can be selected from the group consisting of a branched $C_{20}$ to $C_{60}$ polysulfide represented by general formula $R^{15}S^1$—$[S]_n$—$S^2R^{16}$, wherein n is an integer from 1 to 10, wherein $R^{15}$ and $R^{16}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In still yet other aspects, a $C_{20+}$ polysulfides composition can consist of, or consist essentially of, branched $C_{20}$ to $C_{60}$ polysulfides represented by the general formula $R^{15}S^1$—$[S]_n$—$S^2R^{16}$, wherein n is an integer from 1 to 10, wherein $R^{15}$ and $R^{16}$ are each a branched alkyl group, and wherein $R^{15}$ and $R^{16}$ can each independently have from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspects, the branched $C_{20}$ to $C_{60}$ polysulfides can be selected from the group consisting of a branched $C_{20}$ to $C_{60}$ polysulfide represented by general formula $R^{15}S^1$—$[S]_n$—$S^2R^{16}$, wherein n is an integer from 1 to 10, wherein $R^{15}$ and $R^{16}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In still yet other aspects, a $C_{20+}$ polysulfides composition can comprise at least about 1, 5, 10, 15, 20, 25, 30, 35, 40, 45, 50, 55, 60, 65, 70, 75, 80, 85, 90, 95, or 99 wt. % branched $C_{20}$ to $C_{60}$ polysulfides represented by the general formula $R^{15}S^1$—$[S]_n$—$S^2R^{16}$, wherein n is an integer from 1 to 10, wherein $R^{15}$ and $R^{16}$ are each a branched alkyl group, and wherein $R^{15}$ and $R^{16}$ can each independently have from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspects, the branched $C_{20}$ to $C_{60}$ polysulfides can be selected from the group consisting of a branched $C_{20}$ to $C_{60}$ polysulfide represented by general formula $R^{15}S^1$—$[S]_n$—$S^2R^{16}$, wherein n is an integer from 1 to 10, wherein $R^{15}$ and $R^{16}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In still yet other aspects, a $C_{20+}$ polysulfides composition can comprise polysulfides, wherein at least about 50, 55, 60, 65, 70, 75, 80, 85, 90, 95, or 99 wt. % of the polysulfides are branched $C_{20}$ to $C_{60}$ polysulfides represented by the general formula $R^{15}S^1$—$[S]_n$—$S^2R^{16}$, wherein n is an integer from 1 to 10, wherein $R^{15}$ and $R^{16}$ are each a branched alkyl group, and wherein $R^{15}$ and $R^{16}$ can each independently have from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspects, the branched $C_{20}$ to $C_{60}$ polysulfides can be selected from the group consisting of a branched $C_{20}$ to $C_{60}$ polysulfide represented by general formula $R^{15}S^1$—$[S]_n$—$S^2R^{16}$, wherein n is an integer from 1 to 10, wherein $R^{15}$ and $R^{16}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In an aspect, a $C_{20+}$ monosulfides composition can comprise monosulfides, wherein at least a portion of the monosulfides comprise $C_{20+}$ monosulfides, and wherein at least a portion of the $C_{20+}$ monosulfides comprise branched $C_{20}$ to $C_{60}$ monosulfides. The term monosulfide as used herein refers to a thioether that is characterized by the general formula $R^{17}$—S—$R^{18}$, wherein $R^{17}$ and $R^{18}$ are alkyl groups. The term monosulfide is used herein in place of the term sulfide, which is a common name for a thioether, to distinguish a sulfide comprising a single sulfur atom (i.e., monosulfide), from a sulfide comprising more than one sulfur atom (i.e., polysulfide). In a further aspect, the $C_{20+}$ monosulfides composition of the present disclosure is comparable to a $C_{20+}$ sulfides composition previously disclosed herein that is produced by reacting, in a reactor, a sulfur source (e.g., $H_2S$) and a feedstock comprising one or more branched $C_{10+}$ monoolefins in the presence of an initiating agent. In a further aspect, the components of the $C_{20+}$ monosulfides composition of the present disclosure, (e.g., the monosulfides, the $C_{20+}$ monosulfides and the branched $C_{20}$ to $C_{60}$ monosulfides) are identical to the components of the $C_{20+}$ sulfides composition previously disclosed herein, (e.g., the sulfides, the $C_{20+}$ sulfides and the branched $C_{20}$ to $C_{60}$ sulfides, respectively). It will be appreciated that the $C_{20+}$ monosulfides composition is thoroughly described as the $C_{20+}$ sulfides composition that is produced by reacting, in a reactor, a sulfur source (e.g., $H_2S$) and a feedstock comprising one or more branched $C_{10+}$ monoolefins in the presence of an initiating agent as previously disclosed herein. For the sake of clarity and brevity no further description of the $C_{20+}$ monosulfides composition is provided herein.

In an aspect, a $C_{20+}$ polysulfides/$C_{20+}$ monosulfide composition (i.e., a $C_{20+}$ metasulfides composition) can comprise one or more polysulfides and one or more monosulfides of the type disclosed herein. For purposes of the disclosure herein, a composition comprising (i) polysulfides, wherein at least a portion of the polysulfides are branched $C_{20}$ to $C_{60}$ polysulfides, and (ii) monosulfides, wherein at least a portion of the monosulfides are branched $C_{20}$ to $C_{60}$ monosulfides, can also be referred to as a "branched $C_{20+}$ polysulfides/branched $C_{20+}$ monosulfides composition." In an aspect, the $C_{20+}$ polysulfides/$C_{20+}$ monosulfides composition can comprise any suitable amount of branched $C_{10}$ to $C_{30}$ polysulfides and any suitable amount of branched $C_{20}$ to $C_{60}$ monosulfides.

In an aspect, a $C_{20+}$ polysulfides/$C_{20+}$ monosulfides composition can comprise (A) at least about 1 wt. %, alternatively at least about 5 wt. %, alternatively at least about 10 wt. %, alternatively at least about 15 wt. %, alternatively at least about 20 wt. %, alternatively at least about 25 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % polysulfides, wherein at least a portion of the polysulfides can be branched $C_{20}$ to $C_{60}$ polysulfides represented by the general formula $R^{15}S^1$—$[S]_n$—$S^2R^{16}$, wherein n is an integer from 1 to 10; and (B) at least about 1 wt. %, alternatively at least about 5 wt. %, alternatively at least about 10 wt. %, alternatively at least about 20 wt. %, alternatively at least about 30 wt. %, alternatively at least about 40 wt. %, alternatively at least about 50 wt. %, alternatively at least about 60 wt. %, alternatively at least about 70 wt. %, alternatively at least about 80 wt. %, alternatively at least about 90 wt. %, alternatively at least about 95 wt. %, or alternatively at least about 99 wt. % monosulfides, wherein at least a portion of the monosulfides can be branched $C_{20}$ to $C_{60}$ monosulfides represented by general formula $R^{17}$—S—$R^{18}$; wherein $R^{15}$, $R^{16}$, $R^{17}$, and $R^{18}$ can each independently be a branched alkyl group comprising from 10 to 30 carbon atoms, alternatively from 11 to 30 carbon atoms, alternatively from 12 to 30 carbon atoms, alternatively from 14 to 30 carbon atoms, alternatively from 16 to 28 carbon atoms, or alternatively from 18 to 26 carbon atoms. In such aspect, $R^{15}$ and $R^{16}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and $R^{17}$ and $R^{18}$ can each independently be a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an attachment point with a sulfur atom of the branched $C_{20}$ to $C_{60}$ monosulfide, wherein $R^9$ is a $C_1$ to $C_{21}$ alkyl group, alternatively a $C_2$ to $C_{21}$ alkyl group, alternatively a $C_3$ to $C_{21}$ alkyl group, alternatively a $C_5$ to $C_{21}$ alkyl group, alternatively a $C_7$ to $C_{19}$ alkyl group, or alternatively a $C_9$ to $C_{17}$ alkyl group.

In an aspect, a $C_{20+}$ polysulfides/$C_{20+}$ monosulfides composition can comprise $C_{20}$ to $C_{60}$ polysulfides represented by the general formula $R^{15}S^1$—$[S]_n$—$S^2R^{16}$, and/or $C_{20}$ to $C_{60}$ monosulfides represented by the general formula $R^{17}$—S—$R^{18}$ that are formed by reacting a mercaptan feedstock comprising mercaptans with a sulfur-containing material (e.g., elemental sulfur), as described in more detail herein, wherein the mercaptans present in the mercaptan feedstock provide the alkyl group represented by $R^{15}$, $R^{16}$, $R^{17}$, and $R^{18}$. In such aspects, the $R^{15}$ and $R^{16}$ groups of the $C_{20}$ to $C_{60}$ polysulfides and/or the $R^{17}$ and $R^{18}$ groups of the $C_{20}$ to $C_{60}$ monosulfides are provided by or derived from the counterpart $R^{15}$, $R^{16}$, $R^{17}$, and $R^{18}$ groups present in the mercaptans in the mercaptan feedstock. In an aspect, $R^{15}$, $R^{16}$, $R^{17}$, and $R^{18}$ can each independently be an alkyl group, wherein at least a portion of the alkyl groups can comprise a functional group derived from a mercaptan, wherein the mercaptan is present in a feedstock as disclosed herein (e.g., a first $C_{10}$ to $C_{30}$ mercaptans feedstock; a second $C_{10}$ to $C_{30}$ mercaptans feedstock).

In an aspect, a process of reacting branched mercaptans to produce polysulfides as disclosed herein can advantageously be more facile than an otherwise similar process comprising tertiary mercaptans. For example, tert-butyl polysulfide and tert-dodecyl polysulfide are produced from the tertiary mercaptans tert-butyl mercaptan and tert-dodecyl mercaptan, respectively, by a process similar to the one disclosed herein.

Steric bulk proximal to the sulfur atom of the tertiary mercaptans decreases the reaction rate of the tertiary mercaptans. Conversely, the majority of the branched mercaptans disclosed herein are primary branched mercaptans that have minimal steric bulk proximal to the sulfur atom. The branched mercaptans therefore display much greater reactivity in the reaction with a sulfur-containing material (e.g., elemental sulfur), when compared to tertiary mercaptans. Additional advantages of the $C_{20+}$ polysulfide compositions, $C_{20+}$ monosulfides compositions, and $C_{20+}$ polysulfides/ $C_{20+}$ monosulfides compositions and processes of producing same as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Hydrogen sulfide ($H_2S$) and a feedstock comprising branched $C_{10}$ monoolefins were reacted in the presence of various initiating agents: UV radiation, an acid catalyst, and a hydrodesulfurization (HDS) catalyst.

Various feedstocks (e.g., olefin feedstocks) were used for reacting with $H_2S$ to produce mercaptans and/or sulfides. More specifically, olefin feedstocks obtained from 1-hexene production processes were used as feedstocks for reacting with $H_2S$ to produce mercaptans. Gas chromatography (GC)-mass spectrometry (MS) (GC-MS) and nuclear magnetic resonance (NMR) spectroscopy were used for analyzing the composition of olefin feedstocks obtained from 1-hexene production processes.

The compositions comprising $C_{10}$ monoolefins, i.e., the feedstocks obtained from a 1-hexene production process, were analyzed by gas chromatography-mass spectrometry (GC-MS) using a 15 m×0.25 mm×0.5 µm DB-5 column and/or a 40 m×0.1 mm×0.1 µm DB-1 column to determine component identities, and standard gas chromatography (GC) using a 60 m×0.32 mm×1 µm DB-1 column to determine the quantity of the components present in the compositions. As described previously, these compositions are measured in area %, which is substantially similar and analogous to wt. %.

Table 1 provides representative information about the composition of such an olefin feedstock obtained from 1-hexene production processes to react with $H_2S$ to produce mercaptans—Samples #1-4 in Example 1.

TABLE 1

| Chemical | GC Area % | | Normalized % |
|---|---|---|---|
| cyclohexane | 2.148 | | |
| octene | 0.036 | $C_8$ olefins 1.17 | 1.24 |
| 1-octene | 1.135 | | |
| octane | 0.146 | octane 0.15 | 0.16 |
| ethylbenzene | 1.684 | | |
| 3-propyl-1-heptene | 14.590 | $C_{10}$ olefins 84.16 | 89.11 |
| decene | 0.164 | | |
| 4-ethyl-1-octene | 13.134 | | |
| 5-methyl-1-nonene | 32.144 | | |
| decene | 0.647 | | |
| 2-butyl-1-hexene | 9.960 | | |
| decene | 0.320 | | |
| 4/5 decene | 9.116 | | |
| 1-decene | 4.086 | | |
| decane | 0.360 | decane 0.36 | 0.38 |
| 2-ethyl-1-hexanol | 1.379 | | |
| dodecene isomers | 0.448 | $C_{12}$ olefins 1.29 | 1.37 |
| 1-dodecene | 0.842 | | |
| dodecane | 0.182 | dodecane 0.18 | 0.19 |
| tetradecenes | 6.710 | $C_{14}$ olefins 6.71 | 7.11 |
| tetradecane | 0.198 | tetradecane 0.2 | 0.21 |
| octadecene | 0.222 | $C_{18}$ olefins 0.22 | 0.23 |
| 2-ethylhexyl-2-ethylhexanoate | 0.069 | | |
| Unknowns | 0.281 | | |
| Total | 100.000 | total olefins 94.44 | 99.06 |

Normalized to include only octane, decane, dodecane, tetradecane, and $C_8$, $C_{10}$, $C_{12}$, $C_{14}$, and $C_{18}$ olefins As mentioned previously, the olefin feedstock was produced from the trimerization of ethylene in a 1-hexene production process. As shown in Table 1, the total product content of this particular olefin feedstock sample (excluding the compounds that are not products of the 1-hexene process) is 94.44 area %, and 84.16 area % of the feedstock is $C_{10}$ olefin isomers. The $C_{10}$ olefins represent over 89 area % of the total olefin content when the sample is normalized to remove the compounds that are not products of the 1-hexene process. Cyclohexane, ethylbenzene, and 2-ethylhexanol can be present in the olefin feedstock as residual components of the 1-hexene oligomerization process. The structures of $C_{10}$ isomers that can be present in the olefin feedstock are shown in Table 2.

TABLE 2

| Decene Fraction | Olefin | Major UV Product | Major Acid Catalyst Product |
|---|---|---|---|
| 5-methyl-1-nonene 32.14% (38.19) | [structure of 5-methyl-1-nonene] | [structure with SH on terminal carbon] | [structure with SH on internal carbon] |
| 3-propyl-1-heptene 14.59% (17.33) | [structure of 3-propyl-1-heptene] | [structure with terminal SH] | [structure with internal SH] |

TABLE 2-continued

| Decene Fraction | Olefin | Major UV Product | Major Acid Catalyst Product |
|---|---|---|---|
| 4-ethyl-1-octene 13.13% (15.60) | [structure] | [structure with SH] | [structure with SH] |
| 2-butyl-1-hexene 9.96% (11.83) | [structure] | [structure with SH] | [structure with HS] |
| 4/5 decene 9.12% (10.83) | [two structures] | [two structures with SH] | [two structures with SH] |
| 1-decene 4.09% (4.86) | [structure] | [structure with SH] | [structure with SH] |

In Table 2, the first column provides the name of the isomer, the GC area % of that component in the feedstock from Table 1, and the normalized amount of the isomer typically found in the $C_{10}$ fraction of the feedstock. Table 2 also displays the structure of the mercaptans that are produced from the $C_{10}$ olefin isomers. The second column shows the structure of the major $C_{10}$ olefin isomers in the feedstock; the third column displays the structure of the major mercaptan isomers produced by a UV-initiated reaction with $H_2S$; and the fourth column displays the structure of the major mercaptan isomers produced by acid catalysis, such as Filtrol® 24 or Filtrol® 24X.

A sample of the olefin feedstock was fractionated (e.g., distilled) and only the $C_{10}$ fraction was isolated in high purity (e.g., a purified feedstock). This product was submitted for $H^1$ and $C^{13}$ NMR. The NMR analysis (in mol %) was consistent the GC-MS results. The NMR confirmed that about 11 mol % of the total purified feedstock was vinylidene (2 butyl-1-hexene isomer) and about 11 mol % of the total purified feedstock was internal olefins (linear decene isomers). The nomenclature for the various $C_{10}$ isomer products is shown in Table 3.

TABLE 3

| $C_{10}$ Olefin | UV-initiated Mercaptans | Acid-catalyzed Mercaptans |
|---|---|---|
| 5-methyl-1-nonene | 5-methyl-1-mercapto-nonane | 5-methyl-2-mercapto-nonane |
| 3-propyl-1-heptene | 3-propyl-1-mercapto-heptane | 3-propyl-2-mercapto-heptane |
| 4-ethyl-1-octene | 4-ethyl-1-mercapto-octane | 4-ethyl-mercapto-octane |
| 2-butyl-1-hexene | 2-butyl-1-mercapto-hexane | 5-mercapto-5-methyl-nonane |
| 4-decene | 4-mercapto-decane 5-mercapto-decane | 4-mercapto-decane 5-mercapto-decane |

TABLE 3-continued

| $C_{10}$ Olefin | UV-initiated Mercaptans | Acid-catalyzed Mercaptans |
|---|---|---|
| 5-decene | 4-mercapto-decane 5-mercapto-decane | 4-mercapto-decane 5-mercapto-decane |
| 1-decene | 1-mercapto-decane | 2-mercapto-decane |

Reaction of $H_2S$ with the olefin feedstock (e.g., a feedstock comprising branched $C_{10}$ monoolefins) by UV-initiation (e.g., using UV radiation) yielded mostly primary mercaptans, since the terminal olefin and vinylidene isomers yield predominately the anti-Markovnikov product. The minor components were secondary mercaptans from the terminal olefin and a tertiary mercaptan from the vinylidene isomer. Typically, UV-initiation of a terminal olefin produced primary mercaptans in 92-96 area % range and secondary mercaptans in 4-8 area % range. The linear internal olefin isomers present in the feedstock primarily produced secondary mercaptan isomers. Thus, for the composition of the feedstock disclosed herein, the distribution of mercaptans (i.e., the distribution within the $C_{10}$ fraction) in the resulting reaction product was predominately primary mercaptans at about 80-90 area %. Secondary mercaptans were present at 10-20 area %, and tertiary mercaptans were present at about 0-3 area %. These ranges were calculated by NMR analysis of the reaction product.

Reaction of $H_2S$ with a feedstock comprising branched $C_{10}$ monoolefins over an acid catalyst (such as Filtrol® 24 or Filtrol® 24X) produced as the major product the Markovnikov product. Thus, the major mercaptan isomers comprised secondary mercaptans with some tertiary mercaptans. The relative ratio of mercaptans was estimated at 85-90 area % secondary mercaptans and 10-15 area % tertiary mercaptans.

Reaction of $H_2S$ with a feedstock comprising branched $C_{10}$ monoolefins in the presence of a hydrodesulfurization (HDS) catalyst (such as Haldor Topsoe TK-554 or TK0570) produced mercaptans generally similar in distribution to those produced by acid catalysis, which is the Markovnikov distribution. However, the HDS catalyst also produced a significant amount of the anti-Markovnikov product depending on the conditions used in the reaction step. Thus, under the conditions used in this disclosure, the product produced by the HDS catalyst was a blend of the product produced via acid catalysis with some of the components produced by the UV-initiated reaction.

As will be appreciated by one of skill in the art, and with the help of this disclosure, the actual composition of the resultant crude product will ultimately depend on a number of factors including composition of the feedstock; the ratio of $H_2S$ to olefin that is used to produce the thiols; the catalytic method and reaction conditions used to react the $H_2S$ and olefin (UV-initiated, acid catalysis, or HDS catalysis) to produce the crude product; etc. The final product (e.g., any cuts separated from the crude to form, for example, a commercial product) will also depend on the purification step to remove lights and whether a final product containing both mercaptan and sulfide fractions is desired or just one of the fractions, e.g., a mercaptan fraction or a sulfide fraction, is desired.

$H_2S$ to Olefin Molar Ratio: The $H_2S$ to olefin molar ratio can be an important parameter in determining the amount of mercaptan and sulfide produced during the reaction step. This can be true regardless of the catalytic method employed. Without wishing to be limited by theory and in general, the higher the $H_2S$ to olefin molar ratio, the greater the amount of mercaptans that will be produced compared to the amount of sulfides produced.

A general reaction scheme for addition of $H_2S$ to an olefin is shown in FIG. 1, regardless of catalytic method. For a $C_{10}$ olefin fraction, R, R' and R" can be H or $C_1$-$C_8$ with the total of R+R'+R"=8 carbon atoms. For 1-decene, R=H and R'=H and R"=8 and can be a linear or branched alkyl group. For the major isomers in a $C_{10}$ olefin fraction (e.g., a second feedstock as disclosed herein), 5-methyl-1-nonene: R=H and R'=H and R"=8, but the alkyl group contains branching at the third carbon atom of the $C_8$ fraction.

A sulfide fraction can be produced by further reaction of a mercaptan isomer with an olefin. The generic structures of such sulfides are shown in FIG. 1 and this fraction can consist of a variety of isomers with several possible combinations of sulfide structures depending on whether the sulfide is primary to primary, primary to secondary, primary to tertiary, secondary to secondary, secondary to tertiary, or tertiary to tertiary. The structures are complicated by the fact that on the two portions of the sulfide the R, R' and R" value can be the same or different depending on which mercaptan isomer reacts with which olefin isomer. The total number of carbon atoms of the two portions of the sulfide can also have different values for R+R'+R", although the most dominant combination will be where both sides each have a total sum of 8 carbon atoms since the $C_{10}$ fraction predominates in the first feedstock and in the second feedstock.

Reaction Conditions: Three different reaction methods were used to perform the reaction of $H_2S$ with a feedstock comprising branched $C_{10}$ monoolefins: UV-initiation, acid catalysis, and HDS catalysis.

$H_2S$ Removal: In laboratory experimentation, $H_2S$ was removed using a rotovapor apparatus under conditions of reduced pressure. Under these conditions, $H_2S$ was removed without removing significant quantities of light compounds.

Analytical Methods: The weight percentage of thiol sulfur (wt. % SH) was determined analytically by titration using iodine in water as the titrant and methylene chloride/isopropanol as the solvent system. Such titration can also be done by using a silver nitrate titration method. Total sulfur was measured by X-ray using a model SLFA-20 Horiba sulfur-in-oil analyzer. GC analysis of the reaction product was performed using an Agilent Technologies 7890A GC. A 2 m×0.25 mm×1.0 µm film DB-1 capillary column was used for the separation. Operating conditions were as follows: 70° C. initial temperature, 2 min hold time, 8° C./min ramp rate to 200° C. and then 15° C./min ramp rate to 300° C. and hold for 10 minutes. A 2 ml/min helium flow rate at constant flow conditions was used. A flame ionization detector was used. The injector temperature was set at 275° C. and the detector temperature at 300° C. As described previously, these data from these compositions were reported in area %, which is substantially similar and analogous to wt. %. Olefin conversion was monitored using Raman spectroscopy with a Kaiser Optical System RXN2 4-channel spectrometer. The peak centered at 1640 $cm^{-1}$ was the vinyl olefin, while the peak centered at about 1670 $cm^{-1}$ was the internal olefin.

Example 1

UV-initiation reactions were performed using either a 1.5 L or a 5-liter UV reactor equipped with a 100 watt lamp and ballast. The two reactors are substantially the same configuration, and the only difference in operation is the amount of reactants added to the reactor. To 800 g of mixed $C_{10}$ olefin (or 2.7 kg, if using the larger reactor), 5 g (or 16.7 g) of triethyl phosphite was added and 0.2 kg (or 0.67 kg) $H_2S$ was charged after sealing the reactor. The reaction mixture was stirred at 500-1,000 RPM. The reaction temperature was controlled with a bath set at 25° C., but the heat of reaction did reach about 40° C. The lamp operated at 1.1-1.5 amps and 28-103 volts over the course of the reaction, operating at lower amps and higher voltage as it warmed up. The reaction pressure was 220-280 psig (1,516 kPag-1,930 kPag) during the actual reaction time. The reaction was completed in about 30 minutes based on the results of Raman spectroscopy but was allowed to continue for 60 minutes to ensure completion. Table 4 shows the results of four reactions by UV-initiation, wherein the reactions produced Samples #1, #2, #3, and #4.

TABLE 4

|  | Sample # | | | | | | | |
| --- | --- | --- | --- | --- | --- | --- | --- | --- |
|  | 1 | 1a | 2 | 2a | 3 | 3a | 4 | 4a |
| Olefin Feedstock wt. | 800 |  | 930 |  | 930 |  | 930 |  |
| $H_2S$ wt. | 200 |  | 2300 |  | 2300 |  | 2300 |  |
| H2S:Olefin Molar Ratio | 1.0 |  | 10.2 |  | 10.2 |  | 10.2 |  |
| Phosphite | TEP |  | TEP |  | TEP |  | TBP |  |

TABLE 4-continued

| | Sample # | | | | | | | |
|---|---|---|---|---|---|---|---|---|
| | 1 | 1a | 2 | 2a | 3 | 3a | 4 | 4a |
| Phosphite wt. | 5.0 | | 1.0 | | 1.0 | | 1.0 | |
| wt. % Phosphite | 0.63 | | 0.11 | | 0.11 | | 0.11 | |
| Reaction Time (minutes) | 70.0 | | 40.0 | | 45.0 | | 45.0 | |
| % Raman Conversion | 97.0 | | 98.0 | | 97.3 | | 97.2 | |
| wt. % SH | | 11.2 | 15.8 | 16.6 | 16.8 | | 16.4 | |
| wt. % Total S | | 15.4 | 16.3 | 17.5 | 17.9 | | 16.9 | |
| GC Analysis area % | | | | | | | | |
| Lights | 8.78 | 0.031 | 7.07 | | 3.61 | | 6.96 | |
| Light Intermediate | 1.10 | 0.22 | 1.01 | 0.015 | 3.75 | | 3.45 | |
| $C_{10}$ SH Region | 51.85 | 56.84 | 76.04 | 82.45 | 82.38 | 84.14 | 78.29 | 84.02 |
| Intermediate Heavies | 4.96 | 5.71 | 7.91 | 9.04 | 4.23 | 5.75 | 4.26 | 5.82 |
| Sulfides | 33.31 | 37.20 | 7.98 | 8.50 | 6.03 | 10.10 | 7.05 | 10.15 |

TEP = triethyl phosphite;
TBP = tributyl phosphite.

Samples #1-4 were prepared using samples of an olefin feedstock composition comparable to that shown in Table 1. Samples #1a, #2a, #3a, and #4a were prepared by distilling the crude reaction product, Samples #1, #2, #3, and #4, respectively. The distillation process proceeded as follows: The first 7 fractions removed from the crude reaction product were considered to be the light fractions. This distillation step was considered to be complete when the kettle temperature increased from 100° C. to 121° C. and the head temperature increased from room temperature to 98.9° C. Cuts 8-13 were considered to be the intermediate fractions and included the $C_{10}$ mercaptans. These cuts were collected at a kettle temperature of 122° C. to 154° C. and a head temperature of 99° C. to 105° C. Cuts 14 and 15 were collected at kettle and head temperatures of from 122° C. to 154° C. and 103.4° C. to 107.2° C., respectively. These cuts and whatever remained in the kettle were considered the heavies. The head temperature was allowed to increase from room temperature to 107.2° C. before the distillation was stopped. For a typical distillation, only the light fractions were distilled (e.g., removed) and the reaction product was what remained (e.g., including $C_{10}$ mercaptans and $C_{20}$ sulfides) in the kettle after the lights were removed.

The relative amount of $C_{10}$ mercaptan isomers, intermediate mercaptans (e.g., non-$C_{10}$ mercaptans such as $C_{12}$ to $C_{16}$ mercaptans) and sulfide heavies (e.g., $C_{20}$ sulfides) depended on the ratio of $H_2S$ to olefin during the reaction step. Sample #1 was prepared at a 1:1 ratio of $H_2S$ per olefin to maximize the amount of sulfide content. Conventional wisdom would suggest that the $C_{10}$ mercaptan fraction would have too strong of an odor to be acceptable for certain applications, and that the sulfide fraction might have a better odor. Surprisingly and unexpectedly, after removing Sample #1 from the reactor and venting off the residual $H_2S$ using a rotovapor apparatus, the odor of this crude reaction product (Sample #1) was good.

Figure 2:
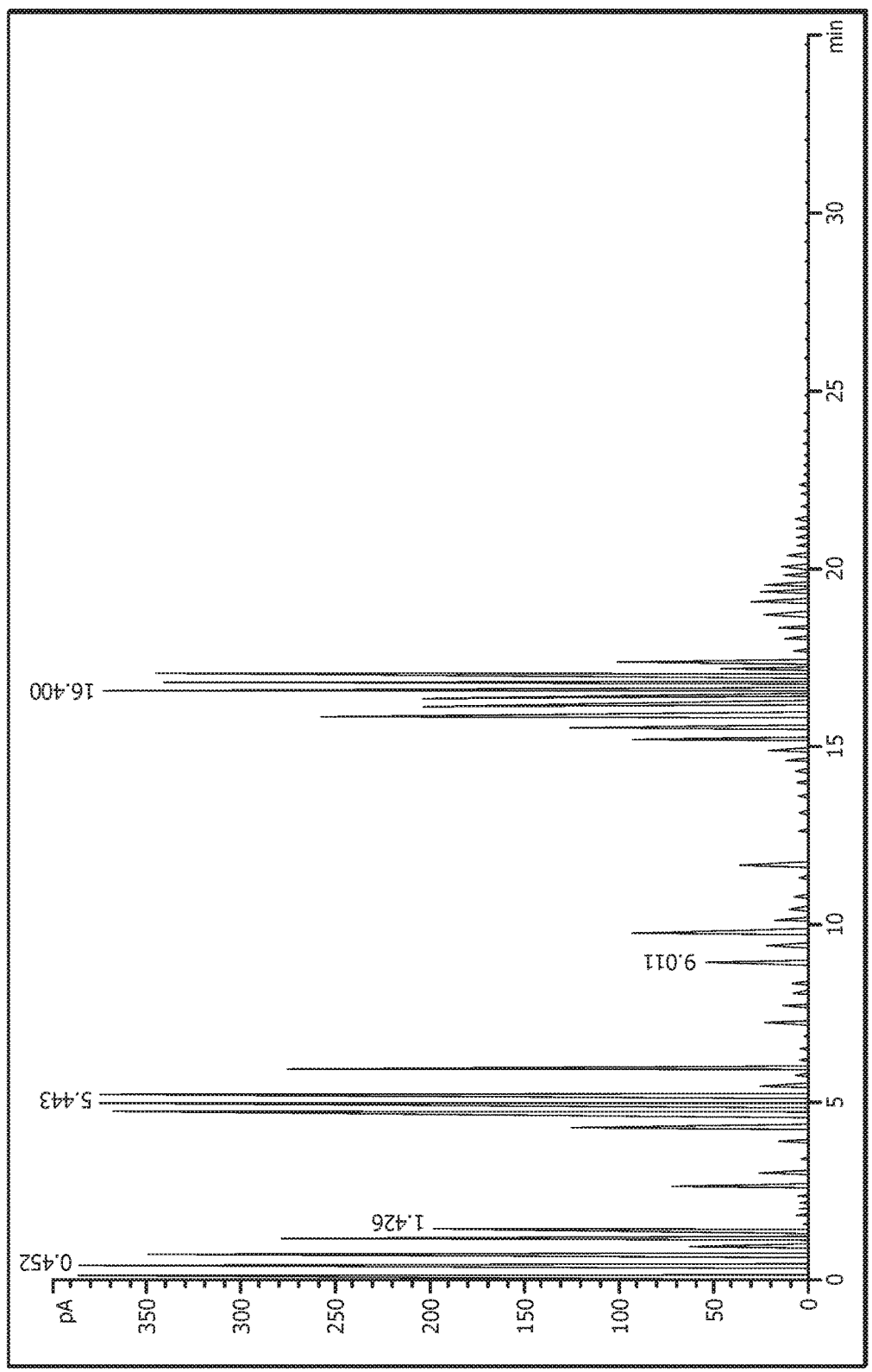
FIG. 2 displays a GC trace of a crude product from an UV initiated reaction after removal of residual $H_2S$.
Figure 3:
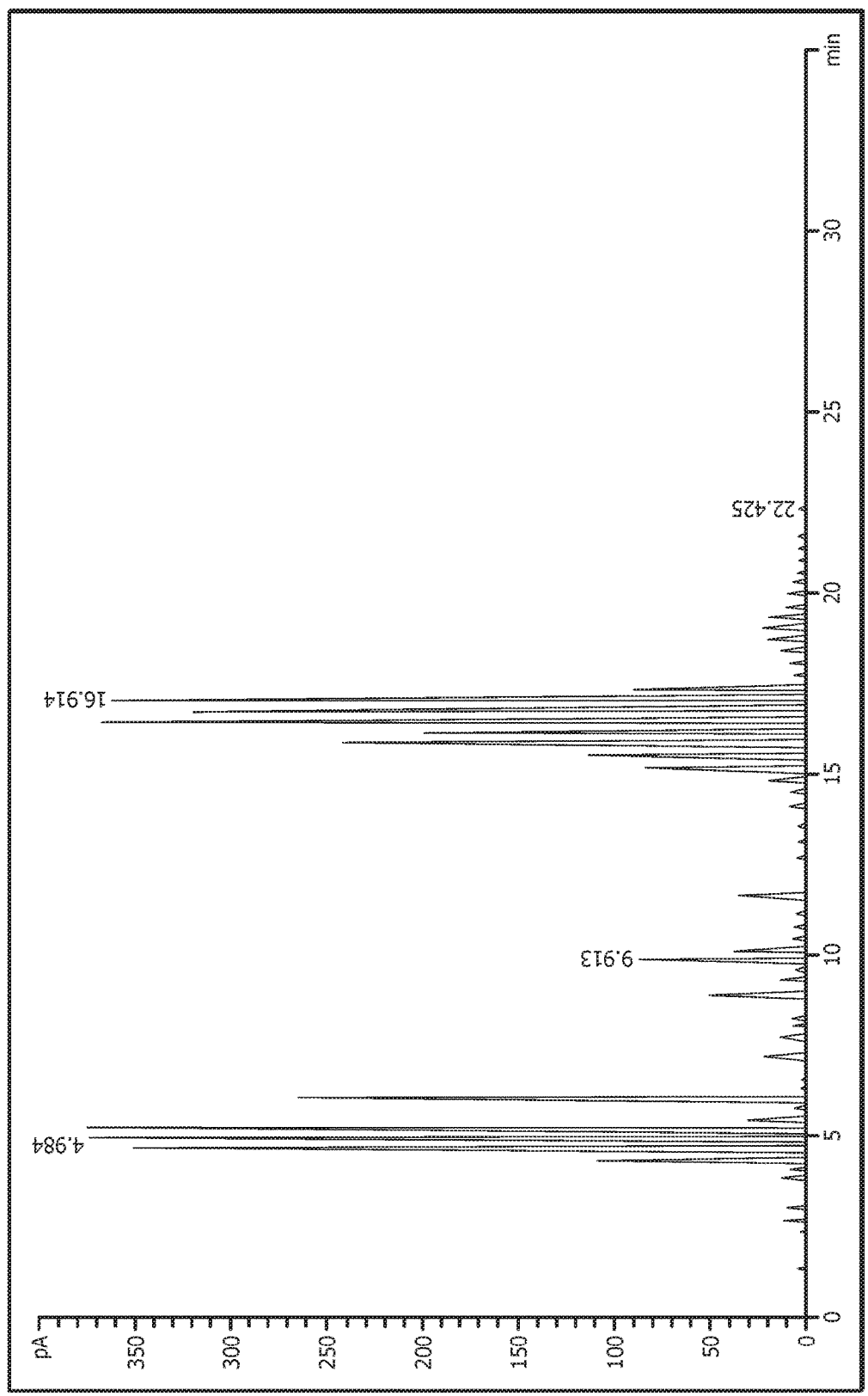
FIG. 3 displays a GC trace of a reaction product from an UV initiated reaction after removal of lights.

FIG. 2 displays a GC trace of reactor crude Sample #1 (after removal of residual $H_2S$). FIG. 3 displays a GC trace of Sample #2 after removal of lights, designated as Sample 2a. Comparison of the GC traces in FIGS. 2 and 3 indicates successful removal of the majority of the lights from the product stream, which include the cyclohexane, ethylbenzene, 2-ethylhexanol and residual octane. Because the run (to obtain Sample #1) was performed at a low $H_2S$ to olefin ratio, the amount of $C_{10}$ mercaptan isomers (peaks at 3.8-6.5 minutes) accounted for 56.8 area % of the kettle product, as shown in FIG. 2. The intermediate cut (peaks at 6.5-14 minutes) included mercaptans produced from the $C_{12}$ to $C_{16}$ olefins present in the olefin feedstock stream and accounted for 5.7 area % of this particular sample. The heavies cut (peaks at >14 minute retention time) included the sulfides, primarily $C_{10}H_{21}$—S—$C_{10}H_{21}$ isomers plus higher sulfides from combinations with other olefins in the mixed feed. It is believed that any $C_{18}$ mercaptans that may have been produced eluted with the sulfide peaks. The amount of $C_{18}$ that could be present was estimated at about 0.2 area %. In Sample #1, the sulfide fraction accounted for about 37.2 area % of the product composition. The amount of the intermediate fraction was primarily dependent on the amount of $C_{14}$ olefin isomers that were present in the olefin feed stream. Analysis of several samples showed that this intermediate fraction ranged from 4-10 area %.

Figure 4:
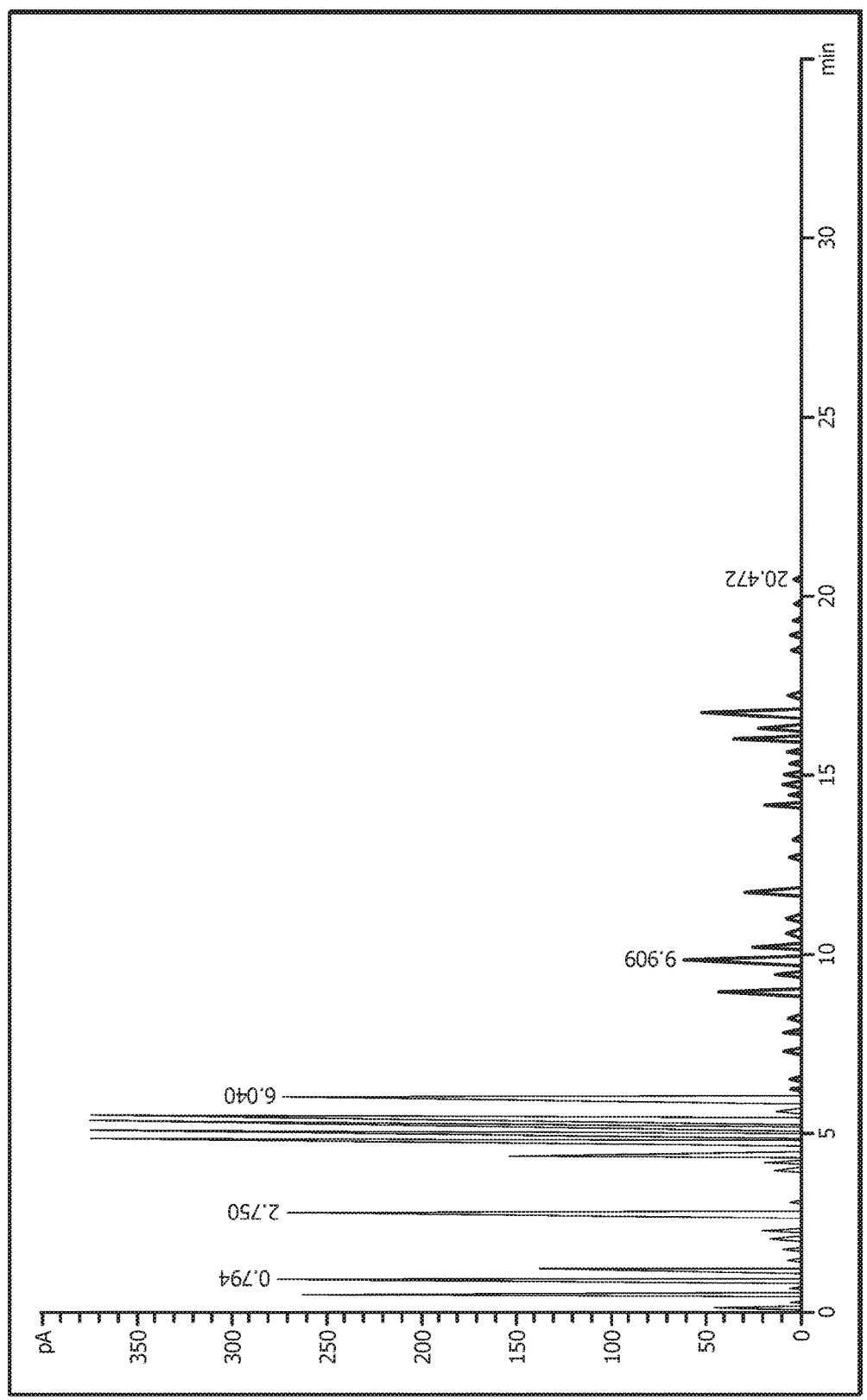
FIG. 4 displays a GC trace of a crude product from an UV initiated reaction after removal of residual $H_2S$.
Figure 5:
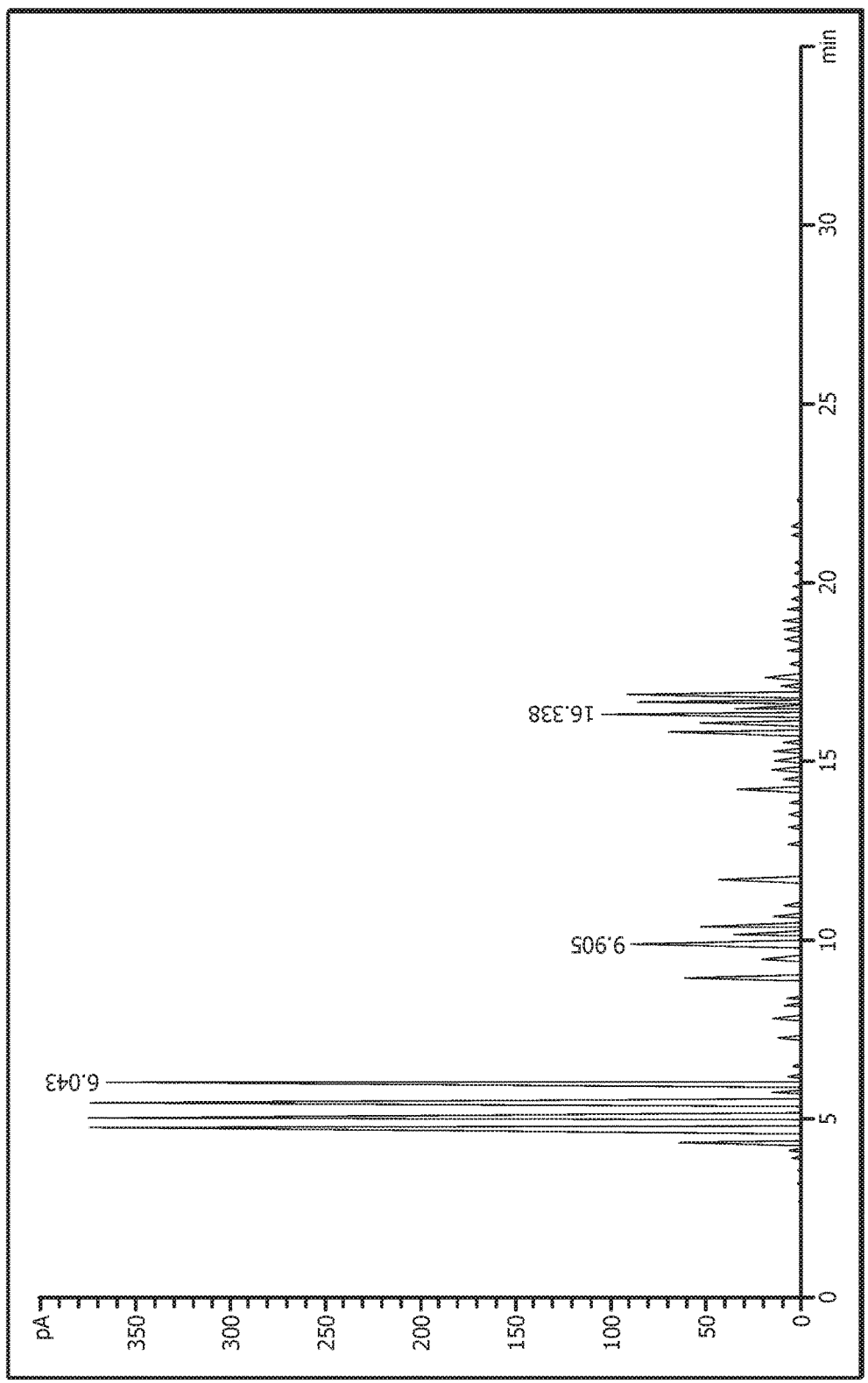
FIG. 5 displays a GC trace of a reaction product from an UV initiated reaction after removal of lights.

FIG. 4 displays a GC trace of reactor crude Sample #3, after removal of residual $H_2S$. FIG. 5 displays a GC trace of kettle product Sample #3a, after removal of lights. FIGS. 4 and 5 compare GC results of product produced at a 10:1 $H_2S$ to olefin molar ratio. The observed trends are similar to the trends seen in FIGS. 2 and 3, and the primary difference is in the ratio of $C_{10}$ mercaptan isomers to the sulfide fraction. This difference is the result of increasing the ratio of $H_2S$ to olefin feedstock used in the reaction. The type and relative amounts of the isomers in the $C_{10}$ mercaptan fraction are essentially unchanged, and the compositions of the sulfide heavies fractions are similar. What is changed is the relative amount of the $C_{10}$ mercaptan fraction compared to the sulfide heavies fraction, as in the sample with a lower $H_2S$:olefins ratio, there is significantly more of the sulfide fraction than the mercaptan fraction. This result is not altogether unexpected, although further experimentation would allow one of skill in the art to optimize the $H_2S$ to olefins ratio to obtain a specific ratio of mercaptans to sulfides.

The main difference between Sample #3a and Sample #1a is the relative amounts of $C_{10}$ mercaptan isomers, intermediate mercaptans, and sulfides. As expected, when the reaction was performed at a higher molar ratio of $H_2S$ per olefin, the resulting reaction product contained a greater amount of $C_{10}$ mercaptan isomers (84.1 area % vs. 56.8 area %) and much less sulfide (10.1 area % vs. 37.2 area %). The removal of lights was done using a simple lab distillation unit, wherein the distillation column was 12" long and 1" in diameter and was packed with a stainless steel sponge. Distillations were performed in batch mode at 9-10 torr vacuum pressure and an overhead temperature of about 100° C.–103° C. and a kettle temperature of about 125° C.–150° C. The lights were collected overhead while trying to minimize the amount of $C_{10}$ mercaptan isomers that were lost with this overhead fraction.

The composition of the UV-produced product can be described in broad terms as follows: a feedstock was reacted with $H_2S$; removal of $H_2S$ after the reaction yielded a crude reaction product. Subsequent removal of the lights fraction to yields a kettle product, which can be used "as is" (e.g., a composition comprising both mercaptans and sulfides) or can be further separated into one or more products or cuts corresponding to a desired compound or combination of compounds (e.g., a $C_{10}$ mercaptan fraction, an intermediate mercaptan fraction, and/or a heavy/sulfide fraction). In broad terms, the product consists of three general fractions as produced from the kettle product after removal of the unwanted lights fraction. The $C_{10}$ mercaptan fraction comprised from 50-100 wt. % of the kettle product. The mercaptan functionality of the $C_{10}$ mercaptan fraction was 80-90% primary mercaptan, 5-18% secondary mercaptan and 0-3% tertiary mercaptan. This was the fraction that eluted in the 3.8-6.5 minute range under the GC conditions used. The intermediate fraction, which eluted in the 6.5-14 minute region, was predominately mercaptan isomers in the $C_{12}$ to $C_{18}$ range with a distribution of functionality that can be similar to that for the $C_{10}$ isomer fraction. The intermediate fraction comprised from 0 to 12 area % of the kettle product. The heavy fraction (>14 minute retention time) consisted essentially of sulfides, primarily of formula $C_{10}H_{21}$—S—$C_{10}H_{21}$ isomers, as well as sulfides from $C_{12}$, $C_{14}$, $C_{16}$ or $C_{18}$ olefins and mercaptans or the asymmetric sulfides produced from the various combinations. These sulfide components comprised from 0-70 area % of the kettle product, depending on the reaction conditions used.

Example 2

Acid Catalysis produced a different distribution of isomer products than those produced by UV-initiation reaction of $H_2S$ and the olefin feedstock comprising branched $C_{10}$ monoolefins.

The product produced via the acid catalyzed addition of $H_2S$ to the feedstock comprising branched $C_{10}$ monoolefins was prepared in a continuous flow reactor over Filtrol® 24 acid catalyst. The reactor contained 43.22 g of catalyst and the WHSV (weight hourly space velocity) was maintained at 1.0 grams of olefin per gram of catalyst per hour. The $H_2S$ to olefin molar ratio ranged from 10:1 to 1:1. The reaction temperature was between 120° C. to 220° C., and the reactor pressure was 450-460 psig (3,100 kPag-3,200 kPag). Optimum results, based on conversion and maximum $C_{10}$ mercaptan, were in the 180-200° C. range and an $H_2S$ to olefin molar ratio of 5:1. A decrease in the $H_2S$ to olefin ratio resulted in a decrease in the $C_{10}$ mercaptan fraction and a corresponding increase in the sulfide fraction. The run data for the acid catalyzed reactions are shown in Table 5.

TABLE 5

| | Sample # | | | | | | | | | | | | | |
|---|---|---|---|---|---|---|---|---|---|---|---|---|---|---|
| | 5 | 6 | 7 | 8 | 9 | 10 | 11 | 12 | 13 | 14 | 15 | 16 | 17 | 18 |
| Mid Temp Actual | 123 | 145 | 167 | 186 | 202 | 221 | 184 | 185 | 202 | 165 | 182 | 201 | 182 | 182 |
| Btm Temp Set | 122 | 142 | 162 | 182 | 202 | 222 | 185 | 185 | 205 | 165 | 185 | 205 | 185 | 185 |
| Btm Temp Actual | 120 | 141 | 160 | 179 | 198 | 219 | 182 | 182 | 201 | 163 | 181 | 201 | 181 | 182 |
| Average Actual Temp | 121 | 142 | 163 | 182 | 200 | 221 | 183 | 184 | 202 | 163 | 182 | 202 | 182 | 182 |
| | GC Analysis area % | | | | | | | | | | | | | |
| Lights | 4.34 | 4.24 | 4.16 | 3.95 | 4.24 | 5.85 | 3.85 | 3.88 | 4.08 | 3.97 | 4.04 | 3.99 | 4.02 | 3.94 |
| Olefin Region | 58.03 | 39.66 | 18.56 | 11.93 | 12.70 | 22.22 | 9.66 | 9.79 | 11.35 | 12.90 | 13.45 | 17.34 | 19.75 | 15.86 |
| Octyl SH | 0.03 | 0.57 | 1.24 | 0.01 | 1.67 | 1.48 | 1.19 | 1.19 | 1.44 | 1.06 | 1.12 | 1.06 | 0.83 | 0.92 |
| Other Lights | 0.51 | 0.18 | 0.13 | 0.00 | 0.73 | 1.26 | 0.40 | 0.33 | 0.54 | 0.00 | 0.01 | 0.02 | 0.24 | 0.21 |
| $C_{10}$ Mercaptan Region | 15.64 | 36.81 | 52.84 | 61.44 | 56.82 | 49.41 | 56.57 | 57.48 | 55.80 | 61.97 | 58.38 | 50.79 | 42.78 | 48.51 |
| Intermediate Heavies | 7.80 | 11.67 | 11.07 | 6.78 | 6.24 | 6.71 | 6.32 | 6.27 | 6.88 | 6.86 | 7.05 | 6.67 | 6.65 | 6.57 |
| Sulfides | 13.65 | 6.88 | 12.00 | 15.88 | 17.59 | 13.08 | 22.01 | 21.06 | 19.91 | 13.24 | 15.95 | 20.13 | 25.73 | 24.00 |
| Raman Olefin Conversion mol % | 31.0% | 56.2% | 81.5% | 91.0% | 92.5% | 89.8% | 93.2% | 92.2% | 91.9% | 86.4% | 85.4% | 81.7% | 76.2% | 78.4% |

The best olefin conversions were in the 88-92 area % range. The $C_{10}$ mercaptan fraction accounted for 50-60 area % of the crude product weight, while the sulfide fraction ranged from 15-25 area % of the crude product weight.

Figure 6:
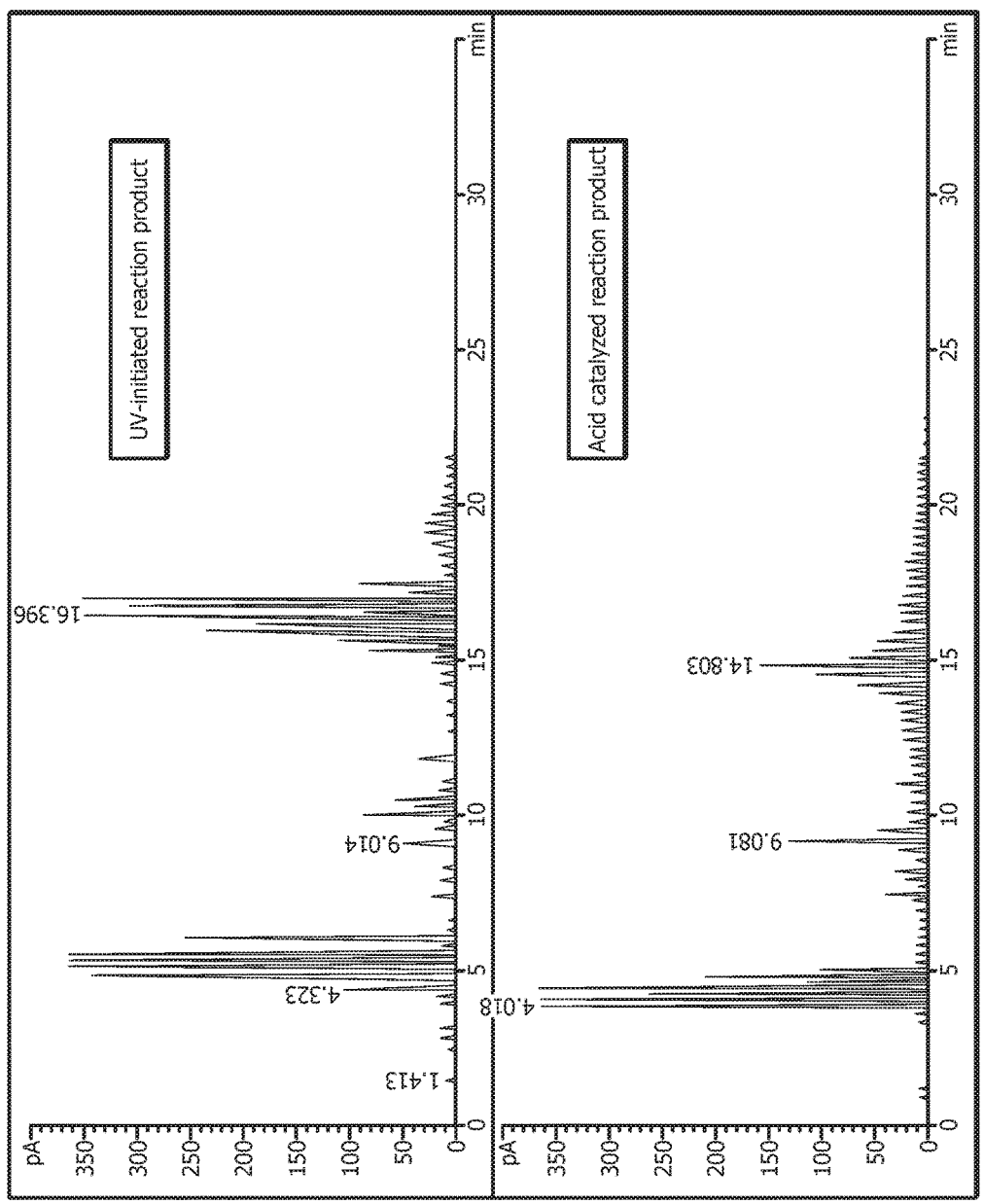
FIG. 6 displays a comparison of GC traces for a product obtained by UV initiation and a product obtained by acid catalysis. The upper chromatogram is the UV-initiated $C_{10}$ mercaptan product, and the lower chromatogram is the acid catalyzed $C_{10}$ mercaptan product.
Figure 7:
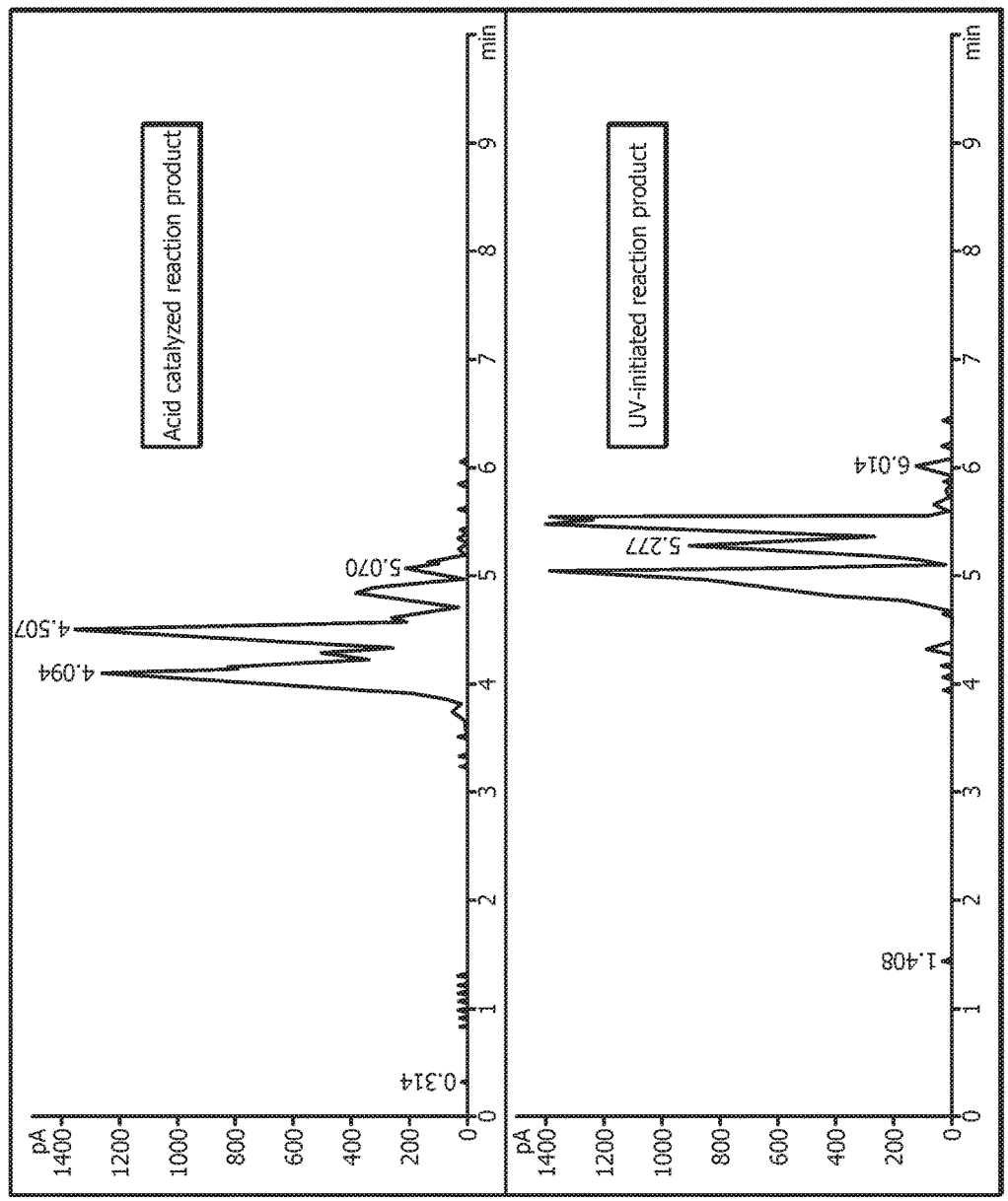
FIG. 7 displays a comparison of GC traces for a $C_{10}$ mercaptan fraction isolated from a product obtained by UV initiation and a $C_{10}$ mercaptan fraction isolated from a product obtained by acid catalysis, and particularly, representative GC profiles of the purified $C_{10}$ mercaptan reaction product. The upper chromatogram is the acid catalyzed $C_{10}$ mercaptan product, and the lower chromatogram is the UV-initiated $C_{10}$ mercaptan product.

Acid catalysis produced the Markovnikov product. The vinyl components of the feedstock comprising branched $C_{10}$ monoolefins produced secondary mercaptans. The internal olefin components produced secondary mercaptans, while the vinylidene components produced tertiary mercaptans. Thus, the composition of the $C_{10}$ mercaptan fraction isomers was different when compared to the composition of the product obtained by UV-initiation. For example, the 5-methyl-1-nonene isomer produced 5-methyl-2-mercapto-nonane by acid catalysis; and 5-methyl-1-mercapto-nonane was the major product produced by UV-initiation, with a minor amount of the 2-mercapto isomer as a by-product. The 2-butyl-1-hexene isomer produced 5-methyl-5-mercapto-nonane by acid catalysis; while UV-initiation produced 2-butyl-1-mercapto-hexane. Comparative GC traces of the product produced by acid catalysis and that produced by UV-initiation are shown in FIG. 6 and FIG. 7. FIG. 6 shows a comparison of crude product (e.g., only $H_2S$ removed) by UV-initiation and acid catalysis routes, and FIG. 7 compares the $C_{10}$ mercaptan fraction produced by the UV-initiation and acid catalysis routes.

The comparative GC traces in FIG. 6 and FIG. 7 demonstrate that different isomer distributions can be obtained depending on how the reaction of the feedstock comprising branched $C_{10}$ monoolefins and $H_2S$ is initiated. One would expect that the tertiary and secondary mercaptans would elute more quickly than primary mercaptans. One would also anticipate that more branching and proximity of the branching to the mercaptan would also cause those isomers to elute more quickly. The peak at 6.01 minutes was clearly n-decyl mercaptan and was expected to be the last of the $C_{10}$ mercaptans to elute in this fraction.

As with the product produced by UV-initiation, the product obtained by acid catalysis consisted of three general fractions as produced as a kettle product after removal of the unwanted lights fraction. The $C_{10}$ mercaptan fraction comprised from 50-100 area % of the crude kettle composition. The mercaptan functionality of the $C_{10}$ fraction was 85-95 area % secondary mercaptan and the remainder tertiary mercaptan. These isomers eluted in the 3.1-6.5 minute range under the utilized GC conditions.

The intermediate fraction consisted of those mercaptan peaks in the 6.5-14 minute range. However, the functionality of the mercaptans was secondary and tertiary $C_{12}$ to $C_{18}$ mercaptans. The intermediate fraction comprised 5-15 area % of the total kettle composition.

The sulfide fraction comprised 0-70 area % of the composition of the kettle product, depending on the specific reaction conditions. The fraction consisted of sulfides primarily of formula $C_{10}H_{21}$—S—$C_{10}H_{21}$. However, the isomer identity was different than that for the product produced by UV-initiation. The acid produced sulfide product was based on secondary and tertiary mercaptans rather than predominately primary mercaptans as in the UV-initiated produced product.

Example 3

HDS Catalysis produced mercaptans that were primarily similar in distribution to those produced by acid catalysis, which is the Markovnikov distribution. However, there was a tendency to also produce some of the anti-Markovnikov distribution depending on the specific conditions utilized in the reaction step. Thus the product produced by the HDS catalyst appeared to be a blend of product produced primarily via acid catalysis with some of the components of the UV-initiated reaction.

The HDS reaction conditions were as follows: WHSV was varied from 0.75 to 2 grams of olefin per gram of catalyst per hour; the molar ratio of $H_2S$ per olefin was varied from 2:1 to 10:1; the average reaction temperature was 180° C. to 220° C. The catalyst used was cobalt molybdenum on alumina, examples being to Haldor Topsoe TK-554, TK-570, or similar. Olefin conversion, as determined by Raman spectroscopy, was in the 88-97 mol % range. The HDS test runs were performed using the feedstock comprising branched $C_{10}$ monoolefins comparable to the composition as outlined in Table 1 are shown in Table 6 and Table 7.

TABLE 6

| | Sample # | | | | | | | | |
|---|---|---|---|---|---|---|---|---|---|
| | 19 | 20 | 21 | 22 | 23 | 24 | 25 | 26 | 27 |
| Ratio $H_2S$/Olefin | 10 | 10 | 10 | 10 | 10 | 5 | 2 | 5 | 5 |
| Olefin Rate (g/hr) | 31.2 | 31 | 31.4 | 31.1 | 30.4 | 31.1 | 30.8 | 31.2 | 31.4 |
| $H_2S$ Rate (g/hr) | 74.8 | 74.2 | 74.7 | 75 | 74.2 | 36.9 | 14.4 | 36.8 | 37 |
| WHSV | 0.75 | 0.75 | 0.75 | 0.75 | 0.75 | 0.75 | 0.75 | 0.75 | 0.75 |
| Average Actual Temp | 204 | 205 | 204 | 223 | 202 | 203 | 203 | 203 | 203 |
| GC Analysis area % | | | | | | | | | |
| Lights | 6.97 | 5.33 | 5.16 | 4.02 | 4.97 | 4.98 | 4.77 | 4.59 | 4.83 |
| Olefin Region | 6.22 | 7.06 | 8.93 | 9.89 | 8.50 | 7.35 | 6.53 | 7.01 | 7.28 |
| Octyl SH | 1.01 | 1.60 | 2.07 | 1.71 | 1.75 | 2.07 | 2.05 | 2.04 | 2.16 |
| $C_{10}$ Mercaptan Region | 51.43 | 60.92 | 75.05 | 59.89 | 73.44 | 80.77 | 79.73 | 78.53 | 80.92 |
| Intermediate heavies | 3.71 | 4.03 | 3.86 | 4.73 | 4.02 | 3.78 | 3.79 | 4.59 | 3.97 |
| Sulfides | 30.62 | 21.05 | 4.93 | 19.74 | 7.32 | 1.06 | 3.13 | 3.24 | 0.83 |
| Raman Olefin Conv. mol % | 96.8% | 96.9% | 96.1% | 94.2% | 96.6% | 97.5% | 97.9% | 97.7% | 97.2% |

Notes:
About 3-4% of olefin region is saturates; lights are primarily cyclohexane, octane, and ethylbenzene

TABLE 7

| | Sample # | | | | | | | | | | | |
|---|---|---|---|---|---|---|---|---|---|---|---|---|
| | 28 | 29 | 30 | 31 | 32 | 33 | 34 | 35 | 36 | 37 | 38 | 39 |
| Ratio $H_2S$/Olefin | 5 | 5 | 2 | 5 | 5 | 5 | 5 | 5 | 5 | 5 | 5 | 5 |
| Olefin Rate (g/hr) | 40.8 | 41.7 | 41.6 | 62.7 | 61.7 | 60.7 | 81.8 | 82.4 | 61.7 | 62.7 | 41.8 | 41.2 |
| $H_2S$ Rate (g/hr) | 50.1 | 49.6 | 20 | 74.7 | 74.5 | 75 | 99.5 | 99 | 74.4 | 74.7 | 49.5 | 50.1 |
| WHSV | 1 | 1 | 1 | 1.50 | 1.50 | 1.50 | 2.00 | 2.00 | 1.50 | 1.50 | 1.00 | 1.00 |
| Average Actual Temp | 203 | 203 | 204 | 203 | 203 | 212 | 203 | 218 | 183 | 183 | 181 | 191 |
| GC Analysis area % | | | | | | | | | | | | |
| Lights | 4.02 | 4.47 | 4.24 | 4.07 | 4.04 | 3.61 | 3.51 | 3.67 | 3.40 | 3.68 | 3.45 | 3.65 |
| Olefin Region | 7.21 | 8.65 | 7.84 | 11.07 | 11.73 | 10.01 | 13.25 | 14.82 | 16.38 | 18.94 | 13.61 | 10.49 |
| Octyl SH | 1.58 | 1.91 | 1.71 | 1.63 | 1.67 | 1.79 | 1.42 | 1.50 | 1.12 | 1.21 | 1.19 | 1.48 |
| $C_{10}$ Mercaptan Region | 66.44 | 77.68 | 77.74 | 73.33 | 73.27 | 63.49 | 59.35 | 65.04 | 58.50 | 64.23 | 65.26 | 71.64 |
| Intermediate Heavies | 5.63 | 5.21 | 5.45 | 5.64 | 5.33 | 7.60 | 7.76 | 8.04 | 8.31 | 7.34 | 8.27 | 8.21 |
| Sulfides | 15.12 | 2.07 | 3.02 | 4.26 | 3.95 | 13.40 | 14.58 | 6.81 | 12.15 | 4.45 | 8.08 | 4.41 |
| Raman Olefin Conv. mol % | 96.6% | 96.6% | 97.0% | 94.9% | 93.9% | 94.4% | 91.1% | 90.4% | 87.3% | 87.0% | 90.9% | 94.9% |

As can be observed from Tables 6 and 7, the trends for sulfide production were less consistent, possibly because the continuous reactor was run at steady state conditions for about 4-5 hours, shut down, and restarted the next day. Further, it appeared that the initial sample each day was initially higher in sulfide content than anticipated and then declined. It appears that under similar conditions of WHSV, ratio and temperature, the HDS catalyzed reaction produces more $C_{10}$ mercaptan fraction and less sulfide fraction than the acid catalyzed reaction. It is expected that the results varied compared to what would be obtained if the reactor was operated continuously at steady state conditions for several weeks.

Figure 8:
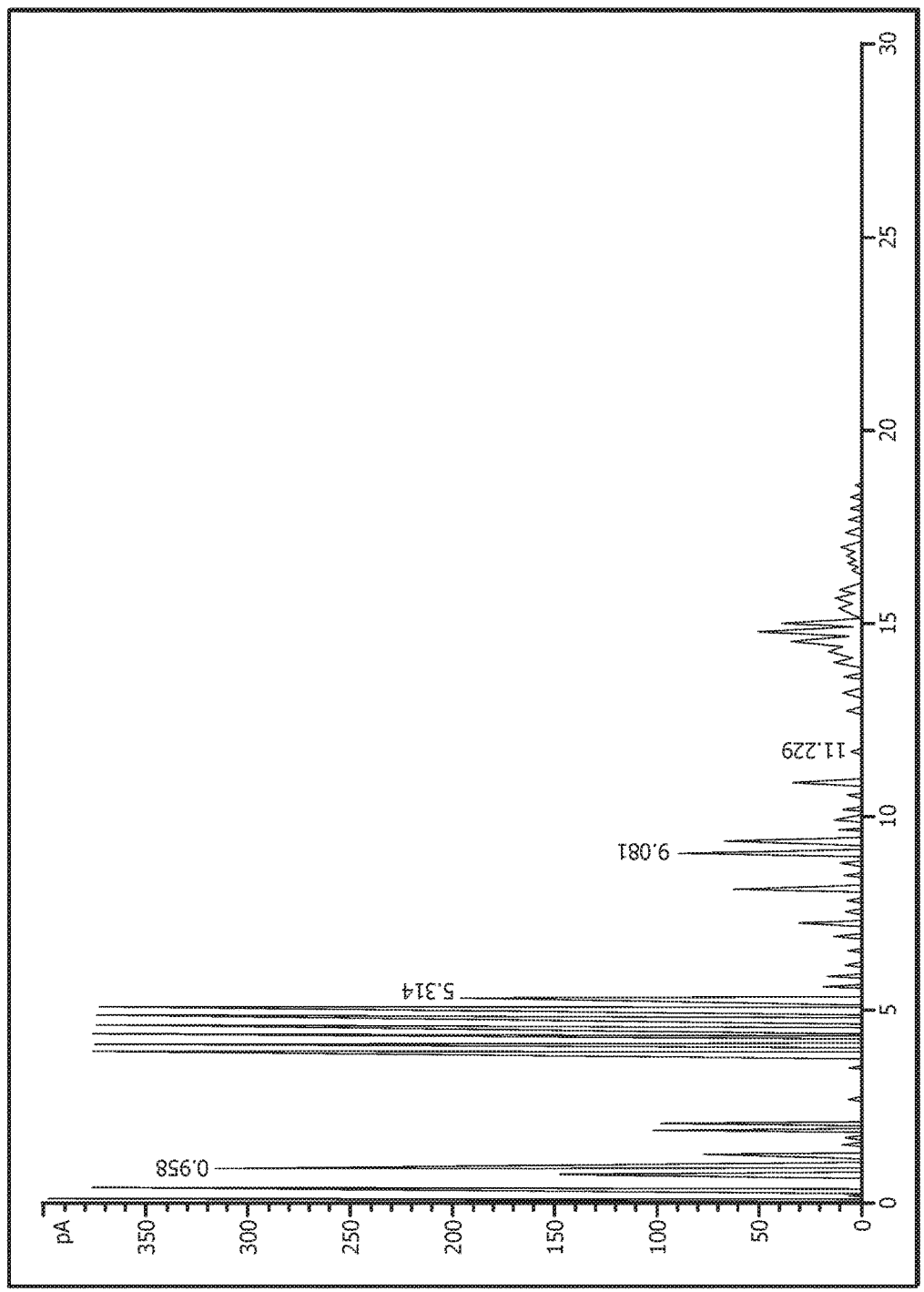
FIG. 8 displays a GC trace of a crude product from a reaction catalyzed by a hydrodesulfurization catalyst after removal of residual $H_2S$.

A typical GC trace of reactor crude produced from the HDS catalyzed reaction of $H_2S$ and branched C10 monoolefins is shown in FIG. 8. Comparison of the $C_{10}$ fraction (3.5 to 6 minute retention time) of the HDS reaction product, as shown in FIG. 8, with the same reaction product for both the acid catalyzed and UV-initiated processes as shown in FIG. 6 or FIG. 7, shows that the HDS product was a blend of the acid catalyzed and UV-initiated products.

Example 4

Purification of Crude Decyl Mercaptan. Purification was performed on some the crude product samples to remove the lights fraction, which consisted of residual $H_2S$, cyclohexane, ethylbenzene, octane, octene, 2-ethylhexanol and as much of the n-octylmercaptan as possible, i.e., all $C_{9-}$. Purification was performed in a conventional laboratory distillation column. Removing the light fraction, especially the n-octylmercaptan, can result in the loss of some $C_{10}$ mercaptan isomers to the overhead distillate product. It is believed that a commercial-scale operation can minimize the loss of $C_{10}$ mercaptans by controlling operating parameters including the number of distillation columns used, the number of theoretical trays in the column(s), the rate of reflux and take-off, and whether the distillation is done in continuous or batch mode. These parameters can readily be determined with research, allowing one of reasonable skill in the art to scale up and optimize the distillation process. It is within the scope of this disclosure that operating a continuous mode distillation system using two columns can provide satisfactory separation. For example, operating a the first column at an overhead temperature of 80° C. to 85° C. at 9 torr and a second column at about 95° C.–97° C. would provide a satisfactory separation.

The distillation column used in the lab was 1"×12" packed with stainless steel sponge. As stated earlier, it is believed that the separation was not as good as desired, and significant $C_{10}$ mercaptan was removed overhead, even with the initial cut. A distillation run at 9 torr and a reflux to take-off ratio of 18:3 required the removal of 12.5 area % of the crude overhead to reach a level of <0.1 area % lights in the kettle product. According to the GC analysis of the crude, only 8.1 area % of the crude product was lights that needed to be removed overhead. The kettle temperature was in the 100° C.-115° C. range at 9 torr. In another distillation batch, 8.8 area % of the crude was taken overhead, while the lights composed only 4.0 area % of the crude. In several other batches, nearly 20 area % of the crude was lost overhead.

For simulation of the distillation, the nearest boiling point impurities are the ethylbenzene, 2-ethylhexanol and n-octylmercaptan. The amount of these impurities that are present will determine how many theoretical trays are be needed, as well as the best pressure and temperature profile to optimize yield and keep the level of the n-octylmercaptan to as low a value as feasible.

Prophetic Example 5

Olefin Feedstock Purification. A feedstock comprising branched $C_{10}$ monoolefins produced in a 1-hexene process can be purified (e.g., distilled), for improved olefin reactivity and resulting mercaptan purity. The lights up to 1-octene can be removed and the $C_{10}$ olefin isomers taken overhead to high purity (>98%). This high purity $C_{10}$ monoolefin cut would then be free of the $C_{12}$ to $C_{18}$ olefins. The high purity $C_{10}$ olefin can then be reacted with $H_2S$ to produce the mercaptan products. The reaction conditions would be identical for the high purity $C_{10}$ olefin stream (e.g., second feedstock) as already indicated for the feedstock comprising branched $C_{10}$ monoolefins produced in a 1-hexene process used as received (e.g., first feedstock). The major difference will be in the composition of the crude stream and product stream. For the second feedstock, the crude product would consist of any residual $H_2S$ and unreacted $C_{10}$ olefin, the $C_{10}$ mercaptan isomers and the $C_{10}H_{21}$—S—$C_{10}H_{21}$ fraction. Once the lights are removed, the product will contain the $C_{10}$ mercaptan isomers and the $C_{20}$-sulfide, but will not contain any of the intermediate mercaptans and asymmetric sulfide components, which come from reaction of $C_{10}$ mercaptan with the other non-$C_{10}$ olefins. The mercaptan functionality for the various routes will be the same as already indicated.

Example 6

UV-initiation reactions of NEODENE 1112 IO higher olefins were performed in a 1.5 L UV reactor equipped with a 100 watt lamp and ballast. To 203.9 g of the NEODENE 1112 IO higher olefins, 650 g of $H_2S$ was charged after sealing the reactor. The reaction mixture was stirred at 500-1,000 RPM. The reaction temperature was controlled with a bath set at 25° C., but the heat of reaction did reach about 40° C. The lamp operated at 1.0-1.7 amps and 25-112 volts over the course of the reaction, operating at lower amps and higher voltages as it warmed up. The reaction pressure varied from 315-350 psig (2,172 kPag-2,413 kPag) during the actual reaction time. The reaction was typically completed in approximately 30 minutes as monitored by RAMAN spectroscopy analysis but was allowed to continue for 90 min to ensure completion. The $H_2S$ was vented and the reaction mixture purged three times with nitrogen to remove excess $H_2S$ to the extent possible. Additional $H_2S$ removal was conducted using a rotary evaporator. The conversion was measured as 98% by gas chromatography (GC) with the constituent components determined to be 41 wt. % $C_{11}$ mercaptan, 41 wt. % $C_{12}$ mercaptan, ~4 wt. % sulfides and 14 wt. % unreacted olefin. Distillation of the $C_{11+}$ mercaptans crude composition sample was performed at a kettle temperature of 137° C. and was complete when the head temperature reached ~120° C. at 9 mm Hg vacuum to give a kettle product with low perceived odor. The product mixture or kettle product (containing the intermediate and heavy fractions recovered from the $C_{11+}$ mercaptans crude composition) was analyzed by GC and determined to be 40.2 wt. % $C_{11}$ mercaptan, 53 wt. % $C_{12}$ mercaptan, 7 wt. % sulfides and 0.3 wt. % light mercaptan/unreacted olefin. Mercaptan sulfur was determined using titration as well and determined to be 16 wt. % vs. a GC calculation of 15.4 wt. %. Total sulfur was determined by X-ray to be 16.8 wt. % versus a GC calculation of ~15.8 wt. %.

Example 7

UV-initiation reactions of NEODENE 1314 IO higher olefins were performed in a 1.5 L UV reactor equipped with a 100 watt lamp and ballast. The UV prepared sample was prepared in the 1.5 L UV reactor equipped with a 100 watt lamp and ballast. To 229.6 g of the NEODENE 1314 IO higher olefins, 650 g of $H_2S$ was charged after sealing the reactor. The reaction mixture was stirred at 500-1,000 RPM. The reaction temperature was controlled with a bath set at 25° C., but the heat of reaction did reach about 40° C. The lamp operated at 1.0-1.5 amps and 25-110 volts over the course of the reaction, operating at lower amps and higher voltages as it warmed up. The reaction pressure varied from 305-340 psig (2,103 kPag-2,344 kPag) during the actual reaction time. The reaction was typically completed in approximately 30 minutes as monitored by RAMAN spectroscopy analysis but was allowed to continue for 70 min to ensure completion. The $H_2S$ was vented and the reaction mixture purged three times with nitrogen to remove excess $H_2S$ to the extent possible. Additional $H_2S$ removal was conducted using a rotary evaporator. The conversion was measured as 79% by GC with the constituent components determined to be 38 wt. % $C_{13}$ mercaptan, 39.4 wt. % $C_{14}$ mercaptan, ~2 wt. % sulfides and 21 wt. % unreacted olefin. Distillation of the $C_{11+}$ mercaptans crude composition sample was performed at a kettle temperature of 149° C. and was complete when the head temperature reached ~100° C. at 3 mm Hg vacuum to give a kettle product with low perceived odor. The product mixture or kettle product (containing the intermediate and heavy fractions recovered from the $C_{11+}$ mercaptans crude composition) was analyzed by GC and determined to be 45 wt. % $C_{13}$ mercaptan, 46 wt. % $C_{14}$ mercaptan, 6 wt. % sulfides and 3 wt. % light mercaptan/unreacted olefin. Mercaptan sulfur was determined using titration as well and determined to be 14 wt. % vs. a GC calculation of 13.1 wt. %. Total sulfur was determined by X-ray to be 14.6 wt. % versus a GC calculation of ~13.5 wt. %.

Example 8

UV-initiation reactions of NEODENE 14/16 higher olefins were performed in a 1.5 L UV reactor equipped with a 100 watt lamp and ballast. To 217.6 g of the NEODENE 14/16 higher olefins, 650 g of $H_2S$ was charged after sealing the reactor. The reaction mixture was stirred at 500-1,000 RPM. The reaction temperature was controlled with a bath set at 25° C., but the heat of reaction did reach about 40° C. The lamp operated at 1.0-1.6 amps and 25-120 volts over the course of the reaction, operating at lower amps and higher voltages as it warmed up. The reaction pressure varied from 310-340 psig (2,137 kPag-2,344 kPag) during the actual reaction time. The reaction was typically completed in approximately 30 minutes as monitored by RAMAN analysis but was allowed to continue for 55 min to ensure completion. The $H_2S$ was vented and the reaction mixture purged three times with nitrogen to remove excess $H_2S$ to the extent possible. Additional $H_2S$ removal was conducted using a rotary evaporator. The conversion was measured as 93% by GC with the constituent components determined to be 57.4 wt. % $C_{14}$ mercaptan, 30.1 wt. % $C_{16}$ mercaptan, ~6 wt. % sulfides and 7 wt. % unreacted olefin. Distillation of the $C_{11+}$ mercaptans crude composition sample was performed at a kettle temperature of 170° C. and was complete when the head temperature reached ~40° C. at 0 mm Hg vacuum to give a kettle product with low perceived odor. The product mixture or kettle product (containing the intermediate and heavy fractions recovered from the $C_{11+}$ mercaptans crude composition) was analyzed by GC and determined to be 57 wt. % $C_{14}$ mercaptan, 30 wt. % $C_{16}$ mercaptan, 13.4 wt. % sulfides and 0 wt. % light mercaptan/unreacted olefin. Mercaptan sulfur was determined using titration as well and determined to be 12 wt. % vs. a GC calculation of 11.6 wt. %. Total sulfur was determined by X-ray to be 12.9 wt. % versus a GC calculation of ~12.5 wt. %.

Example 9

To produce a $C_{20}$ polysulfide composition a feedstock comprising branched $C_{10}$ mercaptans was mixed with a catalyst then heated and reacted with elemental sulfur.

Figure 9:
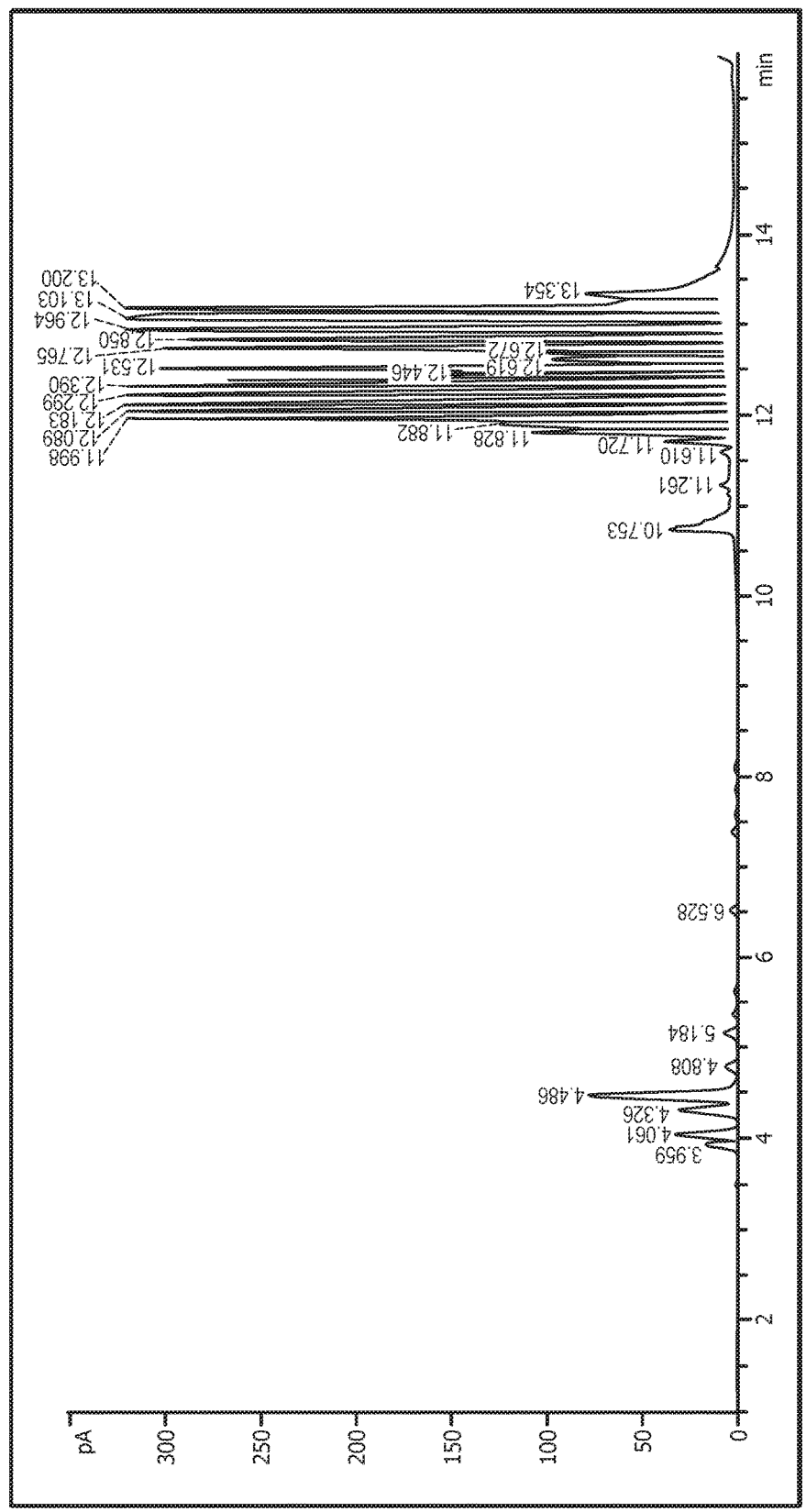
FIG. 9 displays a GC trace of a crude product from a reaction catalyzed by a polysulfidization catalyst.
Figure 10:
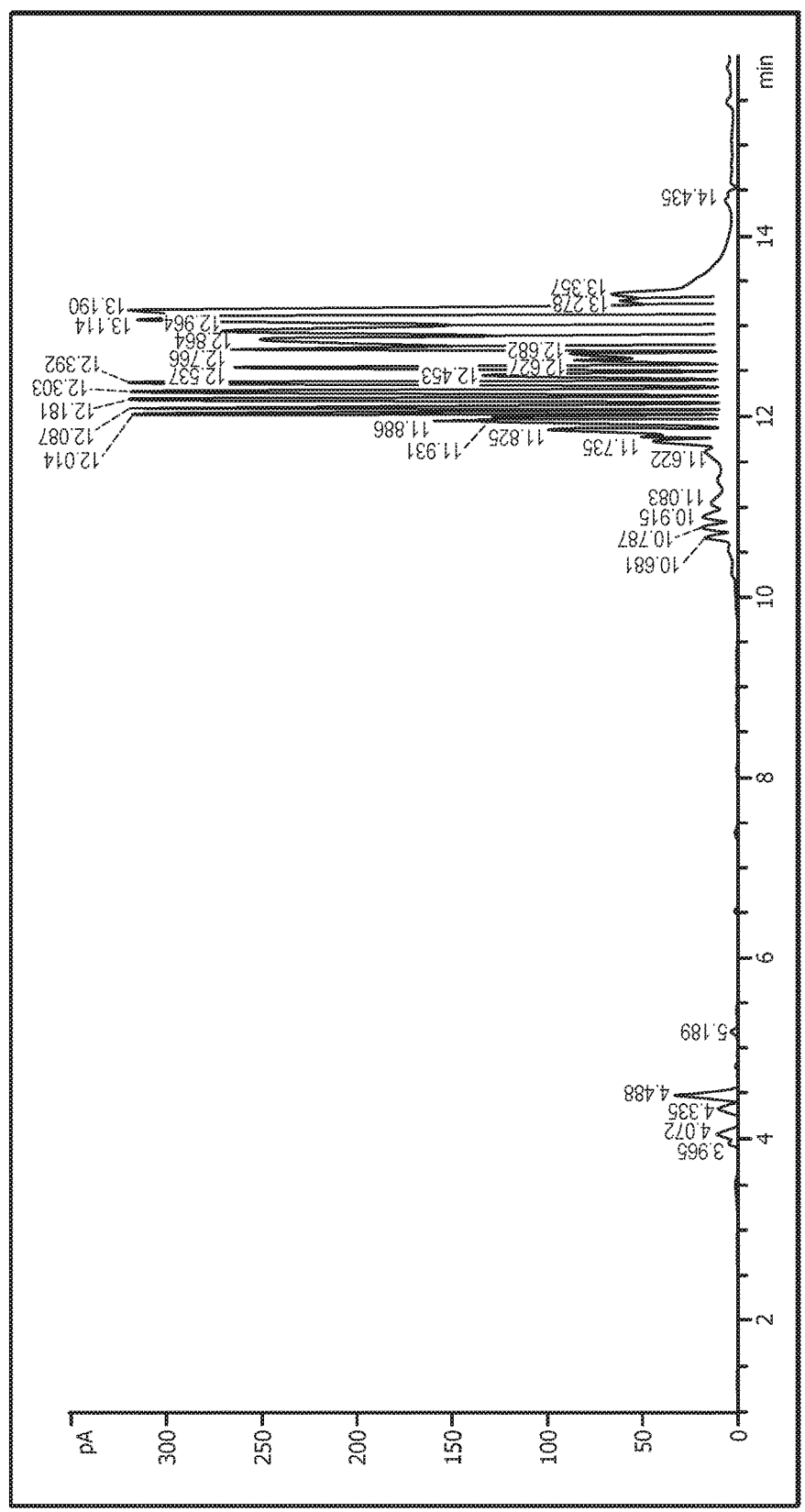
FIG. 10 displays a GC trace of a crude product from a reaction catalyzed by a polysulfidization catalyst after filtration through silica gel.

A 2 L Resin flask was equipped with an overhead stirrer, a heating mantle controlled by an internal thermocouple, a condenser, and a $N_2$ sparge. A quantity of 125.25 grams of branched $C_{10}$ mercaptans was added to the reaction flask followed by 0.08 grams of Tergitol® 15-S-10 and 0.06 grams of aqueous sodium hydroxide solution, 50% (w/w). The mixture of components was placed under an atmosphere of $N_2$ and heated to approximately 100° C. with continuous stirring that was maintained throughout the entire experimental procedure. To the heated mixture was added 17 grams of sulfur in several portions over approximately 30 minutes. The rate of sulfur addition was monitored and managed to maintain the rate of $H_2S$ gas evolution at a controllable level. After the addition of sulfur was complete, $N_2$ was sparged into the mixture to remove $H_2S$. After approximately 30 minutes the temperature was slowly raised (over a period of about 45 min) to 120° C. while $N_2$ sparging continued. The reaction mixture was held at the temperature of 120° C. for approximately 3 h. Then, the mixture was cooled and filtered. Gas chromatography showed conversion of the mercaptan as displayed in FIGS. 9 and 10.

ADDITIONAL DISCLOSURE

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the detailed description of the present disclosure. The disclosures of all patents, patent applications, and publications cited herein are hereby incorporated by reference.

A first aspect which is a composition comprising polysulfides, wherein at least about 50 wt. % of the polysulfides are branched $C_{20}$ to $C_{60}$ polysulfides represented by general formula $R^{15}S^1$—$[S]_n$—$S^2R^{16}$ wherein $R^{15}$ and $R^{16}$ are each independently a branched $C_{10}$ to $C_{30}$ alkyl group and wherein n is an integer from 1 to 10.

A second aspect which is the composition of the first aspect further comprising monosulfides represented by general formula $R^{17}$—S—$R^{18}$, wherein $R^{17}$ and $R^{18}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an attachment point with a sulfur atom of the monosulfide; and $R^9$ is a $C_1$ to $C_{21}$ alkyl group.

A third aspect which is the composition of the first or second aspect wherein the branched $C_{10}$ to $C_{30}$ alkyl group is represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and $R^9$ is a $C_1$ to $C_{21}$ alkyl group.

A fourth aspect which is the composition of any of the first three aspects wherein the branched $C_{10}$ to $C_{30}$ alkyl group is represented by Structure K-A, Structure K-B, Structure K-C, Structure K-D, Structure K-E, Structure K-F, Structure K-G, or Structure K-H, wherein * designates an $S^1$ atom of an $R^{15}S^1$ group or an $S^2$ atom of an $R^{16}S^2$ group.

A fifth aspect which is a process of producing a polysulfides crude product comprising one or more branched $C_{20}$ to $C_{60}$ polysulfides comprising: (A) reacting a feedstock comprising one or more branched $C_{10}$ to $C_{30}$ mercaptans and sulfur in the presence of a catalyst and (B) collecting the polysulfides crude product.

A sixth aspect which is the process of the fifth aspect wherein the one or more branched $C_{10}$ to $C_{30}$ mercaptans are represented by Structure A-1, Structure B-1, Structure C-1, Structure D-1, Structure E-1, Structure F-1, Structure G-1, Structure H-1, or combinations thereof, wherein $R^9$ is a $C_1$ to $C_{21}$ alkyl group.

A seventh aspect which is the process of the fifth or sixth aspect wherein the one or more branched $C_{20}$ to $C_{60}$ polysulfides are polysulfides represented by general formula $R^{15}S^1$—$[S]_n$—$S^2R^{16}$, wherein n is an integer from 1 to 10; $R^{15}$ and $R^{16}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group; and $R^9$ is a $C_1$ to $C_{21}$ alkyl group.

An eighth aspect which is the process of any of the fifth through seventh aspects wherein (A) reacting further comprises: (a) contacting the one or more branched $C_{10}$ to $C_{30}$ mercaptans and the catalyst to form a mixture wherein a weight ratio of catalyst to mercaptans is in a range of from about 0.005:1 to about 0.013:1; (b) heating the mixture to a temperature in a range of from about 60° C. to about 85° C.; (c) heating the mixture to a temperature in a range of from about 90° C. to about 150° C.; and (d) cooling the mixture to a temperature in a range of from about 65° C. to about 85° C.

A ninth aspect which is the process of any of the fifth through eighth aspects wherein (B) collecting the crude product comprises: (e) cooling the mixture to a temperature in a range of from about 20° C. to about 35° C.; and (f) filtering the polysulfides crude product.

A tenth aspect which is the process of any of the fifth through ninth aspects wherein during step (b): (i) the mixture is contacted with elemental sulfur wherein an equivalent molar ratio of sulfur to mercaptans is in a range of from about 0.07:1 to about 1.2:1; and (ii) the mixture is agitated for a time period of from about 2 hours to about 6 hours.

An eleventh aspect which is the process of any of the fifth through tenth aspects wherein during step (c): (i) the mixture is agitated for a time period of from about 2 hours to about 4 hours; and (ii) the mixture is sparged with an inert gas for a time period of from about 0.5 hour to about 4 hours.

A twelfth aspect which is the process of any of the fifth through eleventh aspects wherein during step (d): (i) an epoxide is added to the mixture over a time period of from about 10 min to about 2 hours wherein an equivalent molar ratio of epoxide to mercaptans is in a range of from about 0.05:1 to about 0.1:1; (ii) the mixture is agitated for a time period of from about 1 hour to about 4 hours; and (iii) the mixture is sparged with an inert gas for a time period of from about 0.5 hour to about 4 hours.

A thirteenth aspect which is the process of any of the fifth through twelfth aspects wherein the epoxide comprises ethylene oxide, propylene oxide, or a combination thereof.

A fourteenth aspect which is the process of any of the fifth through thirteenth aspects wherein the catalyst comprises: (i) a surfactant and (ii) a Group 1 or Group 2 metal hydroxide, wherein a weight ratio of (i) to (ii) is in a range of from about 25:1 to about 40:1.

A fifteenth aspect which is the process of any of the fifth through fourteenth aspects wherein prior to contacting the catalyst with the one or more branched $C_{10}$ to $C_{30}$ mercaptans, (i) and (ii) are combined and heated to a temperature in a range of from about 60° C. to about 100° C. and the temperature is maintained for a time period of from about 30 min to about 2 hours.

A sixteenth aspect which is the process of the fourteenth or fifteenth aspects wherein the surfactant comprises a nonionic surfactant.

A seventeenth aspect which is the process of any of the fourteenth through sixteenth aspects wherein the surfactant comprises a polyethoxylated alcohol, a polyethoxylated mercaptan, or a combination thereof.

An eighteenth aspect which is the process of any of the fourteenth through seventeenth aspects wherein the Group 1 or Group 2 metal hydroxide is a solid or is dissolved in an aqueous solution.

A nineteenth aspect which is the process of any of the fourteenth through eighteenth aspects wherein the Group 1 or Group 2 metal hydroxide is sodium hydroxide.

A twentieth aspect which is the process of any of the fifth through nineteenth aspects wherein (A) reacting further comprises: (a) contacting the one or more branched $C_{10}$ to $C_{30}$ mercaptans and the catalyst to form a mixture wherein a weight ratio of catalyst to mercaptans is in a range of from about 0.005:1 to about 0.013:1; (b) contacting the mixture with elemental sulfur wherein an equivalent molar ratio of sulfur to mercaptans is in a range of from about 0.07:1 to about 1.2:1; (c) heating the mixture to a temperature in a range of from about 60° C. to about 85° C. and maintaining the temperature while the mixture is agitated for a time period of from about 2 hours to about 6 hours; (d) heating the mixture to a temperature in a range of from about 90° C. to about 150° C. and maintaining the temperature while the mixture is agitated for a time period of from about 2 hours to about 4 hours and subsequently sparged with an inert gas for a time period of from about 0.5 hour to about 4 hours; and (e) cooling the mixture to a temperature in a range of from about 65° C. to about 85° C. and maintaining the temperature while: (i) an epoxide is added to the mixture over a time period of from about 10 min to about 2 hours wherein an equivalent molar ratio of epoxide to mercaptans is in a range of from about 0.05:1 to about 0.1:1; (ii) the mixture is agitated for a time period for a time period of from about 1 hour to about 4 hours; and (iii) the mixture is sparged with an inert gas for a time period of from about 0.5 hour to about 4 hours.

A twenty-first aspect which is the process of any of the fifth through twentieth aspects wherein after cooling the mixture (d), the process further comprises: (e) adding a decolorizing agent to the mixture, wherein a weight ratio of decolorizing agent to mercaptans is in a range of from about 0.01:1 to about 0.02:1; (f) heating the mixture to a temperature in a range of from about 40° C. to about 60° C., and maintaining the temperature for a time period of from about 30 min to about 2 hours; (g) cooling the mixture to a temperature in a range of from about 20° C. to about 35° C.; and (h) collecting the polysulfides crude product.

A twenty-second aspect which is a process of producing one or more branched $C_{20}$ to $C_{60}$ polysulfides comprising: (a) reacting hydrogen sulfide ($H_2S$) and a feedstock comprising one or more branched $C_{10}$ to $C_{30}$ olefins in the presence of an initiating agent to produce a branched $C_{10+}$ mercaptans crude composition; (b) recovering an intermediate reaction product comprising one or more branched $C_{10}$ to $C_{30}$ mercaptans from the branched $C_{10+}$ mercaptans crude composition; (c) reacting sulfur and the intermediate reaction product comprising one or more branched $C_{10}$ to $C_{30}$ mercaptans in the presence of a catalyst; and (d) collecting a $C_{20+}$ polysulfides crude product comprising the one or more branched $C_{20}$ to $C_{60}$ polysulfides.

A twenty-third aspect which is the process of the twenty-second aspect wherein the one or more branched $C_{10}$ to $C_{30}$ olefins are represented by Structure I-1, Structure J-1, Structure K-1, Structure L-1, or combinations thereof, wherein $R^9$ is a $C_1$ to $C_{21}$ alkyl group.

A twenty-fourth aspect which is the process of the twenty-second or the twenty-third aspect wherein the one or more branched $C_{10}$ to $C_{30}$ mercaptans are represented by Structure A-1, Structure B-1, Structure C-1, Structure D-1, Structure E-1, Structure F-1, Structure G-1, Structure H-1, or combinations thereof, wherein $R^9$ is a $C_1$ to $C_{21}$ alkyl group.

A twenty-fifth aspect which is the process of any of the twenty-second through twenty-fourth aspects wherein the one or more branched $C_{20}$ to $C_{60}$ polysulfides are represented by general formula $R^{15}S^1$—$[S]_n$—$S^2R^{16}$, wherein n is an integer from 1 to 10; and $R^{15}$ and $R^{16}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group; and $R^9$ is a $C_1$ to $C_{21}$ alkyl group.

A twenty-sixth aspect which is the process of any of the twenty-second through twenty-fifth aspects wherein the one or more branched $C_{10}$ to $C_{30}$ olefins comprise 5-methyl-1-nonene (represented by Structure I), 3-propyl-1-heptene (represented by Structure J), 4-ethyl-1-octene (represented by Structure K), 2-butyl-1-hexene (represented by Structure L), or combinations thereof:

A twenty-seventh aspect which is the process of any of the twenty-second through twenty-sixth aspects wherein the one or more branched $C_{10}$ to $C_{30}$ mercaptans comprise 5-methyl-1-mercapto-nonane (represented by Structure A), 3-propyl-1-mercapto-heptane (represented by Structure B), 4-ethyl-1-mercapto-octane (represented by Structure C), 2-butyl-1-mercapto-hexane (represented by Structure D), 5-methyl-2-mercapto-nonane (represented by Structure E), 3-propyl-2-mercapto-heptane (represented by Structure F), 4-ethyl-2-mercapto-octane (represented by Structure G), 5-methyl-5-mercapto-nonane (represented by Structure H), or combinations thereof:

A twenty-eighth aspect which is the process of any of the twenty-second through twenty-seventh aspects wherein the one or more branched $C_{20}$ to $C_{60}$ polysulfides are polysulfides represented by general formula $R^{15}S^1$—$[S]_n$—$S^2R^{16}$, wherein n is an integer from 1 to 10; and $R^{15}$ and $R^{16}$ are each independently a branched $C_{10}$ alkyl group by Structure K-A, Structure K-B, Structure K-C, Structure K-D, Structure K-E, Structure K-F, Structure K-G, or Structure K-H, wherein * designates an $S^1$ atom of an $R^{15}S^1$ group or an $S^2$ atom of an $R^{16}S^2$ group.

A twenty-ninth aspect which is a composition comprising: (A) at least about 25 wt. % branched $C_{20}$ to $C_{60}$ polysulfides represented by general formula $R^{15}S^1$—$[S]_n$—$S^2R^{16}$, wherein n is an integer from 1 to 10, wherein $R^{15}$ and $R^{16}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group; and (B) at least about 5 wt. % branched $C_{20}$ to $C_{60}$ monosulfides represented by general formula $R^{17}$—S—$R^{18}$, wherein $R^{17}$ and $R^{18}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an attachment point with a sulfur atom of the branched $C_{20}$ to $C_{60}$ monosulfide, and wherein $R^9$ is a $C_1$ to $C_{21}$ alkyl group.

A thirtieth aspect which is a composition comprising: (A) from at least about 50 wt. % to at least about 90 wt. % polysulfides, wherein at least about 50 wt. % of the polysulfides are branched $C_{20}$ to $C_{60}$ polysulfides represented by general formula $R^{15}S^1-[S]_n-S^2R^{16}$, wherein n is an integer from 1 to 10, wherein $R^{15}$ and $R^{16}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group; and (B) from at least about 10 wt. % to at least about 30 wt. % monosulfides, wherein at least 50 wt. % of the monosulfides are branched $C_{20}$ to $C_{60}$ monosulfides represented by general formula $R^{17}-S-R^{18}$, wherein $R^{17}$ and $R^{18}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an attachment point with a sulfur atom of the branched $C_{20}$ to $C_{60}$ monosulfide, and wherein $R^9$ is a $C_1$ to $C_{21}$ alkyl group.

A thirty-first aspect which is a composition comprising: (A) at least about 25 wt. % branched $C_{20}$ to $C_{60}$ polysulfides represented by general formula $R^{15}S^1-[S]_n-S^2R^{16}$, wherein n is an integer from 1 to 10, wherein $R^{15}$ and $R^{16}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group, and wherein $R^9$ is a $C_1$ to $C_{21}$ alkyl group; and (B) at least about 5 wt. % branched $C_{20}$ to $C_{60}$ monosulfides represented by general formula $R^{17}-S-R^{18}$, wherein $R^{17}$ and $R^{18}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an attachment point with a sulfur atom of the branched $C_{20}$ to $C_{60}$ monosulfide, and wherein $R^9$ is a $C_1$ to $C_{21}$ alkyl group; and one or more of the following components (C)-(I): (C) less than about 5 wt. % branched $C_{16}$ polysulfides; (D) less than about 15 wt. % branched $C_{64}$ polysulfides; (E) less than about 15 wt. % branched $C_{68}$ polysulfides; (F) less than about 5 wt. % branched $C_{72}$ polysulfides and/or branched $C_{76}$ polysulfides; (G) less than about 1 wt. % branched $C_{16}$ to $C_{76}$ monosulfides represented by general formula $R^{17}-S-R^{18}$, wherein $R^{17}$ and $R^{18}$ are each independently a functional group derived from an olefin selected from the group consisting of $C_8$ monoolefins, $C_{32}$ monoolefins, $C_{34}$ monoolefins, $C_{36}$ monoolefins, and $C_{38}$ monoolefins, wherein $R^{17}$ and $R^{18}$ are not both branched $C_{30}$ monoolefins; (H) less than about 10 wt. % unreacted $C_8$ to $C_{38}$ mercaptans; and (I) less than about 10 wt. % non-mercaptan impurities selected from the group consisting of $C_8$ to $C_{38}$ olefins, $C_8$ to $C_{14}$ alkanes, cyclohexane, methylcyclopentane, methylcyclohexane, benzene, toluene, ethylbenzene, xylene, mesitylene, hexamethylbenzene, $C_4$ to $C_{12}$ alcohols, 2-ethyl-1-hexanol, and 2-ethylhexyl-2-ethylhexanoate.

While aspects and embodiments of the disclosure have been shown and described, modifications thereof can be made without departing from the spirit and teachings of the present disclosure. The embodiments and examples described herein are exemplary only, and are not intended to be limiting. Many variations and modifications of the present disclosure are possible and are within the scope of the subject matter as disclosed herein.

At least one aspect or embodiment is disclosed and variations, combinations, and/or modifications of the embodiment(s) and/or features of the embodiment(s) made by a person having ordinary skill in the art are within the scope of the disclosure. Alternative aspects or embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k \cdot (R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

What is claimed is:

1. A process of producing a polysulfides crude product comprising one or more branched $C_{20}$ to $C_{60}$ polysulfides comprising: (A) reacting a feedstock comprising one or more branched $C_{10}$ to $C_{30}$ mercaptans and sulfur in the presence of a catalyst and (B) collecting the polysulfides crude product, and wherein (A) reacting further comprises:
    (a) contacting the one or more branched $C_{10}$ to $C_{30}$ mercaptans and the catalyst to form a mixture wherein a weight ratio of catalyst to mercaptans is in a range of from about 0.005:1 to about 0.013:1;
    (b) heating the mixture to a temperature in a range of from about 60° C. to about 85° C.;
    (c) heating the mixture to a temperature in a range of from about 90° C. to about 150° C.; and
    (d) cooling the mixture to a temperature in a range of from about 65° C. to about 85° C.

2. The process of claim 1, wherein the one or more branched $C_{10}$ to $C_{30}$ mercaptans are represented by Structure A-1, Structure B-1, Structure C-1, Structure D-1, Structure E-1, Structure F-1, Structure G-1, Structure H-1, or combinations thereof,

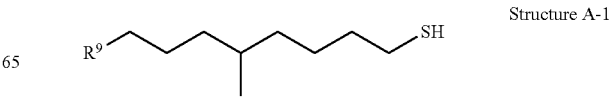

Structure A-1

-continued

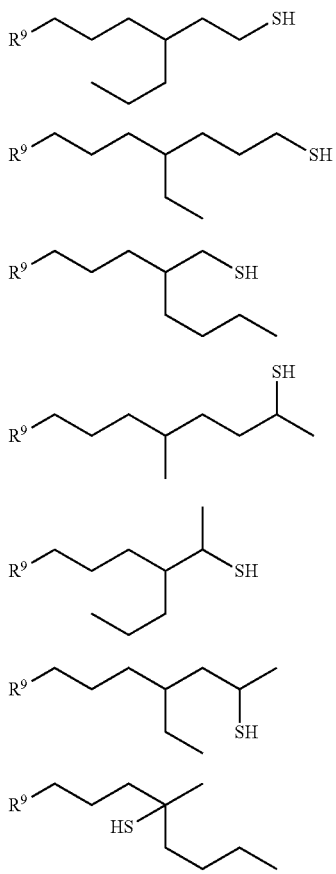

Structure B-1
Structure C-1
Structure D-1
Structure E-1
Structure F-1
Structure G-1
Structure H-1 wherein $R^9$ is a $C_1$ to $C_{21}$ alkyl group.

3. The process of claim 1, wherein the one or more branched $C_{20}$ to $C_{60}$ polysulfides are polysulfides represented by general formula $R^{15}S^1$—$[S]_n S^2 R^{16}$, wherein n is an integer from 1 to 10;

$R^{15}$ and $R^{16}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H;

wherein * designates an $S^1$ atom of an $R^{15}S^1$ group or an $S^2$ atom of an $R^{16}S^2$ group; and $R^9$ is a $C_1$ to $C_{21}$ alkyl group.

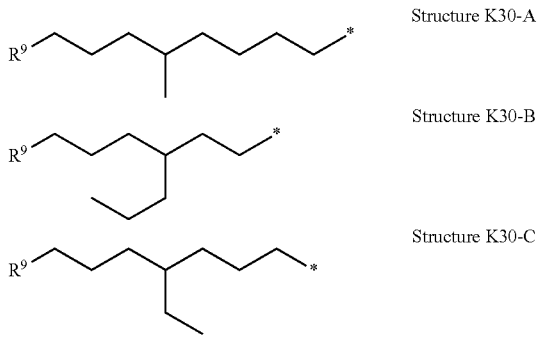

Structure K30-A
Structure K30-B
Structure K30-C

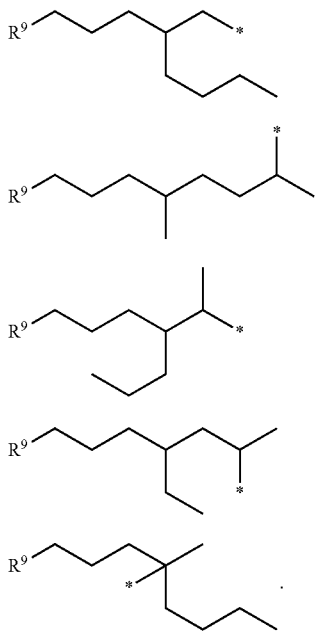

Structure K30-D
Structure K30-E
Structure K30-F
Structure K30-G
Structure K30-H

4. The process of claim 1, wherein (B) collecting the crude product comprises:
   (e) cooling the mixture to a temperature in a range of from about 20° C. to about 35° C.; and
   (f) filtering the polysulfides crude product.

5. The process of claim 1, wherein during step (b):
   (i) the mixture is contacted with elemental sulfur wherein an equivalent molar ratio of sulfur to mercaptans is in a range of from about 0.07:1 to about 1.2:1; and
   (ii) the mixture is agitated for a time period of from about 2 hours to about 6 hours.

6. The process of claim 1, wherein during step (c):
   (i) the mixture is agitated for a time period of from about 2 hours to about 4 hours; and
   (ii) the mixture is sparged with an inert gas for a time period of from about 0.5 hour to about 4 hours.

7. The process of claim 1, wherein during step (d):
   (i) an epoxide is added to the mixture over a time period of from about 10 min to about 2 hours wherein an equivalent molar ratio of epoxide to mercaptans is in a range of from about 0.05:1 to about 0.1:1;
   (ii) the mixture is agitated for a time period of from about 1 hour to about 4 hours; and
   (iii) the mixture is sparged with an inert gas for a time period of from about 0.5 hour to about 4 hours.

8. The process of claim 7, wherein the epoxide comprises ethylene oxide, propylene oxide, or a combination thereof.

9. The process of claim 1, wherein the catalyst comprises: (i) a surfactant and (ii) a Group 1 or Group 2 metal hydroxide, wherein a weight ratio of (i) to (ii) is in a range of from about 25:1 to about 40:1.

10. The process of claim 9, wherein prior to contacting the catalyst with the one or more branched $C_{10}$ to $C_{30}$ mercaptans, (i) and (ii) are combined and heated to a temperature in a range of from about 60° C. to about 100° C. and the temperature is maintained for a time period of from about 30 min to about 2 hours.

11. The process of claim 9, wherein the surfactant comprises a nonionic surfactant.

12. The process of claim 9, wherein the surfactant comprises a polyethoxylated alcohol, a polyethoxylated mercaptan, or a combination thereof.

13. The process of claim 9, wherein the Group 1 or Group 2 metal hydroxide is a solid or is dissolved in an aqueous solution.

14. The process of claim 9, wherein the Group 1 or Group 2 metal hydroxide is sodium hydroxide.

15. The process of claim 1, wherein (A) reacting further comprises:
   (a) contacting the mixture with elemental sulfur wherein an equivalent molar ratio of sulfur to mercaptans is in a range of from about 0.07:1 to about 1.2:1;
   (b) maintaining the temperature of from about 60° C. to about 85° C. while the mixture is agitated for a time period of from about 2 hours to about 6 hours;
   (c) maintaining the temperature in a range of from about 90° C. to about 150° C. while the mixture is agitated for a time period of from about 2 hours to about 4 hours and subsequently sparged with an inert gas for a time period of from about 0.5 hour to about 4 hours; and
   (d) maintaining the mixture at a temperature in a range of from about 65° C. to about 85° C. while:
      (i) an epoxide is added to the mixture over a time period of from about 10 min to about 2 hours wherein an equivalent molar ratio of epoxide to mercaptans is in a range of from about 0.05:1 to about 0.1:1;
      (ii) the mixture is agitated for a time period for a time period of from about 1 hour to about 4 hours; and
      (iii) the mixture is sparged with an inert gas for a time period of from about 0.5 hour to about 4 hours.

16. The process of claim 1, wherein after cooling the mixture (d), the process further comprises:
   (e) adding a decolorizing agent to the mixture, wherein a weight ratio of decolorizing agent to mercaptans is in a range of from about 0.01:1 to about 0.02:1;
   (f) heating the mixture to a temperature in a range of from about 40° C. to about 60° C., and maintaining the temperature for a time period of from about 30 min to about 2 hours;
   (g) cooling the mixture to a temperature in a range of from about 20° C. to about 35° C.; and
   (h) collecting the polysulfides crude product.

17. A process of producing a polysulfides crude product comprising one or more branched $C_{20}$ to $C_{60}$ polysulfides comprising: (A) reacting a feedstock comprising one or more branched $C_{10}$ to $C_{30}$ mercaptans and sulfur in the presence of a catalyst and (B) collecting the polysulfides crude product, and wherein (B) collecting the polysulfides crude product further comprises:
   (e) cooling the mixture to a temperature in a range of from about 20° C. to about 35° C.; and
   (f) filtering the polysulfides crude product.

18. The process of claim 1, wherein (A) reacting further comprises:
   (a) contacting the one or more branched $C_{10}$ to $C_{30}$ mercaptans and the catalyst to form a mixture wherein a weight ratio of catalyst to mercaptans is in a range of from about 0.005:1 to about 0.013:1;
   (b) heating the mixture to a temperature in a range of from about 60° C. to about 85° C.;
   (c) heating the mixture to a temperature in a range of from about 90° C. to about 150° C.; and
   (d) cooling the mixture to a temperature in a range of from about 65° C. to about 85° C.

19. The process of claim 17 wherein the one or more branched $C_{10}$ to $C_{30}$ mercaptans are represented by Structure A-1, Structure B-1, Structure C-1, Structure D-1, Structure E-1, Structure F-1, Structure G-1, Structure H-1, or combinations thereof,

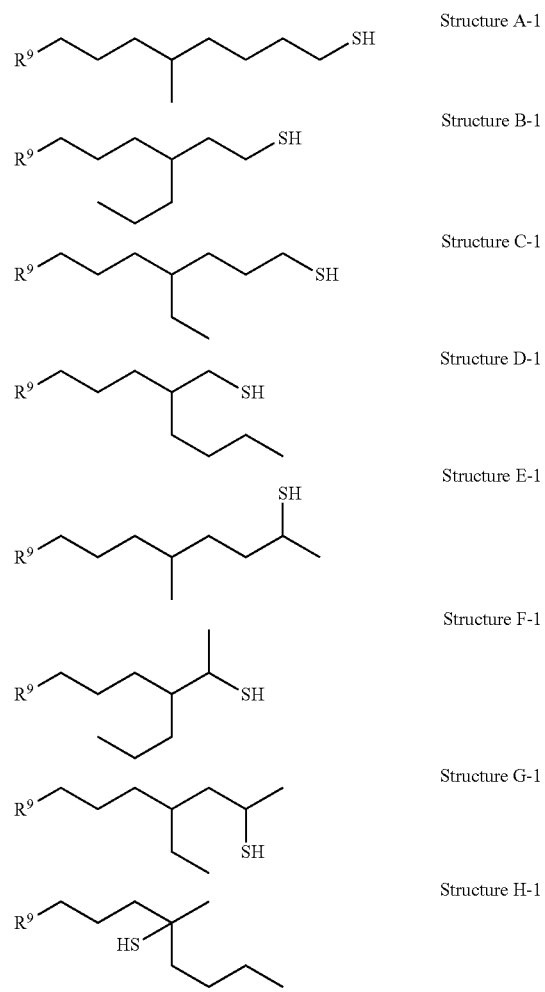

wherein $R^9$ is a $C_1$ to $C_{21}$ alkyl group.

20. The process of claim 17, wherein the one or more branched $C_{20}$ to $C_{60}$ polysulfides are polysulfides represented by general formula $R^{15}S^1—[S]_n—S^2R^{16}$, wherein
   n is an integer from 1 to 10;
   $R^{15}$ and $R^{16}$ are each independently a branched $C_{10}$ to $C_{30}$ alkyl group represented by Structure K30-A, Structure K30-B, Structure K30-C, Structure K30-D, Structure K30-E, Structure K30-F, Structure K30-G, or Structure K30-H, wherein * designates an $S^1$ atom of an $R^{15}S^1$ group or an $S^2$ atom of an $R^{16}S^2$ group; and
   $R^9$ is a $C_1$ to $C_{21}$ alkyl group.

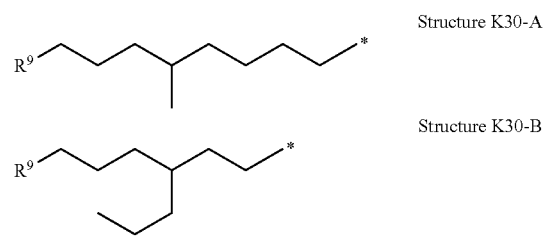

Structure K30-C, Structure K30-D, Structure K30-E, Structure K30-F, Structure K30-G, Structure K30-H 21. The process of claim 18, wherein during step (b):
(i) the mixture is contacted with elemental sulfur wherein an equivalent molar ratio of sulfur to mercaptans is in a range of from about 0.07:1 to about 1.2:1; and
(ii) the mixture is agitated for a time period of from about 2 hours to about 6 hours.

22. The process of claim 18, wherein during step (c):
(i) the mixture is agitated for a time period of from about 2 hours to about 4 hours; and
(ii) the mixture is sparged with an inert gas for a time period of from about 0.5 hour to about 4 hours.

23. The process of claim 18, wherein during step (d):
an epoxide is added to the mixture over a time period of from about 10 min to about 2 hours wherein an equivalent molar ratio of epoxide to mercaptans is in a range of from about 0.05:1 to about 0.1:1;
(ii) the mixture is agitated for a time period of from about 1 hour to about 4 hours; and
(iii) the mixture is sparged with an inert gas for a time period of from about 0.5 hour to about 4 hours.

24. The process of claim 23, wherein the epoxide comprises ethylene oxide, propylene oxide, or a combination thereof.

25. The process of claim 17, wherein the catalyst comprises: (i) a surfactant and (ii) a Group 1 or Group 2 metal hydroxide, wherein a weight ratio of (i) to (ii) is in a range of from about 25:1 to about 40:1.

26. The process of claim 25, wherein prior to contacting the catalyst with the one or more branched $C_{10}$ to $C_{30}$ mercaptans, (i) and (ii) are combined and heated to a temperature in a range of from about 60° C. to about 100° C. and the temperature is maintained for a time period of from about 30 min to about 2 hours.

27. The process of claim 25, wherein the surfactant comprises a nonionic surfactant.

28. The process of claim 25, wherein the surfactant comprises a polyethoxylated alcohol, a polyethoxylated mercaptan, or a combination thereof.

29. The process of claim 25, wherein the Group 1 or Group 2 metal hydroxide is a solid or is dissolved in an aqueous solution.

30. The process of claim 25, wherein the Group 1 or Group 2 metal hydroxide is sodium hydroxide.

31. The process of claim 17, wherein (A) reacting further comprises:
(a) contacting the one or more branched $C_{10}$ to $C_{30}$ mercaptans and the catalyst to form a mixture wherein a weight ratio of catalyst to mercaptans is in a range of from about 0.005:1 to about 0.013:1;
(b) contacting the mixture with elemental sulfur wherein an equivalent molar ratio of sulfur to mercaptans is in a range of from about 0.07:1 to about 1.2:1;
(c) heating the mixture to a temperature in a range of from about 60° C. to about 85° C. and maintaining the temperature while the mixture is agitated for a time period of from about 2 hours to about 6 hours;
(d) heating the mixture to a temperature in a range of from about 90° C. to about 150° C. and maintaining the temperature while the mixture is agitated for a time period of from about 2 hours to about 4 hours and subsequently sparged with an inert gas for a time period of from about 0.5 hour to about 4 hours; and
(e) cooling the mixture to a temperature in a range of from about 65° C. to about 85° C. and maintaining the temperature while:
(i) an epoxide is added to the mixture over a time period of from about 10 min to about 2 hours wherein an equivalent molar ratio of epoxide to mercaptans is in a range of from about 0.05:1 to about 0.1:1;
(ii) the mixture is agitated for a time period for a time period of from about 1 hour to about 4 hours; and
(iii) the mixture is sparged with an inert gas for a time period of from about 0.5 hour to about 4 hours.

32. The process of claim 18, wherein after cooling the mixture (d), the process further comprises:
(e) adding a decolorizing agent to the mixture, wherein a weight ratio of decolorizing agent to mercaptans is in a range of from about 0.01:1 to about 0.02:1;
(f) heating the mixture to a temperature in a range of from about 40° C. to about 60° C., and maintaining the temperature for a time period of from about 30 min to about 2 hours;
(g) cooling the mixture to a temperature in a range of from about 20° C. to about 35° C.; and
(h) collecting the polysulfides crude product.

* * * * *